United States Patent
Yoo et al.

(10) Patent No.: US 12,384,756 B2
(45) Date of Patent: Aug. 12, 2025

(54) PIPERIDINEDIONE DERIVATIVES

(71) Applicant: INNOCURE THERAPEUTICS, INC., Seongnam-si (KR)

(72) Inventors: Hye-Dong Yoo, Seongnam-si (KR); Young-Jun Shin, Suwon-si (KR); Sung Jin Kim, Suwon-si (KR); Bo Kyoung Kim, Yongin-si (KR); Eun Myong Lee, Seoul (KR); So Hyun Shin, Seongnam-si (KR); Yong Hwan Kim, Namyangju-si (KR); Seo Won Choi, Yongin-si (KR); Min Sik Bae, Yongin-si (KR); Dongsik Yang, Pyeongtaek-si (KR); Jeong Hyun Hong, Seoul (KR); Jin Keon Pai, Seoul (KR)

(73) Assignee: INNOCURE THERAPEUTICS, INC., Seongnam-si (KR)

( * ) Notice: Subject to any disclaimer, the term of this patent is extended or adjusted under 35 U.S.C. 154(b) by 823 days.

(21) Appl. No.: 17/626,377

(22) PCT Filed: Nov. 15, 2021

(86) PCT No.: PCT/KR2021/016588
§ 371 (c)(1),
(2) Date: Jan. 11, 2022

(87) PCT Pub. No.: WO2022/250224
PCT Pub. Date: Dec. 1, 2022

(65) Prior Publication Data
US 2023/0295105 A1 Sep. 21, 2023

(30) Foreign Application Priority Data

| May 26, 2021 | (KR) | 10-2021-0067965 |
| Aug. 31, 2021 | (KR) | 10-2021-0116004 |
| Sep. 3, 2021 | (KR) | 10-2021-0118004 |

(51) Int. Cl.
| C07D 401/04 | (2006.01) |
| A61K 47/55 | (2017.01) |
| A61P 35/00 | (2006.01) |
| C07D 401/14 | (2006.01) |
| C07D 495/14 | (2006.01) |

(52) U.S. Cl.
CPC ............ *C07D 401/04* (2013.01); *A61K 47/55* (2017.08); *A61P 35/00* (2018.01); *C07D 401/14* (2013.01); *C07D 495/14* (2013.01)

(58) Field of Classification Search
CPC .. C07D 401/04; C07D 401/14; C07D 495/14; C07D 491/107; A61K 47/55; A61K 31/502
See application file for complete search history.

(56) References Cited

U.S. PATENT DOCUMENTS

| 2018/0215731 A1* | 8/2018 | Crew | A61K 47/55 |
| 2023/0099031 A1* | 3/2023 | Kley | A61K 47/55 |
| | | | 514/275 |

FOREIGN PATENT DOCUMENTS

| WO | WO-2021249534 A1 * | 12/2021 | A61K 31/502 |

OTHER PUBLICATIONS

Sung "A novel cereblon modulator for targeted protein degradation" European Journal of Medicinal Chemistry 2019, 166, 65-74 (Year: 2019).*
Taavi K. Neklesa et al., "Targeted protein degradation by PROTACs", Pharmacology & Therapeutics, 2017, pp. 138-144, vol. 174.

* cited by examiner

*Primary Examiner* — Theodore R. Howell
*Assistant Examiner* — John Josiah Macalipay Lopp
(74) *Attorney, Agent, or Firm* — ArentFox Schiff LLP; Yun H. Choe

(57) ABSTRACT

Disclosed is a novel piperidinedione compound of Formula 1 or a pharmaceutically acceptable salt thereof. Uses of the novel piperidinedione compound of Formula 1 or a pharmaceutically acceptable salt thereof as an anti-tumor agent or an immunomodulatory for treatment of CRBN protein-mediated diseases are disclosed. Also the compound or salt thereof can be used an E3 ligase binder in a PROTAC compound comprising a protein of interest ligand, a linker and an E3 ligase binder. Therefore, a PROTAC compound or a pharmaceutically acceptable salt thereof wherein, as an E3 ligase binder, the compound or salt thereof 1 is connected to the linker is disclosed:

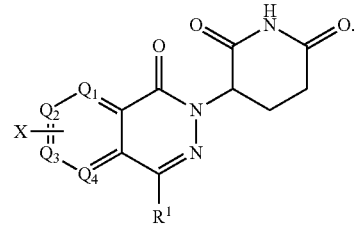

Formula 1

4 Claims, 6 Drawing Sheets

PIPERIDINEDIONE DERIVATIVES

CROSS REFERENCE TO RELATED APPLICATIONS

This application is a National Stage of International Application No. PCT/KR2021/016588, filed Nov. 15, 2021, claiming priorities to Korean Patent Application No. 10-2021-0067965, filed May 26, 2021, Korean Patent Application No. 10-2021-0116004, filed Aug. 31, 2021 and Korean Patent Application No. 10-2021-0118004, filed Sep. 3, 2021.

TECHNICAL FIELD

The present invention relates to a piperidinedione derivative compound. In addition, the present invention relates to a PROTAC compound comprising the piperidinedione derivative compound.

BACKGROUND ART

PROTAC is an abbreviation for PROteolysis TArgeting Chimera and is a technique that induce the degradation of targeted protein (POI: protein of interest).

PROTAC has a structure in which a POI ligand and an E3 ligase binder are linked by a linker. POI ligand has a structure capable of binding to the POI which is related to a disease and E3 ligase binder has a structure capable of binding to E3 ligase.

The E3 ligase (E3 enzyme) can label a ubiquitin on the POI and such ubiquitin-labeled POI is degraded by proteasomes.

When the POI ligand of the PROTAC compound binds to the POI, the E3 ligase is located very close to the POI by the PROTAC compound, and therefore, an environment in which the POI can be removed by the proteasome is created.

In particular, if the PROTAC compound binds to the POI involved in the proliferation of cancer cells, it can induce the degradation of the POI and achieve the effects of cancer treatment.

DISCLOSURE

Technical Problem

The object of the present invention is to provide a PROTAC compound capable of enhancing the degradation effect on the POI. In addition, the object of the present invention is to provide a novel piperidinedione compound that can be used as an E3 ligase binder in a PROTAC compound.

Technical Solution

The present invention relates to a compound of Formula 1 or a pharmaceutically acceptable salt thereof:

[Formula 1]

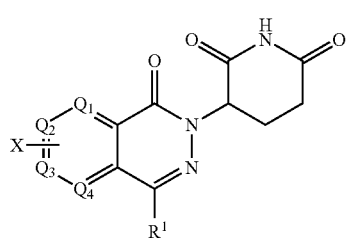

wherein

X is hydrogen, halogen, amino, nitro, hydroxy, $C_1$ to $C_6$ straight or branched alkyloxy, or 4 to 8 membered heterocyclic group including oxygen or nitrogen, $Q_1$ to $Q_4$ are each independently C—F, C—Cl, C—H, C—X or N, provided that at least one of $Q_1$ to $Q_4$ is C—X, $R^1$ is hydrogen, nitro, amino, carbonyl, $C_1$ to $C_6$ straight, branched or cyclic alkyl, or $C_1$ to $C_6$ straight, branched or cyclic alkyl substituted with halogen.

In the compound of Formula 1 according to the present invention, preferably, X is hydrogen, fluoro, chloro, bromo, amino, nitro, hydroxy, piperazinyl group, methoxy or ethoxy, $Q_1$ to $Q_4$ are each independently C—H or C—X, and $R^1$ is hydrogen, amino, methyl, ethyl, cyclopropyl or $CF_3$.

More preferably, embodiments of the present invention encompasses a compound of Formula 1 selected from the group consisting of following compounds:

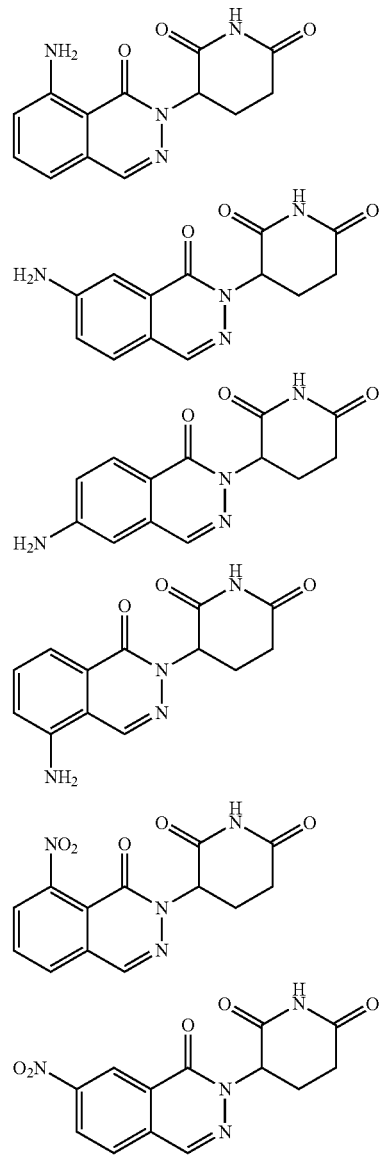

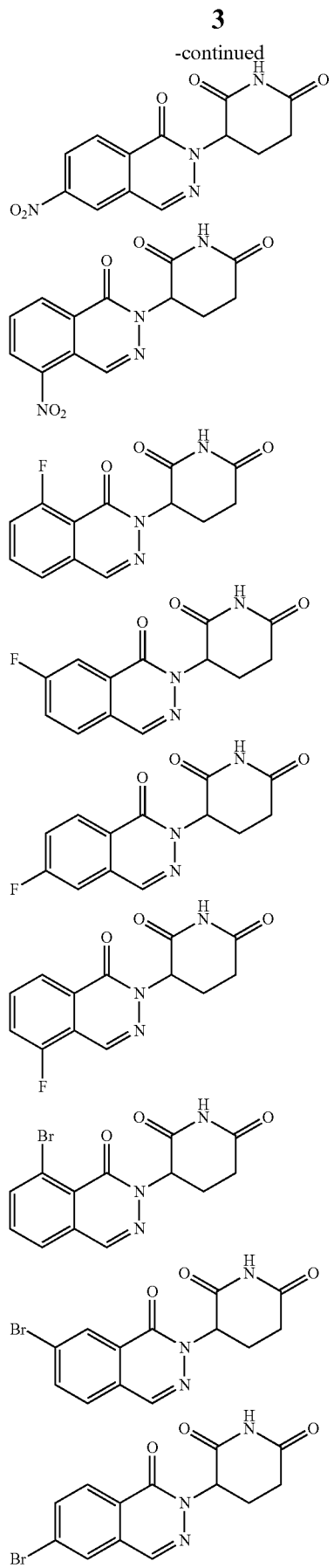
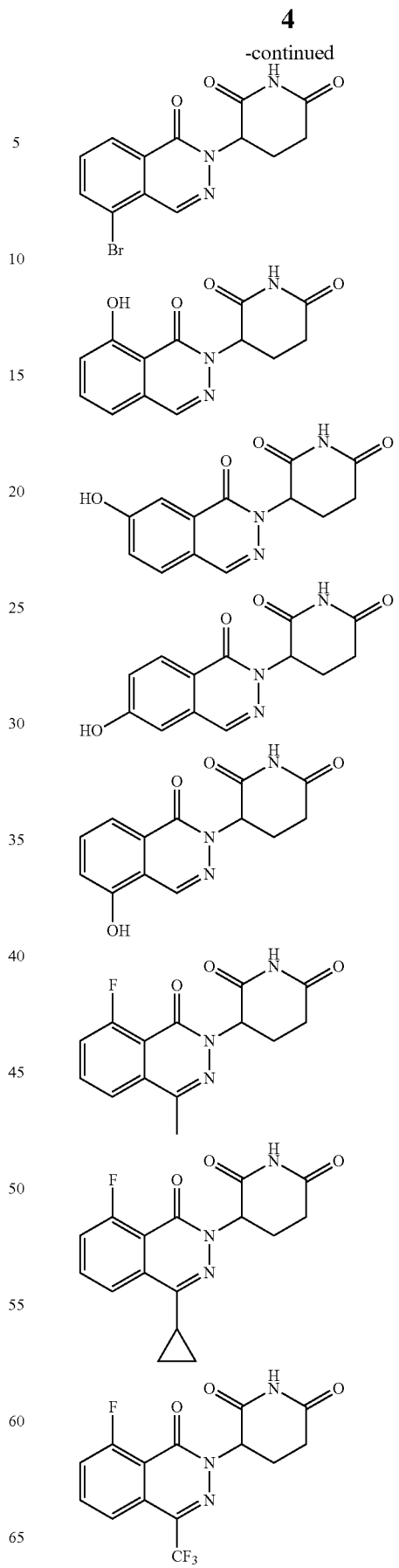

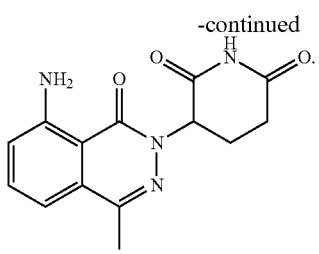

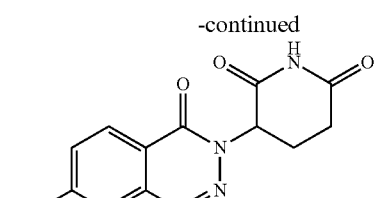

Since the compound of Formula 1 according to the present invention acts on CRBN by itself, it can be usefully used as a treatment for CRBN protein-related diseases (e.g., anti-tumor or immunomodulator).

The compound of Formula 1 according to the present invention can be used as an E3 ligase binder in a PROTAC compound comprising a POI ligand, a linker and an E3 ligase binder.

Accordingly, the present invention relates to a PROTAC compound or a pharmaceutically acceptable salt thereof wherein, as an E3 ligase binder, the compound of Formula 1 is connected to the linker:

[Formula 1]

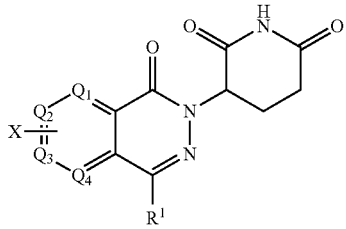

wherein

X is hydrogen, halogen, amino, nitro, hydroxy, $C_1$ to $C_6$ straight or branched alkyloxy, or 4 to 8 membered heterocyclic group including oxygen or nitrogen, $Q_1$ to $Q_4$ are each independently C—F, C—Cl, C—H, C—X or N, provided that at least one of $Q_1$ to $Q_4$ is C—X, $R^1$ is hydrogen, nitro, amino, carbonyl, $C_1$ to $C_6$ straight, branched or cyclic alkyl, or $C_1$ to $C_6$ straight, branched or cyclic alkyl substituted with halogen.

In the PROTAC compound according to the present invention, the compound of Formula 1 is preferably selected from the group consisting of the following compounds:

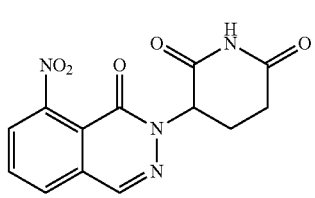

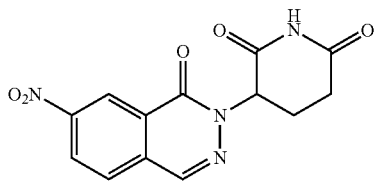

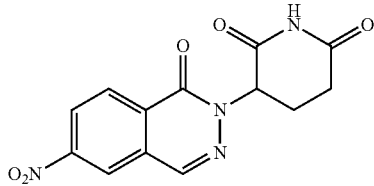

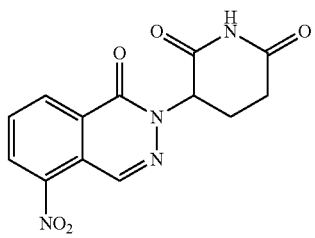

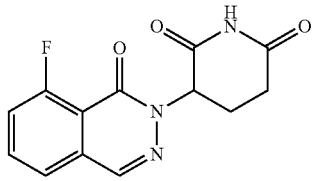

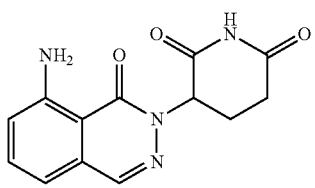

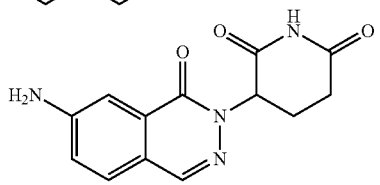

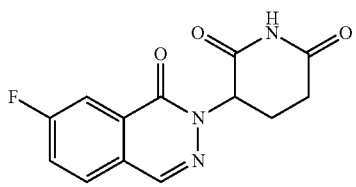

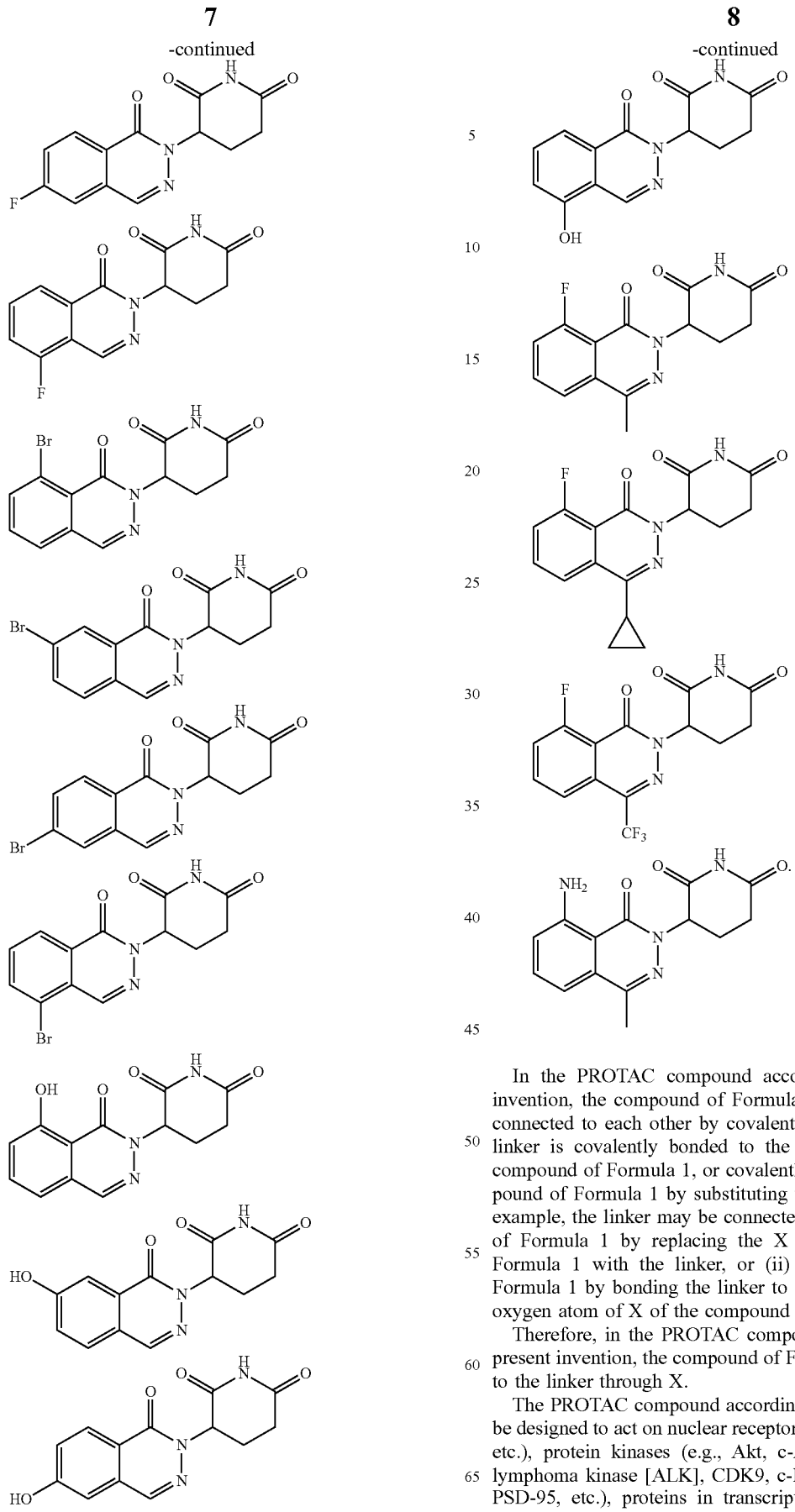

In the PROTAC compound according to the present invention, the compound of Formula 1 and the linker are connected to each other by covalent bond. Especially, the linker is covalently bonded to the substituent X of the compound of Formula 1, or covalently bonded to the compound of Formula 1 by substituting the substituent X. For example, the linker may be connected (i) to the compound of Formula 1 by replacing the X of the compound of Formula 1 with the linker, or (ii) to the compound of Formula 1 by bonding the linker to a nitrogen atom or an oxygen atom of X of the compound of Formula 1.

Therefore, in the PROTAC compound according to the present invention, the compound of Formula 1 is connected to the linker through X.

The PROTAC compound according to the invention can be designed to act on nuclear receptors (e.g., ER, AR, RAR, etc.), protein kinases (e.g., Akt, c-Abl, BTK, anaplastic lymphoma kinase [ALK], CDK9, c-Met, RIPK2, DAPK1, PSD-95, etc.), proteins in transcription regulations (e.g., BRD4, Sir2, HDAC6, TRIM24, IKZH1/3, Smad3, etc.), regulatory proteins (e.g., CRABP-I/II, TACC3, AHR, FKBP12, ERRα, SHP2, X-protein, PTPN11, etc.), neurodegenerative related proteins (e.g., Huntingtin, Tau, a-synuclein, PSD-95, etc.), cellular metabolic enzymes (e.g., MetAP-2, DHODH), fusion proteins (e.g., Alk-fusion, BCR-Abl, Brd-Nut, Ret-fusion, Halo Tags, etc.), mutant proteins (e.g., Braf mutant, EGFR mutant and deletion, Kras mutant, TP53 mutant and splicing variant, etc.), uncommon variant proteins (e.g., EGFRdel19, P53 splicing variant, fusion proteins, etc.) and so on as POI. Therefore, in the PROTAC compound according to the present invention, a compound capable of binding to such a POI is used as a POI ligand. Accordingly, the PROTAC compound according to the present invention can be usefully used to treat or prevent diseases which are related to the POI as described above.

In the PROTAC compound of the present invention, BRD4 inhibitor or SHP2 inhibitor can be a POI ligand. Preferably, the POI ligand is selected from the group consisting of the following compounds:

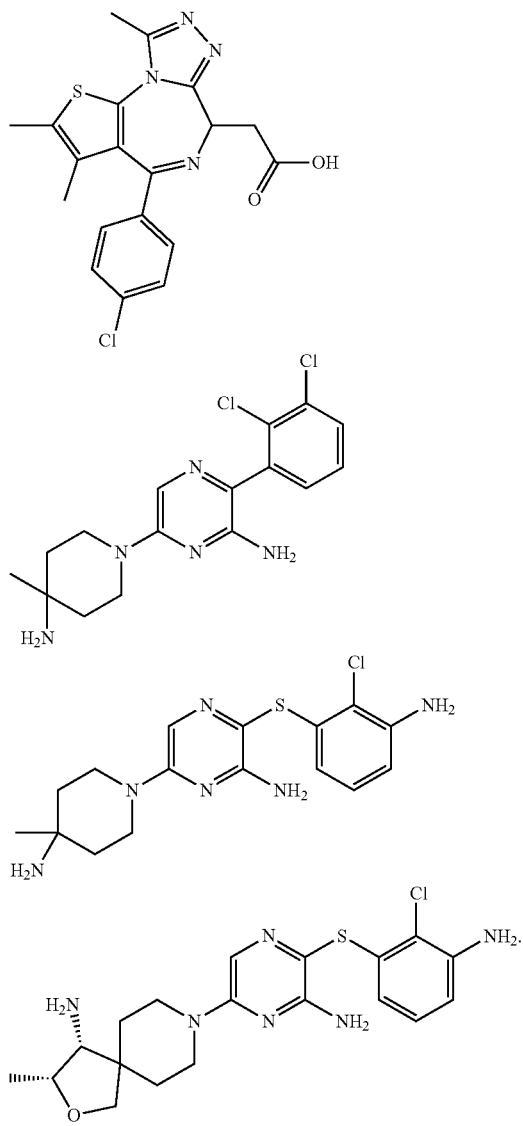

In the PROTAC compound of the present invention, any linker capable of connecting the POI ligand and the compound of Formula 1 can be used as the linker. Preferably, any one compound among Formulae 2 to 9 is used as the linker:

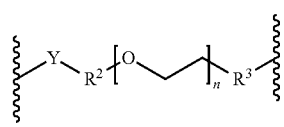
[Formula 2]

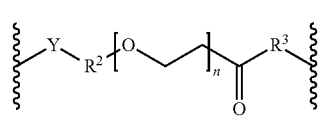
[Formula 3]

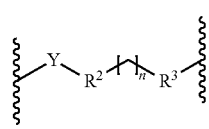
[Formula 4]

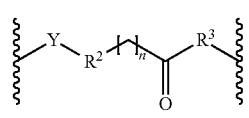
[Formula 5]

—Y—$R^2$-$R^4$— [Formula 7]

—(C=O)—$R^2$—(C=O)— [Formula 8]

—$R^4$—(C=O)—$R^2$— [Formula 9]

wherein n is an integer having a value of any one of 0 to 10, $R^4$ is 4 to 8 membered aryl, heteroaryl or heterocyclic group, $R^2$ is —$(CH_2)$m-; —$(CH_2)$m-$R^4$—$(CH_2)$q-; or —(C=O)—$(CH_2)$m-(CONH)—$(CH_2)$q-, $R^3$ is —$(CH_2)$m-; —$(CH_2)$m-$R^4$—$(CH_2)$q-; —(C=O)—$(CH_2)$m-(CONH)—$(CH_2)$q-; or direct bond, wherein m and q are each independently integers of 0 to 10, Y is —$NR^8$—, —$N(R^8)$—C(O)—, —C(O)—$N(R^8)$—, —$CHR^8$—, —O—, —S—, —S(O)—, —$S(O)NR^8$—, —$S(O)_2$—, —$S(O)_2NR^8$—, —C(=$CH_2$)—, —CH=CH— or —C≡C—, $R^8$ is hydrogen, $C_1$ to $C_6$ straight, branched or cyclic alkyl, or $C_1$ to $C_6$ straight, branched or cyclic alkyl substituted with halogen.

For example, in the above Formula, $R^8$ may be —$CH_2$—$CH_2F$, —$CH_2$—$CHF_2$ or —$CH_2$—$CF_3$.

In the linker represented by Formula, the left side of the structural formula is covalently bonded to POI ligand, and the right side of the structural formula is bonded to an atom such as oxygen or nitrogen in the substituent X of the compound of Formula 1 or be bonded to any one carbon atom of $Q_1$ to $Q_4$.

More preferably, as a linker in the PROTAC compound according to the present invention, a linker selected from the group consisting of the following compounds is used:

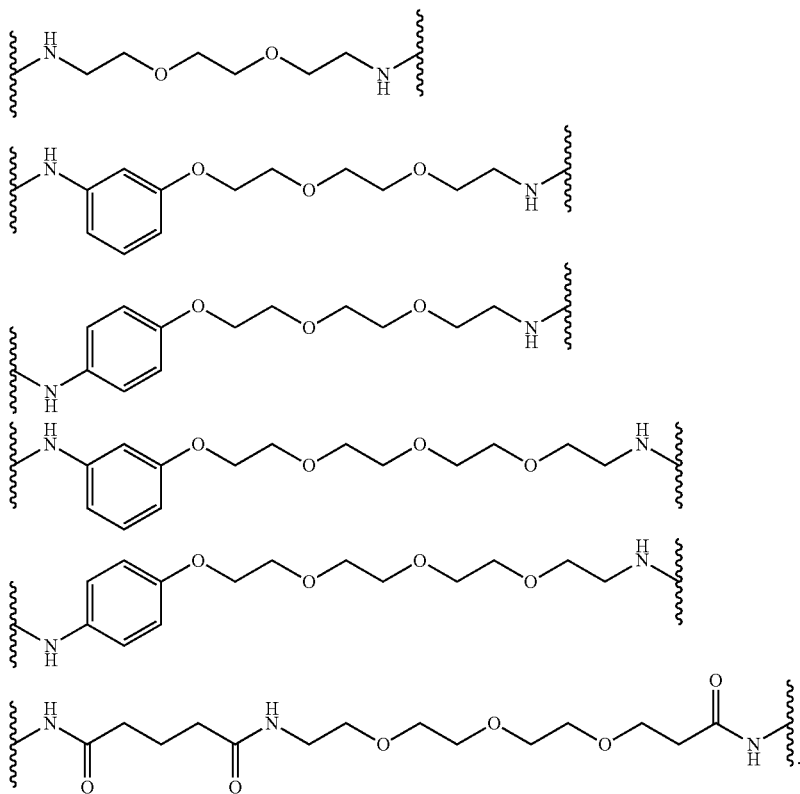
In addition, as a linker in the PROTAC compound according to the present invention, a linker selected from the group consisting of compounds formulae 10 and 11 is used:
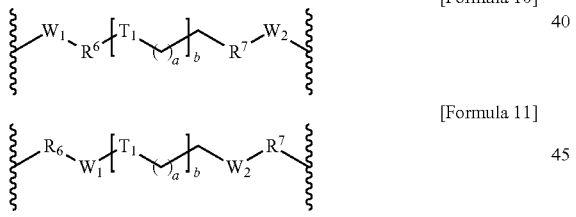
[Formula 10]
[Formula 11]
wherein
b is an integer of 0 to 20.
a is 2 or 3.
$T_1$ is —CH$_2$—, —O—, or —CHR$^g$—, wherein R$^g$ is $C_1$ to $C_4$ alkyl,
$R^6$ and $R^7$ are same or different from each other, and each of them is
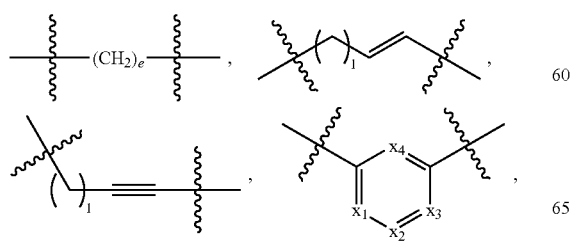
-continued
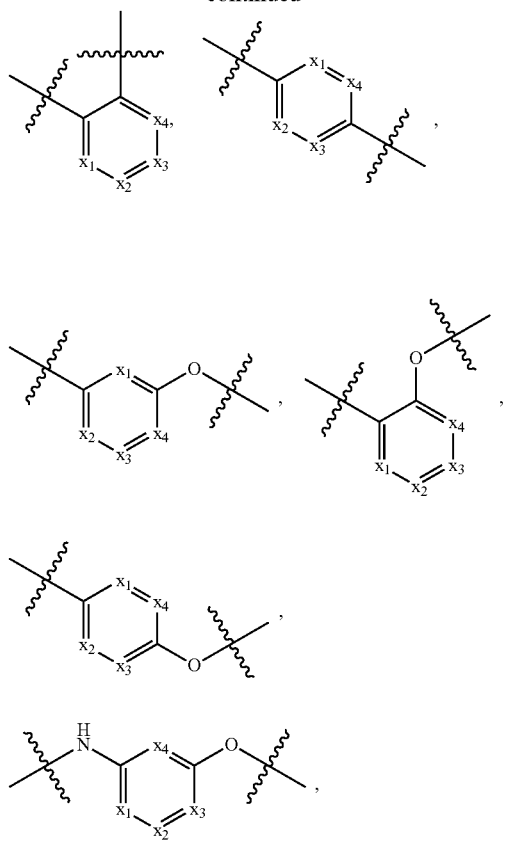

-continued

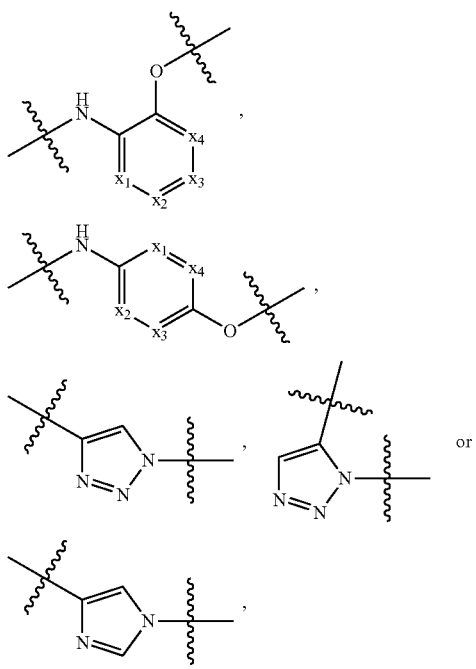

or biaryl, biheterocyclic, heterocyclic, biheterocyclic or spiro biheterocyclic, wherein e is an integer of 1 to 10, $x_1$, $x_2$, $x_3$ and $x_4$ are same or different, and each of them is C—H, C—N, or C—$R^i$, wherein $R^i$ is —F, —Cl, —Br, and $w_1$ and $w_2$ are same or different from each other, and each of them is —(CH2)$_k$—, —(CH2)$_{k-1}$O—,

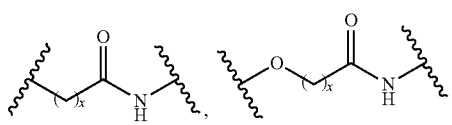

or —(CH$_2$)$_k$NHR$^h$—, wherein k is an integer of 1 to 10 and R$^h$ is C$_1$ to C$_4$ alkyl.

Preferably, R$^6$ and R$^7$ are each independently the following formula:

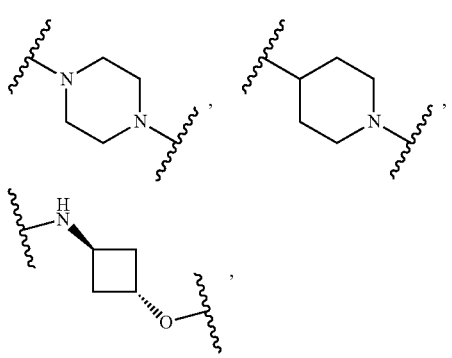

-continued

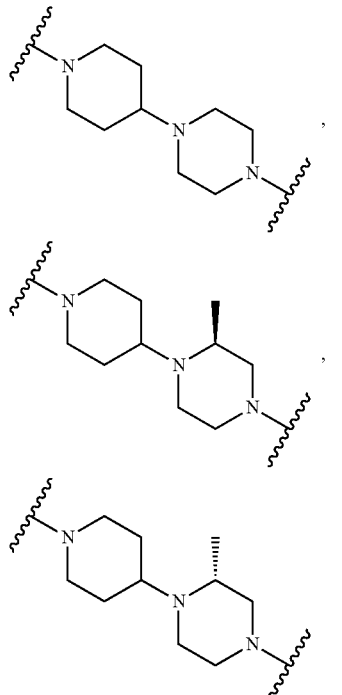

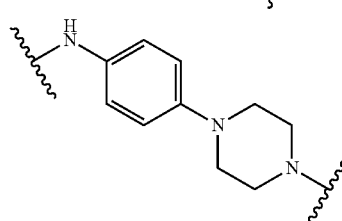

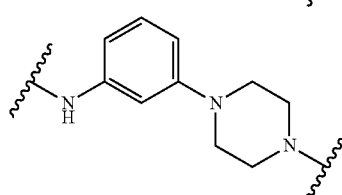

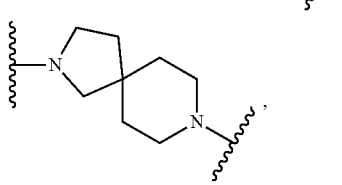

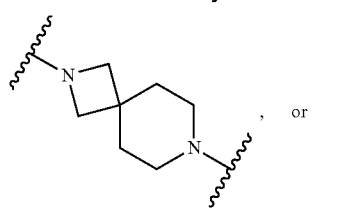

, or

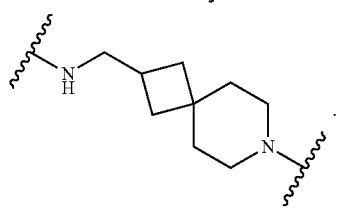

.

In the PROTAC compound according to the present invention, the linker is connected to the POI ligand and the E3 ligase binder, respectively, by covalent bond, thereby connecting the POI ligand and the E3 ligase binder. Those skilled in the art understand that some substituents may be eliminated at the site of covalent bond of linker, POI ligand and E3 ligase binder during the reaction for covalent bonding.

Therefore, the present invention relates to a PROTAC compound including a POI ligand, a linker and an E3 ligase binder, wherein the linker is connected to the POI ligand and the E3 ligase binder, respectively, by covalent bond, and wherein the portion of the E3 ligase binder is represented by the Formula 1.

Accordingly, the PROTAC compound of the present invention is represented by a compound of Formula 6 below:

[Formula 6]

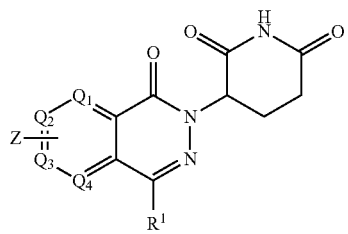

wherein

Z is a POI ligand and a linker connected thereto, $Q_1$ to $Q_4$ are each independently C—F, C—Cl, C—H, C—Z, C—O—Z, C—NH—Z, or N, provided at least one of $Q_1$ to $Q_4$ is C—Z, C—O—Z or C—NH—Z, $R^1$ is hydrogen, nitro, amino, carbonyl, $C_1$ to $C_4$ straight, branched or cyclic alkyl, or $C_1$ to $C_4$ straight, branched or cyclic alkyl substituted with halogen.

In the PROTAC compound according to the present invention, the POI ligand is selected from the group consisting of the following compounds or their derivatives:

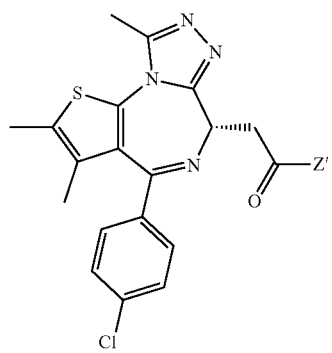

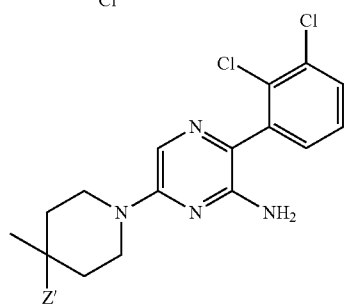

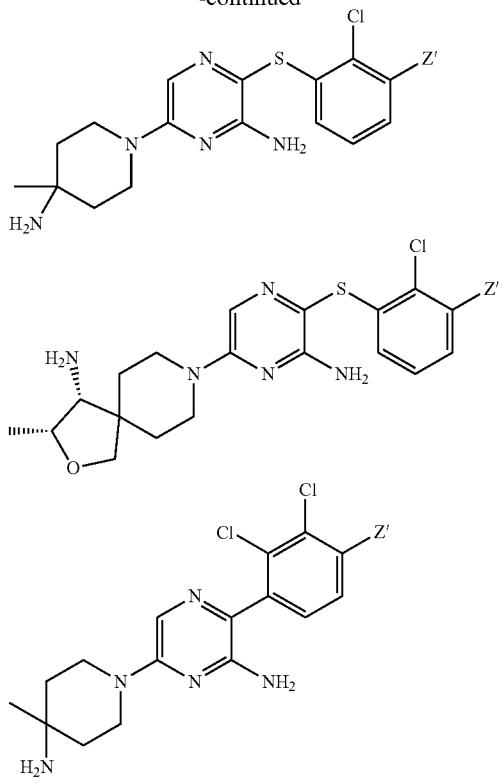

wherein

Z' means the compound of Formula 1 and a linker connected thereto, which is expressed with the intention of representing a moiety of the POI ligand connected to the linker in order to facilitate understanding of the structure of the PROTAC compound illustrated in the present invention.

In particular, when a linker is connected to an amino group contained in a POI ligand or its derivative which may be used in the PROTAC of the invention, the linker (L) will be explained below in viewing the amino group as the part of the linker for convenience.

In the PROTAC compound according to the present invention, as the linker L, any linker capable of connecting the POI ligand and the compound of Formula 1 is used. Preferably, any one of compounds of Formulae 2 to 9 is used as the linker L:

[Formula 2]

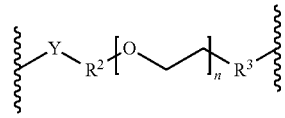

[Formula 3]

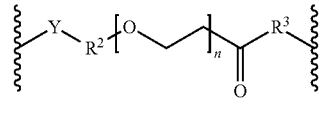

[Formula 4]

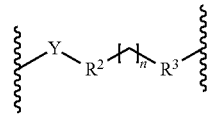

-continued

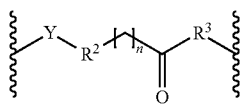
[Formula 5]

—Y—R²-R⁴— [Formula 7]

—(C=O)—R²—(C=O)— [Formula 8]

—R⁴—(C=O)—R²— [Formula 9]

wherein
n is an integer having a value of any one of 0 to 10,
R⁴ is 4 to 8 membered aryl, heteroaryl or heterocyclic group
R² is —(CH₂)m-; —(CH₂)m-R⁴—(CH₂)q-; or —(C=O)—(CH₂)m-(CONH)—(CH₂)q-,
R³ is —(CH₂)m-; —(CH₂)m-R⁴—(CH₂)q-; —(C=O)—(CH₂)m-(CONH)—(CH₂)q-; or direct bond,
wherein
m and q are each independently integers of 0 to 10,
Y is —NR⁸—, —N(R⁸)—C(O)—, —C(O)—N(R⁸)—, —CHR⁸—, —O—, —S—, —S(O)—, —S(O)NR⁸—, —S(O)₂—, —S(O)₂NR⁸—, —C(=CH₂)—, —CH=CH— or —C≡C—, and
R⁸ is hydrogen, C₁ to C₆ straight, branched or cyclic alkyl, or C₁ to C₆ straight, branched or cyclic alkyl substituted with halogen.

In the linker L represented by Formulae, the left side of formula is covalently bonded to the POI ligand.

More preferably, as the linker L in the PROTAC compound according to the present invention, a linker selected from the group consisting of the following compounds is used:

In addition, as the linker in the PROTAC compound according to the present invention, a linker selected from the group consisting of Compounds of formulae 10 and 11 is used:

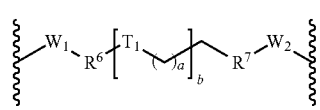
[Formula 10]

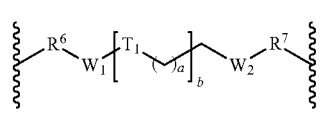
[Formula 11]

wherein
b is an integer of 0 to 20.
a is 2 or 3.
T₁ is —CH₂—, —O—, or —CHR^g—, wherein R^g is C₁ to C₄ alkyl,
R⁶ and R⁷ are same or different from each other, and each of them is

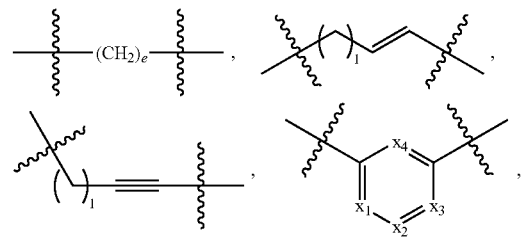

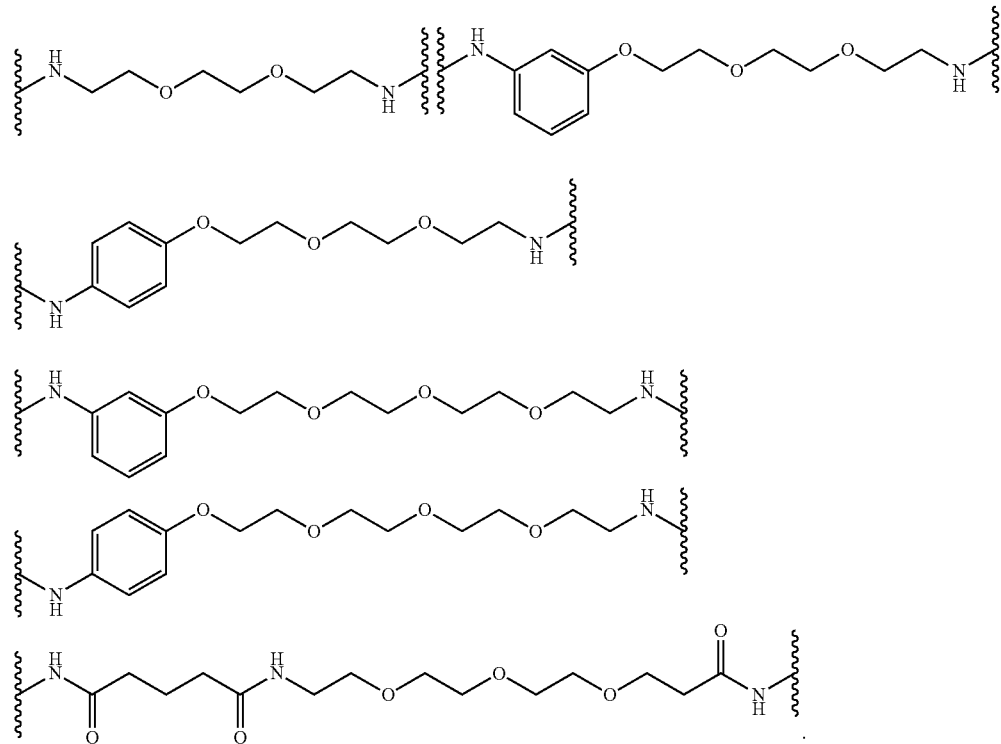

-continued

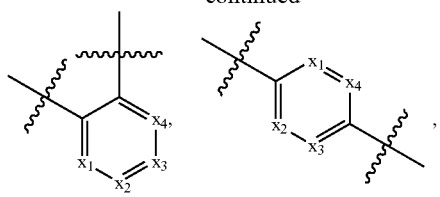

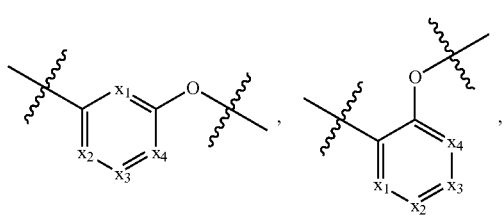

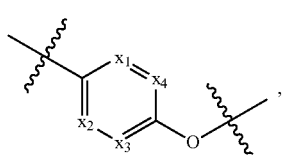

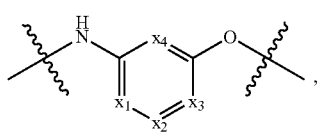

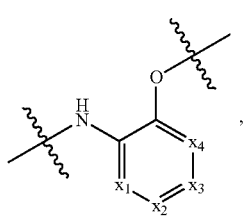

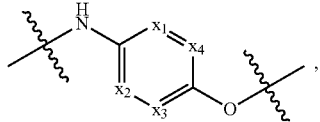

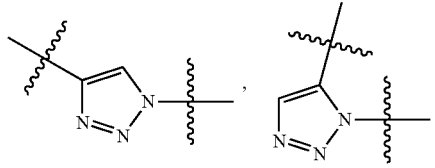

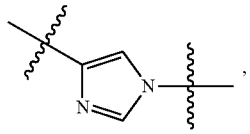

biaryl, biheterocyclic, heterocyclic, biheterocyclic or spiro biheterocyclic wherein e is an integer of 1 to 10, $x_1$, $x_2$, $x_3$ and $x_4$ are same or different, and each of them is C—H, C—N, or C—$R^i$, wherein $R^i$ is —F, —Cl, —Br, and $w_1$ and $w_2$ are same or different from each other, and each of them is —(CH2)$_k$—, —(CH2)$_{k-1}$O—,

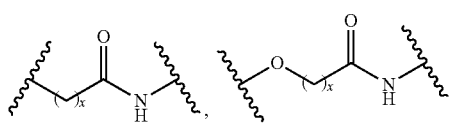

or —(CH$_2$)$_k$NHR$^h$—, wherein k is an integer of 1 to 10 and R$^h$ is C$_1$ to C$_4$ alkyl.

Preferably, R$^6$ and R$^7$ are each independently the following formula:

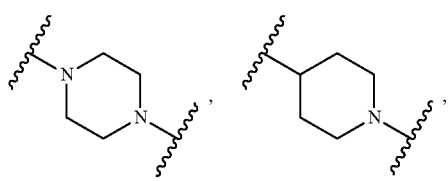

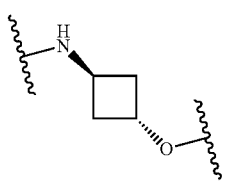

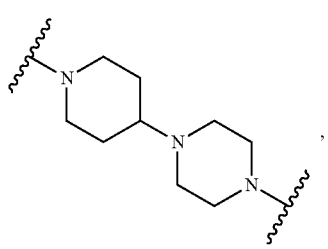

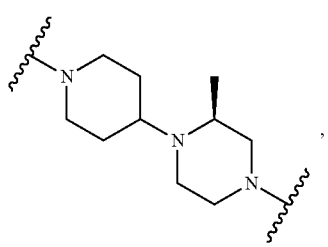

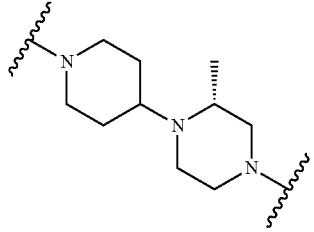

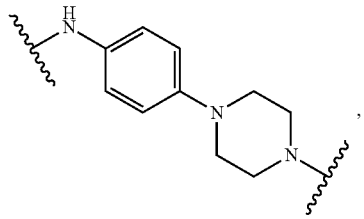

21
-continued
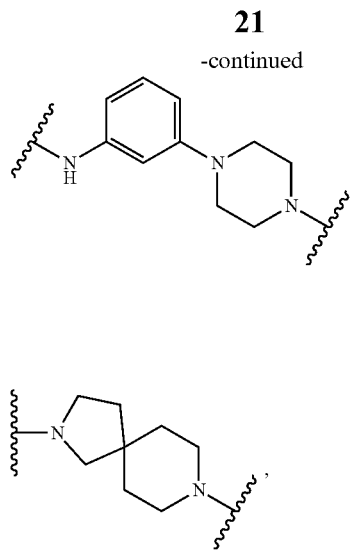
22
-continued
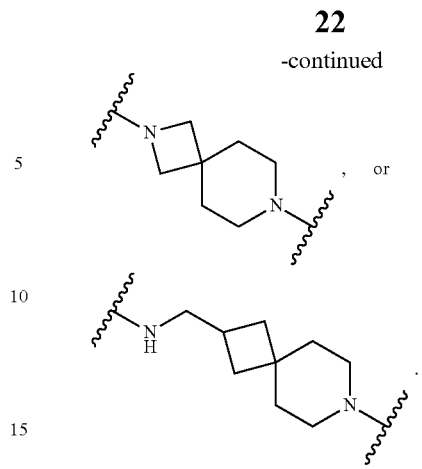
More preferably, in the PROTAC compound of the present invention, the linker is selected from the group consisting of the following compounds:
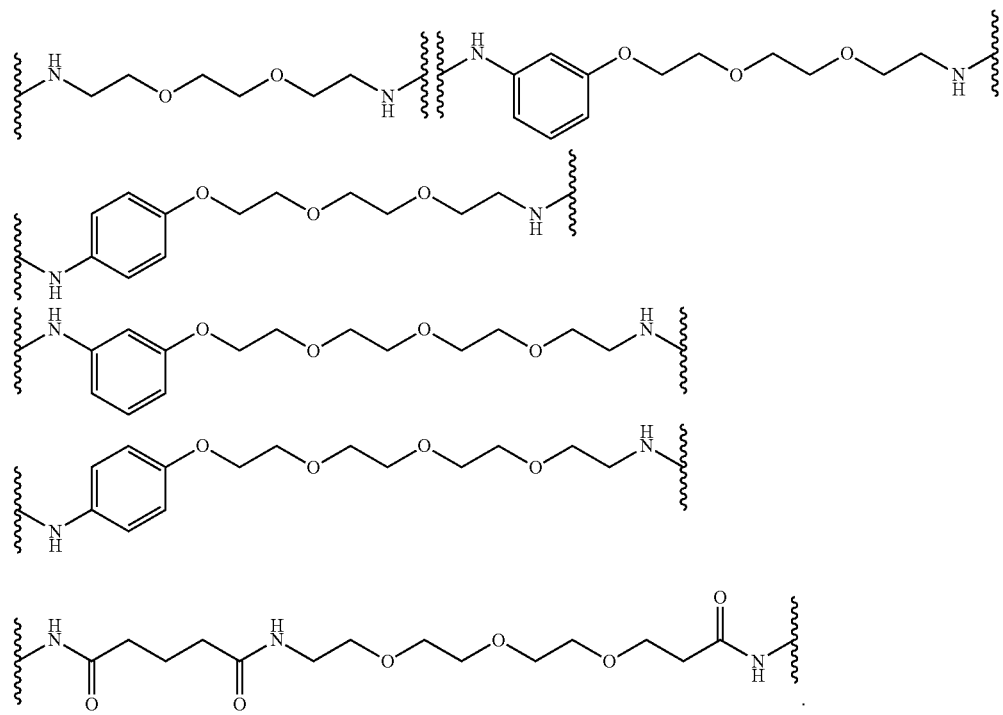
In addition, the PROTAC compound according to the present invention is preferably selected from the group consisting of the following compounds:
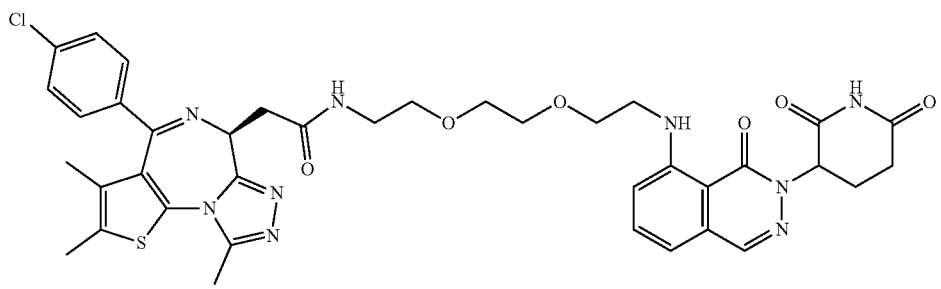

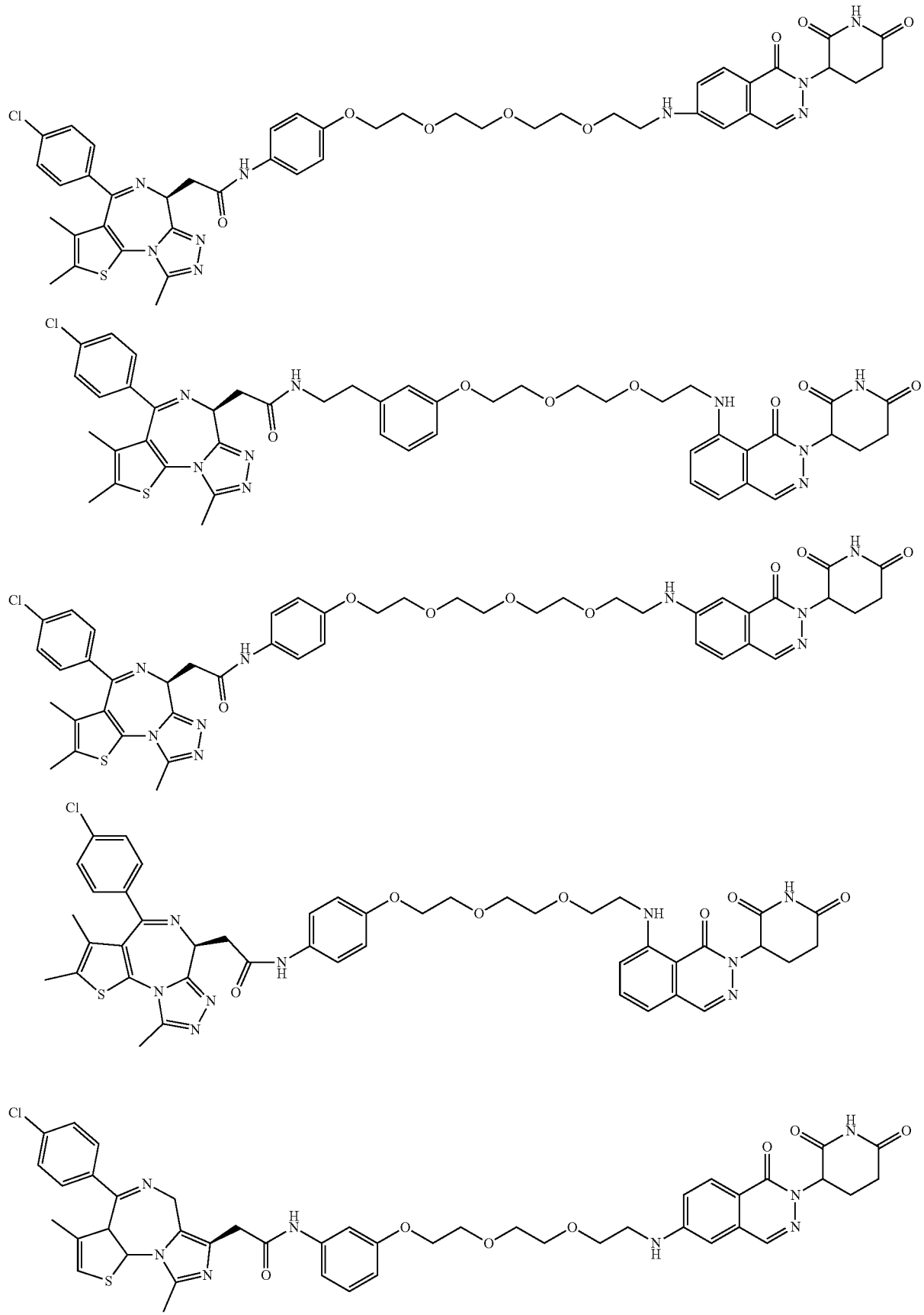

-continued
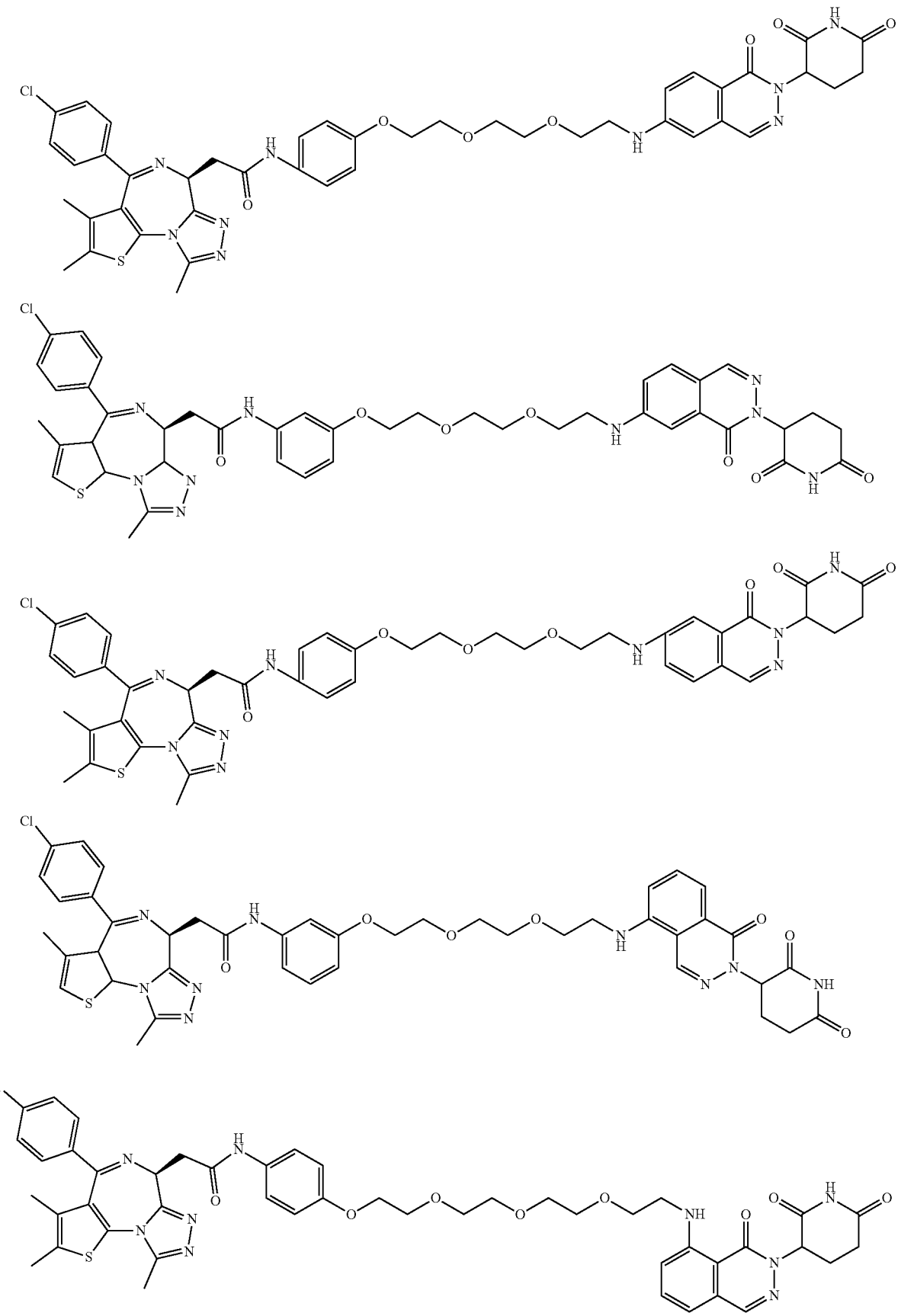

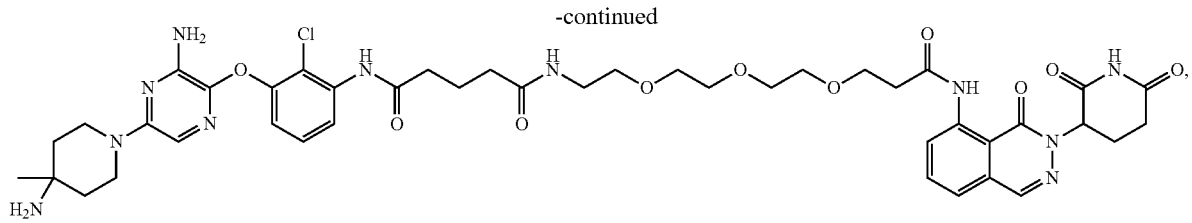

or a pharmaceutically acceptable salt thereof.

Effects

The compound of piperazinedione derivative of the present invention acts on CRBN and can be usefully used as a treatment for CRBN protein-related diseases (e.g., anticancer or immunomodulator).

In addition, the piperazinedione derivative of the present invention can be usefully used as an E3 ligase binder of a PROTAC compound. The PROTAC compound of the present invention is designed to act on nuclear receptors (e.g., ER, AR, RAR, etc.), protein kinases (e.g., Akt, c-Abl, BTK, anaplastic lymphoma kinase [ALK], CDK9, c-Met, RIPK2, DAPK1, PSD-95, etc.), proteins in transcription regulations (e.g., BRD4, Sir2, HDAC6, TRIM24, IKZH1/3, Smad3, etc.), regulatory proteins (e.g., CRABP-I/II, TACC3, AHR, FKBP12, ERRα, SHP2, X-protein, PTPN11, etc.), neurodegenerative related proteins (e.g., Huntingtin, Tau, a-synuclein, PSD-95, etc.), cellular metabolic enzymes (e.g., MetAP-2, DHODH), fusion proteins (e.g., Alk-fusion, BCR-Abl, Brd-Nut, Ret-fusion, Halo Tags, etc.), mutant proteins (e.g., Braf mutant, EGFR mutant and deletion, Kras mutant, TP53 mutant and splicing variant, etc.), uncommon variant proteins (e.g., EGFRdel19, P53 splicing variant, fusion proteins, etc.) and so on as POI. Therefore, in the PROTAC compound according to the present invention, a compound capable of binding to such a POI is used as a POI ligand. Accordingly, the PROTAC compound according to the present invention can be usefully used to treat or prevent diseases which are related to the POI as described above.

For example, the PROTAC compound including the piperazinedione derivative compound of the present invention as an E3 ligase binder has an excellent anticancer effect. Furthermore, the PROTAC compound according to the present invention induces degradation of the specific protein which is related in other diseases than cancer, thereby exhibiting therapeutic effects on the relevant disease.

The term "hetero" described herein means that it comprises atoms such as nitrogen, oxygen or sulfur rather than carbon or hydrogen.

MODE FOR INVENTION

Figure 1:
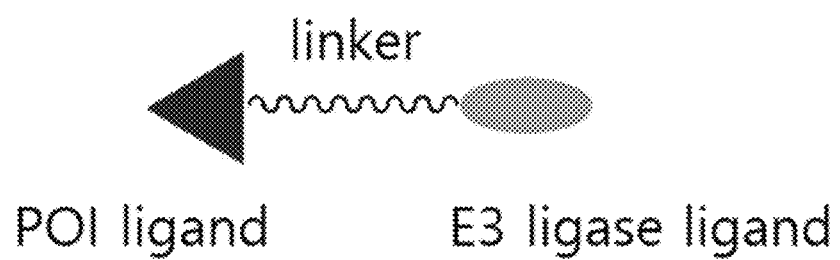
FIG. 1 schematically illustrates a PROTAC compound consisting of a POI ligand, a linker and an E3 ligase binder.

Hereinafter, the present invention will be described in detail according to the embodiments in order to facilitate understanding of the present invention. However, the following embodiments only illustrate the contents of the present invention, and the spirit or scope of the present invention is not limited by the following embodiments in any sense. Embodiments of the present invention are provided to more fully explain the present invention to a person having ordinary skill in the art.

The scaffold of the compound of Formula 1 according to the present invention is prepared through the following reaction steps of Scheme 1 or Scheme 2:

[Scheme 1]

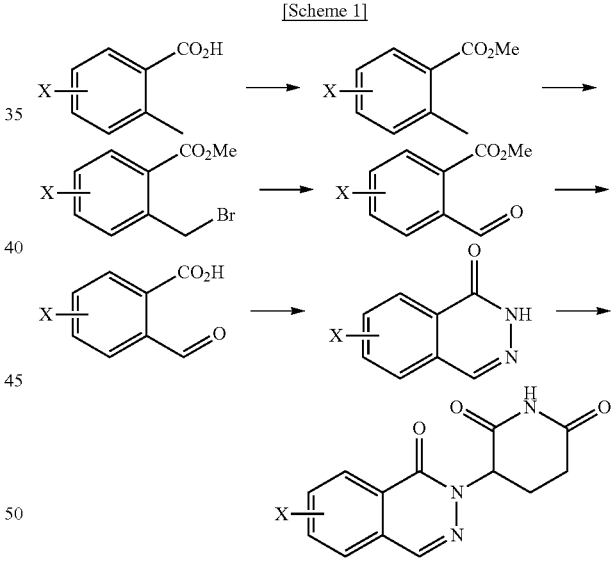

[Scheme 2]

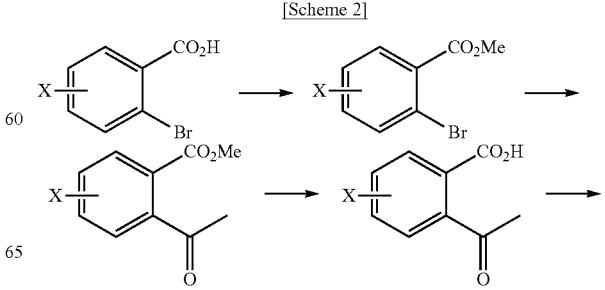

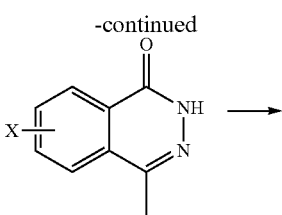

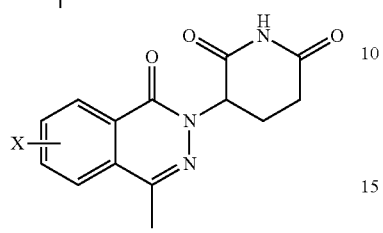

In Scheme 1 or 2, X is hydrogen, halogen, amino, nitro or hydroxy, piperazine group or $C_1$ to $C_4$ alkoxy. However, for convenience of explanation, the display of a substituent that can be bonded to a carbon in $Q_1$ to $Q_4$ of the compounds of Formula 1 was omitted, and only a simple substituent such as hydrogen or methyl was representatively shown among the $R^1$ substituents.

Hereinafter, specific embodiments of the compound of Formula 1 are prepared through examples.

Example A: Synthesis of Piperidinedione Derivatives Compound

Example 1

Synthesis of Compound

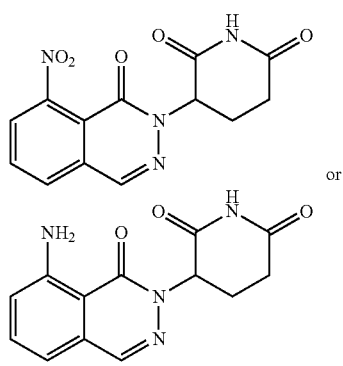

(Prepared Based on Scheme 1)

1-1) Synthesis of methyl 2-methyl-6-nitrobenzoate

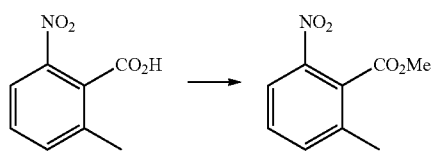

To a solution of 2-methyl-6-nitrobenzoic acid (5 g, 27.6 mmol) in Acetone (100 ml) was added $K_2CO_3$ (19.1 g, 138 mmol) at room temperature. After stirring for 30 min, the reaction mixture was treated with iodomethane (19.6 g, 138 mmol) and heated to 60° C. for 6 hours. After cooling, the reaction mixture was filtered and concentrated under reduced pressure. The product (5.45 g, 98%) was used for the next reaction without further purification. MS (ESI, m/z): $[M+1]^+=[195.2]$.

1-2) Synthesis of methyl 2-(bromomethyl)-6-nitrobenzoate

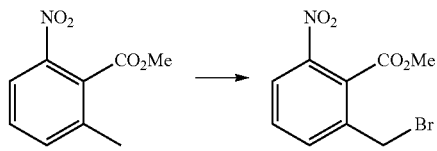

To a solution of methyl 2-methyl-6-nitrobenzoate (5.39 g, 27.6 mmol) in $ClCH_2CH_2Cl$ (100 ml) was added 1-bromopyrrolidine-2,5-dione (7.39 g, 41.4 mmol) followed by benzoyl benzenecarboperoxoate (0.67 g, 7.26 mmol) at room temperature. The reaction mixture was heated to reflux for 3 hours. The reddish color disappeared upon the reaction completion. After cooling, the reaction mixture was washed with water and dried over $MgSO_4$ and concentrated under reduced pressure. The crude product (7.34 g, 98%) was used for the next reaction without further purification. MS (ESI, m/z): $[M+1]^+=[274.4]$.

1-3) Synthesis of methyl 2-formyl-6-nitrobenzoate

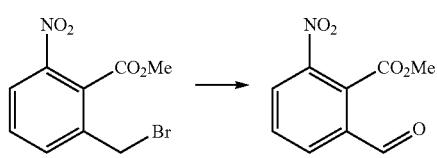 [SMILES: COC(=O)c1c(CBr)cccc1[N+](=O)[O-] ; COC(=O)c1c(C=O)cccc1[N+](=O)[O-]]

To a solution of methyl 2-(bromomethyl)-6-nitrobenzoate (580 mg, 2.12 mmol) in DCM (30 mL) was added NMO (N-methylmorpholine N-oxide) (561 mg, 4.87 mmol) followed by molecular sieve 4 Å at room temperature. The reaction mixture was stirred for 2 hours at room temperature. Molecular sieve was filtered off and washed with DCM (10 mL). The DCM layer was washed with water (50 mL), dried over $MgSO_4$, and then concentrated under reduced pressure. The residue was purified by column chromatography to afford the titled compound (350 mg, 79.07%) as a white solid. MS (ESI, m/z): $[M+^1]+=[210.0]$.

1-4) Synthesis of 2-formyl-6-nitrobenzoic Acid

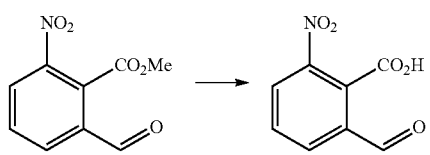 [SMILES: COC(=O)c1c(C=O)cccc1[N+](=O)[O-] ; O=Cc1cccc([N+](=O)[O-])c1C(=O)O]

To a solution of methyl 2-formyl-6-nitrobenzoate (2 g, 9.56 mmol) in THF (10 mL) was added a solution of lithium (1+) hydroxide (1.15 g, 47.8 mmol) in H₂O (10 mL) at room temperature. After stirring for 2 hours, the reaction mixture was concentrated under reduced pressure for drying THF. After cooling to 0° C., the reaction mixture was acidified with 1N—HCl to adjust pH to 4. The reaction mixture was extracted with ethyl acetate (50 mL×2). The combined ethyl acetate layer was dried over MgSO4 and concentrated under reduced pressure to give a white crystal (1.50 g, 80.3%). MS (ESI, m/z): [M+$^1$]+=[195.2].

1-5) Synthesis of 8-nitrophthalazin-1(2H)-one

To a solution of 2-formyl-6-nitrobenzoic acid (1.20 g, 6.15 mmol) in MeOH (10 mL) was added NH₂NH₂ monohydrate (417 mg, 8.33 mmol) at room temperature. After stirring for 30 min, the reaction mixture was heated to 80° C. for 2 hours. The reaction mixture was cooled to room temperature and concentrated under reduced pressure. The residue was poured into water (50 ml) and extracted with ethyl acetate (50 mL×2). The combined ethyl acetate layer was dried over MgSO₄ and concentrated under reduced pressure to give a white crystal (1.0 g, 85.07%). MS (ESI, m/z): [M+$^1$]+=[191.8].

1-6) Synthesis of 3-(8-nitro-1-oxophthalazin-2(1H)-yl)piperidine-2,6-dione

To a solution of 8-nitro-1,2-dihydrophthalazin-1-one (60 mg, 0.314 mmol) in DMF (1 mL) was added 3-bromopiperidine-2,6-dione (90 mg, 0.471 mmol) followed by K₂CO₃ (129 mg, 0.942 mmol). The reaction mixture was heated to 85° C. for 5 hours. After cooling, the reaction mixture was poured into water (5 mL) and extracted with ethyl acetate (5 mL×2). The combined ethyl acetate was dried over MgSO₄ and concentrated under reduced pressure. The residue was purified by column chromatography to furnish the titled compound (68.0 mg, 71.7%) as a white crystal. MS (ESI, m/z): [M+$^1$]+=[302.6].

1-7) Synthesis of 3-(8-nitro-1-oxophthalazin-2(1H)-yl)piperidine-2,6-dione

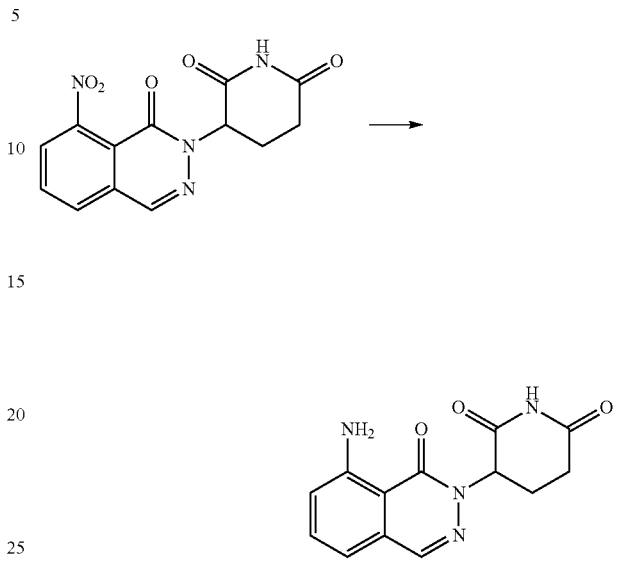

To a solution of 3-(8-nitro-1-oxo-1,2-dihydrophthalazin-2-yl)piperidine-2,6-dione (25 mg, 0.82 mmol) in MeOH (5 mL) was added 20 mg of 10% Pd/C (wet) (5 mg) and stirred under H₂ in a balloon for 1 hour. The solid was filtered off and the filtrate was concentrated under reduced pressure to afford the titled compound in 99%. MS (ESI, m/z): [M+$^1$]+= [272.3]. [NMR] $^1$H NMR (400 MHz, DMSO-d₆) δ 10.95 (s, 1H), 8.10 (s, 1H), 7.46 (t, J=7.83 Hz, 1H), 7.22 (br s, 2H), 6.86 (d, J=7.83 Hz, 1H), 6.81 (d, J=7.34 Hz, 1H), 5.61 (br dd, J=5.2, 11.92 Hz, 1H), 2.77-2.89 (m, 1H), 2.46-2.57 (m, 2H), 1.95-2.08 (m, 1H)

Example 2

Synthesis of Compound

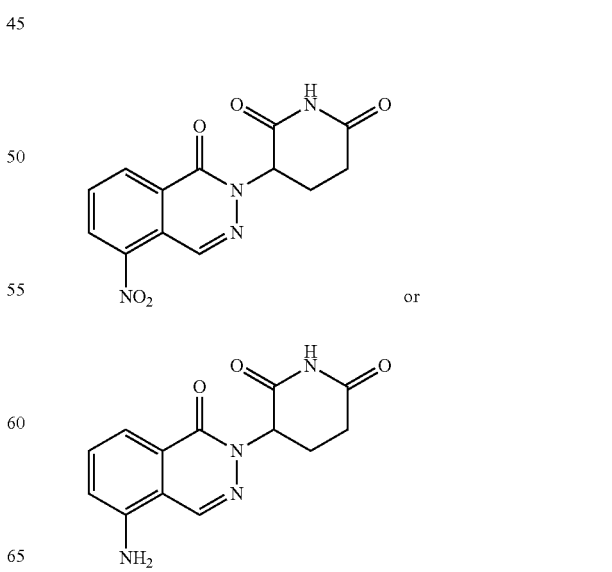

2-1) Synthesis of methyl 2-methyl-3-nitrobenzoate

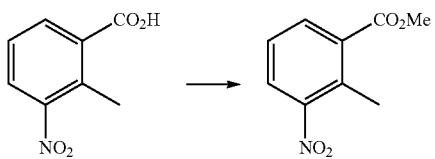

To a solution of 2-methyl-3-nitrobenzoic acid (5 g, 27.6 mmol) in Acetone (100 ml) was added $K_2CO_3$ (19.1 g, 138 mmol) at room temperature. After stirring for 30 min, to the reaction mixture was added iodomethane (19.6 g, 138 mmol) and the mixture was heated to 60° C. for 6 hours. After cooling, the reaction mixture was filtered and concentrated under reduced pressure. The product (5.45 g, 98%) was used for the next reaction without further purification. MS (ESI, m/z): [M+$^1$]+=[195.3].

2-2) Synthesis of methyl 2-(bromomethyl)-3-nitrobenzoate

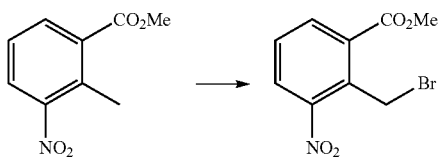

To a solution of methyl 2-methyl-3-nitrobenzoate (5.39 g, 27.6 mmol) in 1,2-dichloroethane (100 ml) was added 1-bromopyrrolidine-2,5-dione (7.39 g, 41.4 mmol) followed by benzoyl benzenecarboperoxoate (0.67 g, 7.26 mmol) at room temperature. The reaction mixture was heated to reflux for 3 hours. The reddish color disappeared upon the reaction completion. After cooling, the reaction mixture was washed with water and dried over $MgSO_4$ and concentrated under reduced pressure. The crude product (7.34 g, 98%) was used for the next reaction without further purification. MS (ESI, m/z): [M+$^1$]+=[274.4]

2-3) Synthesis of methyl 2-formyl-3-nitrobenzoate

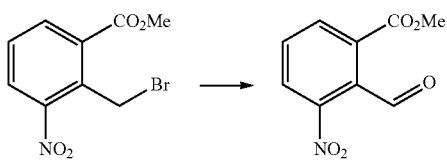 [SMILES: COC(=O)c1cccc([N+](=O)[O-])c1CBr ; COC(=O)c1cccc([N+](=O)[O-])c1C=O]

To a solution of methyl 2-(bromomethyl)-3-nitrobenzoate (580 mg, 2.12 mmol) in DCM (30 mL) was added NMO (561 mg, 4.87 mmol) followed by molecular sieve 4 Å at room temperature. The reaction mixture was stirred for 2 hours at room temperature. Molecular sieve was filtered off and washed with DCM (10 mL). The DCM layer was washed with water (50 mL), dried over $MgSO_4$, and then concentrated under reduced pressure. The residue was purified by column chromatography to afford the titled compound (350 mg, 79.07%) as a white solid. MS (ESI, m/z): [M+$^1$]+=[210.0].

2-4) Synthesis of 2-formyl-3-nitrobenzoic Acid

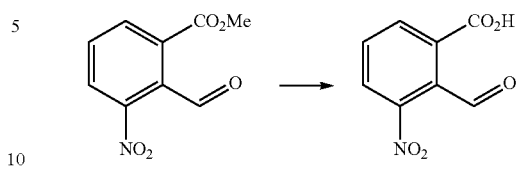

To a solution of methyl 2-formyl-6-nitrobenzoate (2 g, 9.56 mmol) in THF (10 mL) was added a solution of lithium(1+) hydroxide (1.15 g, 47.8 mmol) in $H_2O$ (10 mL) at room temperature. After stirring for 2 hours, the reaction mixture was concentrated under reduced pressure for drying THF. After cooling to 0° C., the reaction was acidified with 1N—HCl to adjust pH to 4. The reaction mixture was extracted with ethyl acetate (50 mL×2). The combined ethyl acetate layer was dried over $MgSO_4$ and concentrated under reduced pressure to give a white crystal (1.50 g, 80.3%). MS (ESI, m/z): [M+$^1$]+=[195.2].

2-5) Synthesis of 5-nitrophthalazin-1(2H)-one

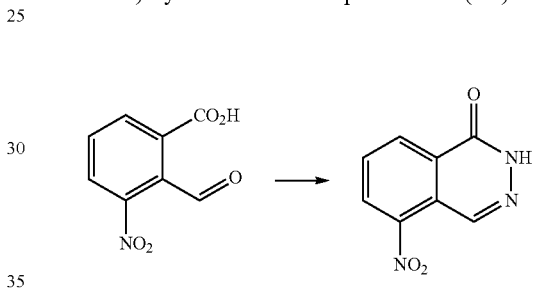

To a solution of 2-formyl-3-nitrobenzoic acid (1.20 g, 6.15 mmol) in MeOH (10 mL) was added hydrazine monohydrate (417 mg, 8.33 mmol) at room temperature. After stirring for 30 min, the reaction mixture was heated to 80° C. for 2 hours. The reaction mixture was cooled to room temperature and concentrated under reduced pressure. The residue was poured into water (50 ml) and extracted with ethyl acetate (50 mL×2). The combined ethyl acetate layer was dried over $MgSO_4$ and concentrated under reduced pressure to give a white crystal (1.0 g, 85.07%). MS (ESI, m/z): [M+$^1$]+=[191.8].

2-6) Synthesis of 3-(5-nitro-1-oxophthalazin-2(1H)-yl)piperidine-2,6-dione

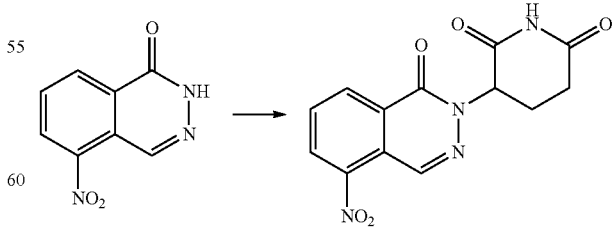

To a solution of 5-nitrophthalazin-1(2H)-one (60 mg, 0.314 mmol) in DMF (1 mL) was added 3-bromopiperidine-2,6-dione (90 mg, 0.471 mmol) followed by $K_2CO_3$ (129 mg, 0.942 mmol). The reaction mixture was heated to 85° C.

for 5 hours. After cooling, the reaction mixture was poured into water (5 mL) and extracted with ethyl acetate (5 mL×2). The combined ethyl acetate was dried over MgSO₄ and concentrated under reduced pressure. The residue was purified by column chromatography to furnish the titled compound (68.0 mg, 71.7%) as a white crystal. MS (ESI, m/z): [M+$^1$]+=[302.4].

2-7) Synthesis of 3-(5-amino-1-oxophthalazin-2 (1H)-yl)piperidine-2,6-dione

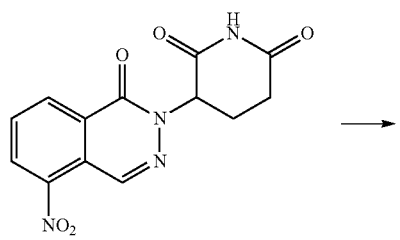

To a solution of 3-(5-nitro-1-oxophthalazin-2(1H)-yl)piperidine-2,6-dione (25 mg, 0.82 mmol) in MeOH (5 mL) was added 20 mg of 10% Pd/C (wet) (5 mg) and stirred under H₂ in a balloon for 1 hour. The solid was filtered off and the filtrate was concentrated under reduced pressure to afford the titled compound in 99%. MS (ESI, m/z): [M+$^1$]+= [272.3]. [NMR] $^1$H NMR (400 MHz, DMSO-d₆) δ 10.95 (s, 1H), 8.20-8.41 (m, 3H), 8.08 (s, 1H), 7.83 (d, J=8.93 Hz, 1H), 6.95 (d, J=10.5 Hz, 1H), 5.64 (br dd. J=4.83, 11.31 Hz, 1H), 2.62-2.89 (M, 1H), 2.52-2.60 (m, 2H), 1.86-2.07 (m, 1H)

Example 3

Synthesis of Compound

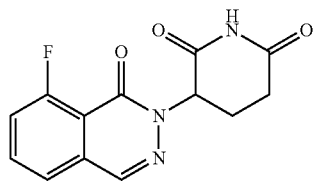 [SMILES: O=C1CCC(n2ncc3cccc(F)c3c2=O)C(=O)N1]

3-1) Synthesis of methyl 2-fluoro-6-methylbenzoate

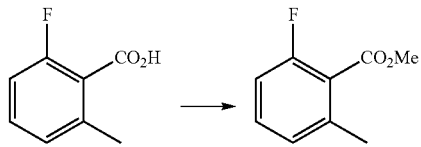

To a solution of 2-fluoro-6-methylbenzoic acid (10 g, 64.9 mmol) in Acetone (200 ml) was added K₂CO₃ (44.8 g, 324 mmol) at room temperature. After stirring for 30 min, the reaction mixture was treated with iodomethane (46 g, 324 mmol) and heated to 60° C. for 6 hours. After cooling, the reaction mixture was filtered and concentrated under reduced pressure. The product (11.2 g, 103%) was used for the next reaction without further purification. MS (ESI, m/z): [M+$^1$]+=[168.3].

3-2) synthesis of methyl 2-(bromomethyl)-6-fluorobenzoate

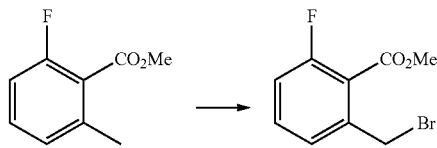

To a solution of methyl 2-fluoro-6-methylbenzoate (21.2 g, 126 mmol) in 1,2-dichloroethane (250 ml) was added 1-bromopyrrolidine-2,5-dione (24.7 g, 139 mmol) followed by benzoyl benzenecarboperoxoate (1.53 g, 6.30 mmol) at room temperature. The reaction mixture was heated to reflux for 16 hours. The reddish color disappeared upon the reaction completion. After cooling, the reaction mixture was washed with water and dried over MgSO₄ and concentrated under reduced pressure. The crude product (35 g, 112%) was used for the next reaction without further purification. MS (ESI, m/z): [M+$^1$]+=[245.9]

3-3) Synthesis of methyl 2-fluoro-6-formylbenzoate

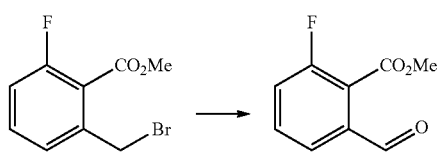 [SMILES: COC(=O)c1c(F)cccc1CBr ; COC(=O)c1c(F)cccc1C=O]

To a solution of methyl 2-(bromomethyl)-6-fluorobenzoate (35 g, 142 mmol) in DCM (280 mL) was added NMO (24.9 g, 212 mmol) at room temperature. The reaction mixture was stirred for 4 hours at room temperature. The DCM layer was washed with water (200 mL), dried over MgSO₄, and then concentrated under reduced pressure. The residue was purified by column chromatography to afford the titled compound (11.52 g, 45%) as a white solid. MS (ESI, m/z): [M+$^1$]+=[183.1]

3-4) Synthesis of 2-fluoro-6-formylbenzoic Acid

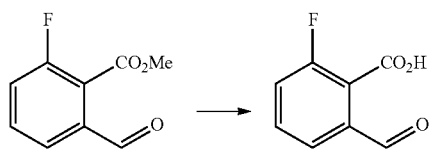 [SMILES: COC(=O)c1c(F)cccc1C=O ; O=Cc1cccc(F)c1C(=O)O]

To a solution of methyl 2-fluoro-6-formylbenzoate (11.5 g, 63.2 mmol) in THF (82 mL) was added a solution of lithium(1+) hydroxide (7.57 g, 180 mmol) in H$_2$O (41 mL) at room temperature. After stirring for 4 hours, the reaction mixture was concentrated under reduced pressure for drying THF. After cooling to 0° C., the reaction mixture was acidified with 1N—HCl to adjust pH to 4. The reaction mixture was extracted with ethyl acetate (100 mL×2). The combined ethyl acetate layer was dried over MgSO$_4$ and concentrated under reduced pressure to give a white crystal (10.4 g, 97.8%). MS (ESI, m/z): [M+1]$^+$=[168.8]

3-5) Synthesis of 8-fluorophthalazin-1(2H)-one

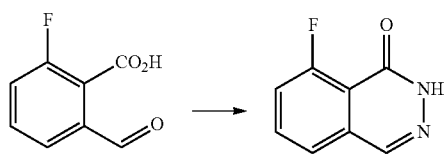 [SMILES: O=Cc1cccc(F)c1C(=O)O ; O=c1[nH]ncc2cccc(F)c12]

To a solution of 2-fluoro-6-formylbenzoic acid (10.4 g, 61.9 mmol) in MeOH (120 mL) was added hydrazine monohydrate (3.72 mg, 61.9 mmol) at room temperature and stirred for 16 hours at room temperature. The white precipitate was filtered and washed with MeOH. The obtained white solid was slurried with 100 ml of EA (ethyl acetate) and filtered to afford a white crystal (3.05 g, 30%). MS (ESI, m/z): [M+1]$^+$=[164.8]

3-6) Synthesis of 3-(8-fluoro-1-oxophthalazin-2 (1H)-yl)piperidine-2,6-dione

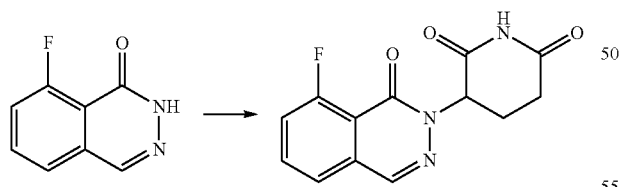

To a solution of 8-fluorophthalazin-1(2H)-one (200 mg, 1.22 mmol) in DMF (5 mL) was added NaH (60%, 53.6 mg, 1.34 mmol) at 0° C. and stirred for 30 mins. To this solution was added 3-bromopiperidine-2,6-dione (468 mg, 2.44 mmol) and stirred for 6 hours at rt (room temperature). The reaction was quenched with water and extracted with ethyl acetate (20 mL×2). The combined ethyl acetate was dried over MgSO$_4$ and concentrated under reduced pressure. The residue was purified by column chromatography to furnish the titled compound (70.0 mg, 20.8%) as a white crystal. MS (ESI, m/z): [M+1]$^+$=[276.1].

[NMR] $^1$H NMR (400 MHz, DMSO-d$_6$) δ 11.06 (s, 1H), 8.48 (s, 1H), 7.99 (ddd, =4.6, 7.2, 8.2 Hz, 1H), 7.80 (d, J=7.2 Hz, 1H), 7.67 (dd, J=8.2, 11.4 Hz, 1H), 5.77 (dd; J=5.3, 12.0 Hz, 1H), 2.99-2.77 (m, 1H), 2.68-2.51 (m, 2H), 2.23-2.02 (m, 1H)

Example 4

Synthesis of Compound

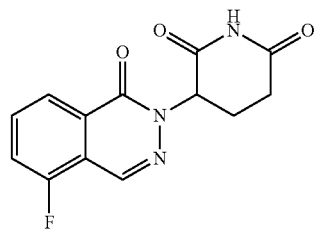 [SMILES: O=C1CCC(n2ncc3c(F)cccc3c2=O)C(=O)N1]

4-1) Synthesis of methyl 5-fluoro-6-methylbenzoate

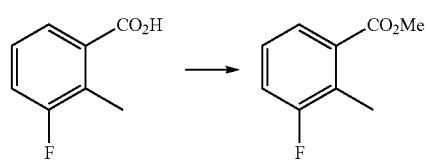

To a solution of 3-fluoro-2-methylbenzoic acid (10 g, 64.9 mmol) in MeOH (60 ml) was added sulfuric acid (2 ml) at room temperature. The reaction mixture was heated to 80° C. and stirred for overnight. After cooling to room temperature, the reaction mixture was evaporated, extracted with NaHCO$_3$ and EA (ethyl acetate), and then dried over MgSO$_4$. The crude product (10.1 g, yield 92%) was used for the next reaction without further purification. MS (ESI, m/z): [M+$^1$]+=[168.3]

4-2) Synthesis of methyl 2-(bromomethyl)-3-fluorobenzoate

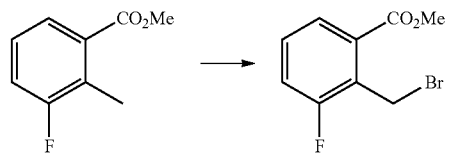

To a solution of methyl 3-fluoro-2-methylbenzoate (10.0 g, 59.5 mmol) in 1,2-dichloroethane (250 ml) was added 1-bromopyrrolidine-2,5-dione (15.9 g, 89.2 mmol) followed by benzoyl benzenecarboperoxoate (0.72 g, 2.97 mmol) at room temperature. The reaction mixture was heated to reflux for 16 hours. The reddish color disappeared upon the reaction completion. After cooling, the reaction mixture was washed with water and dried over MgSO$_4$ and concentrated under reduced pressure. The crude product (10.5 g, yield 71%) was used for the next reaction without further purification. MS (ESI, m/z): [M+$^1$]+=[245.9]

4-3) Synthesis of methyl 3-fluoro-2-formylbenzoate

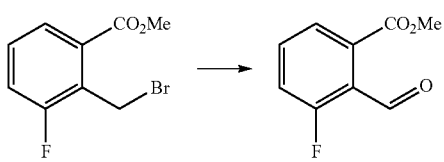 [SMILES: COC(=O)c1cccc(F)c1CBr ; COC(=O)c1cccc(F)c1C=O]

To a solution of methyl 2-(bromomethyl)-3-fluorobenzoate (10 g, 40.5 mmol) in DCM (200 mL) was added NMO (10.4 g, 89.0 mmol), molecular sieve 4 Å at room temperature. The reaction mixture was stirred for 4 hours at room temperature. The DCM layer was washed with water (200 mL), dried over MgSO$_4$, and then concentrated under reduced pressure. The residue was purified by column chromatography to afford the titled compound (5.5 g, 75%). MS (ESI, m/z): [M+$^1$]+=[183.1]

4-4) Synthesis of 3-fluoro-2-formylbenzoic Acid

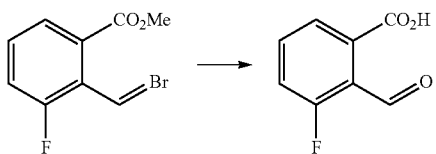

To a solution of methyl 3-fluoro-2-formylbenzoate (2.5 g, 13.7 mmol) in THF (68 mL) was added a solution of lithium(1+)hydroxide monohydrate (2.88 g, 68.6 mmol) in H$_2$O (41 mL) at room temperature. After stirring for 4 hours, the reaction mixture was concentrated under reduced pressure for drying THF. After cooling to 0° C., the reaction mixture was acidified with 1N—HCl to adjust pH to 4. The reaction mixture was extracted with ethyl acetate (100 mL×2). The combined ethyl acetate layer was dried over MgSO$_4$ and concentrated under reduced pressure to give a white crystal (2.5 g, 108%). MS (ESI, m/z): [M+$^1$]+=[168.8]

4-5) Synthesis of
5-fluoro-1,2-dihydrophthalazin-1-one

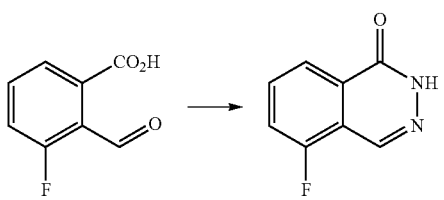 [SMILES: O=Cc1c(F)cccc1C(=O)O ; O=c1[nH]ncc2c(F)cccc12]

To a solution of 3-fluoro-2-formylbenzoic acid (2.5 g, 14.9 mmol) in THF:H$_2$O=1:1 (70 mL) was added hydrazine monohydrate (1.22 mg, 16.4 mmol) at room temperature and stirred for 16 hours at room temperature. The mixture was acidified to pH 4 and the solid was filtered with hexane and dried in vacuo. (1.3 g, 53%). MS (ESI, m/z): [M+$^1$]+= [165.3]

4-6) Synthesis of 3-(5-fluoro-1-oxo-1,2-dihydrophthalazin-2-yl)piperidine-2,6-dione

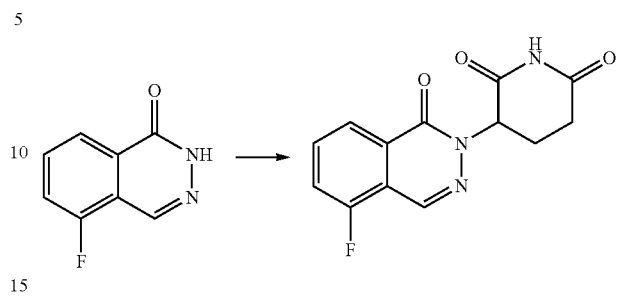

To a solution of 5-fluoro-1,2-dihydrophthalazin-1-one (300 mg, 1.83 mmol) in DMF (10 mL) was added LDA (Lithium diisopropylamide) (2.2 ml, 2.19 mmol) at 0° C. and stirred for 30 mins. To this solution was added 3-bromopiperidine-2,6-dione (526 mg, 2.74 mmol) and stirred for 6 hours at 80° C. Upon the completion of the reaction, the reaction mixture was cooled to room temperature and poured into water (100 ml). The pH of the reaction mixture was adjusted to 3~4 with 6M-HCl. Then, the reaction mixture was extracted with ethyl acetate, dried over MgSO$_4$ and concentrated under reduced pressure. The product was recrystallized with hexane and dried in vacuo to obtain the titled compound. MS (ESI, m/z): [M+1]$^+$=[276.1].

[NMR] $^1$H NMR (400 MHz, DMSO-d$_6$) δ 11.03 (s, 1H), 8.53 (s, 1H), 8.05 (d, J=7.82 Hz, 1H), 7.76-7.90 (m, 2H), 5.78 (dd, J=12.23, 5.26 Hz, 1H), 2.80-2.93 (m, 1H), 2.47-2.61 (m, 2H), 2.01-2.16 (m, 1H)

Example 5

Synthesis of Compound

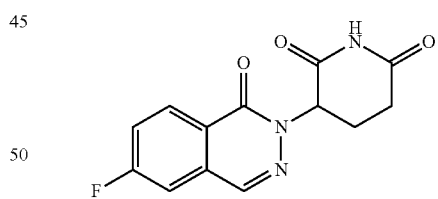

5-1) Synthesis of methyl 4-fluoro-6-methylbenzoate

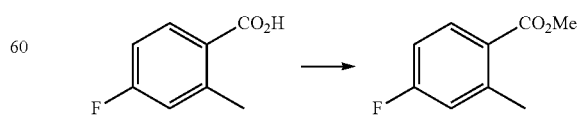

methyl 4-fluoro-2-methylbenzoate was synthesized from 4-fluoro-2-methylbenzoic acid based on the preparation method of Example 4-1.

5-2) Synthesis of methyl 2-(bromomethyl)-4-fluorobenzoate

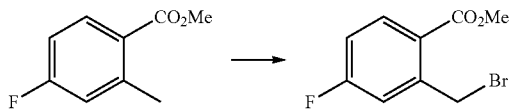

To a solution of methyl 4-fluoro-2-methylbenzoate (20.0 g, 119.0 mmol) in 1,2-dichloroethane (100 ml) was added 1-bromopyrrolidine-2,5-dione (31.8 g, 178.0 mmol) followed by benzoyl benzenecarboperoxoate (1.92 g, 5.95 mmol) at room temperature. The reaction mixture was heated to reflux for 3 hours. The reddish color disappeared upon the reaction completion. After cooling, the reaction was washed with water and dried over $MgSO_4$ and concentrated under reduced pressure. The product was purified by MPLC. (HX/EA EA 0→5%). (22.0 g, yield: 75%). MS (ESI, m/z): [M+$^1$]+=[248.4].

5-3) Synthesis of methyl 3-fluoro-2-formylbenzoate

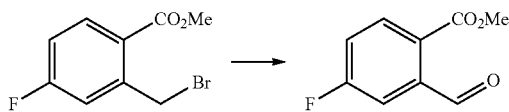 [SMILES: COC(=O)c1ccc(F)cc1CBr ; COC(=O)c1ccc(F)cc1C=O]

To a solution of methyl 2-(bromomethyl)-4-fluorobenzoate (22.0 g, 89 mmol) in DCM (100 mL) was added NMO (15.6 mg, 134 mmol), followed by molecular sieve 4 Å at room temperature. The reaction mixture was stirred for 2 hours at room temperature. Molecular sieve was filtered off and washed with DCM (50 mL). The DCM layer was washed with water (200 mL), dried over $MgSO_4$, and then concentrated under reduced pressure. The residue was purified by column chromatography to afford the titled compound (12.0 g, 73.98%) as a white solid. MS (ESI, m/z): [M+$^1$]+=[183.2].

5-4) Synthesis of 4-fluoro-2-formylbenzoic Acid

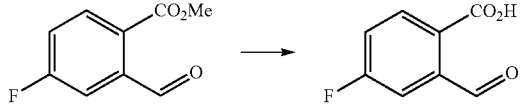 [SMILES: COC(=O)c1ccc(F)cc1C=O ; O=Cc1cc(F)ccc1C(=O)O]

To a solution of methyl 4-fluoro-2-formylbenzoate (12.0 g, 65.9 mmol) in THF (50 mL) was added a solution of lithium(1+) hydroxide (13.8 g, 329 mmol) in $H_2O$ (50 mL) at room temperature. After stirring for 2 hours, the reaction mixture was concentrated under reduced pressure for drying THF. After cooling to 0° C., the reaction was acidified with 1N—HCl to adjust pH to 4. The reaction mixture was extracted with ethyl acetate (50 mL×2). The combined ethyl acetate layer was dried over $MgSO_4$ and concentrated under reduced pressure to give a white crystal (10.0 g, 90.3%). MS (ESI, m/z): [M+$^1$]+=[169.2].

5-5) Synthesis of 6-fluoro-1,2-dihydrophthalazin-1-one

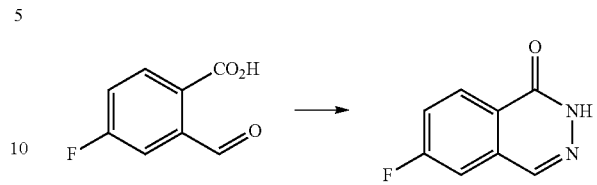

To a solution of 4-fluoro-2-formylbenzoic acid (6.78 g, 40.3 mmol) in MeOH (50 mL) was added hydrazine monohydrate (2.02 mg, 40.3 mmol) at room temperature. After stirring for 30 min, the reaction mixture was heated to 80° C. for 2 hours. The reaction mixture was cooled to room temperature and concentrated under reduced pressure. The residue was poured into water (150 ml) and extracted with ethyl acetate (150 mL×2). The combined ethyl acetate layer was dried over $MgSO_4$ and concentrated under reduced pressure to give a white crystal (5.5 g, 83.07%). MS (ESI, m/z): [M+$^1$]+=[165.3].

5-6) Synthesis of 3-(6-fluoro-1-oxophthalazin-2(1H)-yl)piperidine-2,6-dione

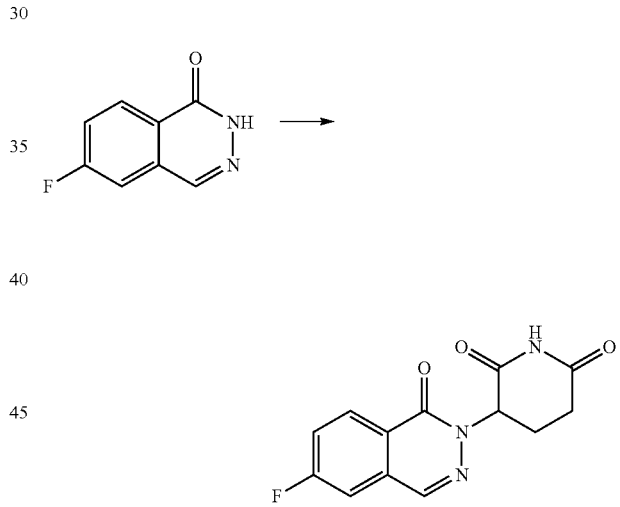

To a solution of 6-fluoro-1,2-dihydrophthalazin-1-one (100 mg, 0.609 mmol) in DMF (2 mL) was added sodium 2-methylpropan-2-olate (175 mg, 0.914 mmol) at 0° C. After stirring for 30 mins. 3-bromopiperidine-2,6-dione (90 mg, 0.471 mmol) was added in reaction mixture and stirred for 6 hours at room temperature. The reaction mixture was poured into water (20 mL) and extracted with ethyl acetate (20 mL×2). The combined ethyl acetate was dried over $MgSO_4$ and concentrated under reduced pressure. The residue was purified by column chromatography to furnish the titled compound (110.0 mg, 65.6%) as a white crystal. MS (ESI, m/z): [M+$^1$]+=[276.6].

[NMR] $^1$H NMR (400 MHz, DMSO-$d_6$) δ 11.11 (s, 1H), 8.50 (s, 1H), 8.38 (dd, =8.86, 5.44 Hz, 1H), 7.72-7.89 (m, 2H), 5.70-5.90 (m, 11H), 2.56-2.70 (m, 2H), 2.11-2.25 (m, 1H)

Example 6

Synthesis of Compound

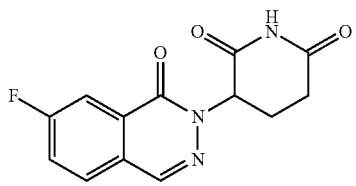

6-1) Synthesis of methyl 4-fluoro-6-methylbenzoate

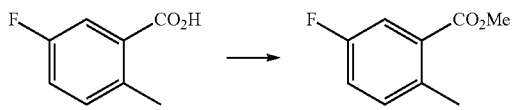

methyl 5-fluoro-2-methylbenzoate was synthesized from 5-fluoro-2-methylbenzoic acid based on the preparation method of Example 4-1.

6-2) Synthesis of methyl 2-(bromomethyl)-5-fluorobenzoate

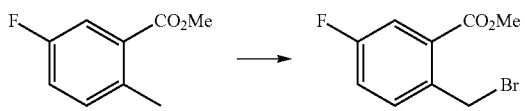

To a solution of methyl 5-fluoro-2-methylbenzoate (20.0 g, 119.0 mmol) in 1,2-dichloroethane (100 m) was added 1-bromopyrrolidine-2,5-dione (31.8 g, 178.0 mmol) followed by benzoyl benzenecarboperoxoate (1.92 g, 5.95 mmol) at room temperature. The reaction mixture was heated to reflux for 3 hours. The reddish color disappeared upon the reaction completion. After cooling, the reaction mixture was washed with water and dried over MgSO$_4$ and concentrated under reduced pressure. The product was purified by MPLC. (HX/EA EA 0→5%). (29.0 g, yield: 98.8%). MS (ESI, m/z): [M+$^1$]+=[248.4].

6-3) Synthesis of methyl 5-fluoro-2-formylbenzoate

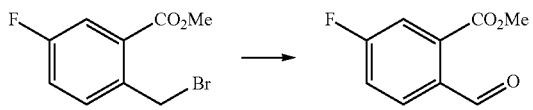 [SMILES: COC(=O)c1cc(F)ccc1CBr ; COC(=O)c1cc(F)ccc1C=O]

To a solution of methyl 2-(bromomethyl)-5-fluorobenzoate (29.0 g, 117 mmol) in DCM (100 mL) was added NMO (20.6 mg, 176 mmol), followed by molecular sieve 4 Å at room temperature. The reaction mixture was stirred for 2 hours at room temperature. Molecular sieve was filtered off and washed with DCM (50 mL). The DCM layer was washed with water (200 mL), dried over MgSO$_4$, and then concentrated under reduced pressure. The residue was purified by column chromatography to afford the titled compound (15.0 g, yield 70.16%) as a white solid. MS (ESI, m/z): [M+$^1$]+=[183.2].

6-4) Synthesis of 5-fluoro-2-formylbenzoic Acid

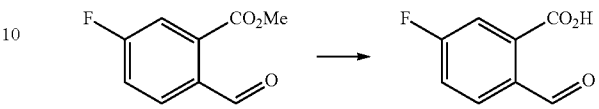

To a solution of methyl 5-fluoro-2-formylbenzoate (15.0 g, 82.3 mmol) in THF (50 mL) was added a solution of lithium(1+) hydroxide (17.3 g, 412 mmol) in H$_2$O (50 mL) at room temperature. After stirring for 2 hours, the reaction mixture was concentrated under reduced pressure for drying THF. After cooling to 0° C., the reaction mixture was acidified with 1 M HCl to adjust pH to 4. The reaction mixture was extracted with ethyl acetate (50 mL×2). The combined ethyl acetate layer was dried over MgSO$_4$ and concentrated under reduced pressure to give a white crystal (12.0 g, 86.67%). MS (ESI, m/z): [M+$^1$]+=[169.2].

6-5) Synthesis of 7-fluoro-1,2-dihydrophthalazin-1-one

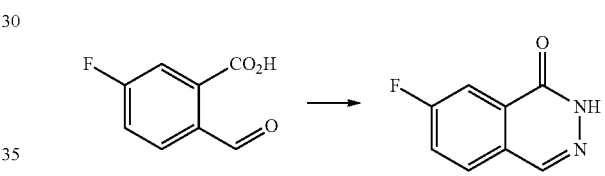

To a solution of 5-fluoro-2-formylbenzoic acid (8.16 g, 48.5 mmol) in MeOH (50 mL) was added hydrazine monohydrate (3.74 mg, 48.5 mmol) at room temperature. After stirring for 30 min, the reaction mixture was heated to 80° C. for 2 hours. The reaction mixture was cooled to room temperature and concentrated under reduced pressure. The residue was poured into water (150 ml) and extracted with ethyl acetate (150 mL×2). The combined ethyl acetate layer was dried over MgSO$_4$ and concentrated under reduced pressure to give a white crystal (6.5 g, 81.59%). MS (ESI, m/z): [M+1]$^+$=[165.3].

6-6) Synthesis of 3-(7-fluoro-1-oxophthalazin-2 (1H)-yl)piperidine-2,6-dione

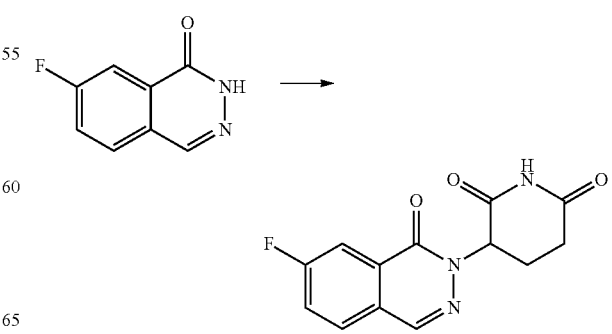

To a solution of 7-fluoro-1,2-dihydrophthalazin-1-one (500 mg, 3.05 mmol) in DMF (5 mL) was added sodium 2-methylpropan-2-olate (586 mg, 6.09 mmol) at 0° C. After stirring for 30 mins, 3-bromopiperidine-2,6-dione (1.05 mg, 5.48 mmol) was added in reaction mixture and stirred for 6 hours at room temperature. The reaction mixture was poured into water (50 mL) and extracted with ethyl acetate (50 mL×2). The combined ethyl acetate was dried over MgSO$_4$ and concentrated under reduced pressure. The residue was purified by column chromatography to furnish the titled compound (300.0 mg, 35.78%) as a white crystal. MS (ESI, m/z): [M+$^1$]+=[276.6].

[NMR] $^1$H NMR (400 MHz, DMSO-d$_6$) δ 11.09 (s, 1H), 8.53 (s, 1H), 8.13 (dd, 1=8.74, 5.20 Hz, 1H), 7.87-8.00 (m, 2H), 5.76-5.88 (m, 11H), 2.54-2.68 (m, 2H), 2.10-2.20 (m, 1H)

Example 7

Synthesis of Compound

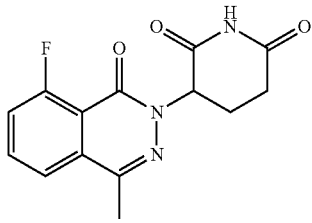 [SMILES: Cc1nn(C2CCC(=O)NC2=O)c(=O)c2c(F)cccc12]

(Prepared Based on Scheme 2)

7-1) Synthesis of methyl 2-acetyl-6-fluorobenzoate

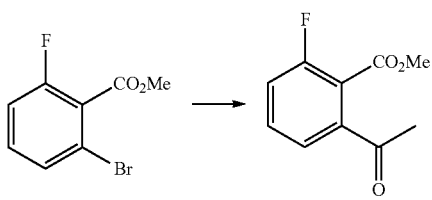

To a solution of methyl 2-acetyl-6-fluorobenzoate (1.12 g, 4.81 mmol) and tributyl(1-ethoxyvinyl)tin (1.91 g, 5.29 mmol) in toluene (20 ml) was added tetrakis(triphenylphosphine)-palladium(0) (557 mg, 0.48 mmol) and stirred for 16 hours at 100° C. After cooling, 5 ml of 1N—HCl was added and the mixture was stirred for 1 hour. The organic layer was dried over MgSO$_4$ and concentrated under reduced pressure. The residue was purified by silica column chromatography to furnish the titled compound (820 mg, yield 87.0%) as a yellow oil. MS (ESI, m/z): [M+$^1$]+=[196.8].

7-2) Synthesis of 2-acetyl-6-fluorobenzoic Acid

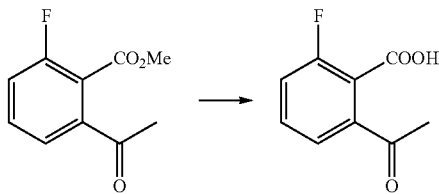

To a solution of methyl 2-acetyl-6-fluorobenzoate (810 mg, 4.13 mmol) in THF (20 ml) and water (10 ml) was added LiOH (494 mg, 20.6 mmol) and stirred for 20 hour at room temperature. The solution was acidified by 1N—HCl until pH was Ca. 3. 100 ml of EA was added and the organic layer was dried over MgSO$_4$ and concentrated under reduced pressure to obtain the tilted compound. MS (ESI, m/z): [M+1]$^+$=[183.1].

7-3) Synthesis of 8-fluoro-4-methylphthalazin-1(2H)-one

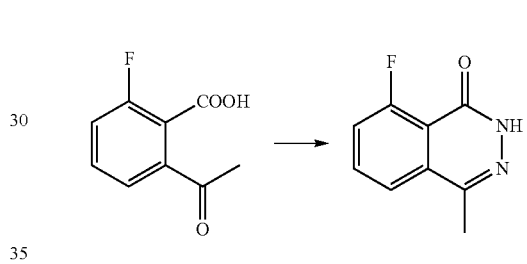

To a solution of 2-acetyl-6-fluorobenzoic acid (790 mg, 4.34 mmol) in methanol (23 mL) was added hydrazine monohydrate (261 mg, 5.20 mmol) and stirred for 16 hours at room temperature. The precipitate was filtered and washed with ACN (acetonitrile) to afford the titled compound (612 mg, 79.2%) as a white solid. MS (ESI, m/z): [M+1]$^+$=[179.1].

7-4) Synthesis of 3-(8-fluoro-4-methyl-1-oxophthalazin-2(1H)-yl)piperidine-2,6-dione

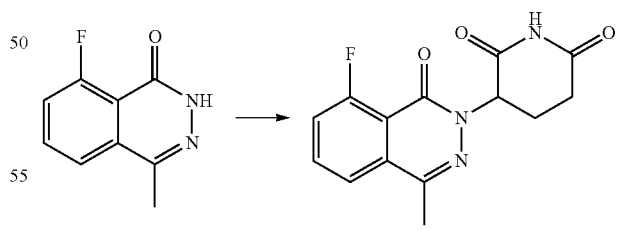

To a solution of 8-fluoro-4-methylphthalazin-1(2H)-one (534 mg, 3 mmol) in THF (30 mL) was added 1M Lithium diisopropylamide (LDA) (3.6 ml, 3.6 mmol) at 0° C., and stirred for 20 min. To a solution was added 3-bromopiperidine-2,6-dione (863 mg, 4.5 mmol) and stirred for 2 hours at 80° C. The reaction mixture was dried under reduced pressure. Water (10 ml) was added and the mixture was stirred for 1 hour. The reaction mixture was acidified with 1N—HCl to adjust pH to 4. The precipitate was filtered and washed with water to afford the titled compound as white solid (760 mg, yield: 86.5%). MS (ESI, m/z): [M+¹]+= [289.8]

[NMR] ¹H NMR (400 MHz, DMSO-$d_6$) δ 11.05 (s, 1H), 8.04-7.94 (m, 1H), 7.79 (d, J=7.9 Hz, 1H), 7.69 (dd, J=7.9, 11.3 Hz, 1H), 5.71 (be dd, J=4.9, 12.1 Hz, 1H), 3.0-2.83 (m, 1H), 2.64-2.56 (m, 2H), 2.55 (s, 3H), 2.17-2.05 (m, 1H).

Example 8

Synthesis of Compound

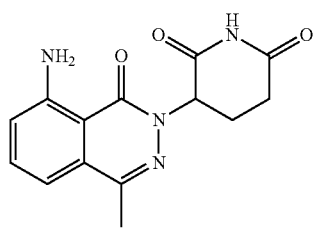 [SMILES: Cc1nn(C2CCC(=O)NC2=O)c(=O)c2c(N)cccc12]

8-1) Synthesis of 3-(8-((2,4-dimethoxybenzyl) amino)-4-methyl-1-oxophthalazin-2(1H)-yl)piperidine-2,6-dione

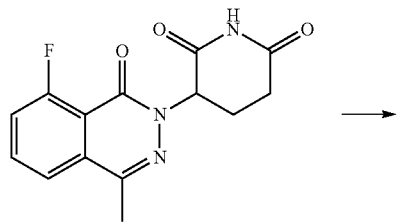

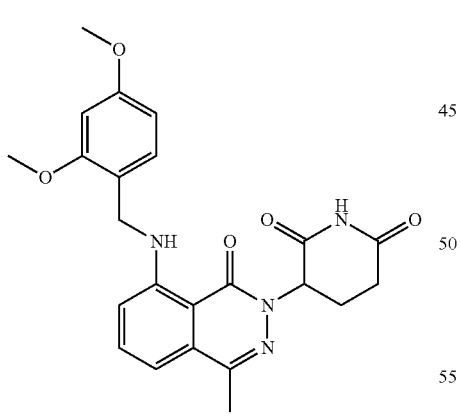

A solution of 3-(8-fluoro-4-methyl-1-oxophthalazin-2 (1H)-yl)piperidine-2,6-dione (0.104 mmol), 2,4-dimethoxybenzylamine (0.207 mmol), and DIPEA (N,N-diisopropyl ethylamine) (0.312 mmol) in NMP (N-methyl-pyrrolidone) (1 mL) was irritated on microwave at 120° C. for 2 hours. The reaction mixture was purified by reverse column chromatography (C18, water (0.1% FA)/ACN (0.1% FA), gradient) to afford 33 mg of white solid. (33 mg, yield=72%). MS (ESI, m/z): [M+¹]+=[437.0]

8-2) Synthesis of 3-(8-amino-4-methyl-1-oxophthalazin-2(1H)-yl)piperidine-2,6-dione

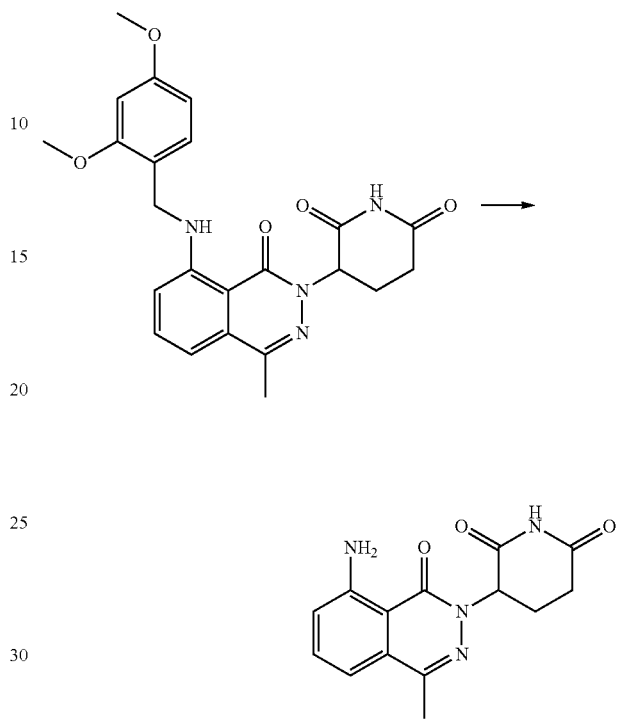

To a solution of 3-(8-((2,4-dimethoxybenzyl)amino)-4-methyl-1-oxophthalazin-2(1H)-yl)piperidine-2,6-dione (14 mg, 0.032 mmol) in 0.7 ml of toluene was added 0.3 ml of TFA (trifluoro acetic acid) and stirred for 1 hour at 80° C. The reaction mixture was purified by reverse column chromatography (C18, water (0.1% FA)/ACN (0.1% FA), gradient) to afford 7.5 mg of white solid, yield=82%. MS (ESI, m/z): [M+¹]+=[287.0].

[NMR] ¹H NMR (400 MHz, DMSO-$d_6$) δ10.98 (s, 1H), 7.54 (t, J=8.0 Hz, 1H), 7.37 (brs, 2H), 6.95 (d, J=8.2 Hz, 1H), 6.88 (d, J=7.6 Hz, 1H), 5.62 (br dd, J=5.3, 12.0 Hz, 1H), 3.0-2.82 (m, 1H), 2.66-2.52 (m, 2H), 2.39 (s, 3H), 2.11-2.02 (m, 1H)

Example 9

Synthesis of Compound

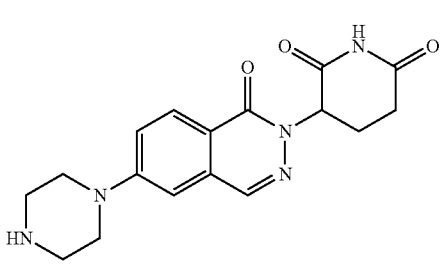 [SMILES: O=C1CCC(n2ncc3cc(N4CCNCC4)ccc3c2=O)C(=O)N1]

9-1) Synthesis of tert-butyl 4-(2-(2,6-dioxopiperidin-3-yl)-1-oxo-1,2-dihydrophthalazin-6-yl)piperazin-1-carboxylate

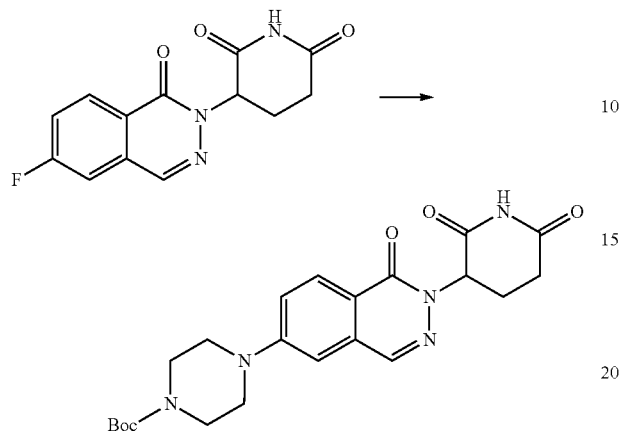

6-fluoro-1,2-dihydrophthalazin-1-one (100 mg, 0.36 mmol) and tert-butyl piperazine-1-carboxylate (81.2 mg, 0.36 mmol) were dissolved in NMP (1 mL), DIPEA (5 eq.) was added in reaction mixture and stirred 120° C. for overnight. The reaction mixture was quenched by water and extracted with EA and washed with NH₄Cl saturated water and brine. The organic layer was dried over MgSO₄. The reaction mixture was loaded on silica and separated by MPLC. (HX/EA 30%→50% for 10 min). product was obtained as oil. (110 mg, yield: 66%), 9-2) Synthesis of 3-(1-oxo-6-(piperazin-1-yl)phthalazin-2(1H)-yl)piperidine-2,6-dione

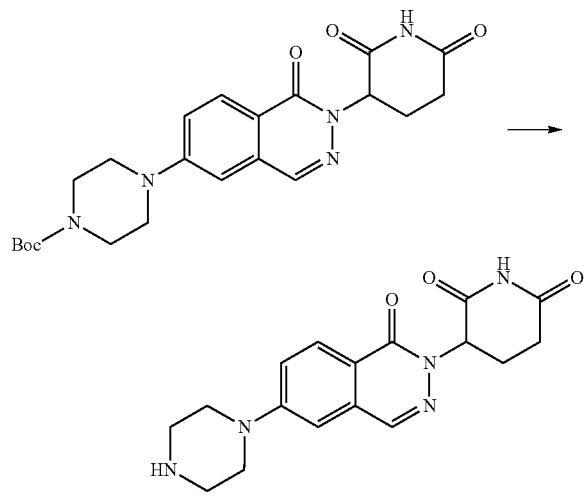

tert-butyl 4-[2-(2,6-dioxopiperidin-3-yl)-1-oxo-1,2-dihydrophthalazin-6-yl]piperazine-1-carboxylate was dissolved in 20% TFA in DCM (1 ml) and reacted for 2 hours at room temperature. The reaction was quenched by NaHCO₃ in sat. water and extracted with EA. The organic layer was dried over MgSO₄ and evaporated. The reaction mixture was purified by MPLC (MC/MEOH, 0→10%). Product was obtained as white solid (yield: 40 mg/86%).

[NMR] ¹H NMR (400 MHz, DMSO-d₆) δ 8.24 (s, 1H) 8.02 (d, J=9.05 Hz, 1H) 7.47 (dd, J=8.93, 2.57 Hz, 1H) 7.31 (s, 0.5H) 7.23 (d, J=2.45 Hz, 1H) 7.13 (s, 0.5H) 5.34 (dd, J=8.93, 4.52 Hz, 1H) 3.28-3.44 (m, 6H) 2.85-2.95 (m, 4H) 2.30-2.40 (m, 1H) 2.16-2.30 (m, 2H)

MS (ESI, m/z): [M+1]⁺=[342.2]

Example 10

Synthesis of Compound

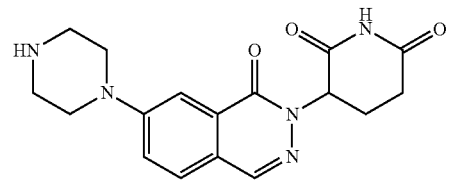 [SMILES: O=C1CCC(n2ncc3ccc(N4CCNCC4)cc3c2=O)C(=O)N1]

10-1) Synthesis of tert-butyl 4-(3-(2,6-dioxopiperidin-3-yl)-4-oxo-3,4-dihydrophthazin-6-yl)piperazin-1-carboxylate

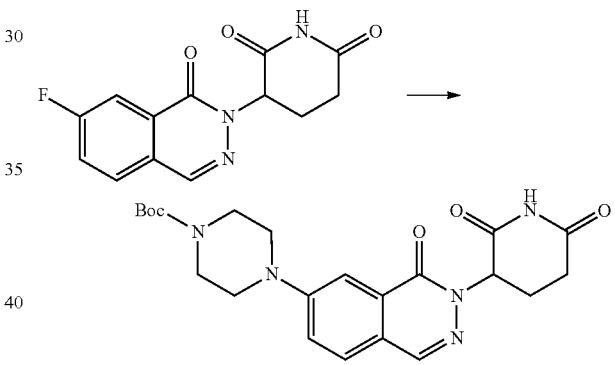

3-(7-fluoro-1-oxo-1,2-dihydrophthalazin-2-yl)piperidine-2,6-dione (100 mg, 0.36 mmol) and tert-butyl piperazine-1-carboxylate (81.2 mg, 0.44 mmol) were dissolved in NMP (1 mL), DIPEA (5 eq.) was added in reaction mixture. and stirred at 120° C. for overnight. The reaction mixture was quenched by water and extracted with EA and washed with NH₄Cl saturated water and brine. The organic layer was dried over MgSO₄. The reaction mixture was loaded on silica and separated by MPLC. (HX/EA 30%→50% for 10 min). product was obtained as oil. (yield: 110 mg, 66%)

10-2) Synthesis of 3-(1-oxo-7-(piperazin-1-yl)phthalazin-2(1H)-yl)piperidine-2,6-dione

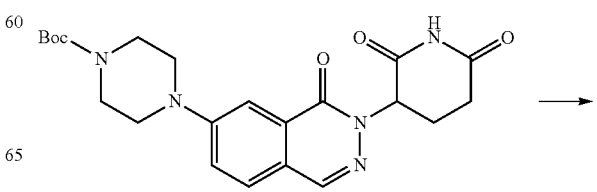

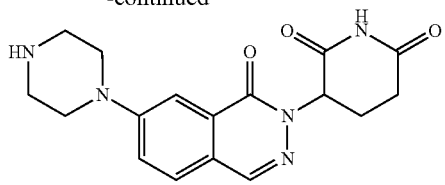

tert-butyl 4-[3-(2,6-dioxopiperidin-3-yl)-4-oxo-3,4-dihydrophthalazin-6-yl]piperazine-1-carboxylate (60 mg, 0.14 mmol) was dissolved in 20% TFA in DCM (1 ml) and reacted for 2 hours at room temperature. The reaction was quenched by NaHCO₃ in sat. water and extracted with EA. The organic layer was dried over MgSO4 and evaporated. The reaction mixture was purified by MPLC (MC/MEOH, 0→10%). Product was obtained as white solid (yield: 40 mg, 86%).

[NMR] $^1$H NMR (400 MHz, DMSO-$d_6$) δ 8.21-8.29 (m, 1H) 7.76 (d, J=8.80 Hz, 1H) 7.58 (dd, J=8.93, 2.57 Hz, 1H) 7.47 (d, J=2.45 Hz, 1H) 7.28 (s, 0.5H) 7.13 (s, 0.5H) 5.34-5.44 ((m, 1H) 3.26-3.33 (m, 4H) 2.81-2.91 (m, 3H) 2.62-2.69 ((m, 1H) 2.55-2.62 ((m, 1H) 2.31-2.44 (m, 1H) 2.15-2.31 (m, 2H)

MS (ESI, m/z): [M+1]$^+$=[342.2].

Example 11: Synthesis of 3-(8-methoxy-1-oxophthalazin-2(1H)-yl)piperidine-2,6-dione Synthesis of Compound

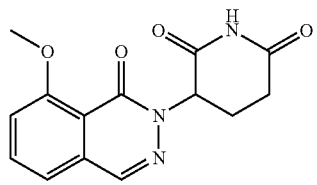 [SMILES: COc1cccc2cnn(C3CCC(=O)NC3=O)c(=O)c12]

3-(6-fluoro-1-oxo-1,2-dihydrophthalazin-2-yl)piperidine-2,6-dione (100 mg, 0.36 mmol) was dissolved in DMSO (1 ml) and NaOMe (19.6 mg, 0.36 mmol) was added in reaction mixture. The reaction mixture was reacted at r.t. for 1 hour. The organic solvent was removed and extracted with EA and H₂O. The mixture was purified by MPLC. Product was obtained as white solid (yield: 80 mg, 76%).

[NMR] $^1$H NMR (400 MHz, DMSO-$d_6$) δ 11.04 (br. s., 1H) 8.40 (s, 1H) 8.14-8.25 (m, 1H) 7.42-7.49 (m, 2H) 5.80 (dd, J=12.23, 5.38 Hz, 1H) 3.94 (s, 3H) 2.86-2.99 (m, 1H) 2.52-2.67 (m, 2H) 2.07-2.17 (m, 1H) MS (ESI, m/z): [M+1]$^+$= [288.2].

Example 12: Synthesis of 3-(7-methoxy-1-oxophthalazin-2(1H)-yl)piperidine-2,6-dione Synthesis of Compound

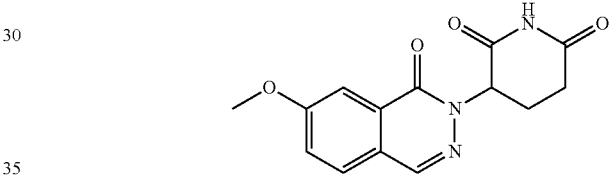

3-(7-fluoro-1-oxophthalazin-2(1H)-yl)piperidine-2,6-dione (100 mg, 0.36 mmol) was dissolved in DMSO (1 ml) and NaOMe (19.6 mg, 0.36 mmol) was added in reaction mixture. The reaction mixture was reacted at r.t. for 1 hour. The organic solvent was removed and extracted with EA and H₂O. The mixture was purified by MPLC. Product was obtained as white solid (yield: 78 mg, 75%).

[NMR] $^1$H NMR (400 MHz, DMSO-$d_6$) δ 11.01-11.11 (m, 1H) 8.38-8.45 (m, 1H) 7.90-7.96 (m, 1H) 7.65 (d, J=2.69 Hz, 1H) 7.56 (dd, J=8.68, 2.57 Hz, 1H) 5.77-5.85 (m, 1H) 3.93-3.98 (m, 3H) 2.87-3.00 (m, 1H) 2.53-2.70 (m, 2H) 2.06-2.18 ((m, 1H)

MS (ESI, m/z): [M+1]$^+$=[288.2].

Example 13: Synthesis of 3-(6-methoxy-1-oxophthalazin-2(1H)-yl)piperidine-2,6-dione Synthesis of Compound

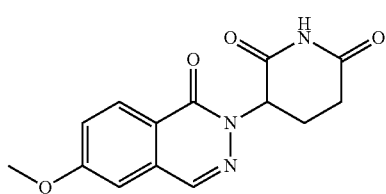 [SMILES: COc1ccc2c(=O)n(C3CCC(=O)NC3=O)ncc2c1]

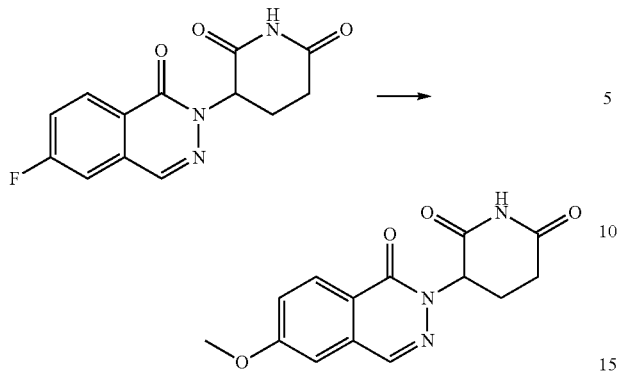

3-(6-fluoro-1-oxophthalazin-2(1H)-yl)piperidine-2,6-dione (100 mg, 0.36 mmol) was dissolved in DMSO (1 ml) and NaOMe (19.6 mg, 0.36 mmol) was added in reaction mixture.

The reaction mixture was reacted at room temperature for 1 hour. The organic solvent was removed and extracted with EA and H$_2$O. The mixture was purified by MPLC. Product was obtained as white solid (yield: 80 mg, 76%).

[NMR] $^1$H NMR (400 MHz, DMSO-d$_6$) δ 11.01 (s, 1H) 8.32 (s, 1H) 7.88 (t, J=8.01 Hz, 1H) 7.40 (d, J=8.31 Hz, 1H) 7.44 (d, J=7.70 Hz, 1H) 5.64 (dd, J=11.49, 4.52 Hz, 1H) 3.90 (s, 3H) 2.83-2.96 (m, 1H) 2.52-2.66 (m, 2H) 2.03-2.13 (m, 1H)

MS (ESI, m/z): [M+1]$^+$=[288.2].

Example 14: Synthesis of 3-(5-methoxy-1-oxophthalazin-2(1H)-yl)piperidine-2,6-dione Synthesis of Compound

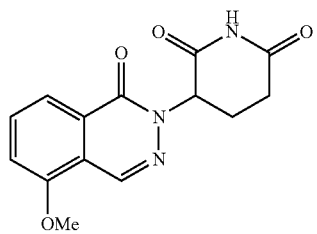 [SMILES: COc1cccc2c(=O)n(C3CCC(=O)NC3=O)ncc12]

14-1) Synthesis of methyl 2-(bromomethyl)-3-methoxybenzoate

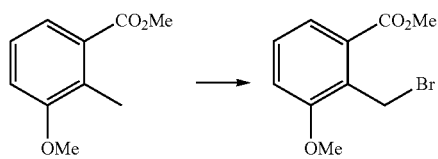

To a solution of methyl 2-methyl-3-methoxybenzoate (11.7 g, 64.9 mmol) in 1,2-dichloroethane (250 ml) was added 1-bromopyrrolidine-2,5-dione (11.5 g, 64.94 mmol) followed by benzoyl benzenecarboperoxoate (786 mg, 3.24 mmol) at room temperature. The reaction mixture was heated to reflux for 3 hours. The reddish color disappeared upon the reaction completion. After cooling, the reaction was washed with water and dried over MgSO$_4$ and concentrated under reduced pressure. The crude product (16.5 g, 98.2%) was used for the next reaction without further purification. MS (ESI, m/z): [M+$^1$]+=[259.4].

14-2) Synthesis of methyl 2-formyl-3-methoxybenzoate

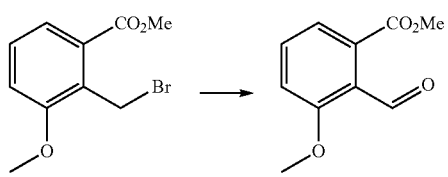

To a solution of methyl 2-(bromomethyl)-3-methoxybenzoate (14.1 g, 54.1 mmol) in DCM (300 mL) was added NMO (12.6 g, 108.1 mmol) followed by molecular sieve 4 Å (50 g) at room temperature. The reaction mixture was stirred for 2 hours at room temperature. Molecular sieve was filtered off and washed with DCM (100 mL). The DCM layer was washed with water (250 mL), dried over MgSO$_4$, and then concentrated under reduced pressure. The residue was purified by column chromatography to afford the titled compound (8.3 g, 80.01%) as a white solid.

MS (ESI, m/z): [M+$^1$]+=[195.0].

14-3) Synthesis of 2-formyl-3-methoxybenzoic Acid

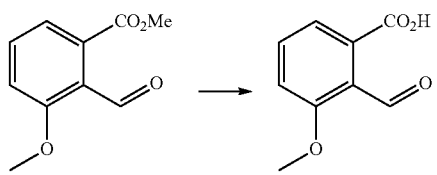

To a solution of methyl 2-formyl-3-methoxybenzoate (6.5 g, 33.6 mmol) in THF (100 mL) was added a solution of lithium(1+) hydroxide (2.4 g, 100.5 mmol) in H$_2$O (100 mL) at room temperature. After stirring for 2 hours, the reaction mixture was concentrated under reduced pressure for drying THF. After cooling to 0° C., the reaction mixture was acidified with 1N—HCl to adjust pH to 4. The reaction mixture was extracted with ethyl acetate (250 mL×2). The combined ethyl acetate layer was dried over MgSO$_4$ and concentrated under reduced pressure to give a white crystal (11.2 g, 82.6%).

MS (ESI, m/z): [M+$^1$]+=[199.2].

14-4) Synthesis of 5-methoxyphthalazin-1(2H)-one

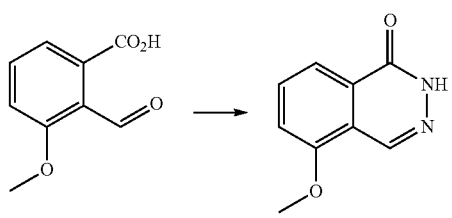

To a solution of 2-formyl-3-methoxybenzoic acid (8.2 g, 45.5 mmol) in MeOH (20 mL) was added hydrazine monohydrate (10.3 g, 342 mmol) at room temperature. After stirring for 2 hours, the reaction mixture was concentrated under reduced pressure, poured into water (50 ml), and extracted with ethyl acetate (150 mL×2). The combined ethyl acetate layer was dried over MgSO$_4$ and concentrated under reduced pressure to give a white crystal (9.2 g, 76.35%).

MS (ESI, m/z): [M+$^1$]+=[176.9].

14-5) Synthesis of 3-(5-methoxy-1-oxophthalazin-2 (1H)-yl)piperidine-2,6-dione

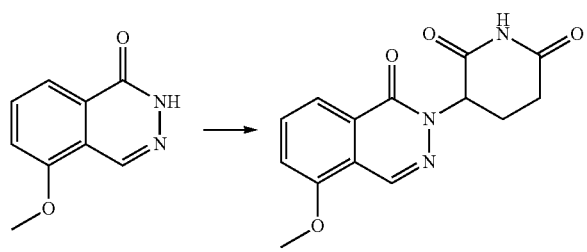 [SMILES: COc1cccc2c(=O)[nH]ncc12 ; COc1cccc2c(=O)n(C3CCC(=O)NC3=O)ncc12]

To a partial suspension of 5-methoxyphthalazin-1(2H)-one (5.1 g, 28.9 mmol) in THF (250 mL) was added 1.0 M LDA (37.4 mL) dropwise at 0° C. After stirring for 30 mins, 3-bromopiperidine-2,6-dione were added to the reaction portionwise. The reaction mixture was heated to 80° C. and stirred for 2 hours. Upon the completion of the reaction, the reaction mixture was cooled to room temperature and poured into water (100 ml), adjusted pH to 3~4 with 6N—HCl, and then extracted with ethyl acetate, which was dried over MgSO$_4$ and concentrated under reduced pressure. The residue was purified by MPLC to afford the titled compound as a white crystal (7.2 g, 86.5%).

MS (ESI, m/z): [M+1]$^+$=[288.3].

[NMR] 1H NMR (400 MHz, DMSO-d6) δ11.06 (s, 1H), 8.51 (s, 1H), 7.87-7.77 (m, 2H), 7.54-7.51 (m, 1H), 5.85 (m, 1H), 4.0 (s, 3H), 2.98-2.90 (m, 1H), 2.65-2.55 (m, 2H), 2.14-2.09 (m, 1H).

Example 15: Synthesis of 3-(6-bromo-1-oxophthalazin-2(1H)-yl)piperidine-2,6-dione

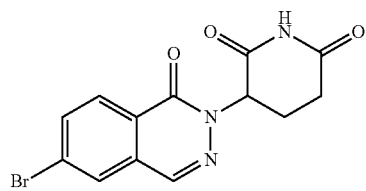 [SMILES: O=C1CCC(n2ncc3cc(Br)ccc3c2=O)C(=O)N1]

15-1) Synthesis of 5-bromo-3-hydroxyisobenzofuran-1(3H)-one

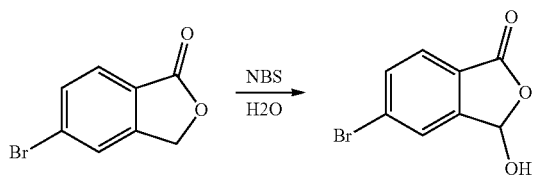

To a mixture of 5-bromophthalide (5.2 g, 24.4 mmol) and N-bromosuccinimide (5.6 g, 31.7 mmol) in 200 ml of 1,2-dichloroethane was added with AIBN (401 mg, 2.44 mmol), and then refluxed for 8 hours. The reaction was followed by TLC. The succinimide was filtered off and the cake was washed with 1,2-dichloroethane (50 mL). The solvent was removed in vacuo leaving a residue 5.2 g, to which was added 50 ml water. This mixture was refluxed with stirring for 4 hours, then the mixture was cooled, and the product filtered off, washed neutrally with water and dried to afford an off-white crystal (4.85 g, 86.7%).

MS (ESI, m/z): [M+1]$^+$=[229.6] and [230.5]

15-2) Synthesis of 6-bromophthalazin-1(2H)-one

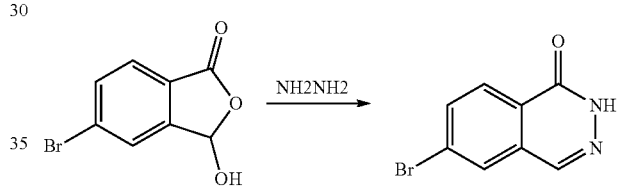

A solution of 5-bromo-3-hydroxy-1,3-dihydro-2-benzofuran-1-one (1.5 g, 6.55 mmol) in MeOH (50 mL) was added with hydrazine monohydrate (315 mg, 9.82 mmol) at room temperature and stirred for 30 mins. The reaction was refluxed for 5 hours. The reaction mixture was cooled to room temperature and concentrated under reduced pressure. The resulting solid was triturated in ethyl acetate to furnish a white crystal (1.31 g, 5.82 mmol).

MS (ESI, m/z): [M+1]$^+$=[226.3].

15-3) Synthesis of 3-(6-bromo-1-oxophthalazin-2 (1H)-yl)piperidine-2,6-dione

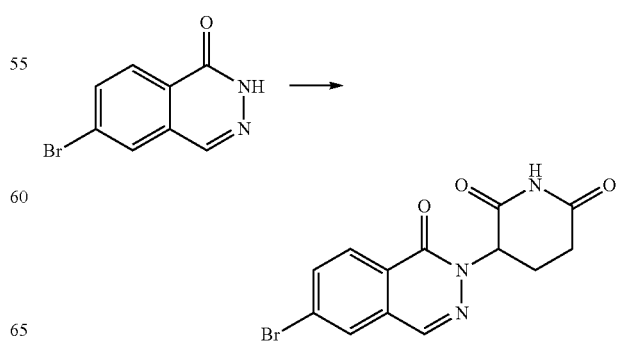

To a suspension of 6-bromo-1,2-dihydrophthalazin-1-one (1.31 g, 5.82 mmol) in THF (150 mL), was added 1.0 M LDA (7.33 mL) dropwise at 0° C. After stirring for 30 mins, 3-bromopiperidine-2,6-dione were added to the reaction mixture portionwise. The reaction mixture was heated to 80° C. and stirred for 2 hours. Upon the completion of the reaction, the reaction mixture was cooled to room temperature and poured into water (100 ml), adjusted pH to 3-4 with 6N—HCl, and then extracted with ethyl acetate, which was dried over MgSO$_4$ and concentrated under reduced pressure. The resulting solid was filtered and washed with ethyl acetate to give a white crystal (1.73 g, 5.15 mmol).

MS (ESI, m/z): [M+1]$^+$=[337.2].

[NMR] 1H NMR (400 MHz, DMSO-d6) δ11.08 (s, 1H), 8.45 (s, 1H), 8.28 (s, 1H), 8.18-8.16 (m, 1H), 8.06-8.04 (m, 1H), 5.84-5.80 (m, 1H), 2.93-2.90 (m, 1H), 2.65-2.54 (m, 2H), 2.15-2.12 (m, 1H).

Example 16: Synthesis of 3-(1-oxo-8-(piperazin-1-yl)phthalazin-2(1H)-yl)piperidine-2,6-dione 2HCl

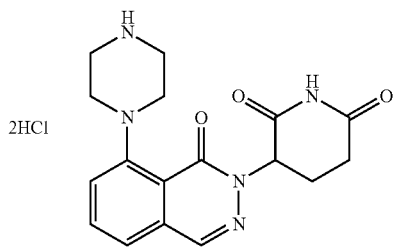 [SMILES: O=C1CCC(n2ncc3cccc(N4CCNCC4)c3c2=O)C(=O)N1]

16-1) Synthesis of 3-(1-oxo-8-(piperazin-1-yl) phthalazin-2(1H)-yl)piperidine-2,6-dione Dihydrochloride

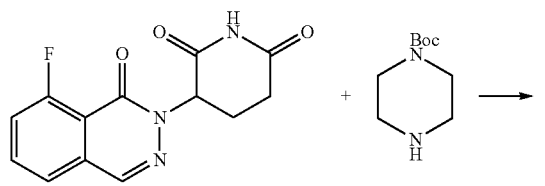

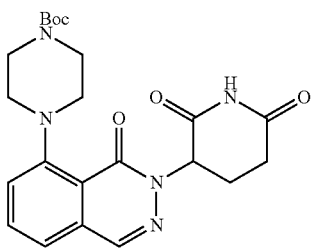

To a solution of 3-(8-fluoro-1-oxo-1,2-dihydrophthalazin-2-yl)piperidine-2,6-dione (0.3 g, 1.09 mmol) in DMA (4 mL) was added tert-butyl piperazine-1-carboxylate (244 mg, 1.13 mmol) followed by ethylbis(propan-2-yl)amine (423 mg, 3.24 mmol). The mixture was stirred at 120° C. for 5 hours. The reaction mixture was diluted with water and extracted with ethyl acetate. The organic layer was washed with brine, dried over Na$_2$SO$_4$, and concentrated. The residue was purified by column chromatography to afford the off-white oil (415 mg, 86.2%).

MS (ESI, m/z): [M+1]$^+$=[442.4]

16-2) Synthesis of 3-(1-oxo-8-(piperazin-1-yl) phthalazin-2(1H)-yl)piperidine-2,6-dione Dihydrochloride

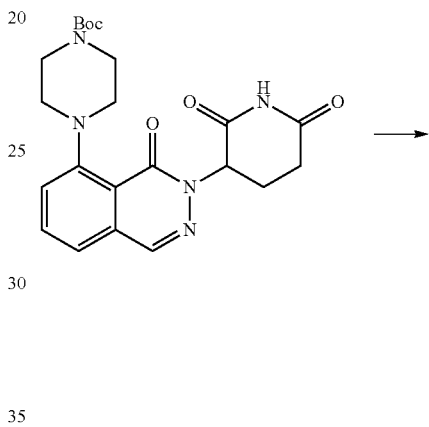

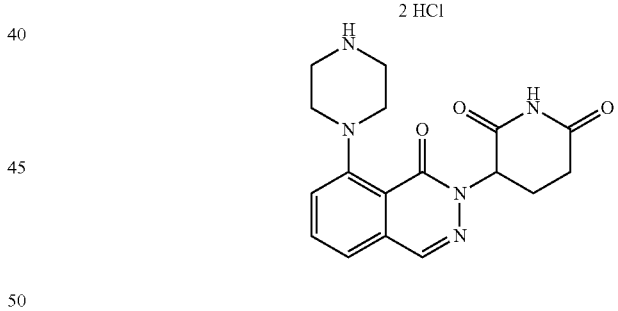

To a solution of 8-nitro-1,2-dihydrophthalazin-1-one (60 mg, 0.314 mmol) in DMF (1 mL) was added 3-bromopiperidine-2,6-dione (90 mg, 0.471 mmol) followed by K$_2$CO$_3$ (129 mg, 0.942 mmol). The reaction mixture was heated to 85° C. for 5 hours. After cooling, the reaction mixture was poured into water (5 mL) and extracted with ethyl acetate (5 mL×2). The combined ethyl acetate was dried over MgSO$_4$ and concentrated under reduced pressure. The residue was purified by column chromatography to furnish the titled compound (68.0 mg, 71.7%) as a white crystal.

MS (ESI, m/z): [M+1]$^+$=[342.6].

[NMR] 1H NMR (400 MHz, DMSO-d6) δ11.02 (s, 1H), 8.35 (s, 1H), 7.87-7.83 (m, 1H), 7.53-7.51 (m, 1H), 7.39-7.41 (m, 1H), 5.55 (m, 1H), 3.31-3.27 (br, 8H), 2.88-2.80 (m, 1H), 2.64-2.57 (m, 2H), 2.50 (br, 1H), 2.13-2.08 (m, 1H).

Example B: PROTAC Synthesis

Example 21: Synthesis of 2-((S)-4-(4-chlorophenyl)-2,3,9-trimethyl-6H-thieno[3,2-f][1,2,4]triazolo[4,3-a][1,4]diazepin-6-yl)-N-((2-(2-(2-((3-(2,6-dioxopiperidin-3-yl)-4-oxo-3,4-dihydrophthalazin-5-yl)amino)ethoxy)ethoxy)ethoxy)methyl)acetamide

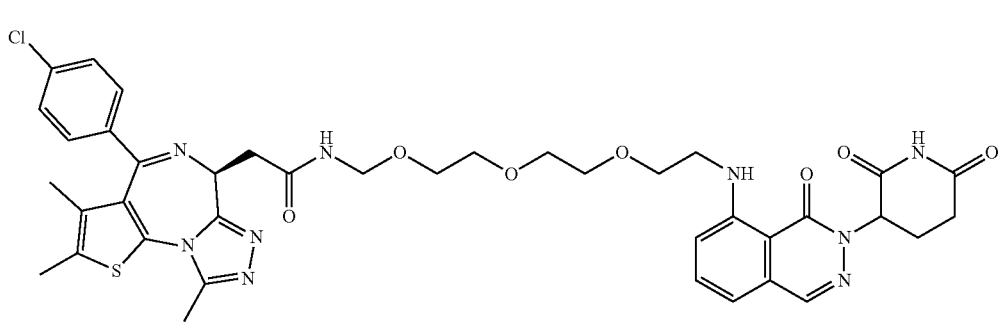 [SMILES: Cc1sc2c(c1C)C(c1ccc(Cl)cc1)=N[C@@H](CC(=O)NCOCCOCCOCCNc1cccc3cnn(C4CCC(=O)NC4=O)c(=O)c13)c1nnc(C)n1-2]

Connecting Linker and E3 Ligase Binder

Step 1) Synthesis of tert-butyl (2-(2-(2-((3-(2,6-dioxopiperidin-3-yl)-4-oxo-3,4-dihydrophthalazin-5-yl)amino)ethoxy)ethoxy)ethyl)carbamate

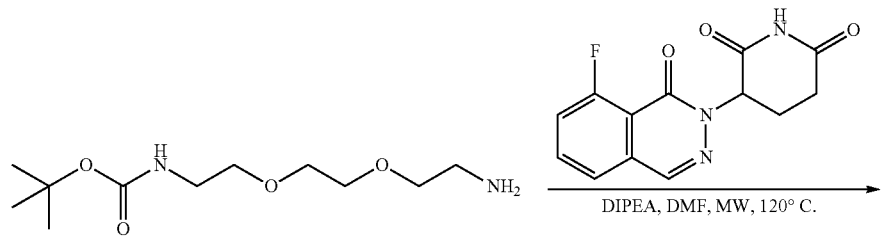

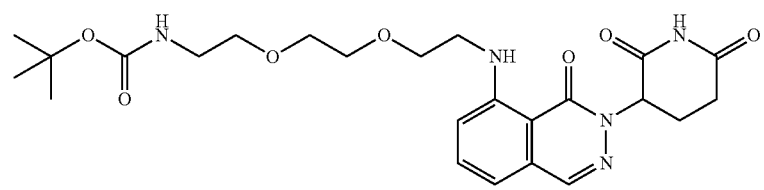

A solution of 3-(8-fluoro-1-oxo-1,2-dihydrophthalazin-2-yl)piperidine-2,6-dione (0.13 mmol), tert-butyl N-{2-[2-(2-aminoethoxy)ethoxy]ethyl}carbamate (0.15 mmol), and DIPEA (N,N-diisopropylethylamine) (0.38 mmol) in DMF (2 mL) was irritated on microwave at 120° C. for 2 hours. The reaction mixture was diluted with water and extracted with EtOAc. The organic layer was washed with brine, dried over MgSO₄, and concentrated. The residue was purified by column chromatography to give the product as above reaction scheme.

MS (ESI, m/z): [M+1]⁺=[504.0]

Step 2) Synthesis of 3-(8-((2-(2-(2-aminoethoxy)ethoxy)ethyl)amino)-1-oxophthalazin-2(1H)-yl)piperidine-2,6-dione HCl

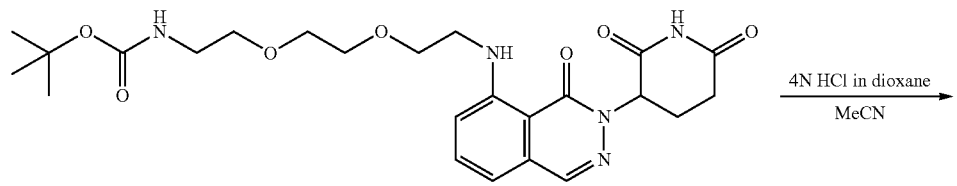

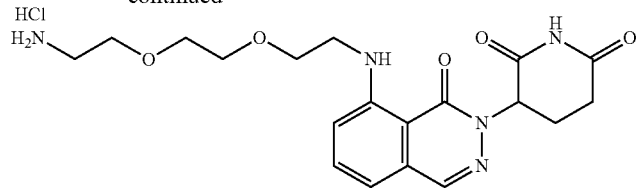

tert-butyl N-{2-[2-(2-{[3-(2,6-dioxopiperidin-3-yl)-4-oxo-3,4-dihydrophthalazin-5-yl]amino}ethoxy)ethoxy]ethyl}carbamate (0.1 mmol) was dissolved in acetonitrile (1 mL) and a solution of 4N—HCl in dioxane was added at room temperature. The reaction was done in 1 hour. The reaction mixture was concentrated in vacuo and used for the next step without further purification.

MS (ESI, m/z): [M+1]$^+$=[404.0]

Connecting Linker and POI Ligand

Step 3) Synthesis of 2-((S)-4-(4-chlorophenyl)-2,3,9-trimethyl-6H-thieno[3,2-f][1,2,4]triazolo[4,3-a][1,4]diazepin-6-yl)-N-((2-(2-(2-((3-(2,6-dioxopiperidin-3-yl)-4-oxo-3,4-dihydrophthalazin-5-yl)amino)ethoxy)ethoxy)ethoxy)methyl)acetamide

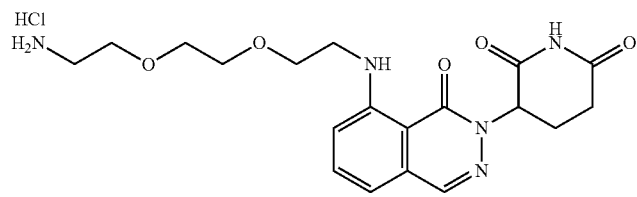
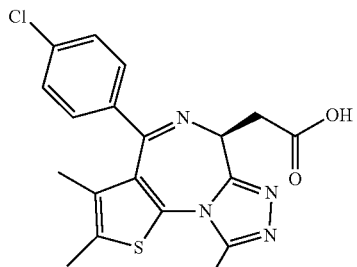

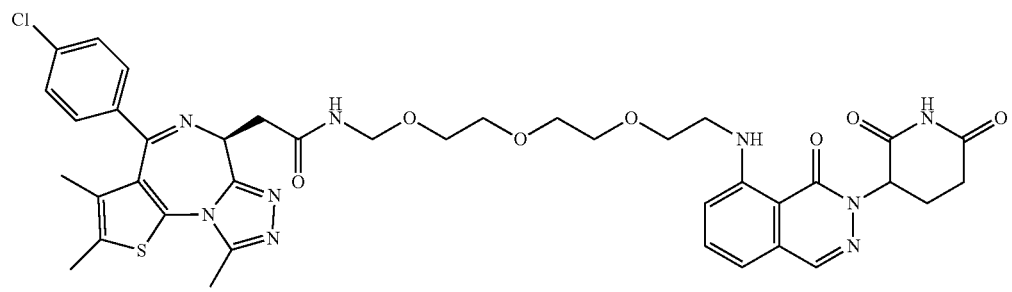

To a solution of JQ-1 carboxylic acid (0.037 mmol), 3-[8-({2-[2-(2-aminoethoxy)ethoxy]ethyl)amino}-1-oxo-1,2-dihydrophthalazin-2-yl]piperidine-2,6-dione hydrochloride (0.041 mmol), EDCl (1-ethyl-3-(3-dimethylaminopropyl)carbodiimide (0.041 mmol), and Cl-HOBt (6-chloro-1-hydroxybenzotriazole) (0.041 mmol) in DMF (1 mL) was added DIPEA (0.13 mmol). The mixture was stirred at room temperature overnight. The reaction mixture was diluted with water and extracted with ethyl acetate. The organic layer was washed with brine, dried over Na$_2$SO$_4$, and concentrated. The titled compound was separated by column chromatography.

1H NMR (400 MHz, CDCl$_3$) δ 8.89 (br, 1H), 8.64-8.57 (m, 1H), 7.95 (s, 1H), 7.41-7.39 (m, 4H), 6.88-6.75 (m, 3H), 5.64 (m, 1H), 4.65 (m, 1H), 3.81-3.45 (m, 14H), 2.66 (s, 3H), 2.39 (s, 3H), 1.66 (s, 3H),

MS (ESI, m/z): [M+1]$^+$=[786.3]

Example 22

2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(3-{2-[2-(2-{[3-(2,6-dioxopiperidin-3-yl)-4-oxo-3,4-dihydro-1,2,3-benzotriazin-5-yl]amino}ethoxy)ethoxy]ethoxy}phenyl)acetamide

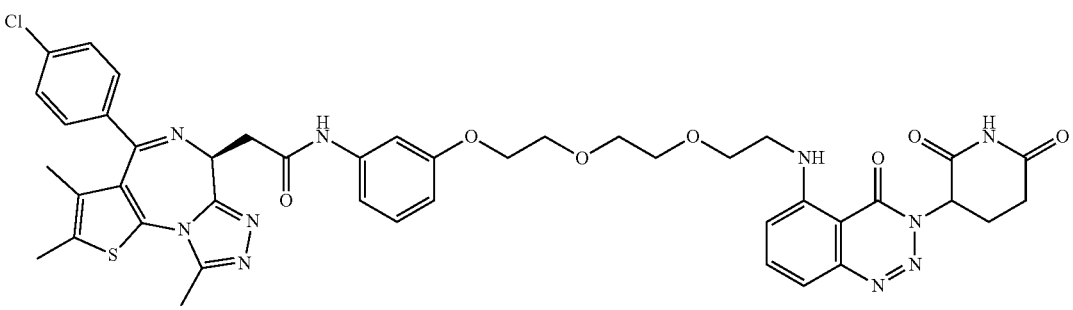 [SMILES: Cc1sc2c(c1C)C(c1ccc(Cl)cc1)=N[C@@H](CC(=O)Nc1cccc(OCCOCCOCCNc3cccc4nnn(C5CCC(=O)NC5=O)c(=O)c34)c1)c1nnc(C)n1-2]

Connecting Linker and E3 Ligase Binder

Step 1) Synthesis of tert-butyl N-(3-{2-[2-(2-{[3-(2,6-dioxopiperidin-3-yl)-4-oxo-3,4-dihydro-1,2,3-benzotriazin-5-yl]amino}ethoxy)ethoxy]ethoxy}phenyl)carbamate

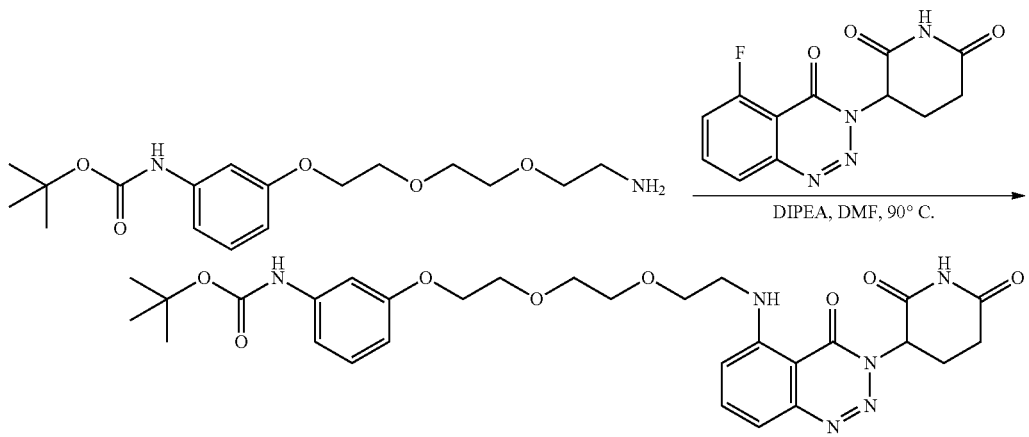

A solution of 3-(5-fluoro-4-oxo-3,4-dihydro-1,2,3-benzotriazin-3-yl)piperidine-2,6-dione (100 mg, 0.36 mmol), tert-butyl N-(3-{2-[2-(2-aminoethoxy)ethoxy]ethoxy}phenyl)carbamate (136 mg, 0.40 mmol) and DIPEA (N,N-diisopropyl ethylamine) in DMF (4 mL) was reacted at 90° C. overnight. The reaction mixture was diluted with water and extracted with EtOAc. The organic layer was washed with brine, dried over MgSO$_4$, and concentrated. The residue was purified by column chromatography to give the product as the above reaction scheme. (Yield: 69.5%, 150 mg)

Step 2) Synthesis of 3-{5-[(2-{2-[2-(3-aminophenoxy)ethoxy]ethoxy}ethyl)amino]-4-oxo-3,4-dihydro-1,2,3-benzotriazin-3-yl}piperidine-2,6-dione Hydrochloride

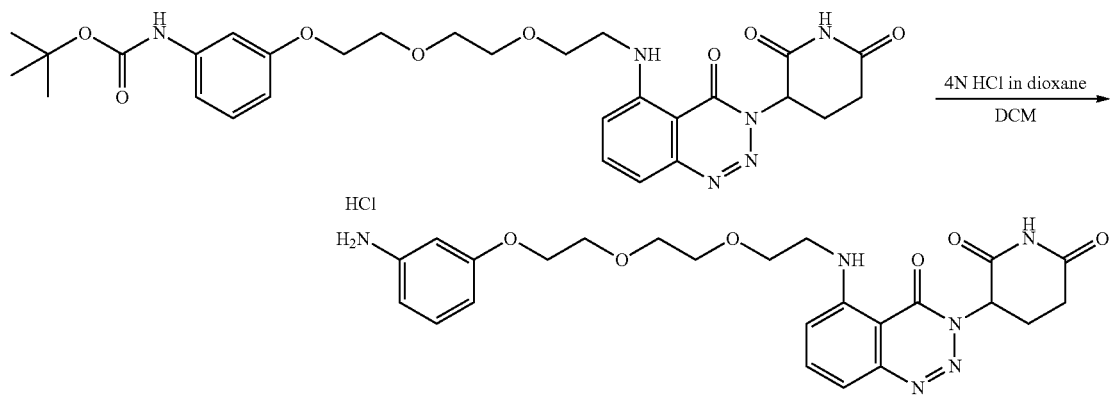

tert-butyl N-(3-{2-[2-(2-{[3-(2,6-dioxopiperidin-3-yl)-4-oxo-3,4-dihydro-1,2,3-benzotriazin-5-yl]amino}ethoxy)ethoxy]ethoxy}phenyl)carbamate (0.10 mmol) was dissolved in DCM (2 ml), and 4N—HCl in dioxane (1 ml) was added to the solution dropwise slowly. The solution was sonicated for 10 minutes. The solvent was evaporated and the residue was dissolved in MeOH. The solvent was evaporated and dried in vacuo to afford the titled compound as the scheme above. (Yield: 75%/~, 100 mg)

Connecting Linker and POI Ligand

Step 3) Synthesis of 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(3-{2-[2-(2-{[3-(2,6-dioxopiperidin-3-yl)-4-oxo-3,4-dihydro-1,2,3-benzotriazin-5-yl]amino}ethoxy)ethoxy]ethoxy}phenyl)acetamide

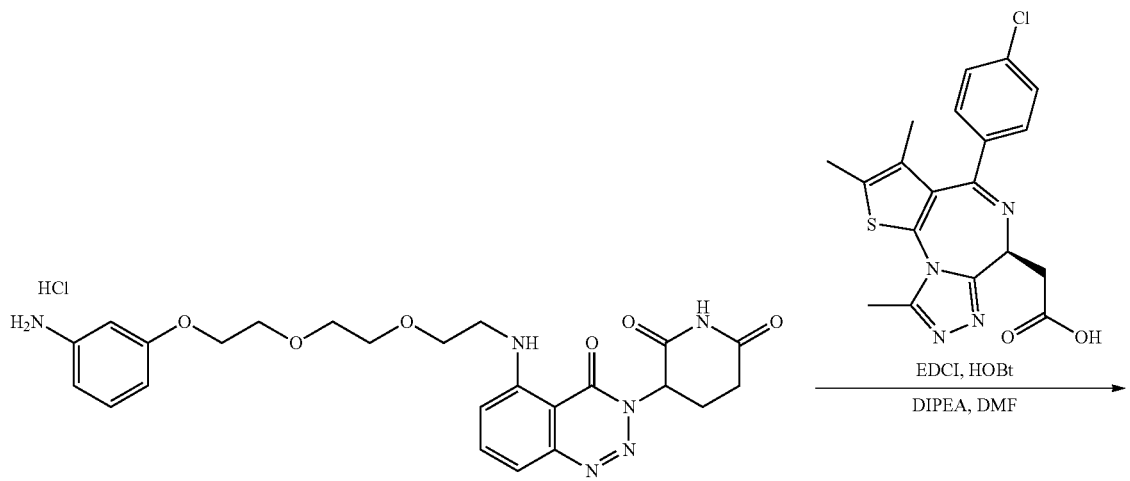

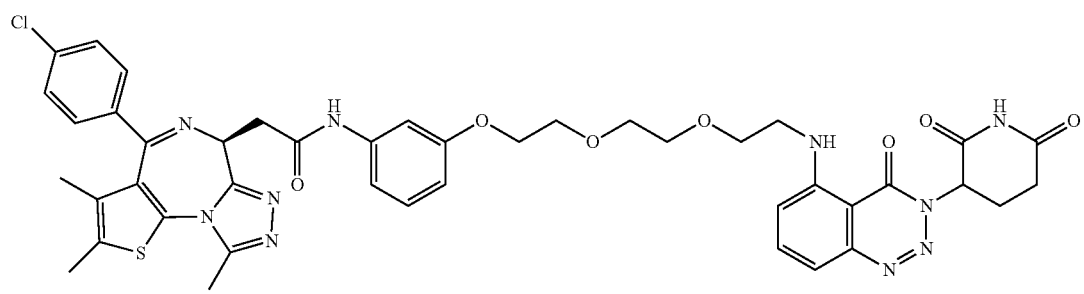

To a solution of 2-[(9S)-7-(4-chlorophenyl)-4,5,13-trimethyl-3-thia-1,8,11,12-tetraazatricyclo[8.3.0.0²,⁶]trideca-2(6),4,7,10,12-pentaen-9-yl]acetic acid (JQ-1 carboxylic acid) (50 mg, 0.13 mmol), 3-{5-[(2-{2-[2-(3-aminophenoxy)ethoxy]ethoxy}ethyl)amino]-4-oxo-3,4-dihydro-1,2,3-benzotriazin-3-yl}piperidine-2,6-dione hydrochloride (73.1 mg, 0.14 mmol), EDCl (1-ethyl-3-(3-dimethylaminopropyl)carbodiimide) (26.3 mg, 0.14 mmol), and Cl-HOBt (6-chloro-1-hydroxybenzotriazole) (23.3 mg, 0.14 mmol) in DMF (2 ml) was added DIPEA (78.4 μL, 0.44 mmol). The mixture was stirred at room temperature overnight. The reaction mixture was diluted with water and extracted with ethyl acetate. The organic layer was washed with brine, dried over Na$_2$SO$_4$, and concentrated. The desired product was separated by column chromatography. (Yield: 15.5%, 17 mg).

MS (ESI, m/z): [M+1]⁺=[881.3].

[NMR] $^1$H NMR (400 MHz, DMSO-d$_6$) δ ppm 11.18 (s, 1H), 10.30 (s, 1H), 8.34 (t, J=5.14 Hz, 1H), 7.77 (t, J=8.07 Hz, 1H), 7.39-7.53 (m, 3H), 7.36 (s, 1H), 7.16-7.25 (m, 2H), 7.09-7.16 (m, 1H), 6.94-7.03 (m, 1H), 6.62 (dd, J=8.19, 1.59 Hz, 1H), 5.86 (dd, J=11.86, 5.01 Hz, 1H), 4.60 (t, J=7.09 Hz, 1H), 3.97-4.08 (m, 2H), 3.64-3.79 (m, 4H), 3.61 (s, 4H), 3.50 (d, J=7.09 Hz, 2H), 3.40 (q, J=5.05 Hz, 2H), 2.83-2.99 (m, 1H), 2.57-2.70 (m, 5H), 2.41 (s, 3H), 2.23 (dd, J=10.15, 5.01 Hz, 1H), 1.96 (d, J=13.69 Hz, 1H), 1.62 (s, 3H)

Example 23: Synthesis of 2-((S)-4-(4-chlorophenyl)-2,3,9-trimethyl-6H-thieno[3,2-f][1,2,4]triazolo[4,3-a][1,4]diazepin-6-yl)-N-(3-(2-(2-(2-((3-(2,6-dioxopiperidin-3-yl)-4-oxo-3,4-dihydrophthalazin-5-yl)amino)ethoxy)ethoxy)ethoxy)phenyl)acetamide

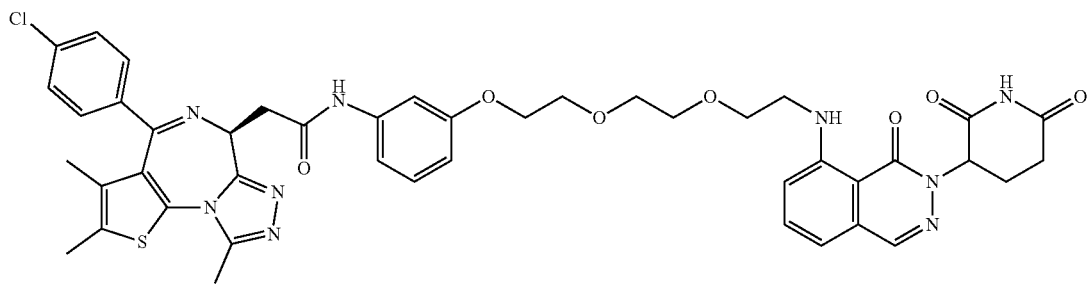 [SMILES: Cc1sc2c(c1C)C(c1ccc(Cl)cc1)=N[C@@H](CC(=O)Nc1cccc(OCCOCCOCCNc3cccc4cnn(C5CCC(=O)NC5=O)c(=O)c34)c1)c1nnc(C)n1-2]

The titled compound is synthesized through following procedure which is similar to that of Example 22.

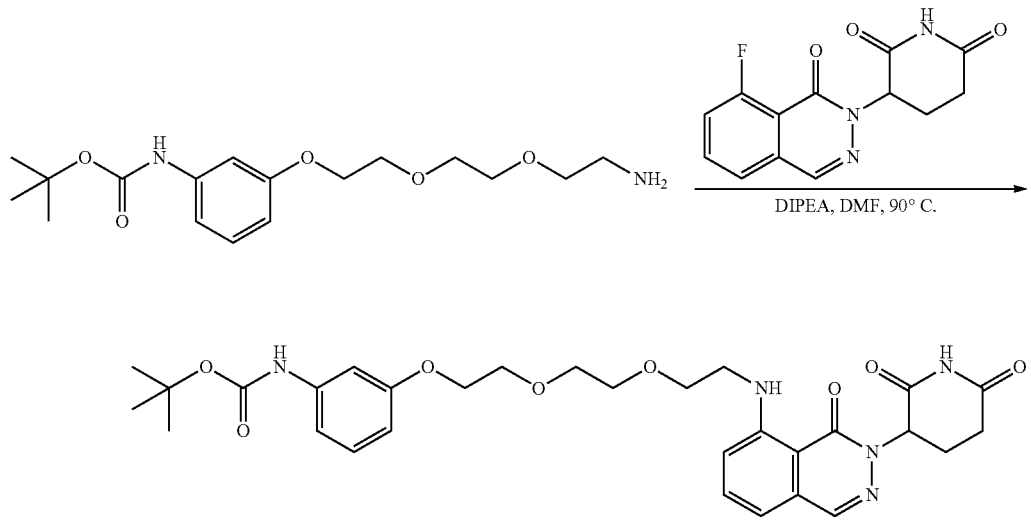

A solution of 3-(8-fluoro-1-oxophthalazin-2(1H)-yl)piperidine-2,6-dione (541 mg, 1.97 mmol), tert-butyl N-(3-{2-[2-(2-aminoethoxy)ethoxy]ethoxy}phenyl)carbamate (870 mg, 2.56 mmol) and DIPEA (1 ml) in NMP (10 mL) was reacted at 100° C. for 6 hours. The reaction mixture was purified by Reverse phase column chromatography (water (0.1% FA)/ACN (0.1% FA)=95/1 to 0/100 gradient) and the corresponding fraction was removed under reduced pressure. 980 mg of light-yellow solid was obtained. (yield=83.6%). MS (ESI, m/z): [M+$^1$]+=[596.2]

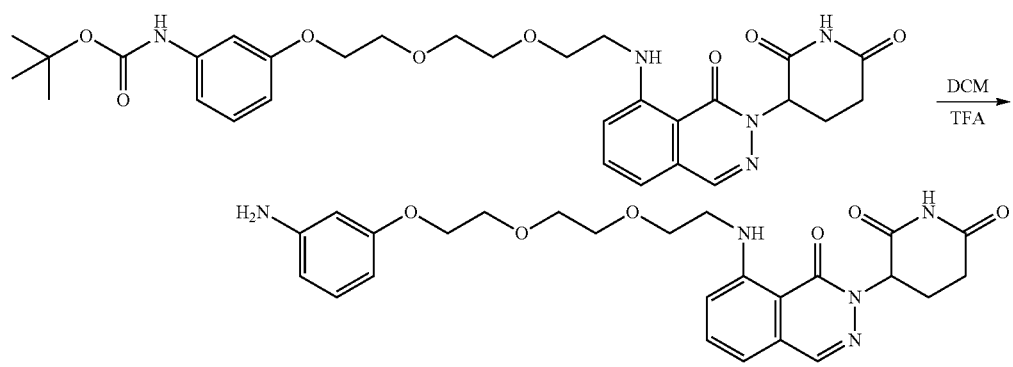
To a solution of tert-butyl (3-(2-(2-(2-((3-(2,6-dioxopiperidin-3-yl)-4-oxo-3,4-dihydrophthalazin-5-yl)amino)ethoxy)ethoxy)ethoxy)phenyl)carbamate (1.35 g, 2.27 mmol) in 27 ml of DCM was added 6.75 ml of TFA and stirred for 1 hour at room temperature. The solvent was evaporated and dried in vacuo. (Yield=2.23 g as Ca 5 eq. of TFA salt). MS (ESI, m/z): [M+$^1$]+=[496.0]
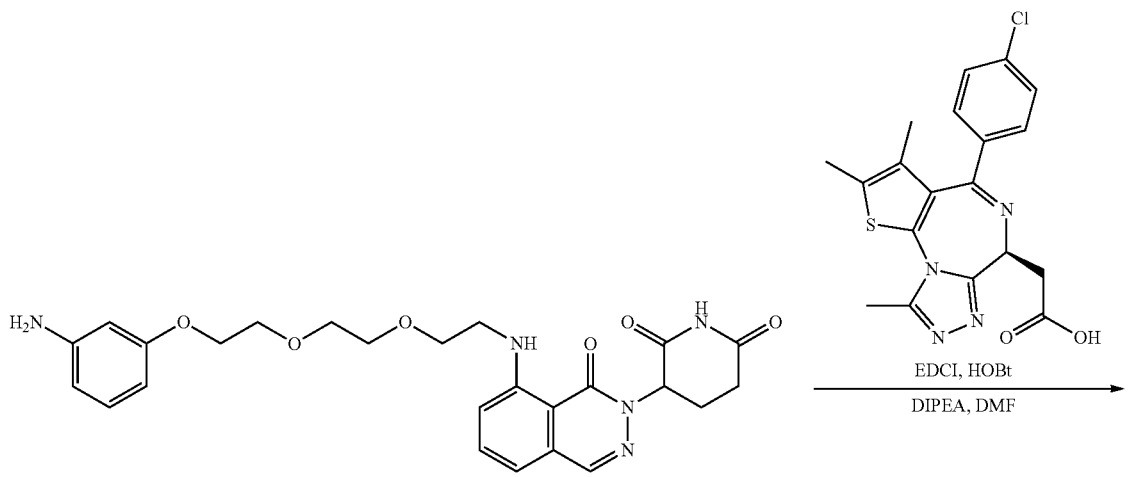
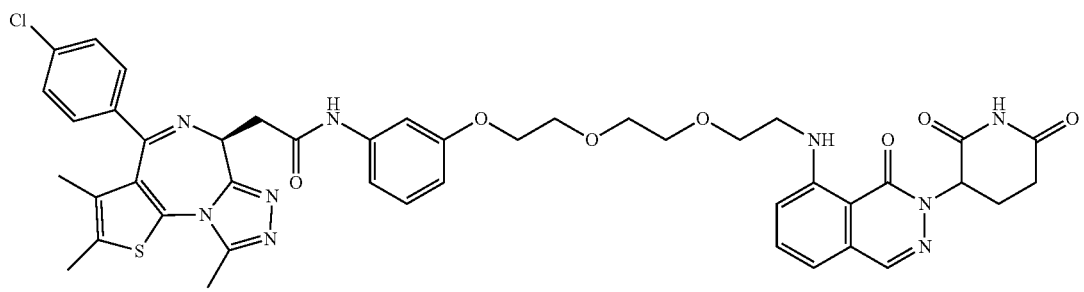

To a solution of 2-[(9S)-7-(4-chlorophenyl)-4,5,13-trimethyl-3-thia-1,8,11,12-tetraazatricyclo[8.3.0.0²,⁶]trideca-2(6),4,7,10,12-pentaen-9-yl]acetic acid (401 mg, 1 mmol), 3-(8-((2-(2-(2-(3-aminophenoxy)ethoxy)ethoxy)ethyl)amino)-1-oxophthalazin-2(1H)-yl)piperidine-2,6-dione (496 mg, 1 mmol) and DIPEA (539 µl, 3 mmol) in 3.3 ml of DMF was added EDCl-HCl (230 mg, 1.2 mmol) and HOBt (187 mg, 1.1 mmol) at 0° C. and stirred for 2 hours at 50° C. The reaction mixture was purified by reverse column chromatography to give the product (Yield: 390 mg, 44.4%).

1H NMR (400 MHz, DMSO-d6) δ=11.03 (s, 1H), 10.30 (s, 1H), 8.83 (t, J=5.14 Hz, 1H), 8.22 (s, 1H), 7.62 (t, J=8.01 Hz, 1H), 7.49 (d, J=8.6 Hz, 2H), 7.43 (d, J=8.6 Hz, 2H), 7.36 (s, 1H), 7.23-7.11 (m, 2H), 6.91 (d, J=7.95 Hz, 2H), 6.62 (d, J=7.49 Hz, 1H), 5.76-5.66 (m, 1H), 4.60 (t, J=7.09 Hz, 1H), 3.76 (m, 2H), 3.67 (m, 2H), 3.60 (m, 4H), 3.50 (m, 2H), 3.38 (m 2H), 2.93-2.82 (m, 1H), 2.63-2.53 (m, 5H), 2.48-2.38 (m, 4H), 2.10 (m, 1H), 1.63 (s, 3H).

MS (ESI, m/z): [M+1]⁺=[878.4] and [880.4].

Example 24

2-[(9S)-7-(4-chlorophenyl)-4,5,13-trimethyl-3-thia-1,8,11,12-tetraazatricyclo[8.3.0.0²,⁶]trideca-2(6),4,7,10,12-pentaen-9-yl]-N-(4-{2-[2-(2-{[3-(2,6-dioxopiperidin-3-yl)-4-oxo-3,4-dihydrophthalazin-5-yl]amino}ethoxy)ethoxy]ethoxy}phenyl)acetamide

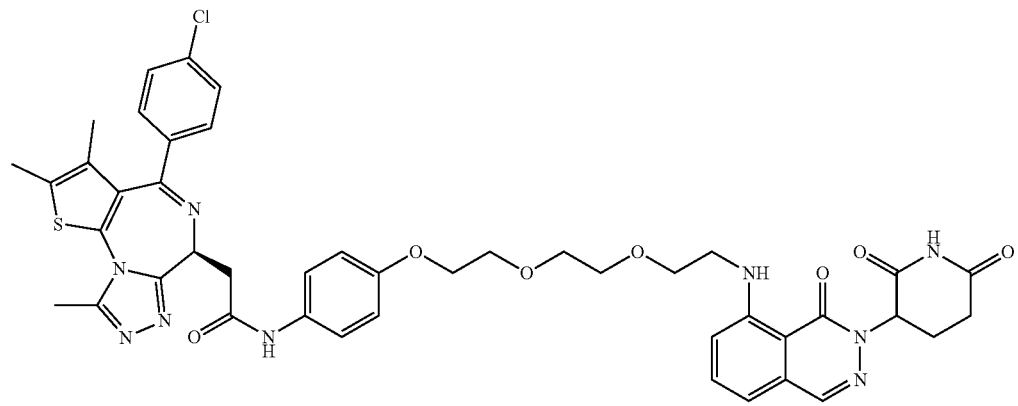 [SMILES: Cc1sc2c(c1C)C(c1ccc(Cl)cc1)=N[C@@H](CC(=O)Nc1ccc(OCCOCCOCCNc3cccc4cnn(C5CCC(=O)NC5=O)c(=O)c34)cc1)c1nnc(C)n1-2]

The titled compound is synthesized through following procedure which is similar to that of Example 23.

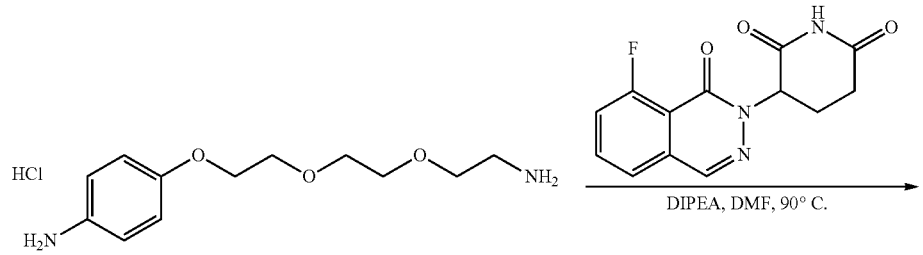

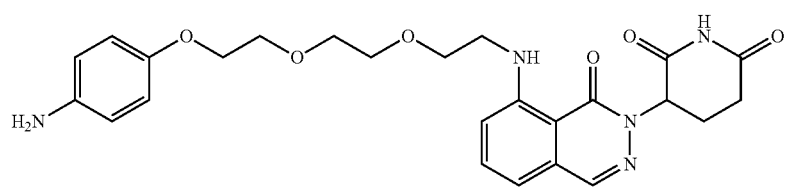

A solution of 3-(8-fluoro-1-oxo-1,2-dihydrophthalazin-2-yl)piperidine-2,6-dione (50 mg, 0.182 mmol), tert-butyl N-(3-{2-[2-(2-aminoethoxy)ethoxy]ethoxy}phenyl)carbamate (74.2 mg, 0.218 mmol) and DIPEA (129 μL, 0.727 mmol) in DMF (4 mL) was reacted at 90° C. overnight. The reaction mixture was diluted with water and extracted with EtOAc. The organic layer was washed with brine, dried over MgSO₄, and concentrated. The residue was purified by column chromatography to give the product. The product was added to a solution of dichloromethane and 4N—HCl in dioxane was added thereto. The reaction mixture was stirred for 1 hour and dried in vacuo. (2 steps Yield: 36.2%, 35 mg)

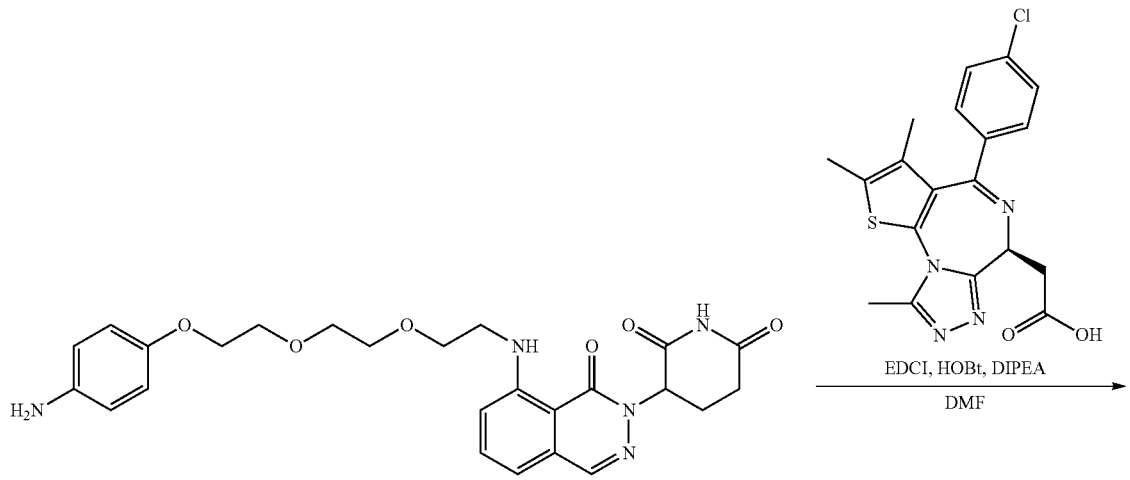

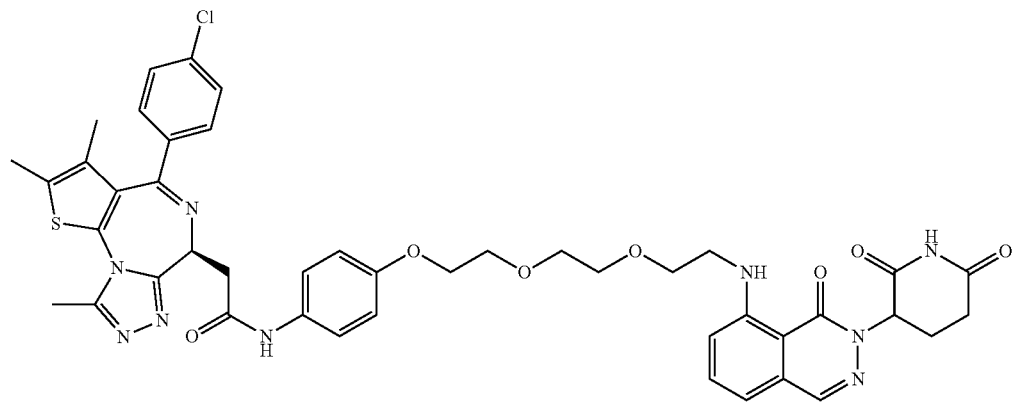

To a solution of JQ-1 carboxylic acid (35 mg, 0.087 mmol), 3-{8-[(2-{2-[2-(4-aminophenoxy)ethoxy]ethoxy}ethyl)amino]-1-oxo-1,2-dihydrophthalazin-2-yl}piperidine-2,6-dione hydrochloride (46.4 mg, 0.087 mmol), EDCl-HCl (18.4 mg, 0.096 mmol) and HOBt (16.3 mg, 0.096 mmol) in DMF was added DIPEA (54.9 μL, 0.306 mmol). The mixture was stirred at room temperature 4 hours. The reaction mixture was diluted with water and extracted with ethyl acetate. The organic layer was washed with brine, dried over Na$_2$SO$_4$, and concentrated. The desired product was separated by column chromatography.

MS (ESI, m/z): [M+1]$^+$=879.3

[NMR] $^1$H NMR (400 MHz, DMSO-d$_6$) d ppm 11.03 (s, 1H), 10.18 (s, 1H), 8.83 (t, J=5.01 Hz, 1H), 8.22 (s, 1H), 7.77 (d, J=8.31 Hz, 2H), 7.60-7.67 (m, 1H), 7.40-7.56 (m, 4H), 7.35-7.42 (m, 2H), 6.80-6.91 (m, 4H), 4.59 (t, J=7.09 Hz, 1H), 4.06-4.14 (m, 1H), 3.96-4.04 (m, 2H), 3.61-3.73 (m, 2H), 3.51-3.60 (m, 6H), 3.38-3.50 (m, 5H), 2.56-2.65 (m, 4H), 2.42 (s, 3H), 1.63 (s, 3H)

Example 25

Synthesis of 2-((S)-4-(4-chlorophenyl)-2,3,9-trimethyl-6H-thieno[3,2-f][1,2,4]triazolo[4,3-a][1,4]diazepin-6-yl)-N-(4-(2-(2-(2-((2-(2,6-dioxopiperidin-3-yl)-1-oxo-1,2-dihydrophthalazin-6-yl)amino)ethoxy)ethoxy)ethoxy)phenyl)acetamide

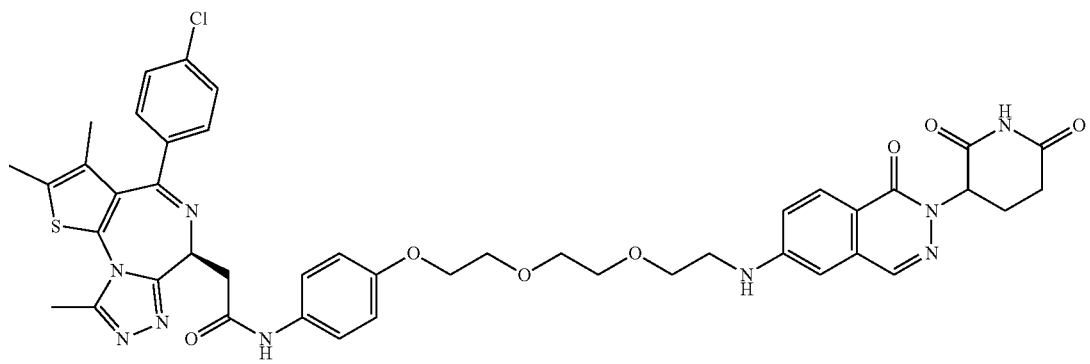 [SMILES: Cc1sc2c(c1C)C(c1ccc(Cl)cc1)=N[C@@H](CC(=O)Nc1ccc(OCCOCCOCCNc3ccc4c(=O)n(C5CCC(=O)NC5=O)ncc4c3)cc1)c1nnc(C)n1-2]

The titled compound is synthesized through following procedure which is similar to that of Example 21.

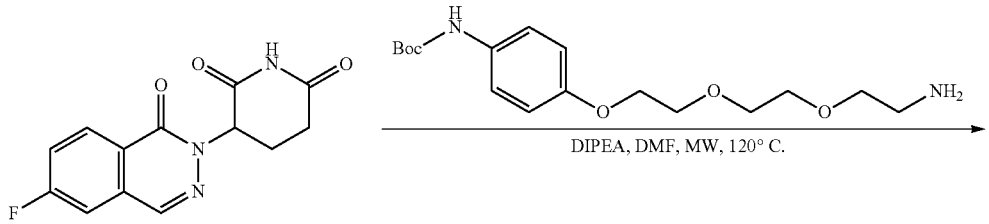

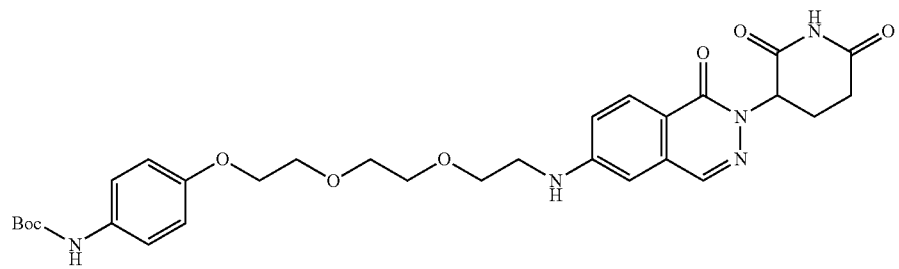

A solution of 3-(6-fluoro-1-oxophthalazin-2(1H)-yl)piperidine-2,6-dione (50.0 mg, 0.182 mmol), tert-butyl (4-(2-(2-(2-aminoethoxy)ethoxy)ethoxy)phenyl)carbamate (68.0 mg, 0.200 mmol) and DIPEA (323 μL, 1.82 mmol) in DMF (2 mL) was irritated on microwave at 120° C. for 5 hour. The reaction mixture was diluted with water and extracted with EtOAc. The organic layer was washed with brine, dried over MgSO$_4$, and concentrated. The residue was purified by column chromatography to give the product (Yield: 20.0 mg, 18.5%). MS (ESI, m/z): [M+$^1$]+=[596.8]

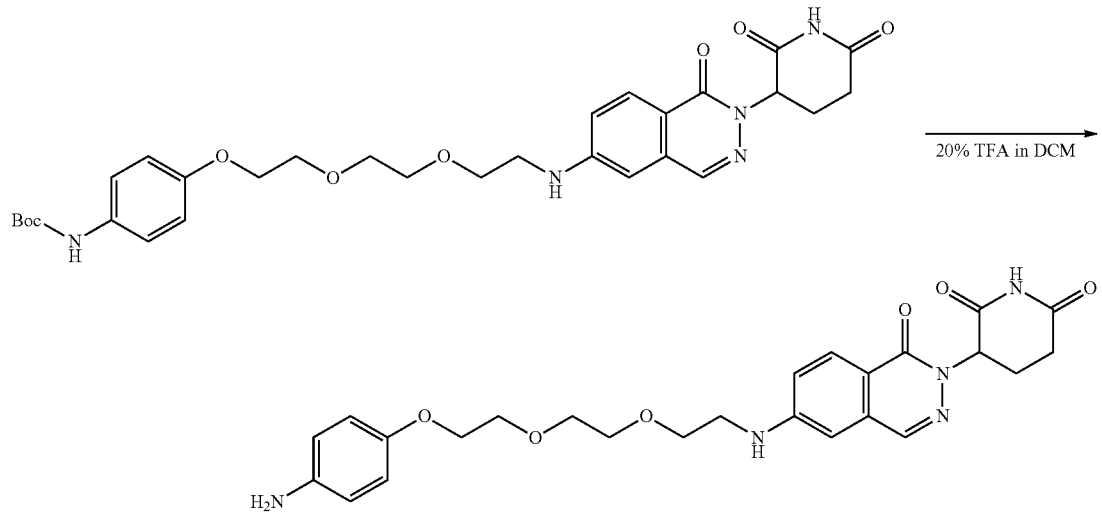

A solution of tert-butyl (4-(2-(2-(2-((2-(2,6-dioxopiperidin-3-yl)-1-oxo-1,2-dihydrophthalazin-6-yl)amino)ethoxy)ethoxy)ethoxy)phenyl)carbamate (15.0 mg, 0.025 mmol) in 20% TFA in DCM (1 mL) was stirred at room temperature. The reaction mixture was concentrated in vacuo and used for the next step without further purification. (yield: 10.0 mg, 80.1%). MS (ESI, m/z): [M+$^1$]+=[496.8]

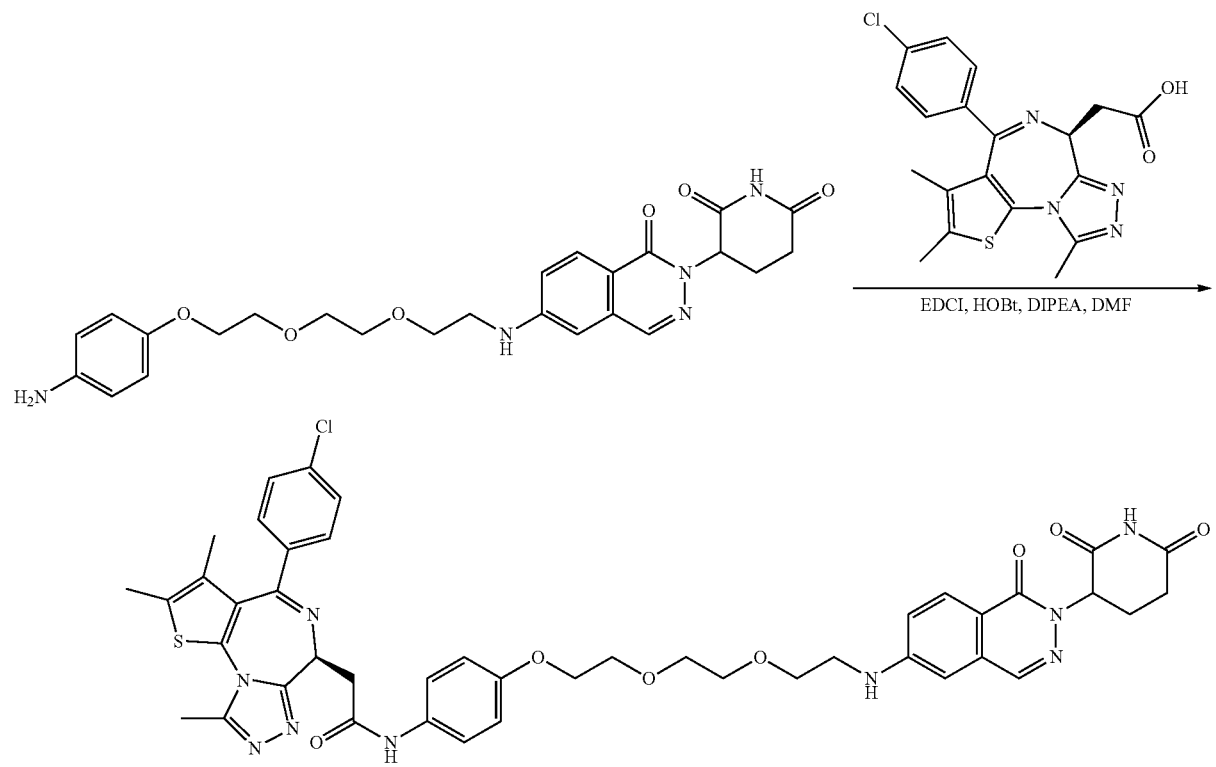

A solution of JQ-1 carboxylic acid (7.02 mg, 0.017 mmol), EDCl (3.36 mg, 0.018 mmol), HOBt (2.97 mg, 0.018 mmol) and DIPEA (0.01 ml, 0.056 mmol) in DMF (1 mL) was stirred at room temperature for 0.5 hour. 3-(6-((2-(2-(2-(4-aminophenoxy)ethoxy)ethoxy)ethyl)amino)-1-oxophthalazin-2(1H)-yl)piperidine-2,6-dione (7.89 mg, 0.016 mmol) was added. The mixture was stirred at room temperature overnight. The reaction mixture was diluted with water and extracted with ethyl acetate. The organic layer was washed with brine, dried over $Na_2SO_4$, and concentrated. The mixture was separated by column chromatography. (yield: 7.0 mg, 50.1%).

MS (ESI, m/z): [M+$^1$]+=879.4

[NMR] 1H NMR (400 MHz, DMSO-d6) δ ppm 10.99 (s, 1H) 10.18 (s, 1H) 8.17 (s, 1H) 7.91 (d, J=8.80 Hz, 1H) 7.39-7.56 (m, 6H) 7.12 (dd, J=8.86, 2.26 Hz, 1H) 6.94 (t, J=5.44 Hz, 1H) 6.88 (d, J=8.93 Hz, 2H) 6.82 (d, J=2.20 Hz, 1H) 5.68-5.76 (m, 1H) 4.59 (t, J=7.09 Hz, 1H) 3.98-4.07 (m, 3H) 3.69-3.76 (m, 2H) 3.57-3.66 (m, 7H) 3.46 (d, J=7.21 Hz, 2H) 2.84-2.95 (m, 1H) 2.42 (s, 2H) 1.96 (d, J=14.31 Hz, 3H) 1.63 (s, 3H) 1.21-1.27 (m, 3H)

Example 26

2-((S)-4-(4-chlorophenyl)-2,3,9-trimethyl-6H-thieno[3,2-f][1,2,4]triazolo[4,3-a][1,4]diazepin-6-yl)-N-(4-(2-(2-(2-((3-(2,6-dioxopiperidin-3-yl)-4-oxo-3,4-dihydrophthalazin-6-yl)amino)ethoxy)ethoxy)ethoxy)phenyl)acetamide

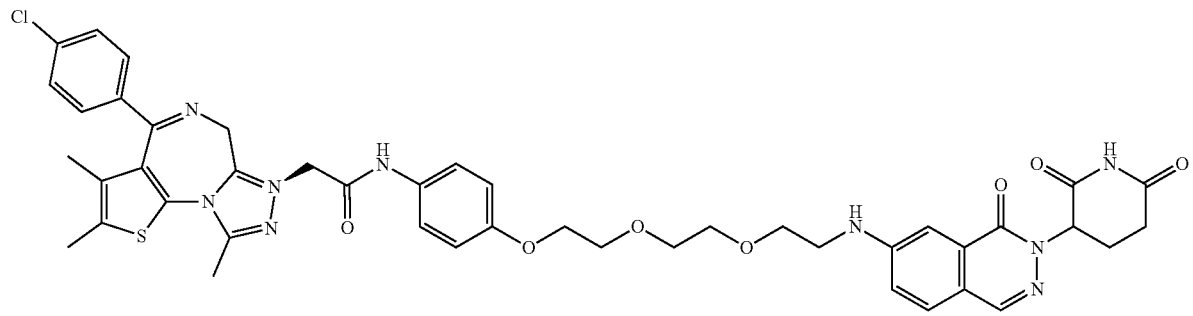

The titled compound is synthesized through following procedure which is similar to that of Example 21.

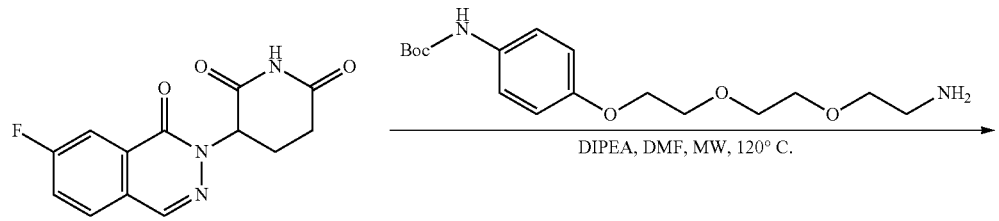

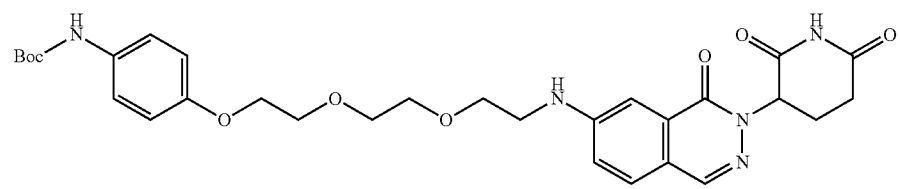

A solution of 3-(7-fluoro-1-oxophthalazin-2(1H)-yl)piperidine-2,6-dione (50.0 mg, 0.182 mmol), tert-butyl (4-(2-(2-(2-aminoethoxy)ethoxy)ethoxy)phenyl)carbamate (68.0 mg, 0.200 mmol) and DIPEA (323 μL, 1.82 mmol) in DMF (2 mL) was irritated on microwave at 120° C. for 5 hours. The reaction mixture was diluted with water and extracted with EtOAc. The organic layer was washed with brine, dried over MgSO$_4$, and concentrated. The residue was purified by column chromatography to give the product. (yield: 25.0 mg, 23.1%). MS (ESI, m/z): [M+$^1$]+=[596.8]

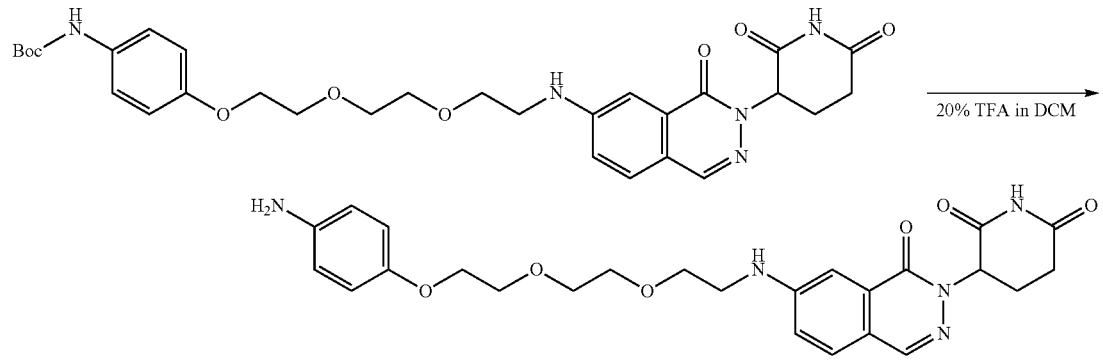

A solution was tert-butyl (4-(2-(2-(2-((3-(2,6-dioxopiperidin-3-yl)-4-oxo-3,4-dihydrophthalazin-6-yl)amino)ethoxy)ethoxy)ethoxy)phenyl)carbamate (15.0 mg, 0.025 mmol) in 20% TFA in DCM (1 mL) was stirred at room temperature. The reaction mixture was concentrated in vacuo and used for the next step without further purification. (yield: 18.0 mg, 86.5%). MS (ESI, m/z): [M+$^1$]+=[496.8]

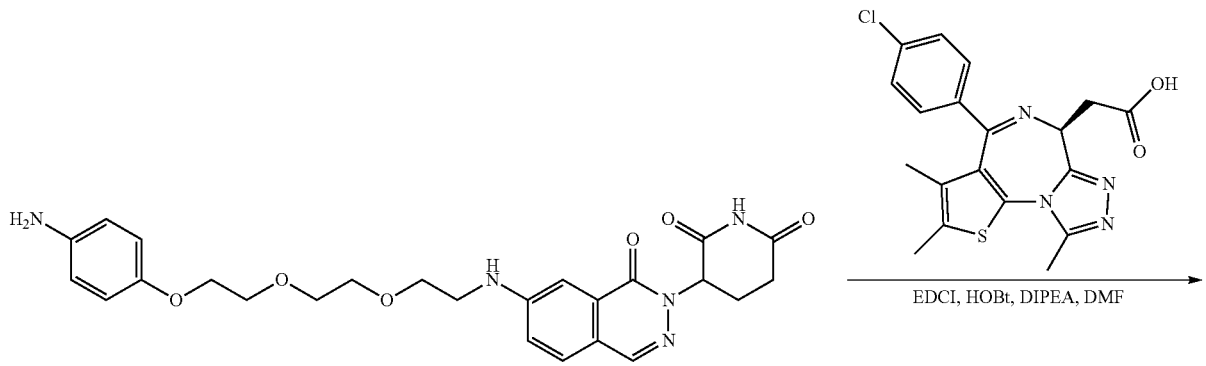

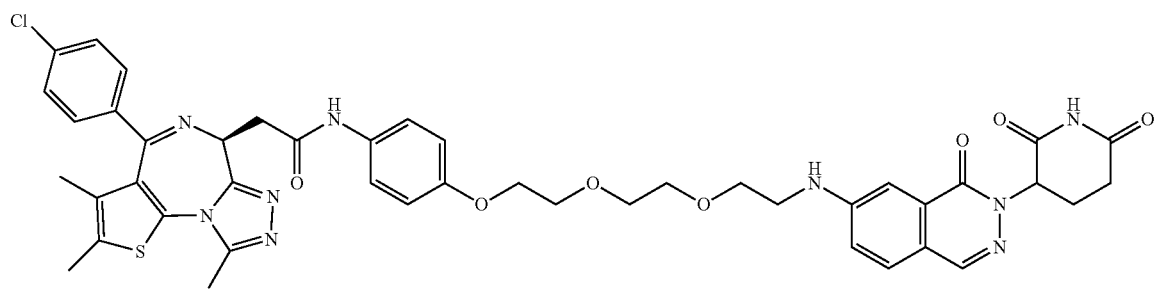

A solution of JQ-1 carboxylic acid (16.0 mg, 0.040 mmol), EDCl (7.66 mg, 0.040 mmol), HOBt (6.78 mg, 0.040 mmol) and DIPEA (33 μl, 0.18 mmol) in DMF (1 mL) was stirred at room temperature for 0.5 hour. 3-(7-((2-(2-(2-(4-aminophenoxy)ethoxy)ethoxy)ethyl)amino)-1-oxophthalazin-2(1H)-yl)piperidine-2,6-dione (18.0 mg, 0.036 mmol) was added. The mixture was stirred at room temperature overnight. The reaction mixture was diluted with water and extracted with ethyl acetate. The organic layer was washed with brine, dried over $Na_2SO_4$, and concentrated. The mixture was separated by column chromatography.

(yield: 8.0 mg, 25.1%)

MS (ESI, m/z): [M+$^1$]+=879.4

[NMR] 1H NMR (400 MHz, DMSO-d6) ppm 11.00 (s, 1H) 10.18 (s, 1H) 8.14 (s, 1H) 7.62 (d, J=9.29 Hz, 1H) 7.39-7.56 (m, 6H) 7.18-7.23 (m, 2H) 6.84-6.97 (m, 2H) 5.70-5.78 (m, 1H) 4.55-4.62 (m, 1H) 3.98-4.08 (m, 3H) 3.69-3.76 (m, 2H) 3.41-3.66 (m, 9H) 2.55-2.64 (m, 2H) 2.42 (s, 2H) 1.89-2.02 (m, 3H) 1.65 (br. s., 3H) 1.19-1.28 (m, 3H)

Example 27

2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[4-(2-{2-[2-(2-{[3-(2,6-dioxopiperidin-3-yl)-4-oxo-3,4-dihydrophthalazin-5-yl]amino}ethoxy)ethoxy]ethoxy}ethoxy)phenyl]acetamide

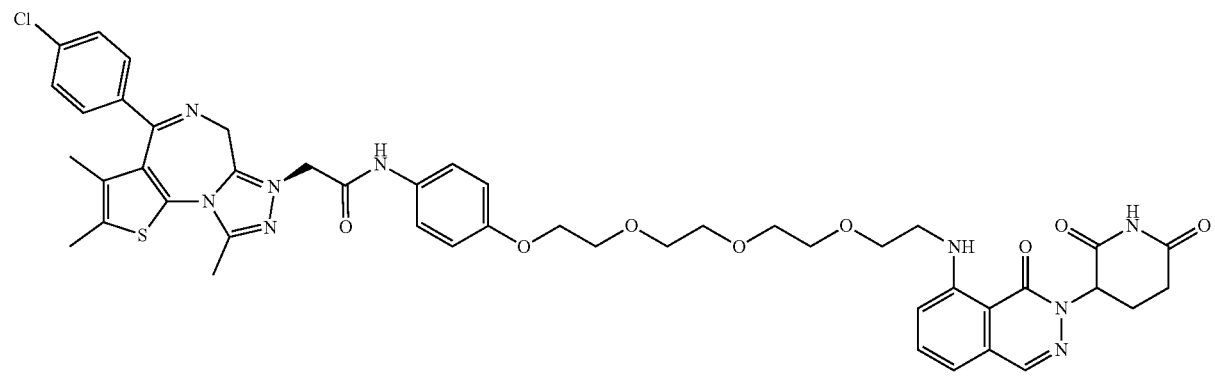

The titled compound is synthesized through following procedure which is similar to that of Example 21.

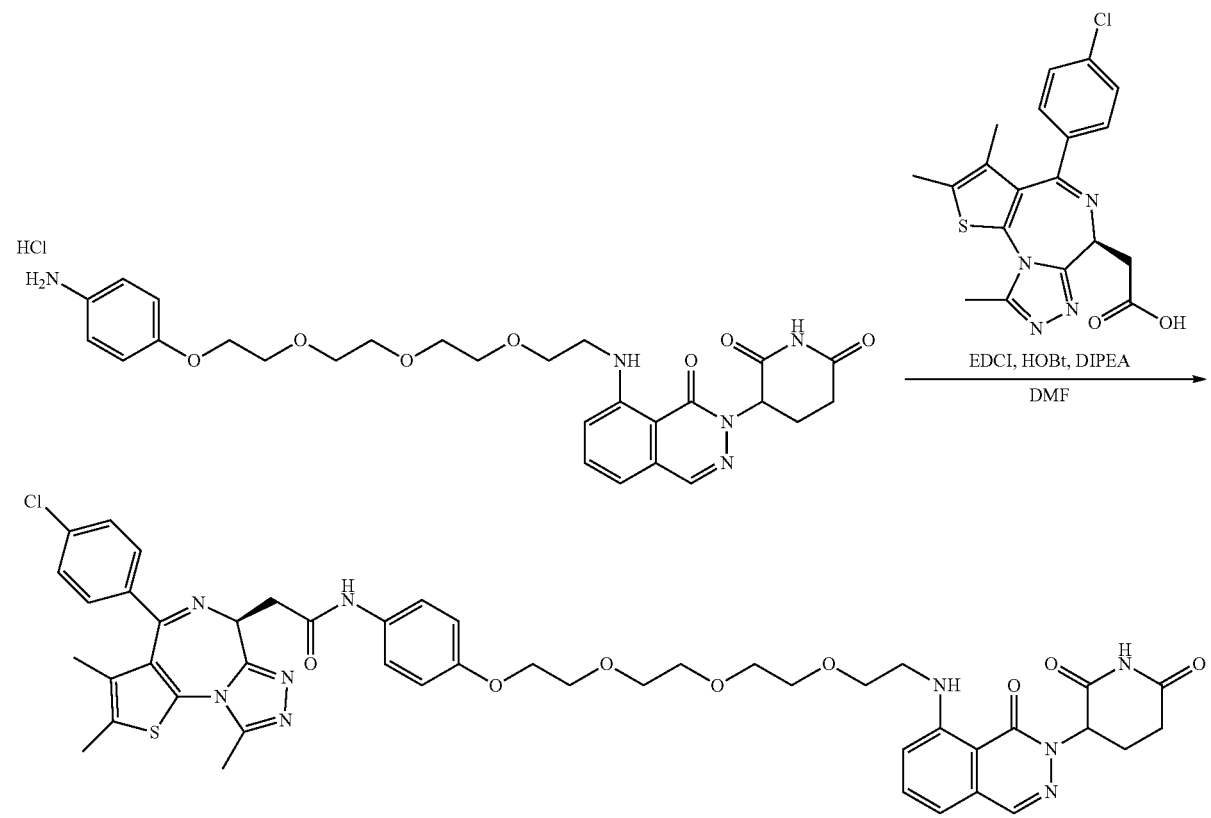

To a solution of 2-[(9S)-7-(4-chlorophenyl)-4,5,13-trimethyl-3-thia-1,8,11,12-tetraazatricyclo[8.3.0.0²,⁶]trideca-2(6),4,7,10,12-pentaen-9-yl]acetic acid (20 mg, 0.050 mmol), 3-{8-[12-(4-aminophenoxy)-4,7,10-trioxa-1-azadodecan-1-yl]-1-oxo-1,2-dihydrophthalazin-2-yl}piperidine-2,6-dione hydrochloride (28.7 mg, 0.050 mmol), EDCl-HCl (10.5 mg, 0.055 mmol) and HOBt (9.31 mg, 0.055 mmol) in DMF was added DIPEA (31.3 µL, 0.175 mmol). The mixture was stirred at room temperature for 4 hours. The reaction mixture was diluted with water and extracted with ethyl acetate. The organic layer was washed with brine, dried over Na$_2$SO$_4$, and concentrated. The desired product was separated by column chromatography.

(yield: 8.7%, 4 mg)

MS (ESI, m/z): [M+$^1$]+=923.5

[NMR] 1H NMR (400 MHz, DMSO-d6) δ ppm 11.03 (s, 1H), 10.18 (s, 1H), 8.83 (t, J=5.01 Hz, 1H), 8.22 (s, 1H), 7.78 (d, J=8.31 Hz, 2H), 7.60-7.67 (m, 1H), 7.44-7.56 (m, 4H), 7.39-7.44 (m, 2H), 6.83-6.94 (m, 4H), 4.59 (t, J=7.09 Hz, 1H), 4.06-4.14 (m, 1H), 3.98-4.06 (m, 2H), 3.63-3.75 (m, 4H), 3.53-3.62 (m, 8H), 3.40-3.53 (m, 5H), 2.56-2.65 (m, 4H), 2.42 (s, 3H), 1.63 (s, 3H)

Example 28

2-((S)-4-(4-chlorophenyl)-2,3,9-trimethyl-6H-thieno[3,2-f][1,2,4]triazolo[4,3-a][1,4]diazepin-6-yl)-N-(4-(2-(2-(2-(2-((2-(2,6-dioxopiperidin-3-yl)-1-oxo-1,2-dihydrophthalazin-6-yl)amino)ethoxy)ethoxy)ethoxy)ethoxy)phenyl)acetamide

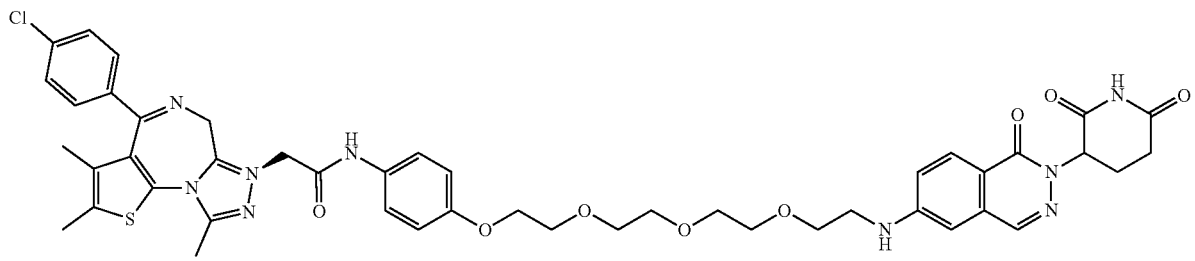

The titled compound is synthesized through following procedure which is similar to that of Example 21:

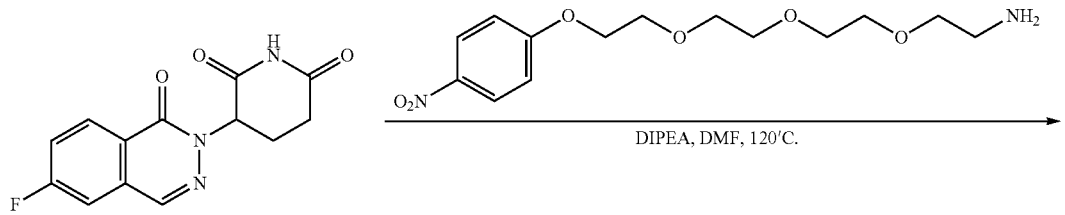

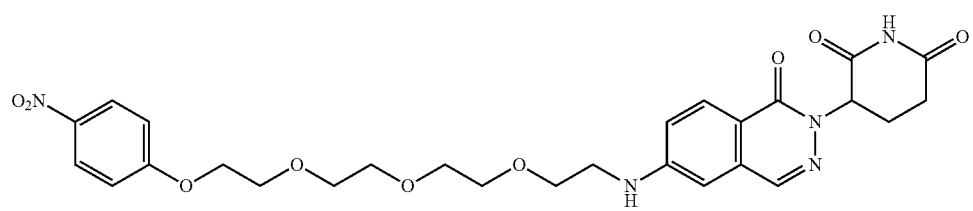

3-(6-fluoro-1-oxo-1,2-dihydrophthalazin-2-yl)piperidine-2,6-dione (1.05 g, 3.82 mmol) and 2-(2-(2-(2-(4-nitrophenoxy)ethoxy)ethoxy)ethoxy)ethan-1-amine (1.0 g, 3.18 mmol) were dissolved in NMP (4 ml). DIPEA (4.53 ml, 25.5 mmol) was added in reaction mixture, which was reacted at 120° C. for overnight. The reaction mixture was diluted with water and extracted with EtOAc. The organic layer was washed with brine, dried over MgSO$_4$, and concentrated. The residue was purified by column chromatography to give the product. (Yield: 70.0 mg, 67.6%). MS (ESI, m/z): [M+1]+=[570.6]

TA solution of JQ-1 carboxylic acid (49.0 mg, 0.12 mmol), EDCI (38.4 mg, 0.20 mmol), HOBt (33.9 mg, 0.20 mmol) and DIPEA (0.10 ml, 0.556 mmol) in DMF (1 mL) was stirred at room temperature for 0.5 hour. 3-(6-((2-(2-(2-(2-(4-aminophenoxy)ethoxy)ethoxy)ethoxy)ethyl)amino)-1-oxophthalazin-2(1H)-yl)piperidine-2,6-dione (60.0 mg, 0.11 mmol) was added. The mixture was stirred at room temperature overnight. The reaction mixture was diluted with water and extracted with ethyl acetate. The

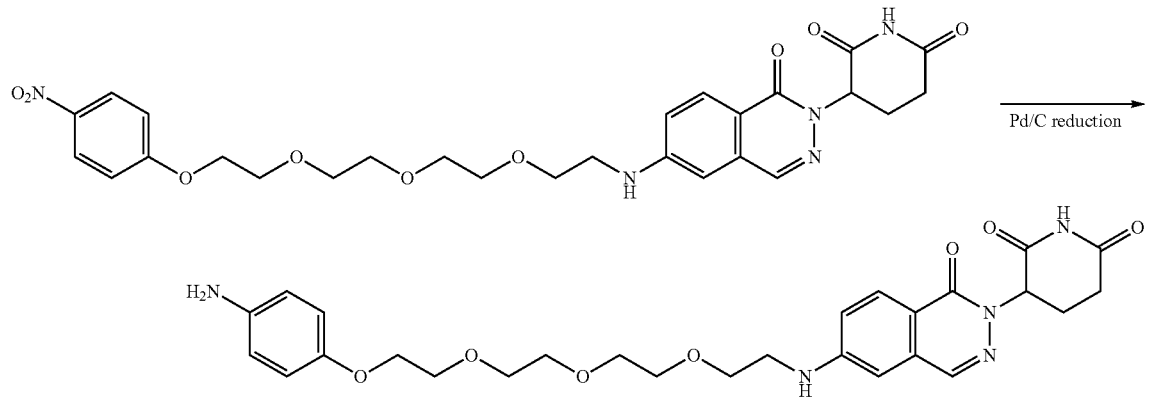

3-(6-((2-(2-(2-(2-(4-nitrophenoxy)ethoxy)ethoxy)ethoxy)ethyl)amino)-1-oxophthalazin-2(1H)-yl)piperidine-2,6-dione (70.0 mg, 0.123 mmol) was dissolved in MeOH (3 ml), and 20 mg of 10% Pd/C (wet) was added thereto. The solution was stirred under H$_2$ in a balloon for 1 hour. The Pd/C was filtered and the mixture was concentrated under reduced pressure to afford the titled compound in 99% purity. (Yield: 60.0 mg, 90.4%).
MS (ESI, m/z): [M+1]$^+$=540.6 organic layer was washed with brine, dried over Na$_2$SO$_4$, and concentrated. The mixture was separated by column chromatography.
(yield: 25.0 mg, 24.4%)
MS (ESI, m/z): [M+1]+=923.5
[NMR] $^1$H NMR (400 MHz, DMSO-d6) δ 10.99 (s, 1H), 10.19 (s, 1H), 8.15-8.19 (m, 1H), 7.91 (d, J=8.80 Hz, 1H), 7.40-7.56 (m, 6H), 7.12 (dd, J=8.86, 2.02 Hz, 1H), 6.86-6.97 (m, 3H), 6.81 (d, J=1.96 Hz, 1H), 5.73 (br dd, J=11.98, 4.89

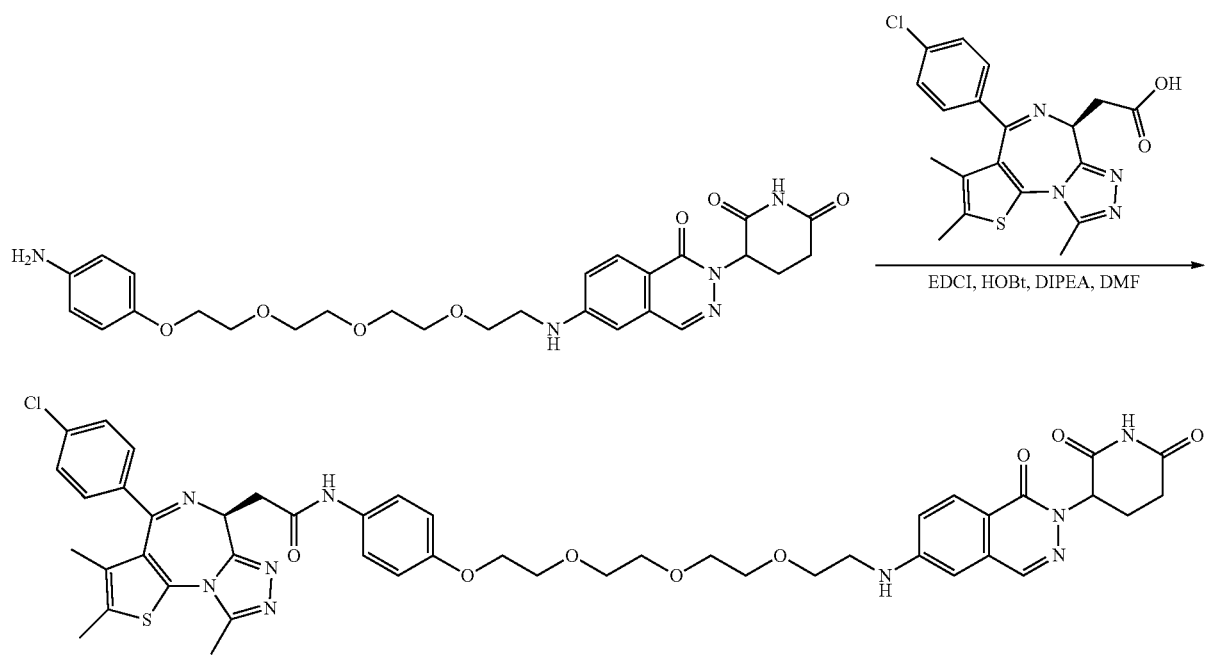

Hz, 1H), 4.59 (t, J=7.03 HZ, 1H), 3.99-4.08 (m, 2H), 3.67-3.76 (m, 2H), 3.52-3.64 (m, 10H), 3.38-3.51 (m, 3H), 3.16 (br, 1H), 2.69-2.95 (m, 1H), 2.55-2.65 (m, 5H), 2.38-2.47 (m, 4H), 1.98-2.14 (m, 1H), 1.63 (s, 3H).

Example 29

2-((S)-4-(4-chlorophenyl)-2,3,9-trimethyl-6H-thieno[3,2-f][1,2,4]triazolo[4,3-a][1,4]diazepin-6-yl)-N-(4-(2-(2-(2-(2-((3-(2,6-dioxopiperidin-3-yl)-4-oxo-3,4-dihydrophthalazin-6-yl)amino)ethoxy)ethoxy)ethoxy)ethoxy)phenyl)acetamide

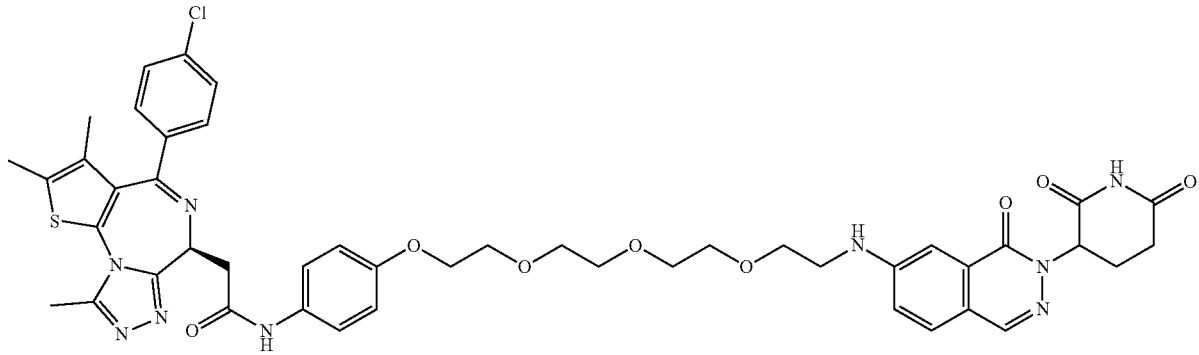 [SMILES: Cc1sc2c(c1C)C(c1ccc(Cl)cc1)=N[C@@H](CC(=O)Nc1ccc(OCCOCCOCCOCCNc3ccc4cnn(C5CCC(=O)NC5=O)c(=O)c4c3)cc1)c1nnc(C)n1-2]

The titled compound is synthesized through following procedure which is similar to that of Example 21.

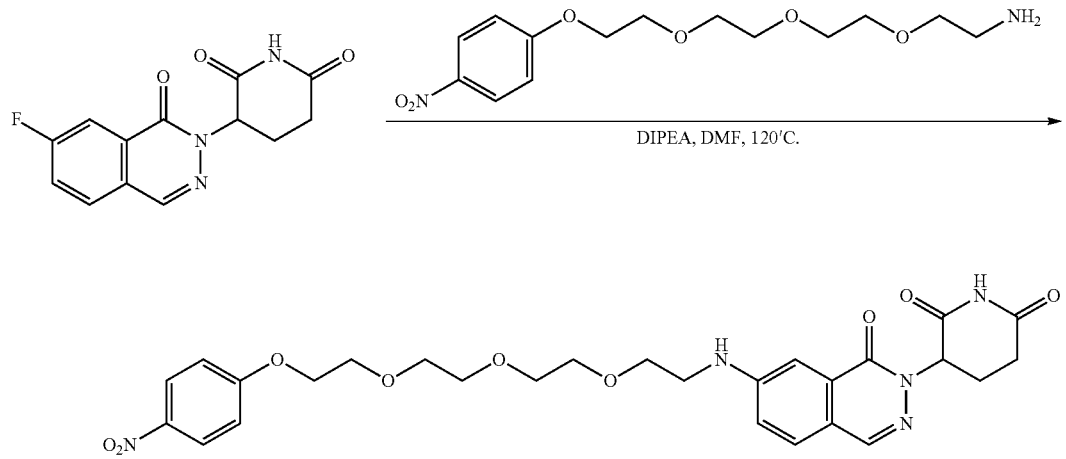

3-(7-fluoro-1-oxophthalazin-2(1H)-yl)piperidine-2,6-dione (50 mg, 0.182 mmol) and 2-(2-(2-(2-(4-nitrophenoxy)ethoxy)ethoxy)ethoxy)ethan-1-amine (68.5 mg, 0.218 mmol) were dissolved in NMP (4 ml), and DIPEA (0.323 mL, 1.82 mmol) was added in reaction mixture, which was reacted at 120° C. for overnight. The reaction mixture was diluted with water and extracted with EtOAc. The organic layer was washed with brine, dried over MgSO₄, and concentrated. The residue was purified by column chromatography to give the product (yield: 70.0 mg, 67.6%)

MS (ESI, m/z): [M+1]⁺=570.6

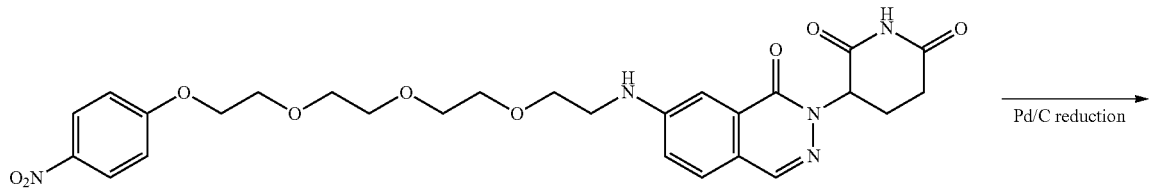

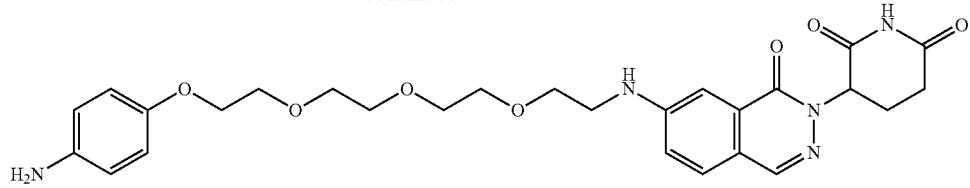

3-(7-((2-(2-(2-(2-(4-nitrophenoxy)ethoxy)ethoxy)ethoxy)ethyl)amino)-1-oxophthalazin-2(1H)-yl)piperidine-2,6-dione (70.0 mg, 0.123 mmol) was dissolved in MeOH (3 ml), and 20 mg of 10% Pd/C (wet) was added thereto. The solution was stirred under $H_2$ in a balloon for 1 hour. The Pd/C was filtered and the mixture was concentrated under reduced pressure to afford the titled compound in 99% purity.

(yield: 60.0 mg, 90.4%) MS (ESI, m/z): [M+$^1$]+=540.6

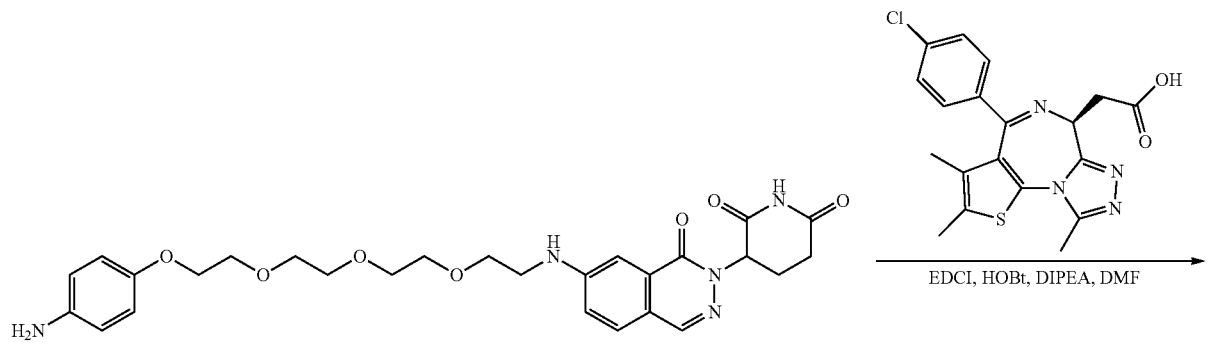

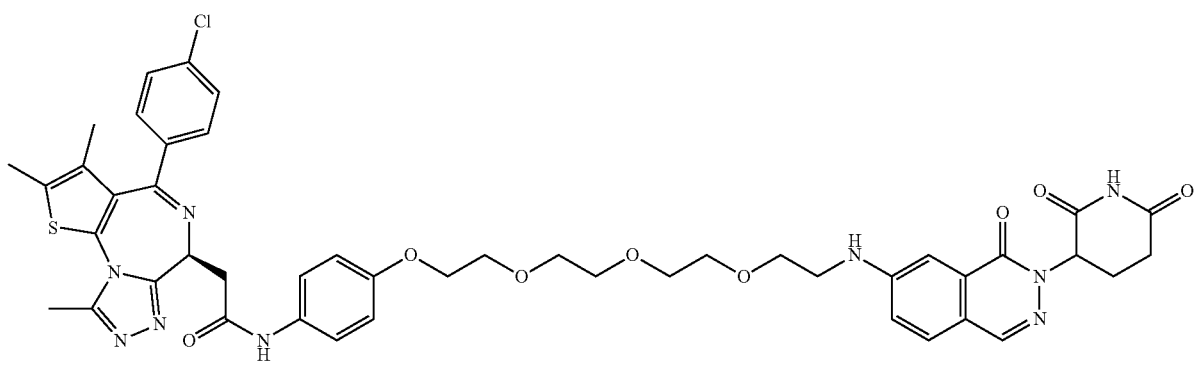

A solution of JQ-1 carboxylic acid (49.0 mg, 0.12 mmol), EDCl (38.4 mg, 0.20 mmol), HOBt (33.9 mg, 0.20 mmol) and DIPEA (0.10 ml, 0.556 mmol) in DMF (1 mL) was stirred at room temperature for 0.5 hour. 3-(7-((2-(2-(2-(2-(4-aminophenoxy)ethoxy)ethoxy)ethoxy)ethyl)amino)-1-oxophthalazin-2(1H)-yl)piperidine-2,6-dione (60.0 mg, 0.11 mmol) was added. The mixture was stirred at room temperature overnight. The reaction mixture was diluted with water and extracted with ethyl acetate. The organic layer was washed with brine, dried over $Na_2SO_4$, and concentrated. The mixture was separated by column chromatography.

(yield: 25.0 mg, 20.4%)

MS (ESI, m/z): [M+1]$^+$=923.5

[NMR] $^1$H NMR (400 MHz, DMSO-d) S 11.00 (s, 1H), 10.19 (s, 1H), 8.14 (s, 1H), 7.63 (d, J=8.44 Hz, 1H), 7.38-7.56 (m, 6H), 7.17-7.24 (m, 2H), 6.86-7.11 (m, 3H), 5.75 (br dd, J=12.04, 5.07 Hz, 1H), 4.47-4.68 (m, 1H), 3.98-4.24 (m, 2H), 3.66-3.78 (m, 2H), 3.43-3.64 (m, 11H), 3.07-3.29 (m, 2H), 2.84-3.00 (m, 1H), 2.53-2.64 (m, 6H) 2.42 (s, 3H), 1.89-2.15 (m, 1H), 1.63 (s, 3H).

Example 30

2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(3-{2-[2-(2-{[2-(2,6-dioxopiperidin-3-yl)-1-oxo-1,2-dihydrophthalazin-5-yl]amino}ethoxy)ethoxy]ethoxy}phenyl)acetamide

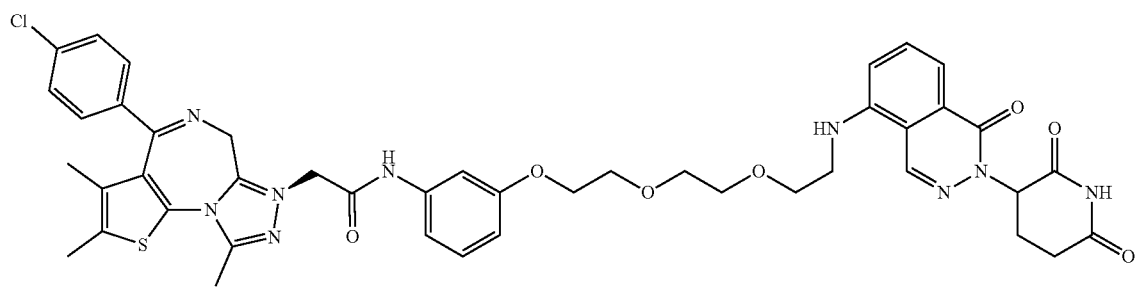

The titled compound is synthesized through following procedure which is similar to that of Example 20.

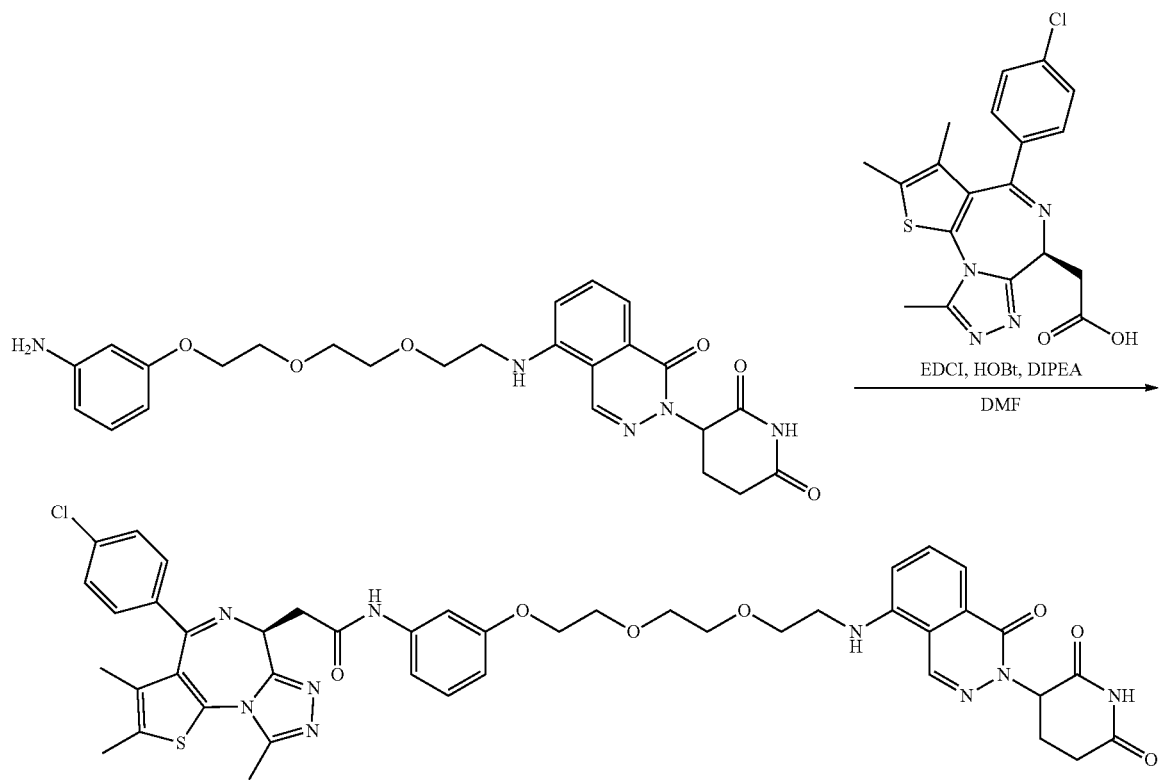

To a solution of 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetic acid (50 mg, 0.125 mmol), 3-{8-[(2-{2-[2-(3-aminophenoxy)ethoxy]ethoxy}ethyl)amino]-1-oxo-1,2-dihydrophthalazin-2-yl}piperidine-2,6-dione hydrochloride (66.4 mg, 0.125 mmol), EDCl·HCl (26.3 mg, 0.137 mmol) and HOBt (23.3 mg, 0.137 mmol) in DMF was added DIPEA (78.4 µL, 0.437 mmol). The mixture was stirred at room temperature overnight. The reaction mixture was diluted with water and extracted with ethyl acetate. The organic layer was washed with brine, dried over Na$_2$SO$_4$, and concentrated. The desired product was separated by column chromatography.

(Yield: 7.8%, 8.61 mg)

MS (ESI, m/z): [M+1]$^+$=878.4

[NMR] 1H NMR (400 MHz, DMSO-d6) δ 11.03 (s, 1H), 10.30 (s, 1H), 8.65 (s, 1H), 7.52-7.61 (m, 1H), 7.45-7.52 (m, 2H), 7.31-7.45 (m, 4H), 7.09-7.24 (m, 2H), 7.02 (d, J=8.31 Hz, 1H), 6.83 (t, J=5.62 Hz, 1H), 6.62 (dd, J=8.07, 1.71 Hz, 1H), 5.75 (dd, J=12.10, 5.01 Hz, 1H), 4.60 (t, J=7.09 Hz, 1H), 3.95-4.08 (m, 2H), 3.69-3.76 (m, 2H), 3.55-3.69 (m,

6H), 3.50 (d, J=7.09 Hz, 2H), 3.41 (q, J=5.62 Hz, 2H), 2.83-2.98 (m, 1H), 2.41 (s, 3H), 1.99-2.14 (m, 1H), 1.62 (s, 3H)

Example 31

2-((S)-4-(4-chlorophenyl)-2,3,9-trimethyl-6H-thieno[3,2-f][1,2,4]triazolo[4,3-a][1,4]diazepin-6-yl)-N-((1-(2-(2-(2-((3-(2,6-dioxopiperidin-3-yl)-4-oxo-3,4-dihydrophthalazin-5-yl)amino)ethoxy)ethoxy)ethyl)-1H-1,2,3-triazol-4-yl)methyl)acetamide

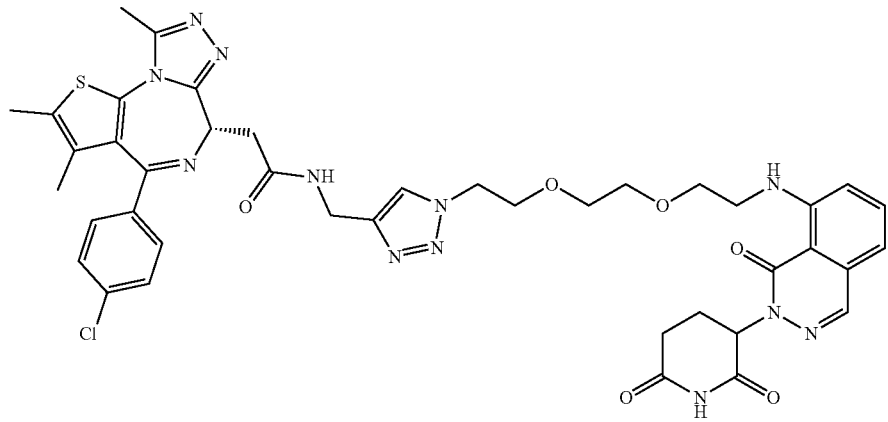 [SMILES: Cc1sc2c(c1C)C(c1ccc(Cl)cc1)=N[C@@H](CC(=O)NCc1cn(CCOCCOCCNc3cccc4cnn(C5CCC(=O)NC5=O)c(=O)c34)nn1)c1nnc(C)n1-2]

Step 1) Synthesis of (S)-2-(4-(4-chlorophenyl)-2,3,9-trimethyl-6H-thieno[3,2-f][1,2,4]triazolo[4,3-a][1,4]diazepin-6-yl)-N-(prop-2-yn-1-yl)acetamide

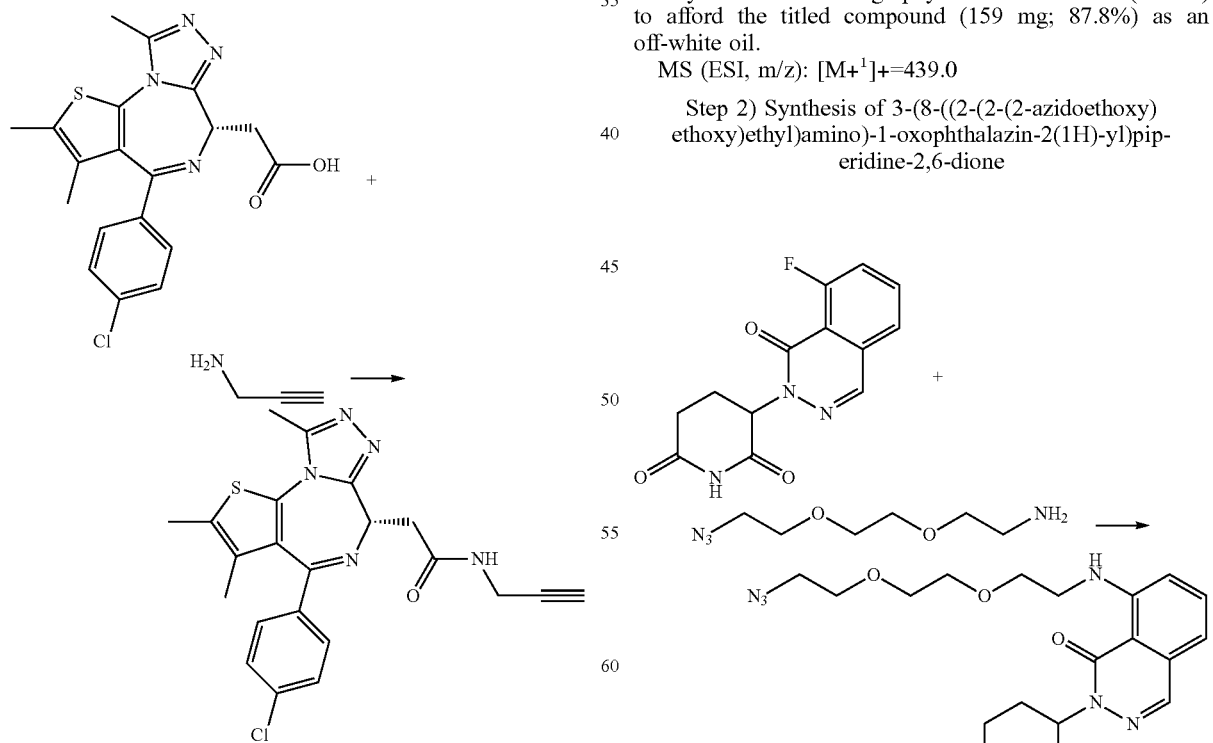

To a solution of JQ-1 carboxylic acid (160 mg; 0.4 mmol), prop-2-yn-1-amine (26.4 mg; 0.5 mmol) EDCl·HCl (84.2 mg; 0.44 mmol) and HOBt (74.4 mmol; 0.44 mmol) in DMF (2 ml) was added DIPEA (181 mg; 1.4 mmol). The mixture was stirred at room temperature overnight. The reaction mixture was diluted with water and extracted with ethyl acetate. The organic layer was washed with brine, dried over $Na_2SO_4$, and concentrated. The resulting residue was purified by column chromatography with DCM: MeOH (0-10%) to afford the titled compound (159 mg; 87.8%) as an off-white oil.

MS (ESI, m/z): $[M+^1]+$=439.0

Step 2) Synthesis of 3-(8-((2-(2-(2-azidoethoxy)ethoxy)ethyl)amino)-1-oxophthalazin-2(1H)-yl)piperidine-2,6-dione To a solution of 3-(8-fluoro-1-oxo-1,2-dihydrophthalazin-2-yl)piperidine-2,6-dione (100 mg; 0.36 mmol) and 1-(2-aminoethoxy)-2-(2-azidoethoxy)ethane (76 mg; 0.44 mmol) in NMP (3 mL) was added ethylbis(propan-2-yl)amine at room temperature. The reaction mixture was heated at 110° C. for 16 hours. After cooling, the reaction mixture was poured into water (10 mL) and extracted with ethyl acetate (20 mL×2). The combined ethyl acetate was dried over MgSO4 and concentrated under reduced pressure. The residue was purified by column chromatography with DCM/MeOH (0-10%) to afford the titled compound (89 mg, 57%).

MS (ESI, m/z): [M+$^1$]+=430.3

Step 3) 2-((S)-4-(4-chlorophenyl)-2,3,9-trimethyl-6H-thieno[3,2-f][1,2,4]triazolo[4,3-a][1,4]diazepin-6-yl)-N-((1-(2-(2-(2-((3-(2,6-dioxopiperidin-3-yl)-4-oxo-3,4-dihydrophthazin-5-yl)amino)ethoxy)ethoxy)ethyl)-1H-1,2,3-triazol-4-yl)methyl)acetamide

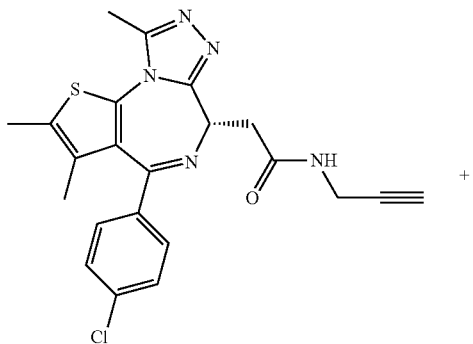 + 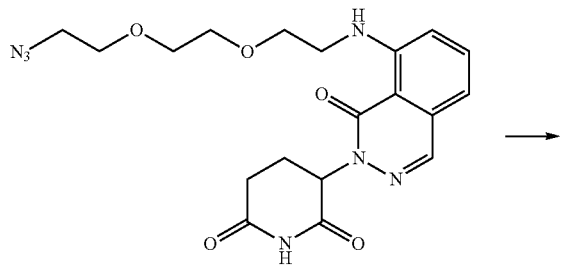 →

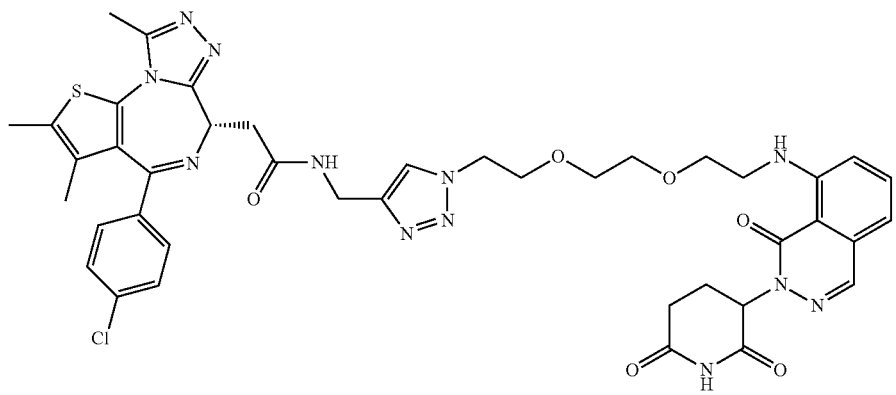

To a 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(prop-2-yn-1-yl)acetamide (20 mg; 0.045 mmol) and 3-(8-((2-(2-(2-azidoethoxy)ethoxy)ethyl)amino)-1-oxophthalazin-2(1H)-yl)piperidine-2,6-dione (18.7 mg, 0.045 mmol) in THF/H$_2$O (5 mL/5 mL) were added Sodium ascorbate (1.81 mg, 0.0091 mmol) and copper sulfate (1.46 mg, 0.0091 mmol) at 25° C. The reaction was done in 2 hours. The reaction mixture was poured into 50 mL of water, extracted with EA (50 mL×2), and dried over MgSO$_4$. The reaction mixture was loaded on silica and separated by column chromatography. (DCM/MeOH 0%→10%) to afford the titled compound as a white crystal (18.0 mg, 16.1%).

MS (ESI, m/z): [M+$^1$]+=867.3

Example 32

2-((S)-4-(4-chlorophenyl)-2,3,9-trimethyl-6H-thieno[3,2-f][1,2,4]triazolo[4,3-a][1,4]diazepin-6-yl)-N-((1-(2-(2-(2-(2-((3-(2,6-dioxopiperidin-3-yl)-4-oxo-3,4-dihydrophthalazin-5-yl)amino)ethoxy)ethoxy)ethoxy)ethyl)-1H-1,2,3-triazol-4-yl)methyl)acetamide

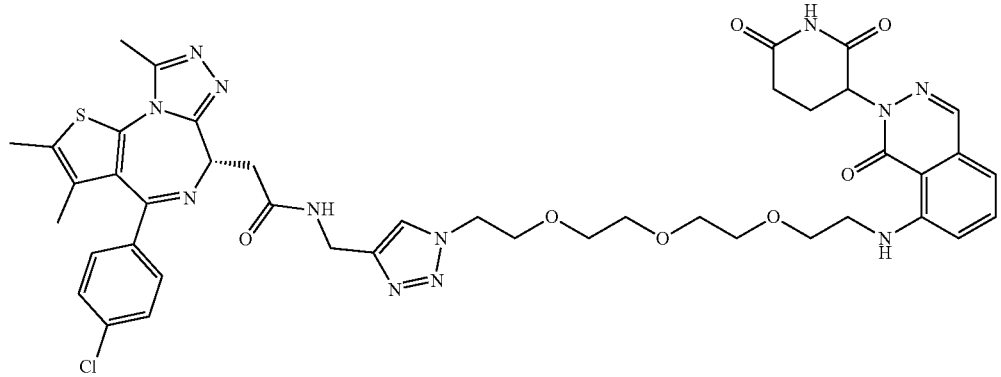 [SMILES: Cc1sc2c(c1C)C(c1ccc(Cl)cc1)=N[C@@H](CC(=O)NCc1cn(CCOCCOCCOCCNc3cccc4cnn(C5CCC(=O)NC5=O)c(=O)c34)nn1)c1nnc(C)n1-2]

The titled compound is synthesized through following procedure which is similar to that of Example 31.

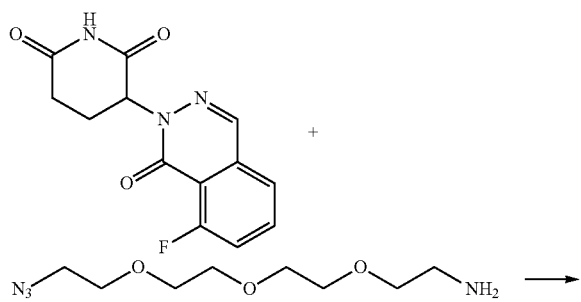

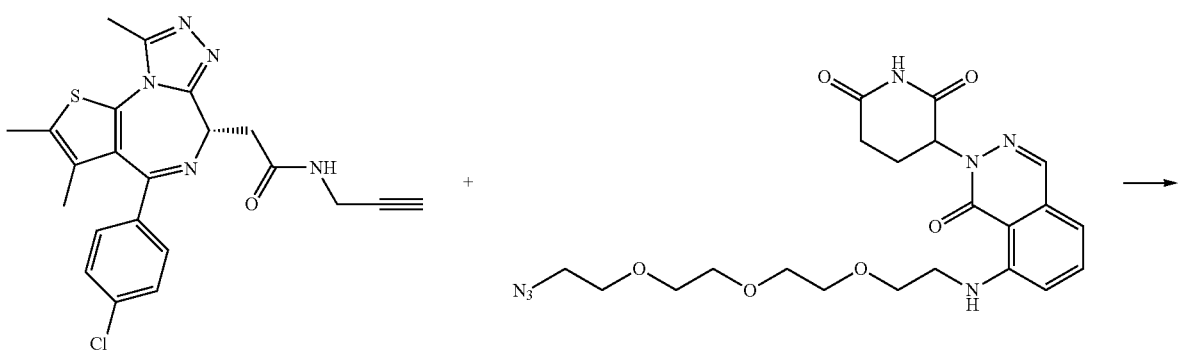

To a solution of 3-(8-fluoro-1-oxo-1,2-dihydrophthalazin-2-yl)piperidine-2,6-dione (100 mg, 0.36 mmol) and 2-(2-(2-(2-azidoethoxy)ethoxy)ethoxy)ethan-1-amine (96.3, 0.44 mmol) in NMP (3 mL) was added ethylbis(propan-2-yl)amine (141 mg, 1.1 mmol) at room temperature. The reaction mixture was heated at 110° C. for 16 hours. After cooling, the reaction mixture was poured into water (10 mL) and extracted with ethyl acetate (20 mL×2). The combined ethyl acetate was dried over MgSO$_4$ and concentrated under reduced pressure. The resulting residue was purified by column chromatography with DCM/MeOH (0-10%) to afford the titled compound (92 mg. 54%). MS (ESI, m/z): [M+$^1$]+=[474.5]

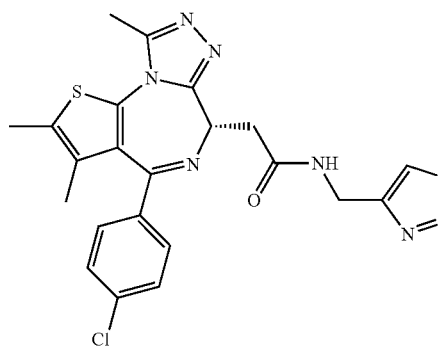
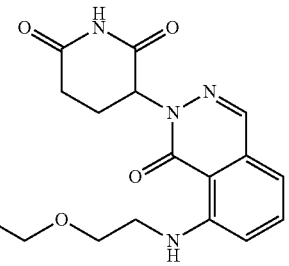

-continued

To a 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(prop-2-yn-1-yl)acetamide (20 mg, 0.045 mmol) and 3-[8-(12-azido-4,7,10-trioxa-1-azadodecan-1-yl)-1-oxo-1,2-dihydrophthalazin-2-yl]piperidine-2,6-dione (21.6 mg, 0.045 mmol) in THF/H$_2$O (5 mL/5 mL) were added Sodium ascorbate (1.81 mg, 0.0091 mmol) and copper sulfate (1.46 mg, 0.0091 mmol) at 25° C. The reaction was done in 2 hours. The reaction mixture was poured into 50 mL of water and extracted with EA (50 mL×2), and dried over MgSO$_4$. The reaction mixture was loaded on silica and separated by column chromatography to afford the titled compound as a white crystal (18.0 mg, 43.3%).

MS (ESI, m/z): [M+$^1$]+=912.5

Example 33

2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-[(1-{2-[2-(2-{[2-(2,6-di-oxopiperidin-3-yl)-1-oxo-1,2-dihydrophthalazin-5-yl]amino}ethoxy)ethoxy]ethyl}-1H-1,2,3-triazol-4-yl)methyl]acetamide

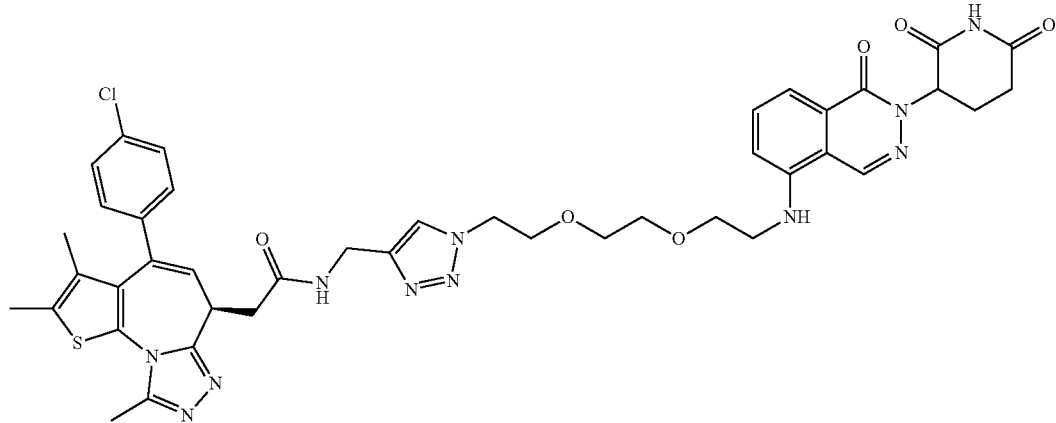 [SMILES: Cc1sc2c(c1C)C(c1ccc(Cl)cc1)=C[C@@H](CC(=O)NCc1cn(CCOCCOCCNc3cccc4c(=O)n(C5CCC(=O)NC5=O)ncc34)nn1)c1nnc(C)n1-2]

The titled compound is synthesized through following procedure which is similar to that of Example 31.

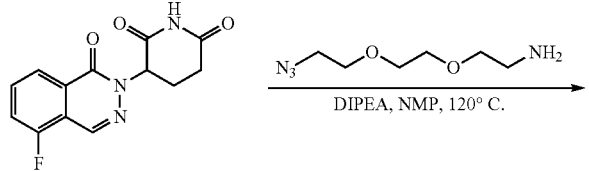

A solution of 3-(5-fluoro-1-oxo-1,2-dihydrophthalazin-2-yl)piperidine-2,6-dione (100 mg, 0.36 mmol), 1-(2-amino-ethoxy)-2-(2-azidoethoxy)ethane (82.3 mg, 0.47 mmol) and DIPEA (259 μL, 1.45 mmol) in NMP (4 mL) was reacted at 120° C. overnight. The reaction mixture was diluted with water and extracted with EtOAc. The organic layer was washed with brine, dried over MgSO$_4$, and concentrated. The residue was purified by column chromatography to give the product. (Yield: 12.8%, 20 mg)

MS (ESI, m/z): [M+$^1$]+=430.8

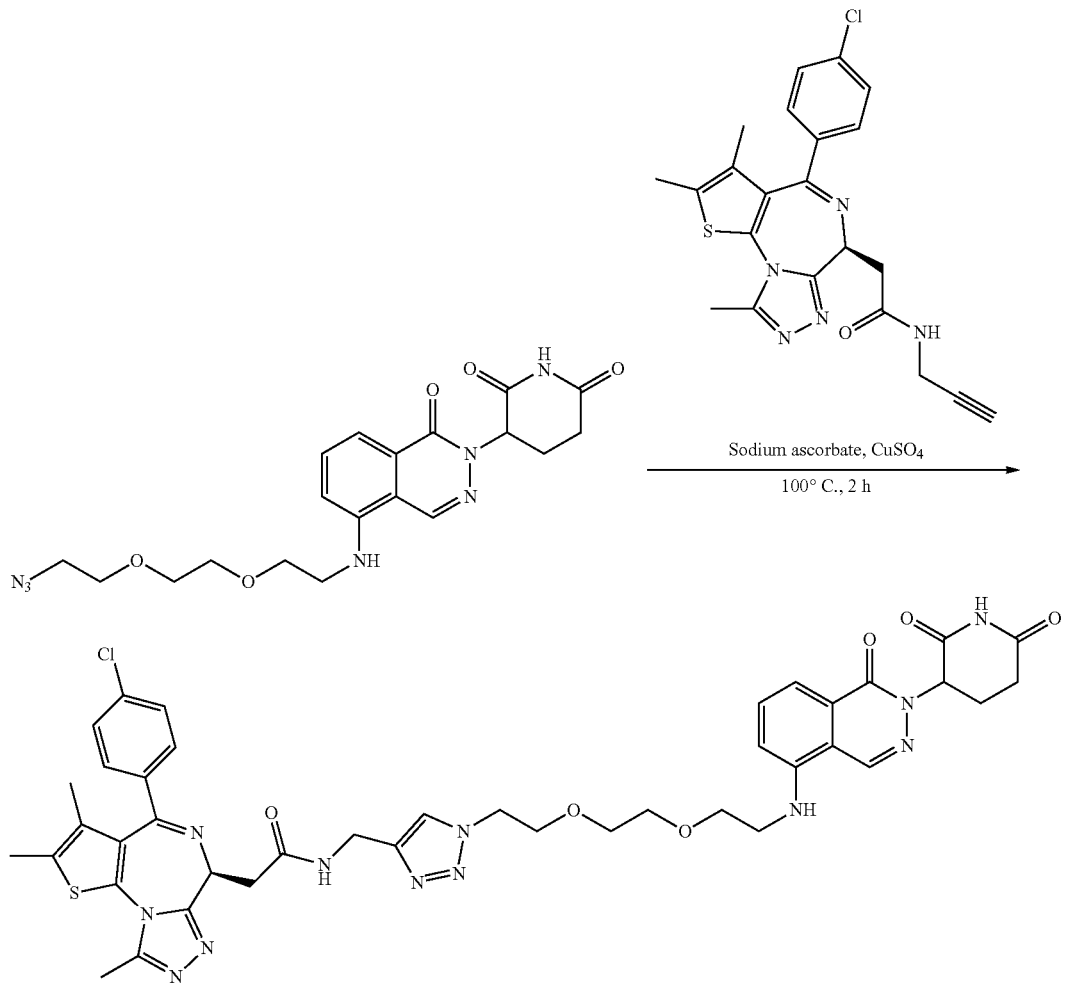

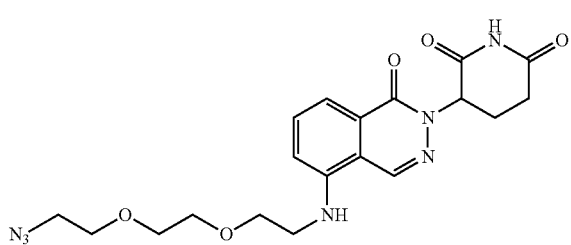

2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(prop-2-yn-1-yl)acetamide, and 3-[5-({2-[2-(2-azidoethoxy)ethoxy]ethyl}amino)-1-oxo-1,2-dihydrophthalazin-2-yl]piperidine-2,6-dione were added in THF: H$_2$O (1:1). The sodium ascorbate and copper sulfate were added to the mixture. The reaction mixture was heated to 100° C. for 2 hours. The reaction mixture was cooled to room temperature and extracted with EA, and dried over MgSO$_4$. The desired product was separated by column chromatography.

(Yield: 38.4%, 15.2 mg).

MS (ESI, m/z): [M+$^1$]+=870.4

[NMR] $^1$H NMR (400 MHz, DMSO-$d_6$) δ ppm 11.02 (s, 1H), 8.76 (t, J=5.87 Hz, 1H), 8.63 (s, 1H), 7.93 (s, 1H), 7.55 (t, J=7.95 Hz, 1H), 7.46 (d, J=8.31 Hz, 2H), 7.38 (d, J=8.07 Hz, 3H), 7.01 (d, J=8.07 Hz, 1H), 6.80 (t, J=5.50 Hz, 1H), 5.69-5.80 (m, 1H), 4.52 (t, J=6.97 Hz, 1H), 4.44-4.49 (m, 2H), 4.36 (d, J=5.38 Hz, 2H), 3.80 (t, J=5.26 Hz, 2H), 3.58 (t, J=5.75 Hz, 2H), 3.53 (s, 4H), 3.37 (q, J=5.79 Hz, 2H), 3.23-3.30 (m, 2H), 2.81-2.99 (m, 1H), 2.60-2.65 (m, 1H), 2.58 (s, 4H), 2.38 (s, 3H), 2.01-2.14 (m, 1H), 1.59 (s, 3H)

Example 34

2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-{[1-(2-{2-[2-(2-{[2-(2,6-dioxopiperidin-3-yl)-1-oxo-1,2-dihydrophthalazin-5-yl]amino}ethoxy)ethoxy]ethoxy}ethyl)-1H-1,2,3-triazol-4-yl]methyl}acetamide

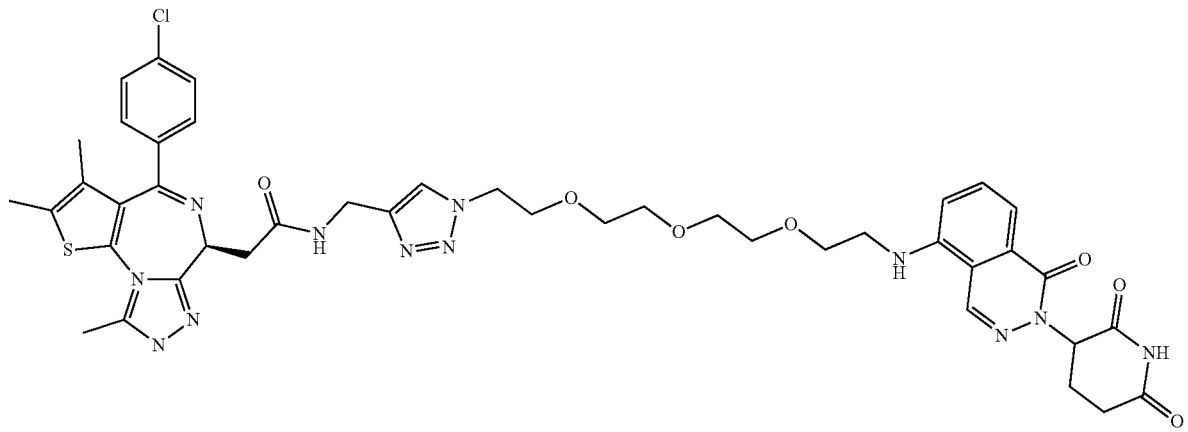

The titled compound is synthesized through following procedure which is similar to that of Example 31.

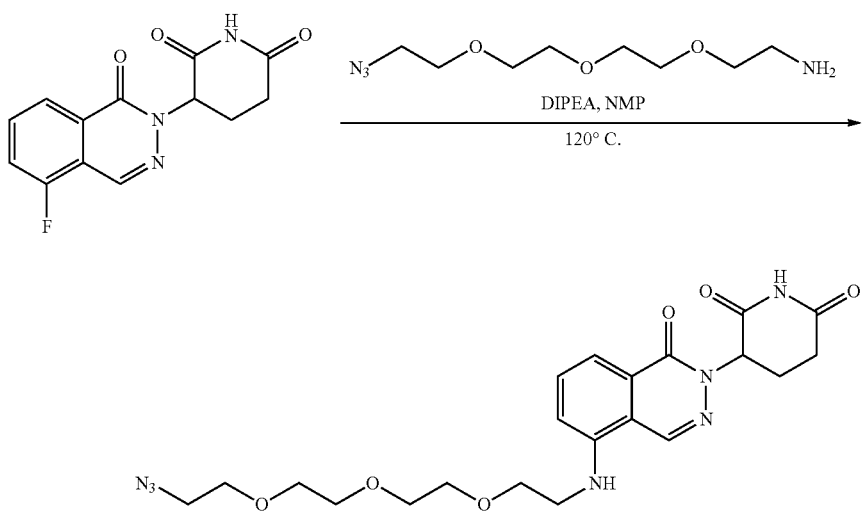

A solution of 3-(5-fluoro-1-oxo-1,2-dihydrophthalazin-2-yl)piperidine-2,6-dione (100 mg, 0.36 mmol), 1-[2-(2-aminoethoxy)ethoxy]-2-(2-azidoethoxy)ethane (103 mg, 0.472 mmol) and DIPEA (259 μL, 1.45 mmol) in NMP (4 mL) was reacted at 120° C. overnight. The reaction mixture was diluted with water and extracted with EtOAc. The organic layer was washed with brine, dried over MgSO$_4$, and concentrated. The residue was purified by column chromatography to give the product. (Yield: 11.6%, 20 mg)

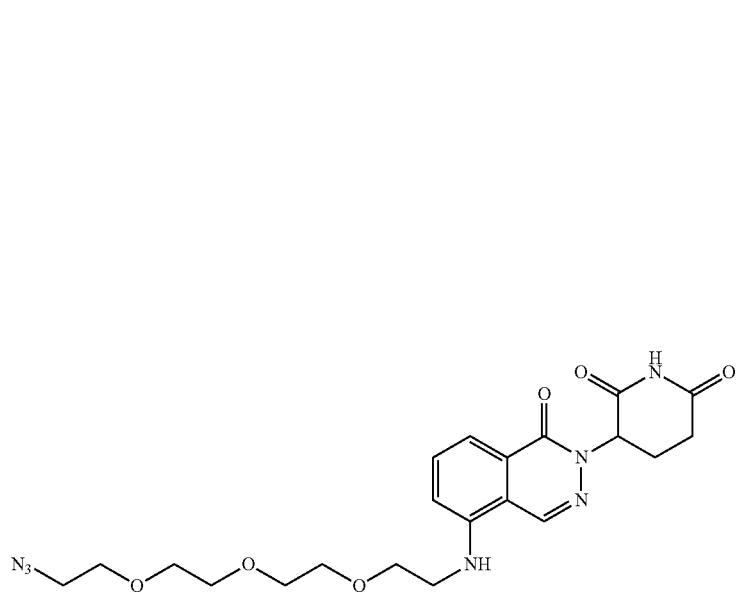
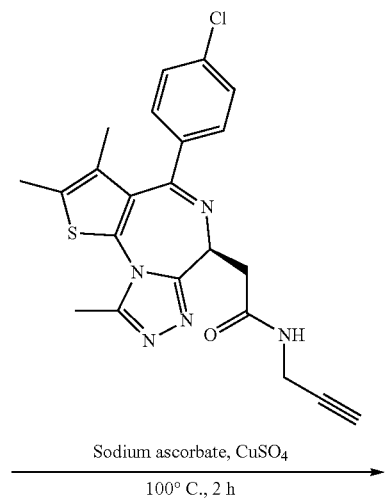
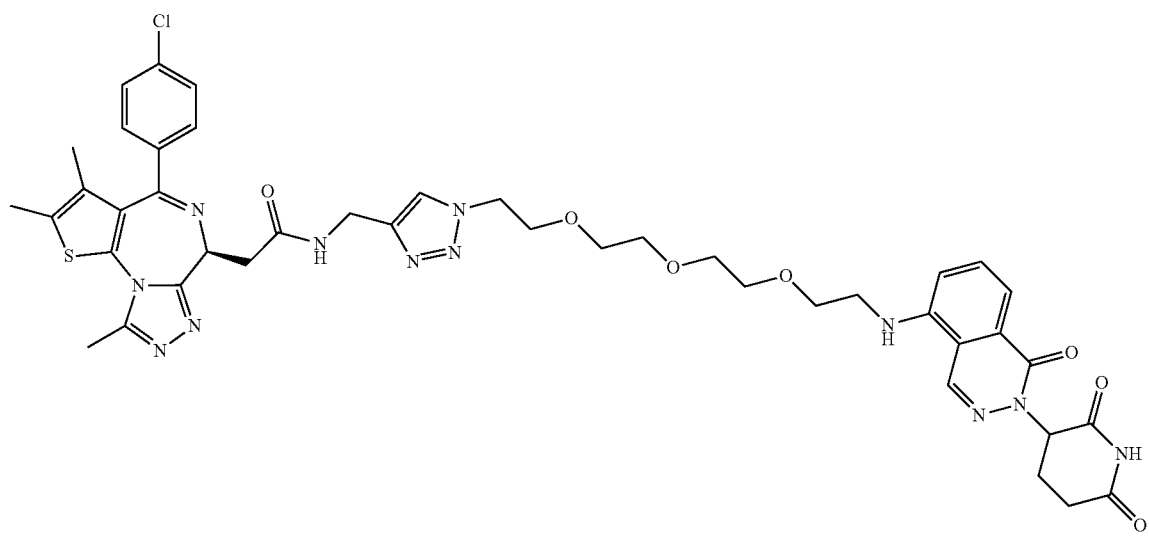

2-[(9S)-7-(4-chlorophenyl)-4,5,13-trimethyl-3-thia-1,8,11,12-tetraazatricyclo[8.3.0.0²,⁶]trideca-2(6),4,7,10,12-pentaen-9-yl]-N-(prop-2-yn-1-yl)acetamide (20 mg, 0.046 mmol) and 3-[5-(12-azido-4,7,10-trioxa-1-azadodecan-1-yl)-1-oxo-1,2-dihydrophthalazin-2-yl]piperidine-2,6-dione (21.6 mg, 0.046 mmol) were added in THF:H₂O (1:1, 2 mL). The sodium ascorbate (1.81 mg, 0.009 mmol) and copper sulfate (1.46 mg, 0.009 mmol) were added to the mixture. The reaction mixture was heated to 100° C. for 2 hours. The reaction mixture was cooled to room temperature, extracted with EA, and then dried over MgSO₄. The desired product was separated by column chromatography.

(Yield: 12.6%, 5.23 mg).

MS (ESI, m/z): [M+¹]+=914.4

[NMR] ¹H NMR (400 MHz, DMSO-d₆) δ ppm 11.02 (s, 1H), 8.74 (t, J=5.87 Hz, 1H), 8.64 (s, 1H), 7.92 (s, 1H), 7.57 (t, J=7.95 Hz, 1H), 7.47 (d, J=8.80 Hz, 3H), 7.38 (d, J=8.31 Hz, 4H), 7.02 (d, J=8.31 Hz, 1H), 6.81 (t, J=5.62 Hz, 1H), 4.52 (t, J=7.21 Hz, 1H), 4.43-4.56 (m, 2H), 4.36 (d, J=5.87 Hz, 2H), 3.78 (t, J=5.26 Hz, 2H), 3.61 (t, J=5.75 Hz, 2H), 3.51-3.56 (m, 2H), 3.48 (t, J=4.52 Hz, 7H), 3.39 (d, J=5.62 Hz, 2H), 3.27 (t, J=6.72 Hz, 2H), 2.59 (s, 3H), 2.36-2.44 (m, 3H), 1.56-1.66 (m, 3H)

Example 35

2-[(9S)-7-(4-chlorophenyl)-4,5,13-trimethyl-3-thia-1,8,11,12-tetraazatricyclo[8.3.0.0²,⁶]trideca-2(6),4,7,10,12-pentaen-9-yl]-N-[2-(2-{2-[4-({[3-(2,6-dioxopiperidin-3-yl)-4-oxo-3,4-dihydrophthalazin-5-yl]amino}methyl)-1H-1,2,3-triazol-1-yl]ethoxy}ethoxy)ethyl]acetamide

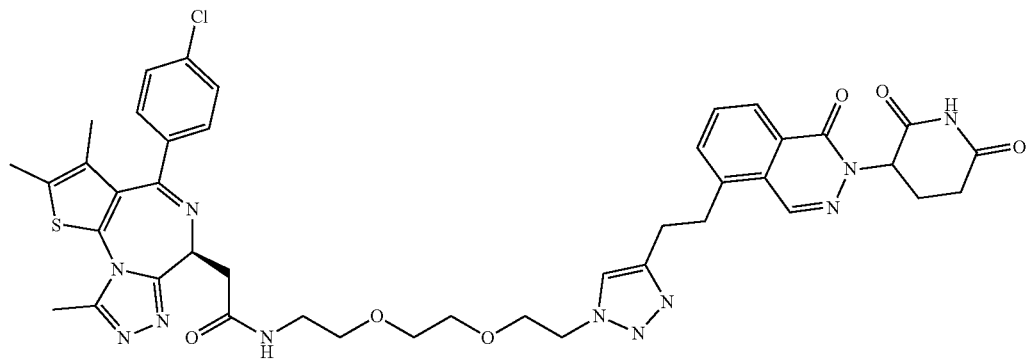 [SMILES: Cc1sc2c(c1C)C(c1ccc(Cl)cc1)=N[C@@H](CC(=O)NCCOCCOCCN1C=C(CCc3cccc4c(=O)n(C5CCC(=O)NC5=O)ncc34)NN1)c1nnc(C)n1-2]

The titled compound is synthesized through following procedure which is similar to that of Example 31:

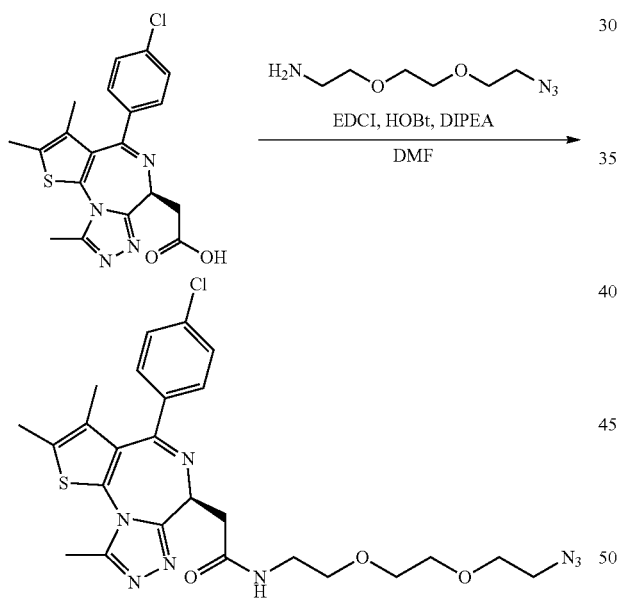

To a solution of 2-[(9S)-7-(4-chlorophenyl)-4,5,13-trimethyl-3-thia-1,8,11,12-tetraazatricyclo[8.3.0.0²,⁶]trideca-2(6),4,7,10,12-pentaen-9-yl]acetic acid (50 mg, 0.125 mmol), 1-(2-aminoethoxy)-2-(2-azidoethoxy)ethane (28.2 mg, 0.162 mmol), EDCl-HCl (26.3 mg, 0.137 mmol) and HOBt (23.3 mg, 0.137 mmol) in DMF was added DIPEA (78.4 μL, 0.437 mmol). The mixture was stirred at room temperature overnight. The reaction mixture was diluted with water and extracted with ethyl acetate. The organic layer was washed with brine, dried over $Na_2SO_4$, and concentrated. The desired product was separated by column chromatography. (Yield: 72.0%, 50 mg)

MS (ESI, m/z): [M+1]⁺=557.5

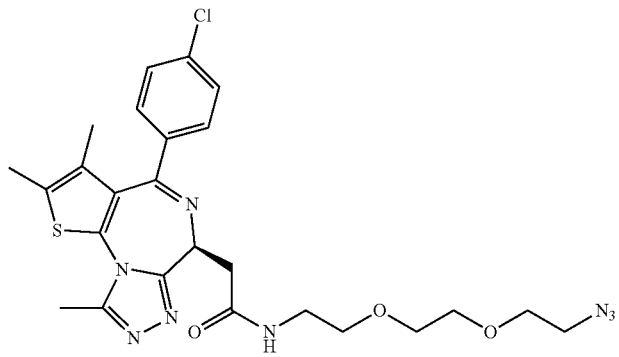
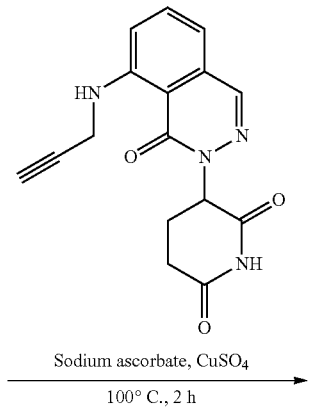

Sodium ascorbate, CuSO₄
100° C., 2 h

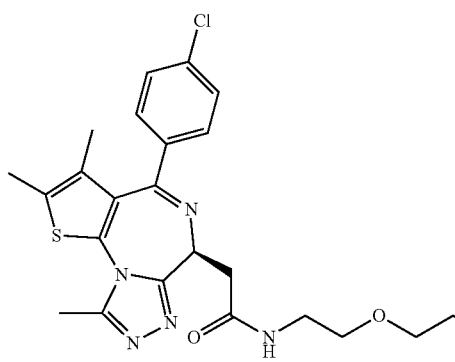
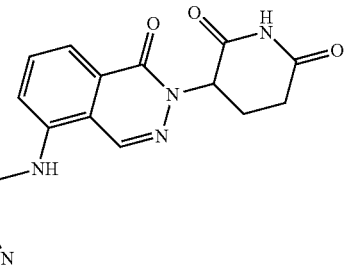

N-{2-[2-(2-azidoethoxy)ethoxy]ethyl}-2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamide (50 mg, 0.090 mmol) and 3-{1-oxo-5-[(prop-2-yn-1-yl)amino]-1,2-dihydrophthalazin-2-yl}piperidine-2,6-dione (36.2 mg, 0.117 mmol) were added in THF:H₂O (1:1, 3 mL). The sodium ascorbate (3.56 mmol, 0.018 mmol) and copper sulfate (2.86 mg, 0.018 mmol) were added to the mixture. The reaction mixture was heated to 100° C. for 2 hours. The reaction mixture was cooled to room temperature, extracted with EA, and then dried over MgSO₄. The desired product was separated by column chromatography.

(Yield: 20.4%, 15.8 mg).

MS (ESI, m/z): [M+¹]+=867.4

[NMR] ¹H NMR (400 MHz, DMSO-d₆) d ppm 11.02 (s, 1H), 9.07 (t, J=5.26 Hz, 1H), 8.20-8.30 (m, 2H), 8.03 (s, 1H), 7.63 (t, J=7.95 Hz, 1H), 7.38-7.51 (m, 4H), 6.91-7.05 (m, 2H), 4.45-4.55 (m, 5H), 3.80 (t, J=5.14 Hz, 2H), 3.45-3.56 (m, 5H), 3.37-3.44 (m, 2H), 3.15-3.29 (m, 4H), 2.80-2.95 (m, 1H), 2.56-2.65 (m, 5H), 2.36-2.42 (m, 3H), 1.57-1.65 (m, 4H)

Example 36
2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-{2-[2-(2-{2-[4-({[3-(2,6-dioxopiperidin-3-yl)-4-oxo-3,4-dihydrophthalazin-5-yl]amino}methyl)-1H-1,2,3-triazol-1-yl]ethoxy}ethoxy)ethoxy]ethyl}acetamide
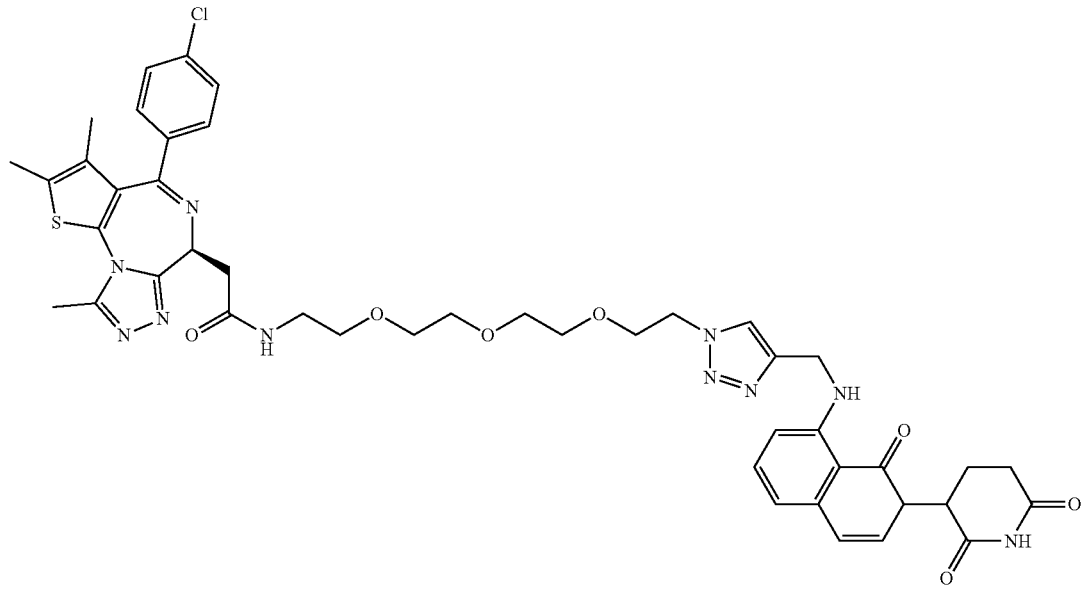 [SMILES: Cc1sc2c(c1C)C(c1ccc(Cl)cc1)=N[C@@H](CC(=O)NCCOCCOCCOCCn1cc(CNc3cccc4c3C(=O)C(C3CCC(=O)NC3=O)C=C4)nn1)c1nnc(C)n1-2]
The titled compound is synthesized through following procedure which is similar to that of Example 31.
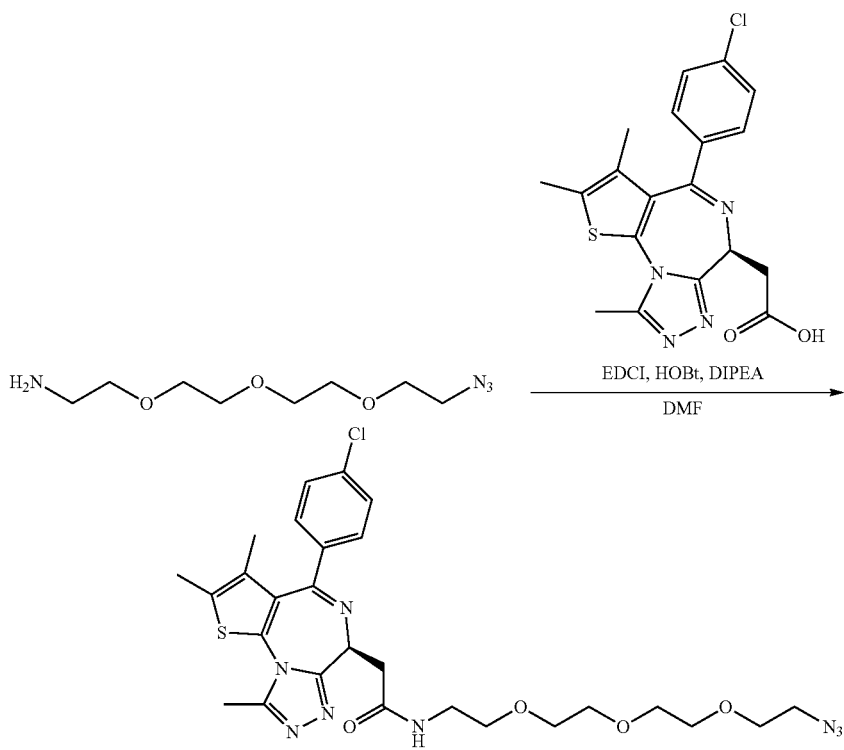

To a solution of 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetic acid (50 mg, 0.125 mmol), 1-[2-(2-aminoethoxy)ethoxy]-2-(2-azidoethoxy)ethane (40.8 mg, 0.187 mmol), EDCl-HCl (26.3 mg, 0.137 mmol) and HOBt (23.3 mg, 0.137 mmol) in DMF was added DIPEA (78.4 μL, 0.437 mmol). The mixture was stirred at room temperature overnight. The reaction mixture was diluted with water and extracted with ethyl acetate. The organic layer was washed with brine, dried over Na$_2$SO$_4$, and concentrated. The desired product was separated by column chromatography (Yield: 66.5%, 50 mg)

MS (ESI, m/z): [M+$^1$]+=601.3

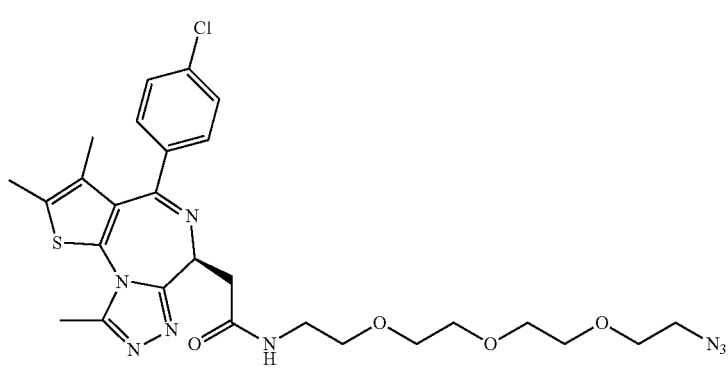
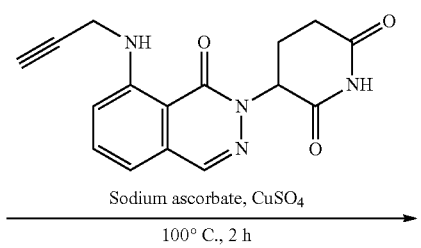
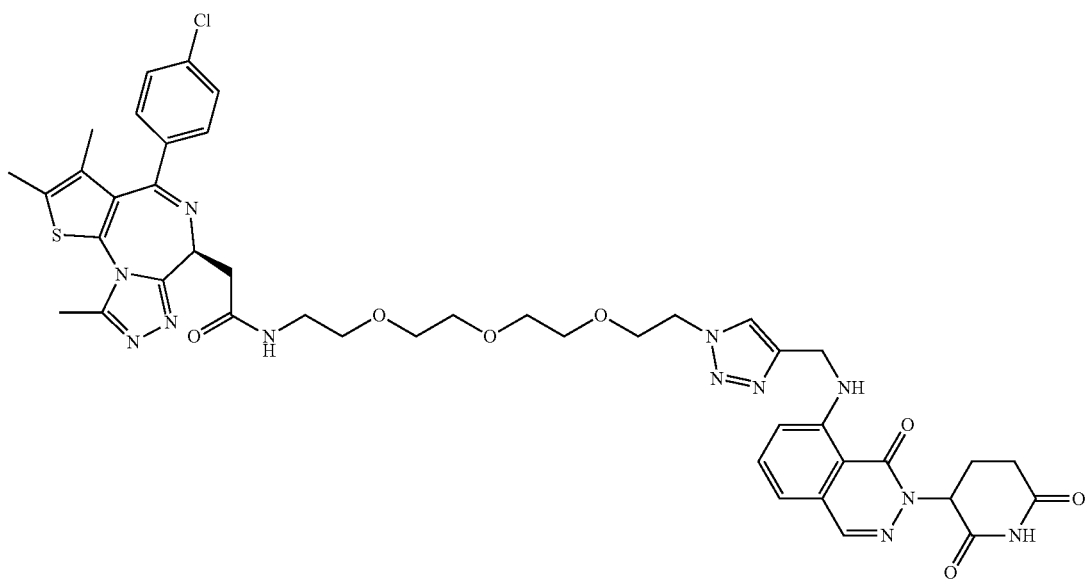

N-(2-{2-[2-(2-azidoethoxy)ethoxy]ethoxy}ethyl)-2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetamide (50 mg, 0.083 mmol) and 3-{1-oxo-8-[(prop-2-yn-1-yl)amino]-1,2-dihydrophthalazin-2-yl}piperidine-2,6-dione (33.6 mg, 0.108 mmol) were added in THF:H$_2$O (1:1, 3 mL). The sodium ascorbate (3.3 mg, 0.0167 mmol) and copper sulfate (2.66 mg, 0.017 mmol) were added to the mixture. The reaction mixture was heated to 100° C. for 2 hours. The reaction mixture was cooled to room temperature, extracted with EA, and then dried over MgSO$_4$. The desired product was separated by column chromatography. (Yield 18.9%, 14.3 mg)

MS (ESI, m/z): [M+$^1$]+=911.4

[NMR] $^1$H NMR (400 MHz, DMSO-d$_6$) d ppm 11.02 (s, 1H), 9.07 (s, 1H), 8.20-8.31 (m, 2H), 8.03 (s, 1H), 7.59-7.72 (m, 1H), 7.37-7.52 (m, 4H), 6.91-7.05 (m, 2H), 4.44-4.55 (m, 5H), 3.79 (t, J=5.14 Hz, 2H), 3.38-3.53 (m, 12H), 3.15-3.29 (m, 4H), 2.59 (s, 4H), 2.40 (s, 3H), 1.61 (s, 3H), 1.23 (s, 1H)

Example 37

Synthesis of 2-((S)-4-(4-chlorophenyl)-2,3,9-trimethyl-6H-thieno[3,2-f][1,2,4]triazolo[4,3-a][1,4]diazepin-6-yl)-N-(5-((2-(2,6-dioxopiperidin-3-yl)-1-oxo-1,2-dihydrophthalazin-6-yl)amino)pentyl)acetamide

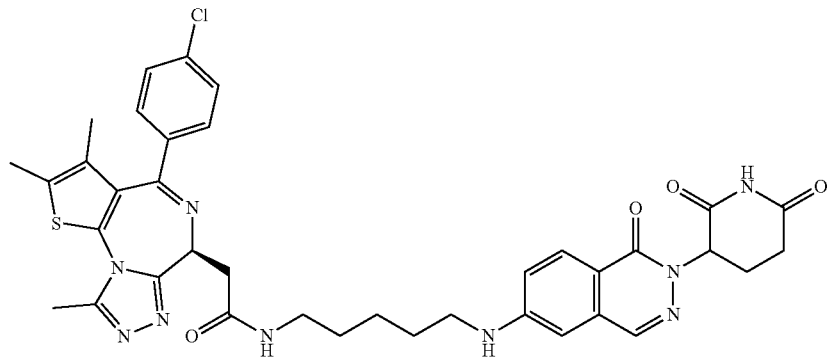 [SMILES: Cc1sc2c(c1C)C(c1ccc(Cl)cc1)=N[C@@H](CC(=O)NCCCCCNc1ccc3c(=O)n(C4CCC(=O)NC4=O)ncc3c1)c1nnc(C)n1-2]

Step 1) Synthesis of tert-butyl (5-((2-(2,6-dioxopiperidin-3-yl)-1-oxo-1,2-dihydrophthazin-6-yl)amino)pentyl)carbamate

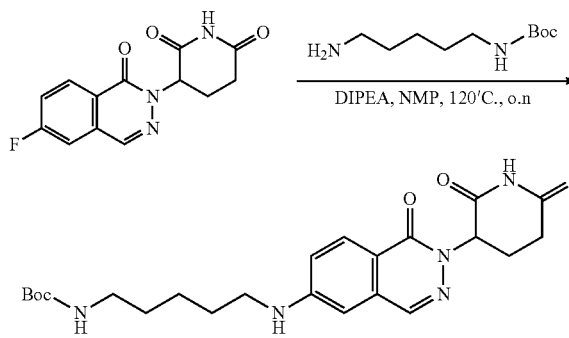

3-(6-fluoro-1-oxo-1,2-dihydrophthalazin-2-yl)piperidine-2,6-dione (1 g, 3.63 mmol) and tert-butyl N-(5-aminopentyl) carbamate (0.74 g, 3.63 mmol) were dissolved in NMP (10 mL), and DIPEA (5.17 ml, 29.04 mmol) was added in reaction mixture. The mixture was stirred 120° C. for overnight. The reaction was quenched by water and extracted with DCM, NH₄Cl and brine, and then dried over MgSO₄. The reaction mixture was loaded on silica and separated by MPLC. The product was obtained as oil. (Yield: 1.3 g, 66%)

Step 2) Synthesis of 3-(6-((5-aminopentyl)amino)-1-oxophthalazin-2(1H)-yl)piperidine-2,6-dione

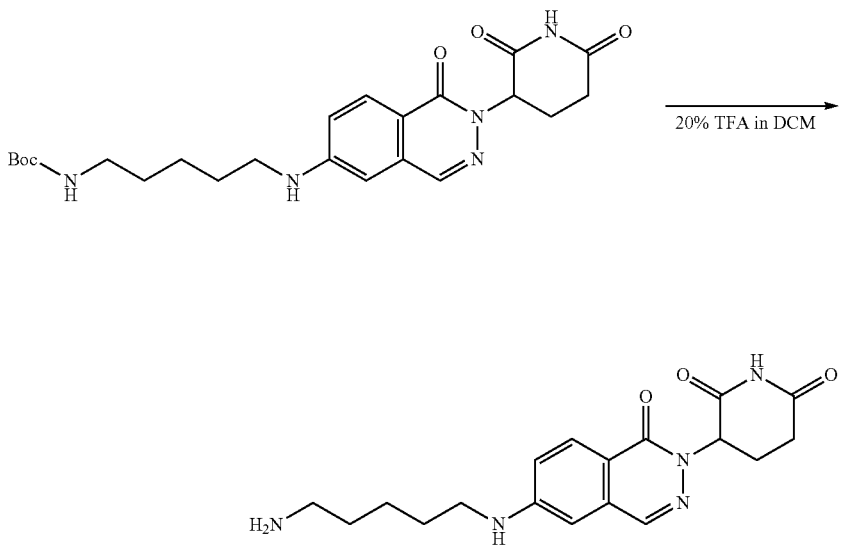

tert-butyl N-(5-{[2-(2,6-dioxopiperidin-3-yl)-1-oxo-1,2-dihydrophthalazin-6-yl]amino}pentyl) carbamate (1 g, 2.19 mmol) was dissolved in 20% TFA in DCM (30 ml) and reacted for 2 hours at room temperature. After reaction finished, solvent was removed under high vacuum. The product was used in next step without no further purification. The product was obtained as pure oil. (Yield: 0.78 g, 99%), Step 3) Synthesis of 2-((S)-4-(4-chlorophenyl)-2,3,9-trimethyl-6H-thieno[3,2-f][1,2,4]triazolo[4,3-a][1,4]diazepin-6-yl)-N-(5-((2-(2,6-dioxopiperidin-3-yl)-1-oxo-1,2-dihydrophthalazin-6-yl)amino)pentyl) acetamide

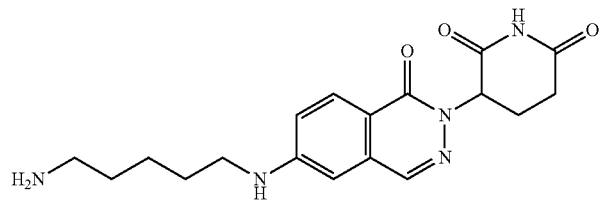
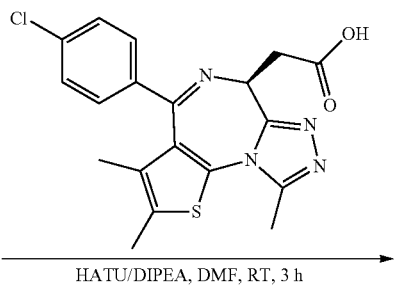

HATU/DIPEA, DMF, RT, 3 h

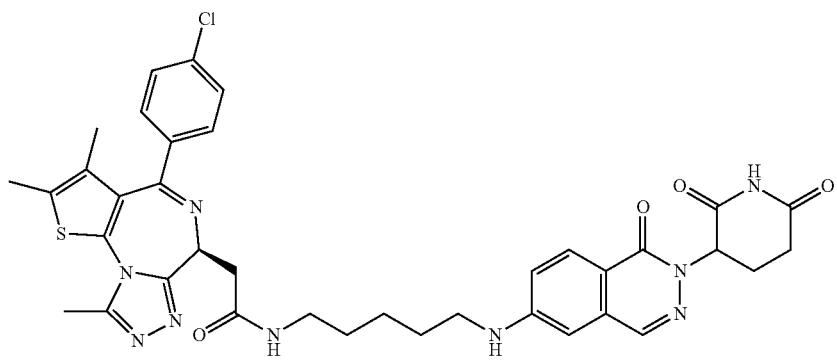

JQ-1 carboxylic acid (1.05 g, 2.62 mmol), HATU (1.08 g, 2.84 mmol) and DIPEA (2.74 µL, 15.3 mmol) were dissolved in DMF (25 ml) and stirred for 1 hour at room temperature. 3-{6-[(5-aminopentyl)amino]-1-oxo-1,2-dihydrophthalazin-2-yl}piperidine-2,6-dione (780 mg, 2.18 mmol) was added to reaction mixture. The mixture was stirred at room temperature for overnight. The reaction mixture was diluted with water and extracted with EA. The organic layer was washed with brine, dried over $Na_2SO_4$, and concentrated. Product was purified by MPLC. The product was obtained as white solid (yield: 0.66 g, 41%).

MS (ESI, m/z): [M+$^1$]+=741.3

[NMR] $^1$H NMR (400 MHz, DMSO-$d_6$) δ ppm 10.98 (s, 1H) 8.24 (t, J=5.56 Hz, 1H) 8.15 (d, J=1.22 Hz, 1H) 7.89 (d, J=8.80 Hz, 1H) 7.39-7.50 (m, 5H) 7.05 (dd, J=8.86, 2.26 Hz, 1H) 6.87 (t, J=5.14 Hz, 1H) 6.73 (d, J=2.08 Hz, 1H) 5.72 (dd, J=11.92, 5.07 Hz, 1H) 4.53 (dd, J=7.95, 6.24 Hz, 1H) 3.17-3.30 (m, 3H) 3.10 (d, J=6.11 Hz, 3H) 2.85-2.96 (m, 1H) 2.59 (m, 4H) 2.37 (s, 3H) 2.02-2.11 (m, 1H) 1.62 (d, J=7.34 Hz, 2H) 1.56 (d, J=1.71 Hz, 2H) 1.39-1.54 (m, 4H)

Example 38

Synthesis of 2-((S)-4-(4-chlorophenyl)-2,3,9-trimethyl-6H-thieno[3,2-f][1,2,4]triazolo[4,3-a][1,4]diazepin-6-yl)-N-(3-(4-(3-((3-(2,6-dioxopiperidin-3-yl)-4-oxo-3,4-dihydrophthalazin-5-yl)amino)propyl)piperazin-1-yl)propyl)acetamide

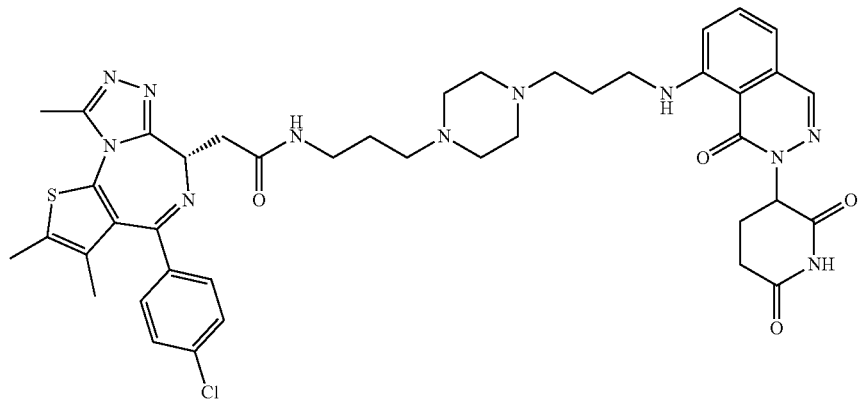 [SMILES: Cc1sc2c(c1C)C(c1ccc(Cl)cc1)=N[C@@H](CC(=O)NCCCN1CCN(CCCNc3cccc4cnn(C5CCC(=O)NC5=O)c(=O)c34)CC1)c1nnc(C)n1-2]

The titled compound is synthesized through following procedure.

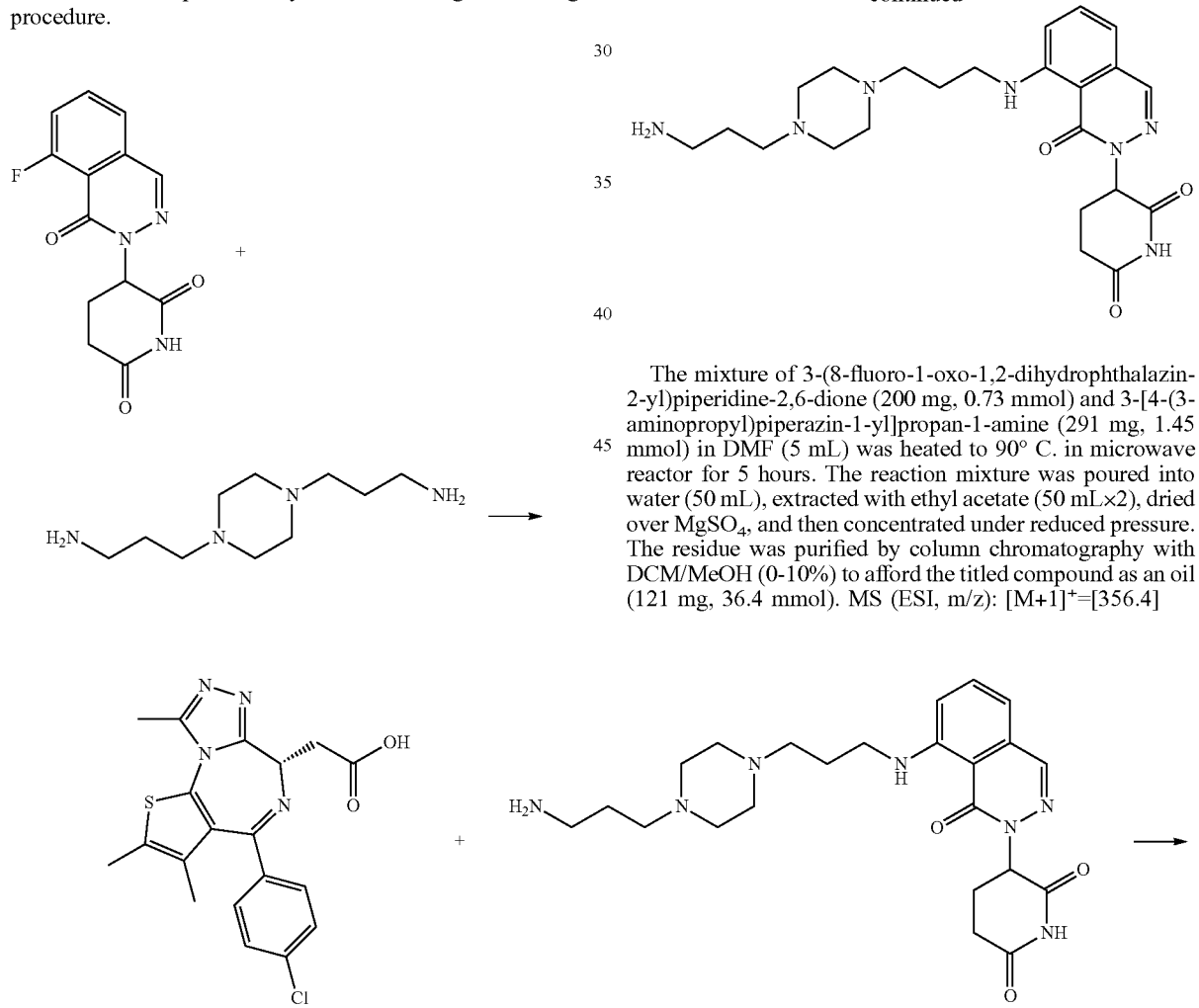

The mixture of 3-(8-fluoro-1-oxo-1,2-dihydrophthalazin-2-yl)piperidine-2,6-dione (200 mg, 0.73 mmol) and 3-[4-(3-aminopropyl)piperazin-1-yl]propan-1-amine (291 mg, 1.45 mmol) in DMF (5 mL) was heated to 90° C. in microwave reactor for 5 hours. The reaction mixture was poured into water (50 mL), extracted with ethyl acetate (50 mL×2), dried over MgSO$_4$, and then concentrated under reduced pressure. The residue was purified by column chromatography with DCM/MeOH (0-10%) to afford the titled compound as an oil (121 mg, 36.4 mmol). MS (ESI, m/z): [M+1]$^+$=[356.4]

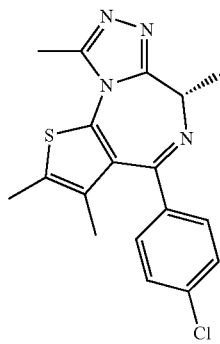
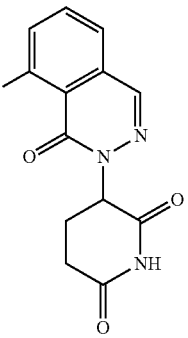

To a solution of JQ-1 carboxylic acid (17 mg, 0.042 mmol) and HATU (11 mg, 0.0046 mmol) in DMF (4 mL) was added DIPEA (27.4 mg, 0.21 mmol). The mixture was treated with 3-[8-({3-[4-(3-aminopropyl)piperazin-1-yl]propyl}amino)-1-oxo-1,2-dihydrophthalazin-2-yl]piperidine-2,6-dione (19.3 mg, 0.042 mmol) in DMF (1 mL) and stirred at room temperature overnight. The reaction mixture was diluted with water and extracted with ethyl acetate. The organic layer was washed with brine, dried over $Na_2SO_4$, and concentrated. The residue was purified by column chromatography with DCM/MeOH (0-10%) to afford the titled compound.

MS (ESI, m/z): $[M+^1]+=838.4$.

$^1$H NMR (400 MHz, DMSO-$d_6$) δ ppm 11.03 (s, 1H) 8.75 (m, 1H) 8.23 (s, 1H) 7.65 (dd, J=8.1, 2.3 Hz, 1H) 7.42 (d, J=2.1 Hz, 2H) 7.44 (d, J=2.1 Hz, 2H) 6.92 (d, J=2.1 Hz, 2H), 5.20 (m, 1H), 4.51 (m, 1H), 3.75-3.48 (m, 14H), 3.33 (m, 6H), 3.22-3.24 (m, 2H), 2.80 (m, 2H), 2.57 (m, 2H), 2.59 (s, 3H), 2.41 (s, 3H), 2.09 (m, 1H), 1.75 (m, 1H), 1.62 (s, 3H).

Example 39: Synthesis of 2-((S)-4-(4-chlorophenyl)-2,3,9-trimethyl-6H-thieno[3,2-f][1,2,4]triazolo[4,3-a][1,4]diazepin-6-yl)-N-(3-(2-(2-(2-((3-(2,6-dioxopiperidin-3-yl)-1-methyl-4-oxo-3,4-dihydrophthalazin-5-yl)amino)ethoxy)ethoxy)ethoxy)phenyl)acetamide

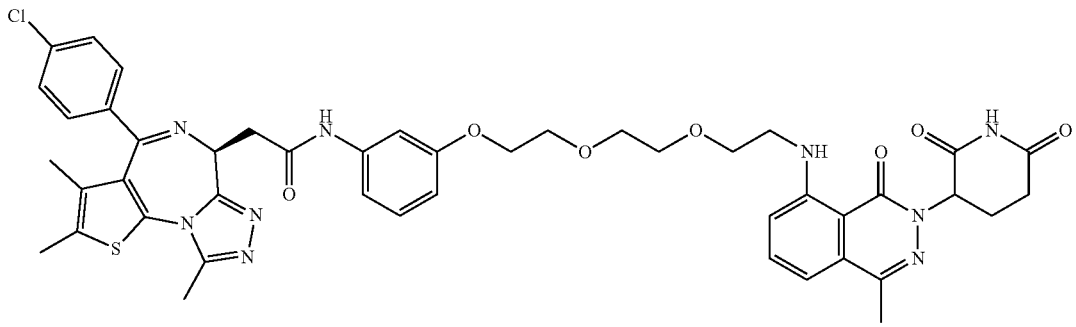 [SMILES: Cc1sc2c(c1C)C(c1ccc(Cl)cc1)=N[C@@H](CC(=O)Nc1cccc(OCCOCCOCCNc3cccc4c(C)nn(C5CCC(=O)NC5=O)c(=O)c34)c1)c1nnc(C)n1-2]

39-1) Synthesis of tert-butyl (3-(2-(2-(2-((3-(2,6-dioxopiperidin-3-yl)-1-methyl-4-oxo-3,4-dihydrophthalazin-5-yl)amino)ethoxy)ethoxy)ethoxy)phenyl)carbamate

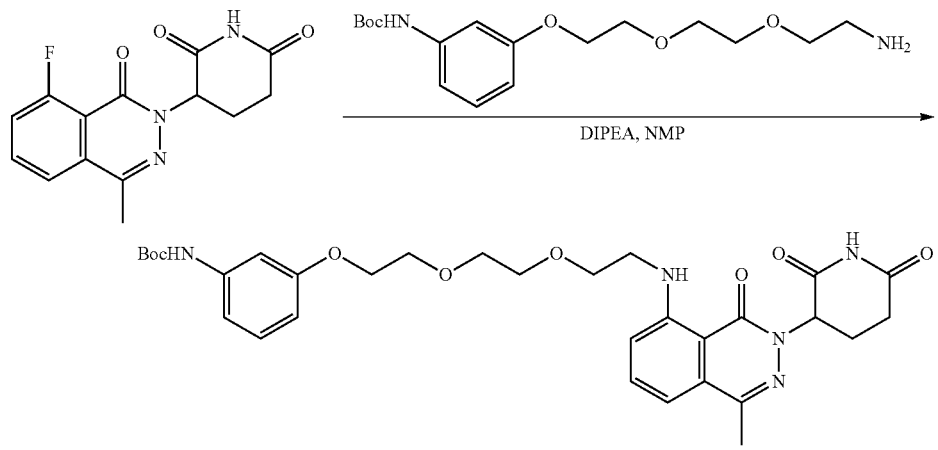

A solution of 3-(8-fluoro-4-methyl-1-oxophthalazin-2(1H)-yl)piperidine-2,6-dione (30.0 mg, 0.104 mmol), tert-butyl (3-(2-(2-(2-aminoethoxy)ethoxy)ethoxy)phenyl)carbamate (45.9 mg, 0.135 mmol) and DIPEA (0.067 mL, 0.407 mmol) in NMP (1 mL) was stirred for 16 hours at 120° C. The reaction mixture was purified by reverse column chromatography to give the product.
(Yield: 41 mg, 64.8%)
MS (ESI, m/z): [M+1]$^+$=610.2

39-2) Synthesis of 3-(8-((2-(2-(2-(3-aminophenoxy)ethoxy)ethoxy)ethyl)amino)-4-methyl-1-oxophthalazin-2(1H)-yl)piperidine-2,6-dione

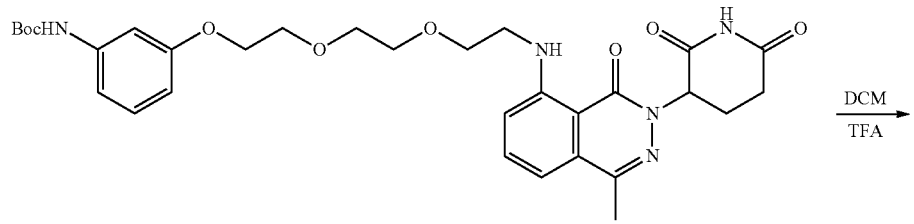

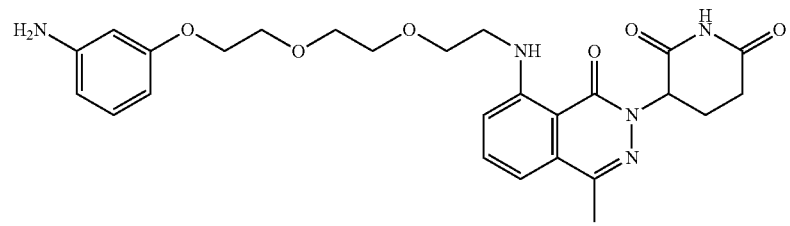

A solution of tert-butyl (3-(2-(2-(2-((3-(2,6-dioxopiperidin-3-yl)-1-methyl-4-oxo-3,4-dihydrophthalazin-5-yl)amino)ethoxy)ethoxy)ethoxy)phenyl)carbamate (41 mg, 0.076 mmol) in 20% TFA in DCM (0.6 mL) was stirred at room temperature. The reaction mixture was concentrated in vacuo and used for the next step without further purification.
(Yield: 34.3 mg, quant.).
MS (ESI, m/z): [M+1]$^+$=[510.0]

39-3) Synthesis of 2-((S)-4-(4-chlorophenyl)-2,3,9-trimethyl-6H-thieno[3,2-f][1,2,4]triazolo[4,3-a][1,4]diazepin-6-yl)-N-(3-(2-(2-(2-((3-(2,6-dioxopiperidin-3-yl)-1-methyl-4-oxo-3,4-dihydrophthalazin-5-yl)amino)ethoxy)ethoxy)ethoxy)phenyl)acetamide

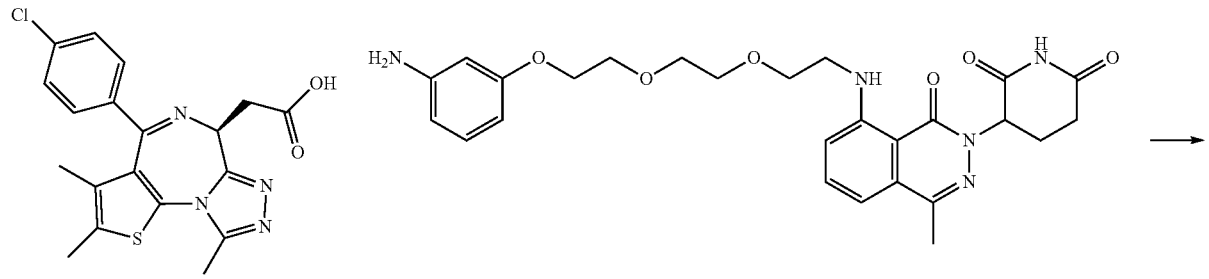

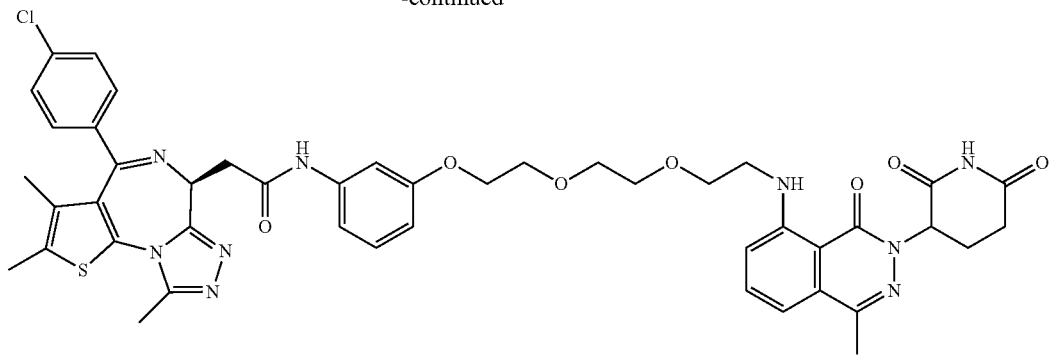

To a solution of 3-(8-((2-(2-(2-(3-aminophenoxy)ethoxy)ethoxy)ethyl)amino)-4-methyl-1-oxophthalazin-2(1H)-yl)piperidine-2,6-dione (34.3 mg, 0.067 mmol), JQ-1 carboxylic acid (27 mg, 0.067 mmol), DIPEA (0.073 ml, 0.404 mmol) and HOBT (12.6 mg, 0.074 mmol) in DMF (1 mL) was added EDCI (16.8 mg, 0.088 mmol) at 0° C. and the mixture was stirred at room temperature for 2 hours. The reaction mixture was purified by reverse column chromatography to give the product (Yield: 20.1 mg, 33.5%).

1H NMR (400 MHz, DMSO-d6) δ=11.00 (s, 1H), 10.30 (s, 1H), 9.05 (t, J=5.2 Hz, 1H), 7.63 (t, J=8.1 Hz, 1H), 7.49 (d, J=8.8 Hz, 2H), 7.42 (d, J=8.8 Hz, 2H), 7.35 (s, 1H), 7.23-7.11 (m, 2H), 6.93 (d, J=9.5 Hz, 1H), 6.90 (d, J=8.6 Hz, 1H), 6.62 (d, J=7.5 Hz, 1H), 5.66 (m, 1H), 4.60 (t, J=7.1 Hz, 1H), 4.02 (t, J=4.1 Hz, 2H), 3.74 (t, J=4.1 Hz, 2H), 3.68 (t, J=5.4 Hz, 2H), 3.61 (s, 4H), 3.50 (d, J=7.0 Hz, 2H), 3.38 (m 2H), 2.92-2.81 (m, 1H), 2.63-2.53 (m, 5H), 2.41 (s, 3H), 2.40 (s, 3H), 2.06 (m, 1H), 1.62 (s, 3H).

MS (ESI, m/z): [M+$^1$]+=894.4 and 892.4

Example 40: Synthesis of 2-((S)-4-(4-chlorophenyl)-2,3,9-trimethyl-6H-thieno[3,2-f][1,2,4]triazolo[4,3-a][1,4]diazepin-6-yl)-N-(3-(2-(2,6-dioxopiperidin-3-yl)-1-oxo-1,2-dihydrophthalazin-6-yl)prop-2-yn-1-yl)acetamide 40-1) 3-(6-(3-aminoprop-1-yn-1-yl)-1-oxophthalazin-2(1H)-yl)piperidine-2,6-dione

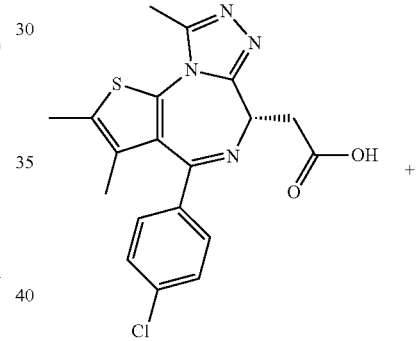

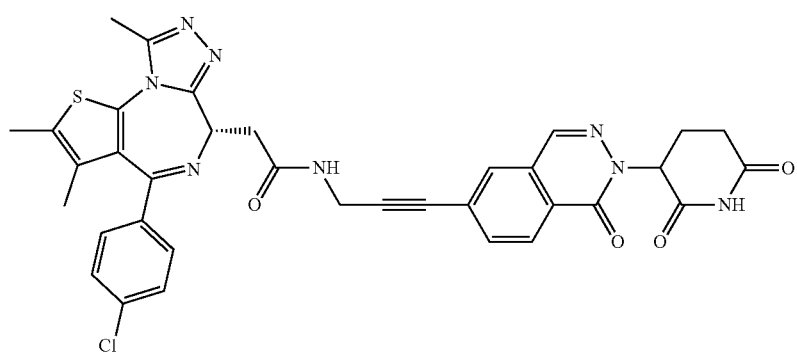 [SMILES: Cc1sc2c(c1C)C(c1ccc(Cl)cc1)=N[C@@H](CC(=O)NCC#Cc1ccc3c(=O)n(C4CCC(=O)NC4=O)ncc3c1)c1nnc(C)n1-2]

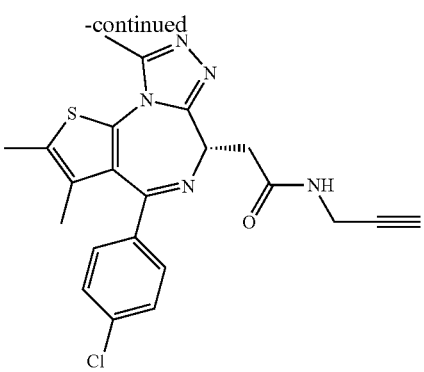

To a solution of JQ-1 carboxylic acid (160 mg, 0.40 mmol), prop-2-yn-1-amine (26.4 mg, 0.48 mmol), EDCl-HCl (84.2 mg, 0.44 mmol) in DMF (5 mL) was added DIPEA (182.2 mg, 1.44 mmol). The mixture was stirred at room temperature overnight. The reaction mixture was diluted with water (50 ml) and extracted with ethyl acetate (50 ml×2). The organic layer was washed with brine, dried over Na$_2$SO$_4$, and concentrated. The resulting residue was purified by column chromatography with DCM:MeOH=10:1 to afford the titled compound (159 mg, 87.7%). MS (ESI, m/z): [M+$^1$]+=438.8.

40-2) Synthesis of 2-((S)-4-(4-chlorophenyl)-2,3,9-trimethyl-6H-thieno[3,2-f][1,2,4]triazolo[4,3-a][1,4]diazepin-6-yl)-N-(3-(2-(2,6-dioxopiperidin-3-yl)-1-oxo-1,2-dihydrophthalazin-6-yl)prop-2-yn-1-yl)acetamide

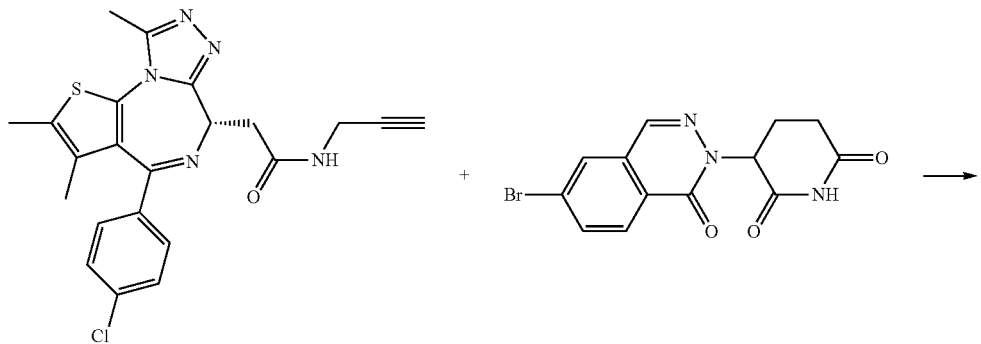

To a solution of 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(prop-2-yn-1-yl)acetamide (50 mg, 0.11 mmol) and 3-(6-bromo-1-oxo-1,2-dihydrophthalazin-2-yl)piperidine-2,6-dione (38.4 mg, 0.11 mmol) in DMF (2 mL) were added CuI (2.19 mg, 0.011 mmol) and Pd(PPh3)2Cl2 (8.0 mg, 0.011 mmol) followed by TEA (34.7 mg, 0.34 mmol). The mixture was irradiated in microwave reactor at 80° C. for 1.5 hours. The reaction mixture was diluted with water (50 ml) and extracted with ethyl acetate (50 ml×2). The organic layer was washed with brine, dried over Na$_2$SO$_4$, and concentrated under reduced pressure. The residue was purified by MPLC with EA/Hex (20-80%) to afford the titled compound as an off-white solid.

MS (ESI, m/z): [M+$^1$]+=694.8

$^1$H NMR (400 MHz, DMSO-d$_6$) δ ppm 11.09 (s, 1H) 8.92 (m, 1H) 8.47 (s, 1H) 8.25 (d. J=2.5 Hz, 1H) 8.10 (s, 1H) 794 (d, J=2.5 Hz, 1H) 7.32 (d, J=1.8 Hz, 2H), 7.23 (d, J=1.8 Hz, 2H), 5.72 (m, 1H) 4.62 (m, 2H) 4.25 (m., 2H) 2.50-3.31 (m, 4H) 2.60 (s, 3H), 2.41 (s, 3H) 2.15 (m, 1H) 1.60 (s., 3H).

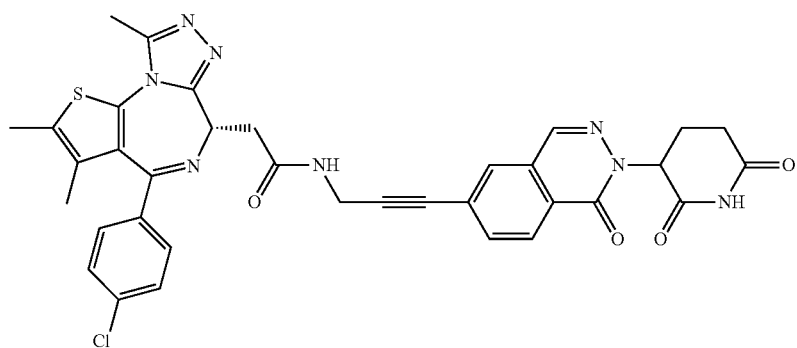

Example 41: 2-((S)-4-(4-chlorophenyl)-2,3,9-trimethyl-6H-thieno[3,2-f][1,2,4]triazolo[4,3-a][1,4]diazepin-6-yl)-N-(3-(2-(2-(2-((2-(2,6-dioxopiperidin-3-yl)-1-oxo-1,2-dihydrophthaazin-6-yl)amino)ethoxy)ethoxy)ethoxy)phenyl)acetamide

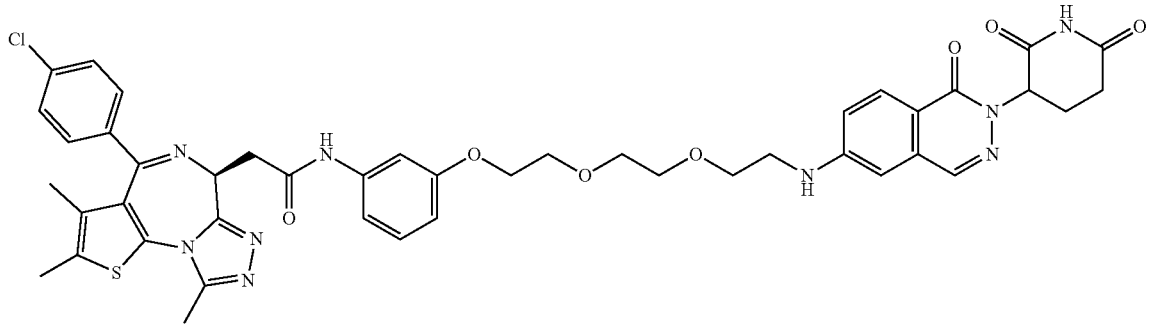 [SMILES: Cc1sc2c(c1C)C(c1ccc(Cl)cc1)=N[C@@H](CC(=O)Nc1cccc(OCCOCCOCCNc3ccc4c(=O)n(C5CCC(=O)NC5=O)ncc4c3)c1)c1nnc(C)n1-2]

The titled compound is synthesized through following procedure.

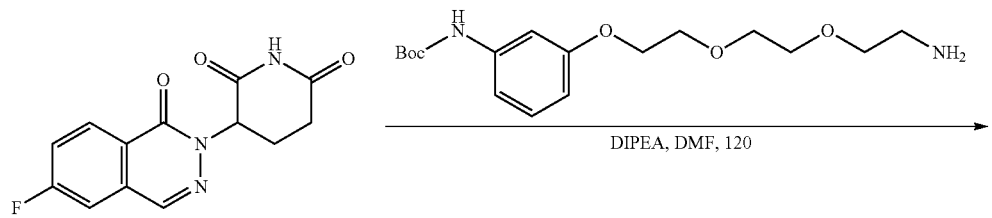

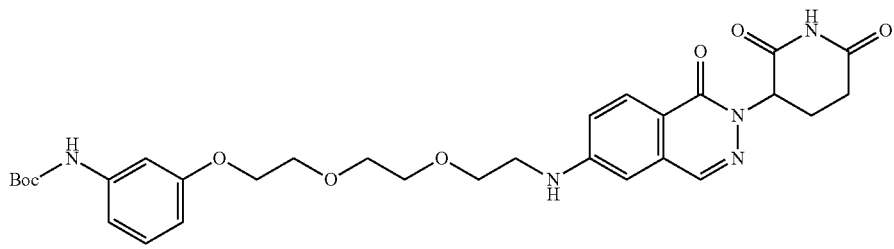

A solution of 3-(6-fluoro-1-oxophthalazin-2(1H)-yl)piperidine-2,6-dione (80.0 mg, 0.291 mmol), tert-butyl (3-(2-(2-(2-aminoethoxy)ethoxy)ethoxy)phenyl)carbamate (109.0 mg, 0.320 mmol) and DIPEA (363 μL, 2.03 mmol) in DMF (2 mL) was irritated on microwave at 120° C. for 5 hours. The reaction mixture was diluted with water and extracted with EtOAc. The organic layer was washed with brine, dried over MgSO₄, and concentrated. The residue was purified by column chromatography to give the product. (Yield: 130.0 mg, 75.1%). MS (ESI, m/z): [M+¹]+=[596.8]

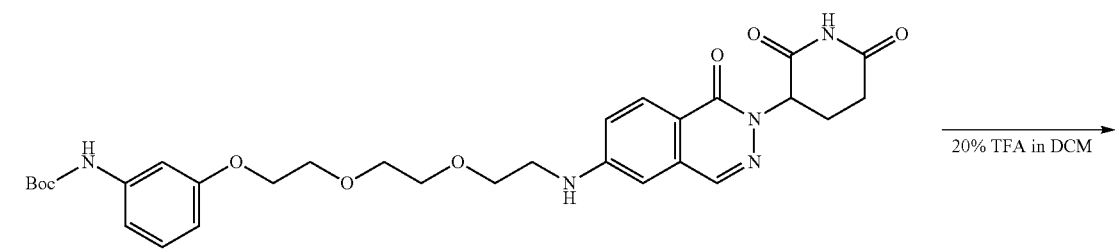

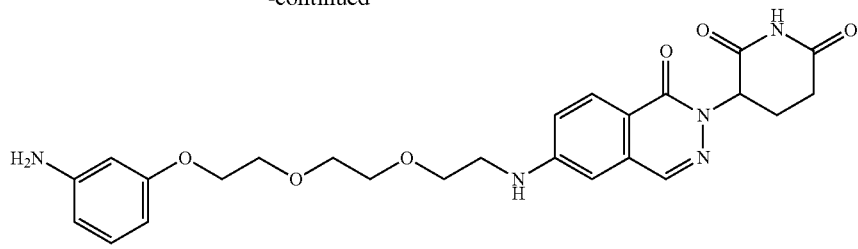

A solution of tert-butyl (3-(2-(2-(2-((2-(2,6-dioxopiperidin-3-yl)-1-oxo-1,2-dihydrophthalazin-6-yl)amino)ethoxy)ethoxy)ethoxy)phenyl)carbamate (74.0 mg, 0.124 mmol) in 20% TFA in DCM (1 mL) was stirred at room temperature. The reaction mixture was concentrated in vacuo and used for the next step without further purification. (Yield: 60.0 mg, 97.5%). MS (ESI, m/z): [M+¹]+=[496.8]

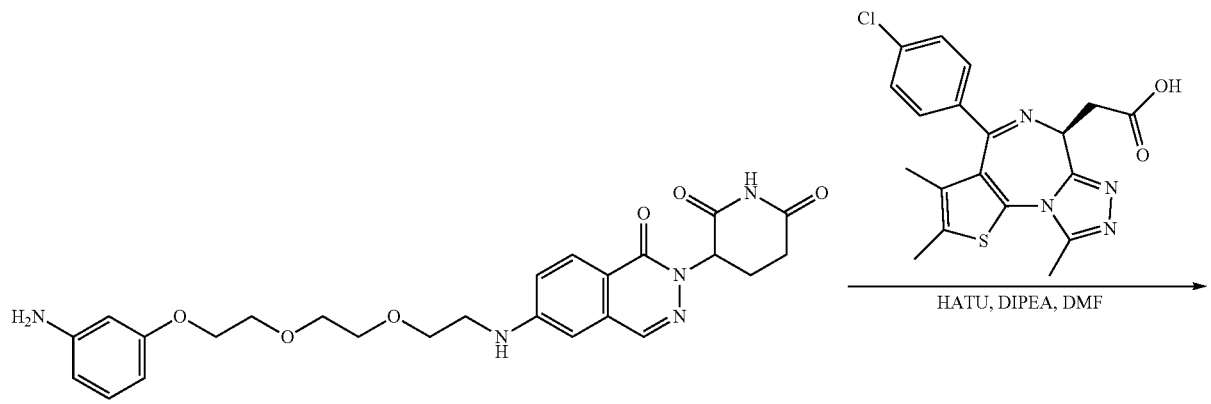

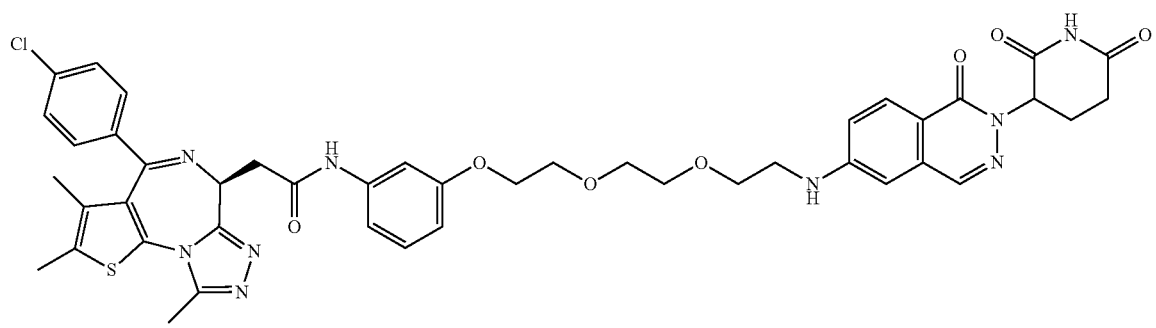

A solution of JQ-1 carboxylic acid (53.4 mg, 0.133 mmol), HATU (55.2 mg, 0.145 mmol) and DIPEA (0.1 ml, 0.605 mmol) in DMF (2 mL) was stirred at room temperature for 0.5 hour. 3-(6-((2-(2-(2-(3-aminophenoxy)ethoxy)ethoxy)ethyl)amino)-1-oxophthalazin-2(1H)-yl)piperidine-2,6-dione (60.0 mg, 0.121 mmol) was added. The mixture was stirred at room temperature overnight. The reaction mixture was diluted with water and extracted with ethyl acetate. The organic layer was washed with brine, dried over $Na_2SO_4$, and concentrated. The mixture was separated by column chromatography.

(yield: 45.0 mg, 42.3%)

MS (ESI, m/z): [M+¹]+=879.4

[NMR] 1H NMR (400 MHz, DMSO-d6) δ ppm 10.99 (s, 1H) 10.31 (s, 1H) 8.16 (s, 1H) 7.90 (d, J=8.80 Hz, 1H) 7.34-7.52 (m, 5H) 7.17-7.24 (m, 1H) 7.08-7.16 (m, 2H) 6.93 (t, J=5.44 Hz, 1H) 6.80 (d, J=2.08 Hz, 1H) 6.58-6.67 (m, 1H) 5.72 (dd, J=12.04, 4.95 Hz, 1H) 4.60 (t, J=7.15 Hz, 1H) 4.00-4.07 (m, 2H) 3.70-3.78 (m, 2H) 3.56-3.66 (m, 8H) 3.50 (d, J=6.97 Hz, 2H) 2.85-2.96 (m, 1H) 2.55-2.65 (m, 4H) 2.41 (s, 3H) 2.01-2.10 (m, 1H) 1.62 (s, 3H)

Example 42: Synthesis of 2-((S)-4-(4-chlorophenyl)-2,3,9-trimethyl-6H-thieno[3,2-f][1,2,4]triazolo[4,3-a][1,4]diazepin-6-yl)-N-(3-(2-(2-(2-((3-(2,6-dioxopiperidin-3-yl)-4-oxo-3,4-dihydrophthalazin-6-yl)amino)ethoxy)ethoxy)ethoxy)phenyl)acetamide

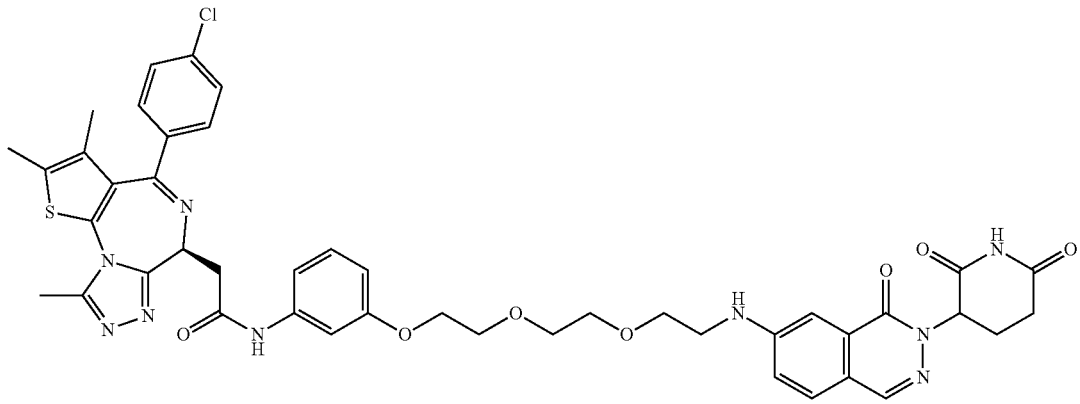 [SMILES: Cc1sc2c(c1C)C(c1ccc(Cl)cc1)=N[C@@H](CC(=O)Nc1cccc(OCCOCCOCCNc3ccc4cnn(C5CCC(=O)NC5=O)c(=O)c4c3)c1)c1nnc(C)n1-2]

The titled compound is synthesized through following procedure.

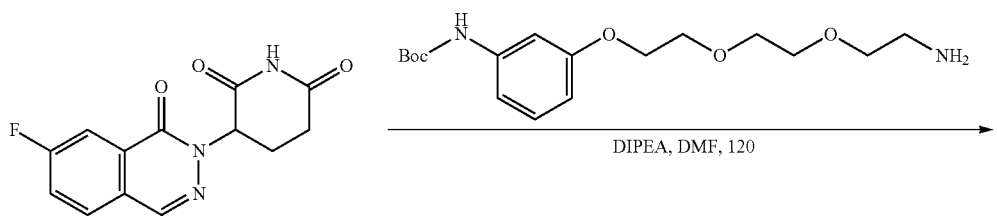

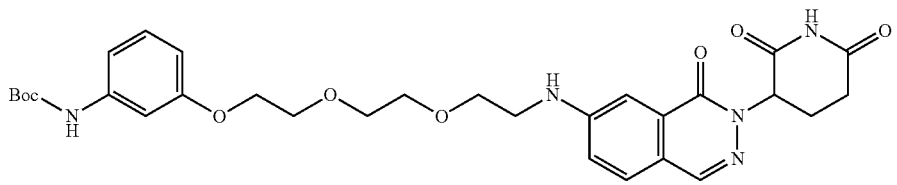

A solution of 3-(7-fluoro-1-oxophthalazin-2(1H)-yl)piperidine-2,6-dione (80.0 mg, 0.291 mmol), tert-butyl (3-(2-(2-(2-aminoethoxy)ethoxy)ethoxy)phenyl)carbazate (109.0 mg, 0.320 mmol) and DIPEA (363 µL, 2.03 mmol) in DMF (2 mL) was irritated on microwave at 120° C. for 5 hours. The reaction mixture was diluted with water and extracted with EtOAc. The organic layer was washed with brine, dried over MgSO$_4$, and concentrated. The residue was purified by column chromatography to give the product. (Yield: 80.0 mg, 46.21%). MS (ESI, m/z): [M+1]$^+$=[596.8]

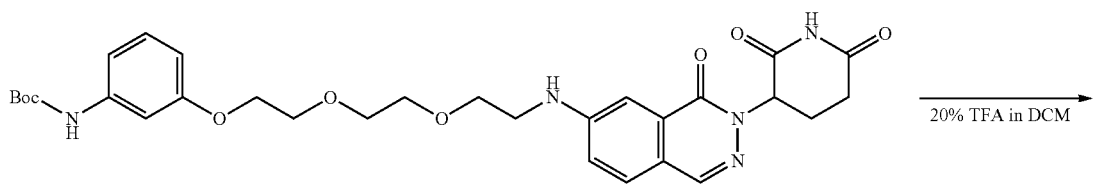

-continued

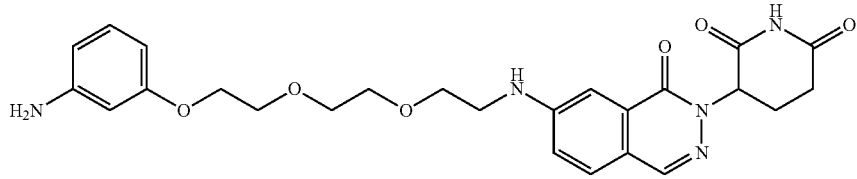

A solution of tert-butyl (3-(2-(2-(2-((3-(2,6-dioxopiperidin-3-yl)-4-oxo-3,4-dihydrophthalazin-6-yl)amino)ethoxy)ethoxy)ethoxy)phenyl)carbamate (80.0 mg, 0.134 mmol) in 20% TFA in DCM (1 mL) was stirred at room temperature. The reaction mixture was concentrated in vacuo and used for the next step without further purification. (Yield: 65.0 mg, 97.5%). MS (ESI, m/z): [M+$^1$]+=[496.8]

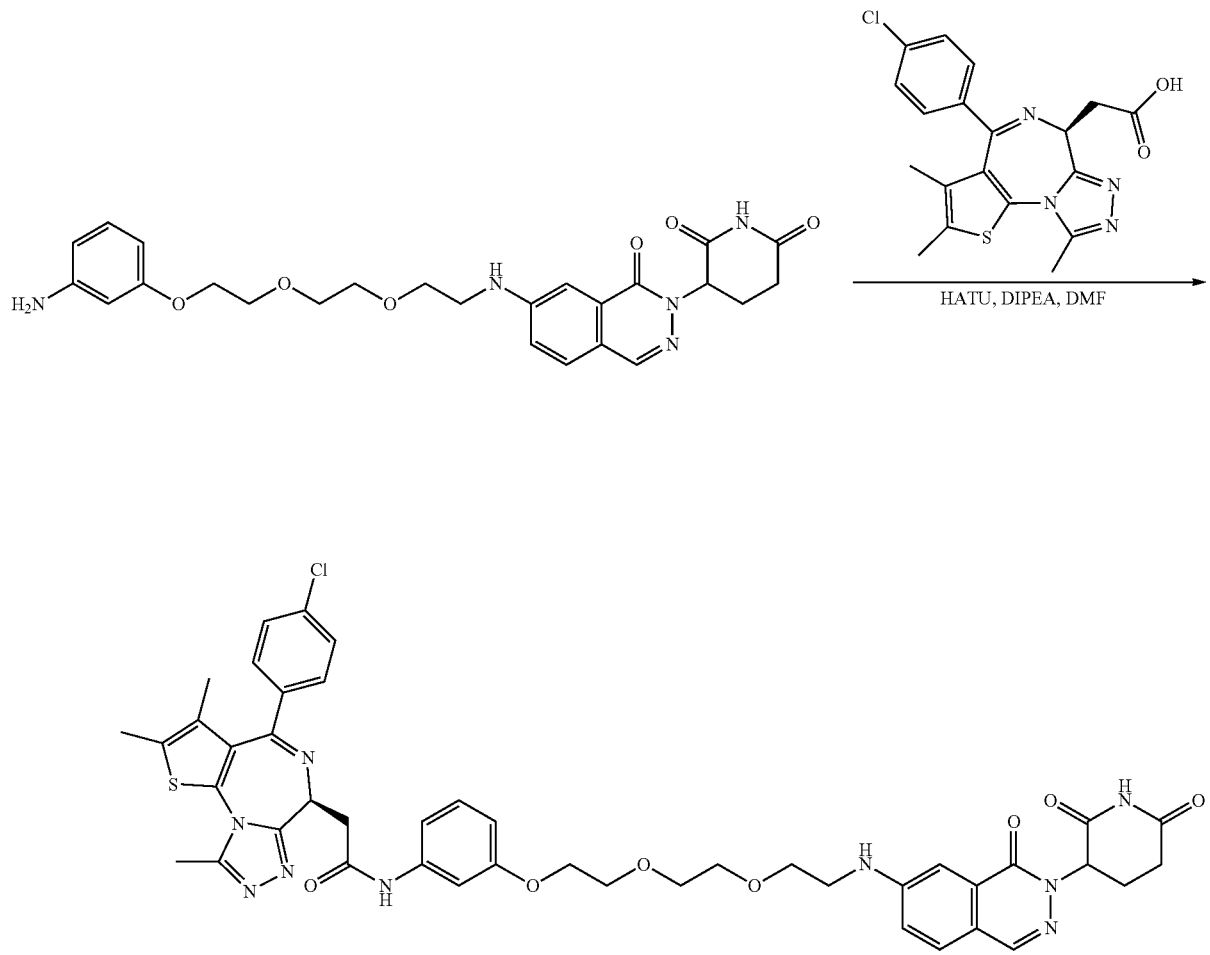

A solution of JQ-1 carboxylic acid (57.8 mg, 0.144 mmol), HATU (59.9 mg, 0.157 mmol) and DIPEA (0.12 ml, 0.656 mmol) in DMF (2 mL) was stirred at room temperature for 0.5 hour. 3-(7-((2-(2-(2-(3-aminophenoxy)ethoxy)ethoxy)ethyl)amino)-1-oxophthalazin-2(1H)-yl)piperidine-2,6-dione (65.0 mg, 0.131 mmol) was added. The mixture was stirred at room temperature overnight. The reaction mixture was diluted with water and extracted with ethyl acetate. The organic layer was washed with brine, dried over Na$_2$SO$_4$, and concentrated. The mixture was separated by column chromatography.

(yield: 54.0 mg, 46.8%)

MS (ESI, m/z): [M+$^1$]+=879.4

[NMR] 1H NMR (400 MHz, DMSO-d6) d ppm 11.00 (s, 1H) 10.31 (s, 1H) 8.13 (s, 1H) 7.61 (d, J=9.17 Hz, 1H) 7.34-7.52 (m, 6H) 7.10-7.26 (m, 4H) 6.92 (t, J=5.38 Hz, 1H) 6.62 (dd, J=7.89, 1.65 Hz, 1H) 5.74 (d, J=7.58 Hz, 1H) 4.56-4.64 (m, 1H) 3.98-4.08 (m, 2H) 3.67-3.78 (m, 2H) 3.54-3.67 (m, 6H) 3.50 (d, J=7.09 Hz, 2H) 2.82-2.97 (m, 2H) 2.54-2.65 (m, 4H) 2.37-2.45 (m, 3H) 2.00-2.13 (m, 1H) 1.52-1.68 (m, 3H)

Example 43: Synthesis of 2-((S)-4-(4-chlorophenyl)-2,3,9-trimethyl-6H-thieno[3,2-f][1,2,4]triazolo[4,3-a][1,4]diazepin-6-yl)-N-(2-((3-(2,6-dioxopiperidin-3-yl)-4-oxo-3,4-dihydrophthalazin-5-yl)amino)ethyl)acetamide

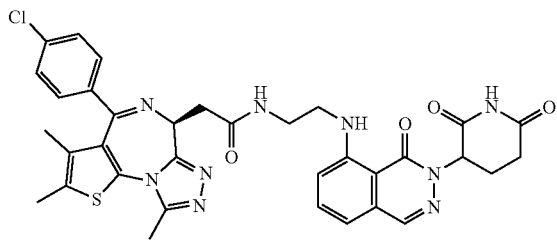 [SMILES: Cc1sc2c(c1C)C(c1ccc(Cl)cc1)=N[C@@H](CC(=O)NCCNc1cccc3cnn(C4CCC(=O)NC4=O)c(=O)c13)c1nnc(C)n1-2]

The titled compound is synthesized through following procedure.

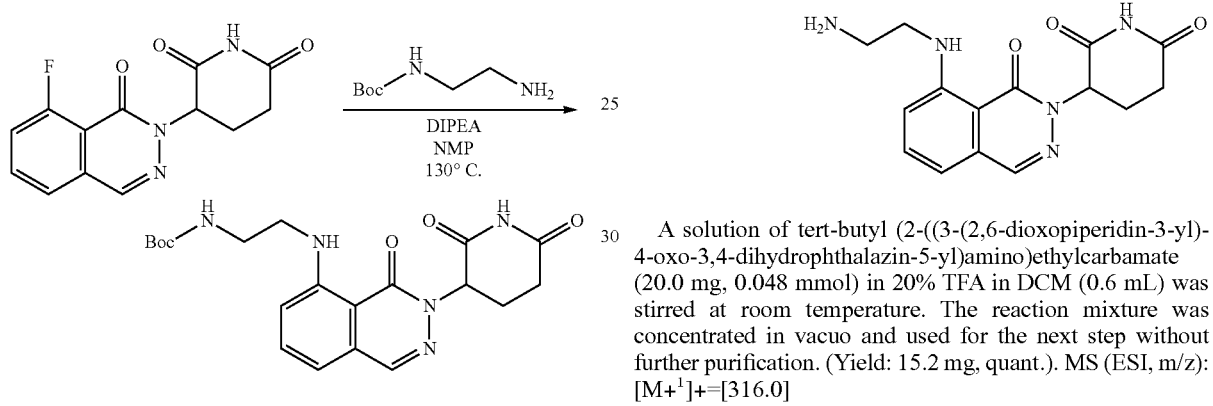

A solution of 3-(8-fluoro-1-oxophthalazin-2(1H)-yl)piperidine-2,6-dione (56.0 mg, 0.203 mmol), tert-butyl (2-aminoethyl)carbamate (48.9 mg, 0.305 mmol) and DIPEA (0.134 mL, 0.814 mmol) in NMP (1 mL) was stirred for 3 hours at 130° C. The reaction mixture was purified by reverse column chromatography to give the product (Yield: 68 mg, 80.5%). MS (ESI, m/z): [M+$^1$]+=[416.0]

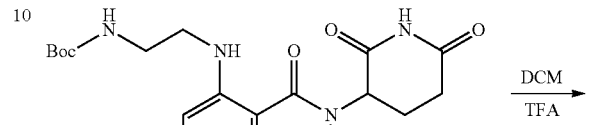

A solution of tert-butyl (2-((3-(2,6-dioxopiperidin-3-yl)-4-oxo-3,4-dihydrophthalazin-5-yl)amino)ethylcarbamate (20.0 mg, 0.048 mmol) in 20% TFA in DCM (0.6 mL) was stirred at room temperature. The reaction mixture was concentrated in vacuo and used for the next step without further purification. (Yield: 15.2 mg, quant.). MS (ESI, m/z): [M+$^1$]+=[316.0]

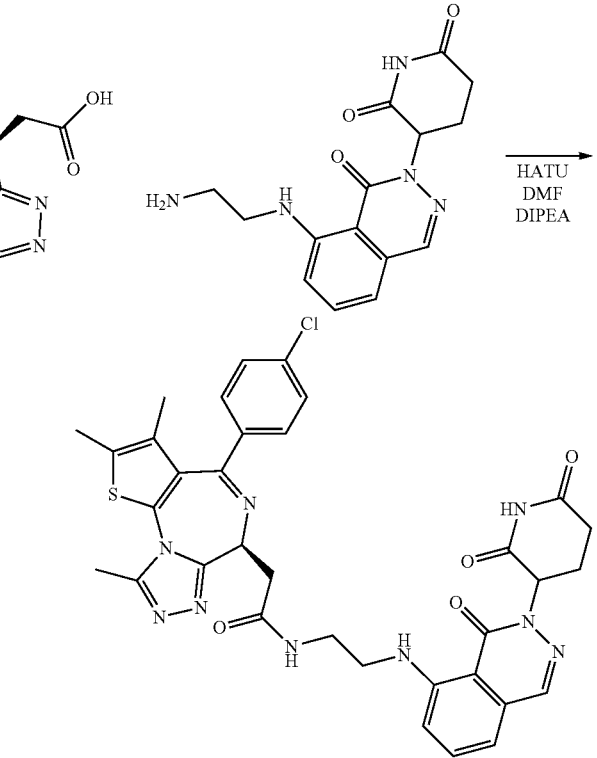

To a solution of 3-(8-((2-aminoethyl)amino)-1-oxophthalazin-2(1H)-yl)piperidine-2,6-dione (15.2 mg, 0.048 mmol), JQ-1 carboxylic acid (19.3 mg, 0.048 mmol), DIPEA (0.052 ml, 0.288 mmol) in DMF (0.5 mL) was added HATU (21.9 mg, 0.058 mmol) at 0° C. and the mixture was stirred at room temperature for 16 hours. The reaction mixture was purified by reverse column chromatography to give the product. (Yield: 18 mg, 53.7%).

1H NMR (400 MHz, DMSO-d6) δ=11.03 (s, 1H), 8.83 (t, J=5.14 Hz, 1H), 8.51 (s, 1H), 8.24 (s, 1H), 7.66 (t, J=7.90 Hz, 1H), 7.49-7.38 (m, 4H), 7.03 (d, J=8.5 Hz, 1H), 6.94 (d, J=7.6 Hz, 1H), 5.67 (m, 1H), 4.53 (m, 1H), 3.31 (m, 2H), 3.26 (m, 4H), 2.93-2.82 (m, 1H), 2.63-2.53 (m, 5H), 2.41 (s, 3H), 2.05 (m, 1H), 1.61 (s, 3H).

MS (ESI, m/z): [M+$^1$]+=698.2 and 700.2

Example 44: 2-((S)-4-(4-chlorophenyl)-2,3,9-trimethyl-6H-thieno[3,2-f][1,2,4]triazolo[4,3-a][1,4]diazepin-6-yl)-N-(2-((2-(2,6-dioxopiperidin-3-yl)-1-oxo-1,2-dihydrophthalazin-5-yl)amino)ethyl)acetamide

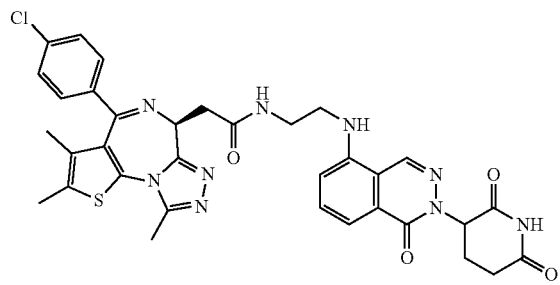 [SMILES: Cc1sc2c(c1C)C(c1ccc(Cl)cc1)=N[C@@H](CC(=O)NCCNc1cccc3c(=O)n(C4CCC(=O)NC4=O)ncc13)c1nnc(C)n1-2]

The titled compound is synthesized through following procedure.

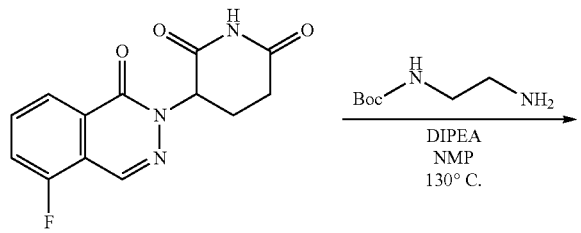

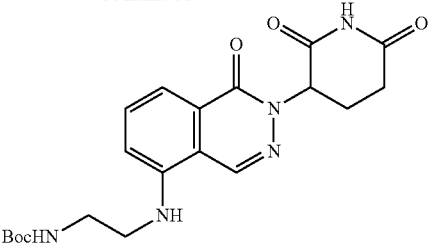

A solution of 3-(5-fluoro-1-oxophthalazin-2(1H)-yl)piperidine-2,6-dione (56.0 mg, 0.203 mmol), tert-butyl (2-aminoethyl)carbamate (48.9 mg, 0.305 mmol) and DIPEA (0.134 mL, 0.814 mmol) in NMP (1 mL) was stirred for 3 hours at 130° C. The reaction mixture was purified by reverse column chromatography to give the product (Yield: 27.2 mg, 32.2%). MS (ESI, m/z): [M+$^1$]+=[416.0]

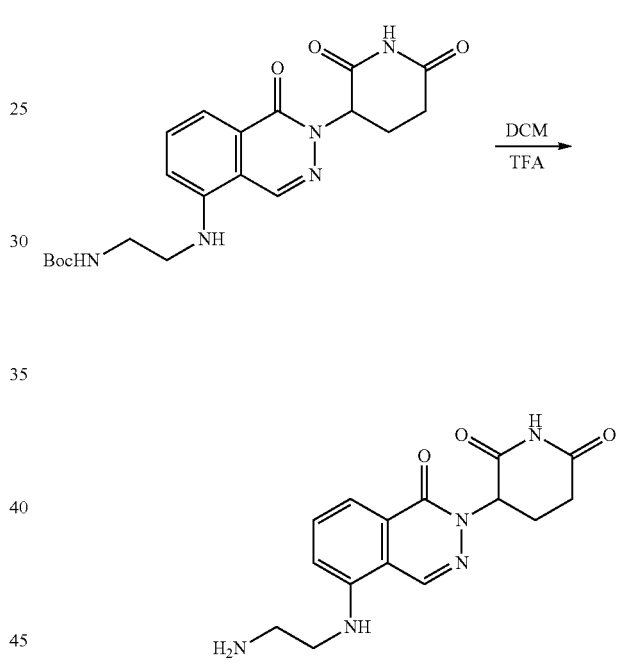

To a tert-butyl (2-((2-(2,6-dioxopiperidin-3-yl)-1-oxo-1,2-dihydrophthalazin-5-yl)amino)ethyl)carbamate (15 mg, 0.036 mmol) in 20% TFA in DCM (0.6 mL), and stirred at room temperature. The reaction mixture was concentrated in vacuo and used for the next step without further purification. (yield: 11.4 mg, quant.). MS (ESI, m/z): [M+$^1$]+=[316.0]

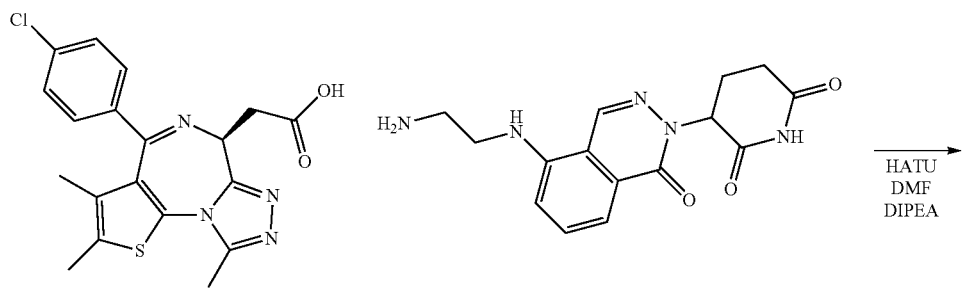

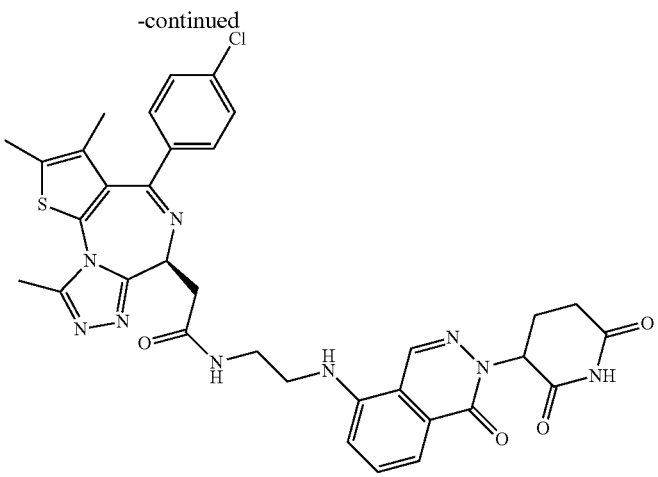

To a solution of 3-(5-((2-aminoethyl)amino)-1-oxophthalazin-2(1H)-yl)piperidine-2,6-dione (11.4 mg, 0.036 mmol), JQ-1 carboxylic acid (18.8 mg, 0.044 mmol), DIPEA (0.0378 ml, 0.217 mmol) in DMF (0.5 mL) was added HATU (20.6 mg, 0.054 mmol) at 0° C. and the mixture was stirred at room temperature for 16 hours. The reaction mixture was purified by reverse column chromatography to give the product. (Yield: 14 mg, 55.5%).

1H NMR (400 MHz, DMSO-d6) δ=11.03 (s, 1H), 8.53 (m, 2H), 7.62 (t, J=7.9 Hz, 1H), 7.45-7.38 (m, 5H), 7.08 (d, J=8.3 Hz, 1H), 6.90 (m, 1H), 5.73 (m, 1H), 4.53 (m, 1H), 3.31 (m, 2H), 3.32-3.26 (m, 4H), 2.93-2.82 (m, 1H), 2.63-2.53 (m, 5H), 2.41 (s, 3H), 2.05 (m, 1H), 1.59 (s, 3H).

MS (ESI, m/z): [M+$^1$]+=698.2 and 700.2

Example 45: Synthesis of 2-((S)-4-(4-chlorophenyl)-2,3,9-trimethyl-6H-thieno[3,2-f][1,2,4]triazolo[4,3-a][1,4]diazepin-6-yl)-N-(2-((3-(2,6-dioxopiperidin-3-yl)-4-oxo-3,4-dihydrophthalazin-5-yl)oxy)ethyl)acetamide

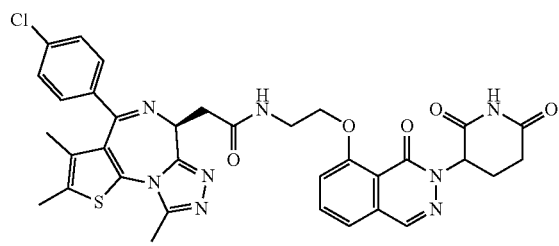 [SMILES: Cc1sc2c(c1C)C(c1ccc(Cl)cc1)=N[C@@H](CC(=O)NCCOc1cccc3cnn(C4CCC(=O)NC4=O)c(=O)c13)c1nnc(C)n1-2]

The titled compound is synthesized through following procedure.

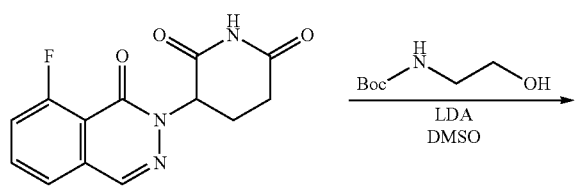

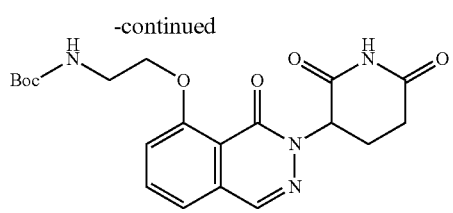

A solution of 3-(8-fluoro-1-oxophthalazin-2(1H)-yl)piperidine-2,6-dione (30.0 mg, 0.109 mmol) and tert-butyl (2-hydroxyethyl)carbamate (35.1 mg, 0.218 mmol) in DMSO (1 mL) was added LDA (1M sol. 0.218 ml, 0.218 mmol) at 0° C. and the mixture was stirred for 2 hours at room temperature. The reaction mixture was purified by reverse column chromatography to give the product. (Yield: 29.1 mg, 64.1%). MS (ESI, m/z): [M+$^1$]+=[417.0]

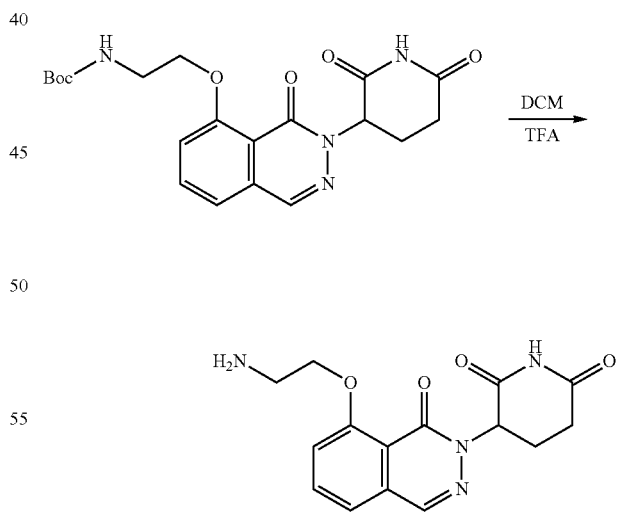

A solution of tert-butyl (2-((3-(2,6-dioxopiperidin-3-yl)-4-oxo-3,4-dihydrophthalazin-5-yl)oxy)ethyl)carbamate (15 mg, 0.036 mmol) in 20% TFA in DCM (0.6 mL) was stirred at room temperature. The reaction mixture was concentrated in vacuo and used for the next step without further purification. (Yield: 11.4 mg, quant.). MS (ESI, m/z): [M+$^1$]+=[317.0]

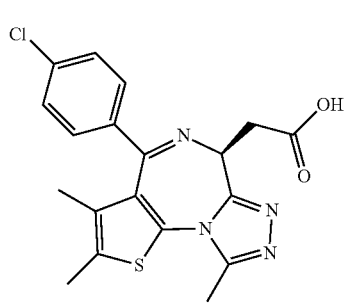
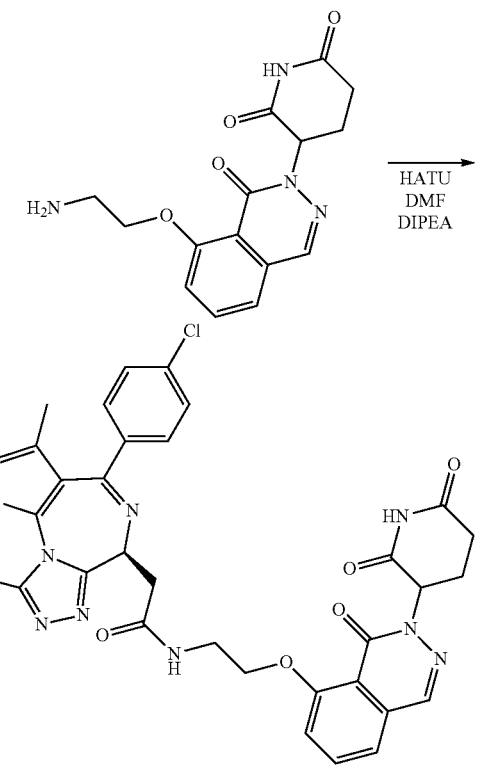

To a solution of 3-(8-(2-aminoethoxy)-1-oxophthalazin-2(1H)-yl)piperidine-2,6-dione (11.4 mg, 0.036 mmol), JQ-1 carboxylic acid (18.8 mg, 0.047 mmol), DIPEA (0.038 ml, 0.217 mmol) in DMF (0.5 mL) was added HATU (20.6 mg, 0.054 mmol) at 0° C. and the mixture was stirred at room temperature for 1 hour at room temperature. The reaction mixture was purified by reverse column chromatography to give the product (Yield: 16.7 mg, 66%).

1H NMR (400 MHz, DMSO-d6) δ=11.06 (d, J=9.8 Hz, 1H), 8.51 (m, 1H), 8.36 (s, 1H), 7.89 (t, J=8.0 Hz, 1H), 7.51 (m, 2H), 7.39 (m, 4H), 5.67 (m, 1H), 4.52 (m, 1H), 4.20 (m, 2H), 3.57 (m, 2H), 3.33-3.25 (m, 2H), 2.93-2.82 (m, 1H), 2.63-2.53 (m, 5H), 2.41 (s, 3H), 2.05 (m, 1H), 1.60 (s, 3H).
MS (ESI, m/z): [M+$^1$]+=699.2 and 701.2

Example 46: Synthesis of 2-((S)-4-(4-chlorophenyl)-2,3,9-trimethyl-6H-thieno[3,2-f][1,2,4]triazolo[4,3-a][1,4]diazepin-6-yl)-N-(2-((2-(2,6-dioxopiperidin-3-yl)-1-oxo-1,2-dihydrophthalazin-5-yl)oxy)ethyl)acetamide

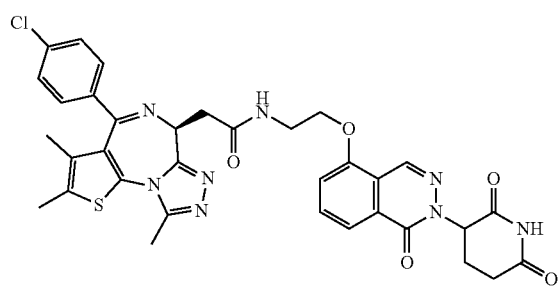 [SMILES: Cc1sc2c(c1C)C(c1ccc(Cl)cc1)=N[C@@H](CC(=O)NCCOc1cccc3c(=O)n(C4CCC(=O)NC4=O)ncc13)c1nnc(C)n1-2]

The titled compound is synthesized through following procedure.

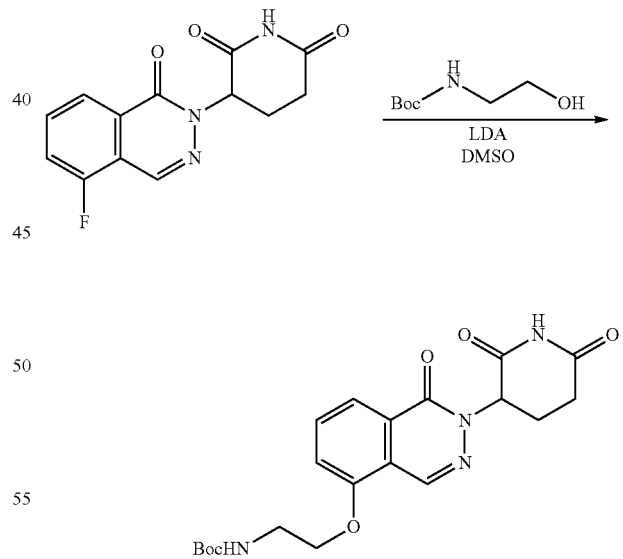

To a solution of 3-(5-fluoro-1-oxophthalazin-2(1H)-yl)piperidine-2,6-dione (30.0 mg, 0.109 mmol) and tert-butyl (2-hydroxyethyl)carbamate (35.1 mg, 0.218 mmol) in DMSO (1 mL) was added LDA (1M sol. 0.218 ml, 0.218 mmol) at 0° C. and the mixture was stirred for 2 hours at room temperature. The reaction mixture was purified by reverse column chromatography to give the product. (yield: 13.1 mg, 28.9%) MS (ESI, m/z): [M+$^1$]+=[439.0]

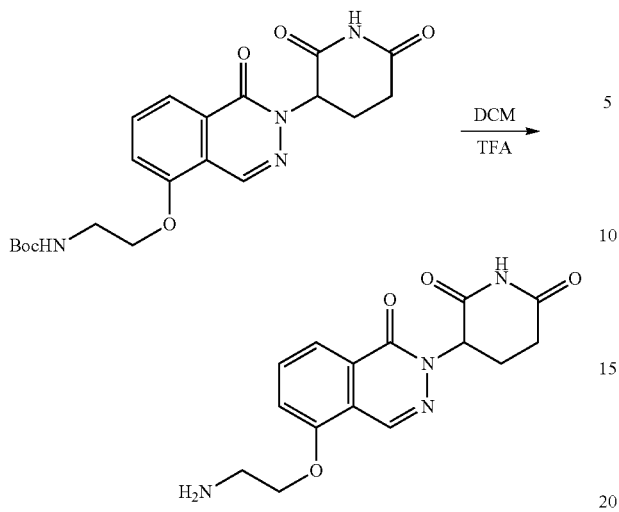

A solution of tert-butyl (2-((2-(2,6-dioxopiperidin-3-yl)-1-oxo-1,2-dihydrophthalazin-5-yl)oxy)ethyl)carbamate (13.1 mg, 0.032 mmol) in 20% TFA in DCM (0.6 mL) was stirred at room temperature. The reaction mixture was concentrated in vacuo and used for the next step without further purification. (Yield: 9.9 mg, quant.). MS (ESI, m/z): [M+$^1$]+=[317.0]

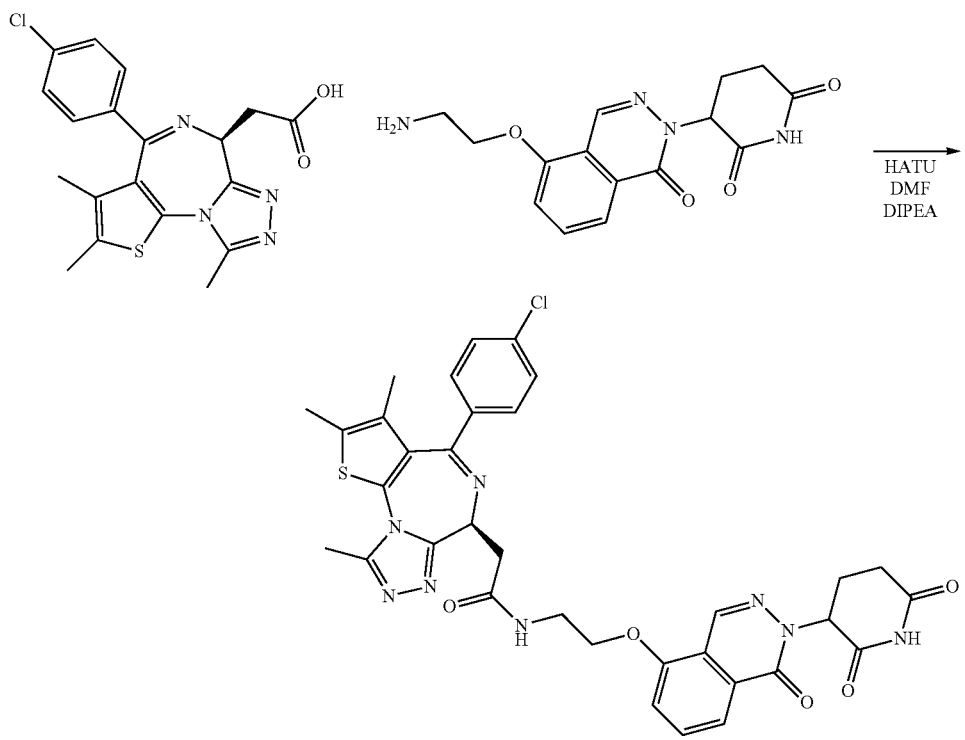

To a solution of 3-(5-(2-aminoethoxy)-1-oxophthalazin-2(1H)-yl)piperidine-2,6-dione (9.9 mg, 0.032 mmol), JQ-1 carboxylic acid (16.4 mg, 0.041 mmol), DIPEA (0.033 ml, 0.189 mmol) in DMF (0.5 mL) was added HATU (18 mg, 0.047 mmol) at 0° C. and the mixture was stirred at room temperature for 16 hours. The reaction mixture was purified by reverse column chromatography to give the product. (Yield: 17 mg, 77%).

1H NMR (400 MHz, DMSO-d6) δ=11.06 (s, 1H), 8.62 (brs, 1H), 8.59 (m, 1H), 7.82 (m, 2H), 7.55 (m, 1H), 7.40-7.25 (m, 4H), 5.79 (m, 1H), 4.54 (m, 1H), 4.20 (m, 2H), 3.79-3.50 (m, 2H), 3.35-3.20 (m, 2H), 2.93-2.82 (m, 1H), 2.63-2.53 (m, 5H), 2.40 (s, 3H), 2.07 (m, 1H), 1.57 (s, 3H).

MS (ESI, m/z): [M+$^1$]+=699.2 and 701.2

Example 47: Synthesis of N-(4-(2-(2,6-dioxopiperidin-3-yl)-1-oxo-1,2-dihydrophthalazin-6-yl)butyl)-2-((S)-2,3,9-trimethyl-4-phenyl-6H-thieno[3,2-f][1,2,4]triazolo[4,3-a][1,4]diazepin-6-yl)acetamide The titled compound is synthesized through following procedure.

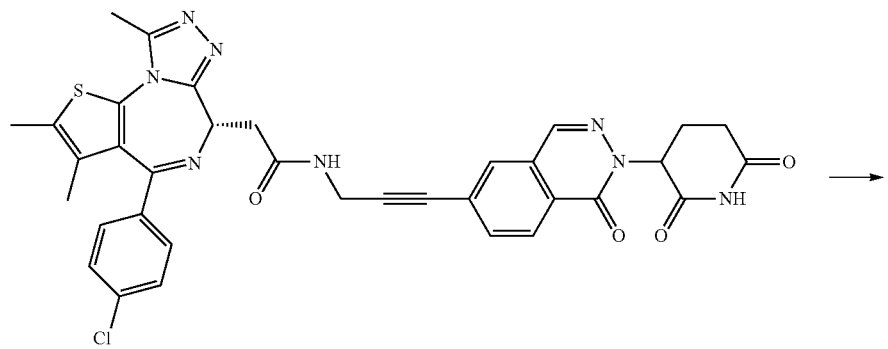

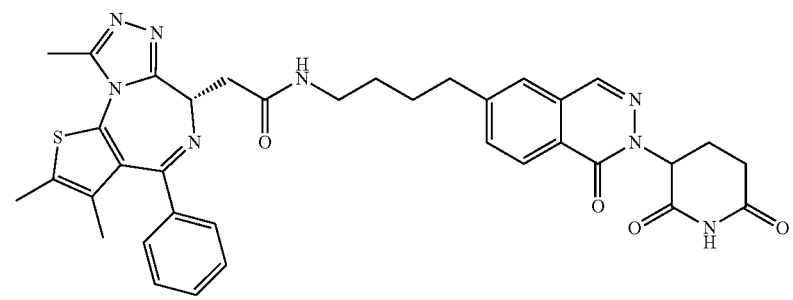

To a solution of 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-{3-[2-(2,6-dioxopiperidin-3-yl)-1-oxo-1,2-dihydrophthalazin-6-yl]prop-2-yn-1-yl}acetamide (11.0 mg, 0.012 mmol) in MeOH (10 mL) was added 10% Pd/C (5 mg) with a H$_2$ balloon. The reaction mixture was stirred for 4 hours. After filtration of solid material, the filtrate was concentrated under reduced pressure. The residue was purified by column chromatograph to afford the titled compound as a white-off oil (yield 8.2 mg; 78.0%)

MS (ESI, m/z): [M+$^1$]+=663.2.

$^1$H NMR (400 MHz, DMSO-d$_6$) δ 11.15 (s, 1H), 8.45 (s, 1H), 8.20 (d, J=2.3 Hz, 2H), 7.80 (s, 1H), 7.75 (d, J=2.3 Hz, 2H), 7.42 (m, 3H), 5.75 (br, 1H), 4.52 (m, 1H), 3.25-3.27 (m, 2H), 3.17 (m, 2H), 2.75-2.80 (m, 2H), 2.50-2.62 (m, 6H), 1.75 (m, 1H), 1.58 (m, 2H), 1.56 (s, 3H), 1.24 (s, 6H).

Example 48: Synthesis of 2-((S)-4-(4-chlorophenyl)-2,3,9-trimethyl-6H-thieno[3,2-f][1,2,4]triazolo[4,3-a][1,4]diazepin-6-yl)-N-(2-(4-(2-(2,6-dioxopiperidin-3-yl)-1-oxo-1,2-dihydrophthalazin-6-yl)piperazin-1-yl)ethyl)acetamide

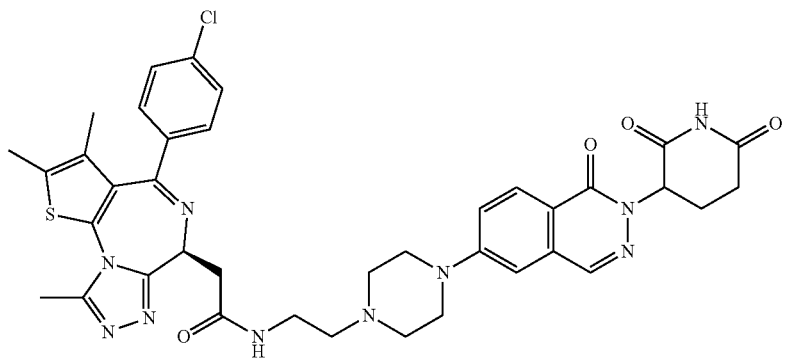 [SMILES: Cc1sc2c(c1C)C(c1ccc(Cl)cc1)=N[C@@H](CC(=O)NCCN1CCN(c3ccc4c(=O)n(C5CCC(=O)NC5=O)ncc4c3)CC1)c1nnc(C)n1-2]

The titled compound is synthesized through following procedure.

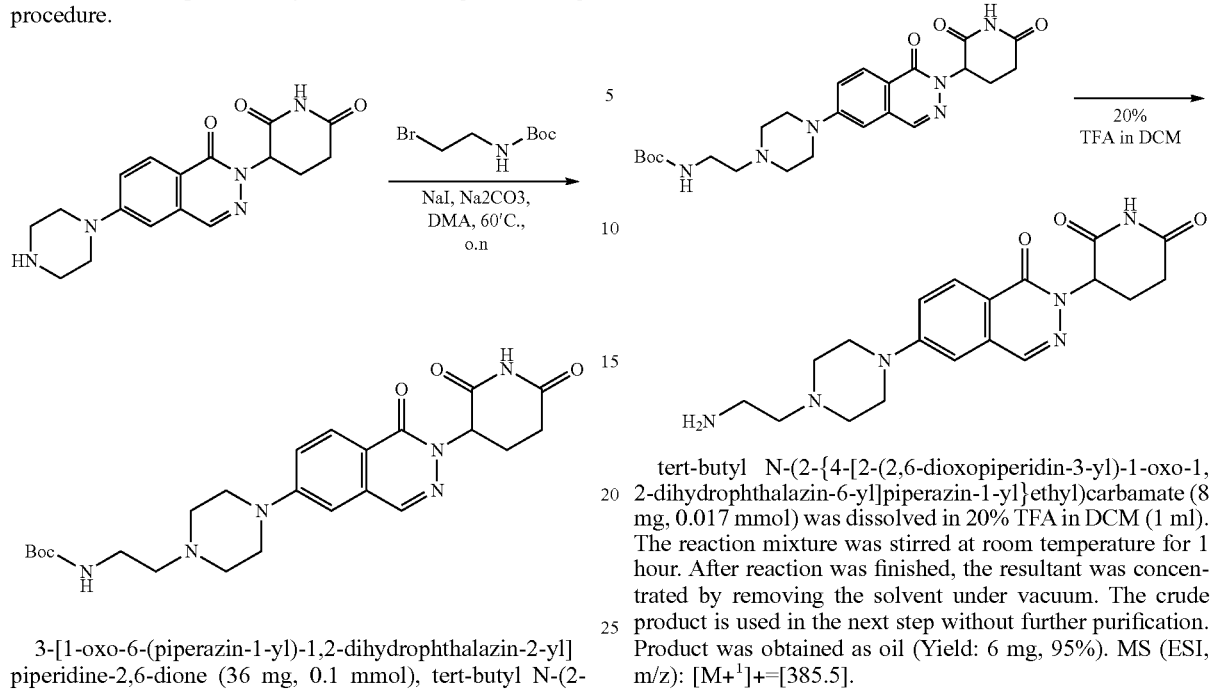

3-[1-oxo-6-(piperazin-1-yl)-1,2-dihydrophthalazin-2-yl]piperidine-2,6-dione (36 mg, 0.1 mmol), tert-butyl N-(2-bromoethyl)carbamate (35.4 mg, 0.16 mmol), sodium iodide (31.6 mg, 0.21 mmol), Sodium Carbonate (33.5 mg, 0.32 mmol) were dissolved in DMAC (1 ml). The reaction mixture was stirred at 60° C. for 3 hours. After reaction was finished, the mixture was extracted with EtOAc and water. The organic layer was concentrated under vacuum. The reaction mixture was purified by MPLC. Product was obtained as yellow solid. (Yield: 8 mg, 16%). MS (ESI, m/z): [M+$^1$]+=[485.5].

tert-butyl N-(2-{4-[2-(2,6-dioxopiperidin-3-yl)-1-oxo-1,2-dihydrophthalazin-6-yl]piperazin-1-yl}ethyl)carbamate (8 mg, 0.017 mmol) was dissolved in 20% TFA in DCM (1 ml). The reaction mixture was stirred at room temperature for 1 hour. After reaction was finished, the resultant was concentrated by removing the solvent under vacuum. The crude product is used in the next step without further purification. Product was obtained as oil (Yield: 6 mg, 95%). MS (ESI, m/z): [M+$^1$]+=[385.5].

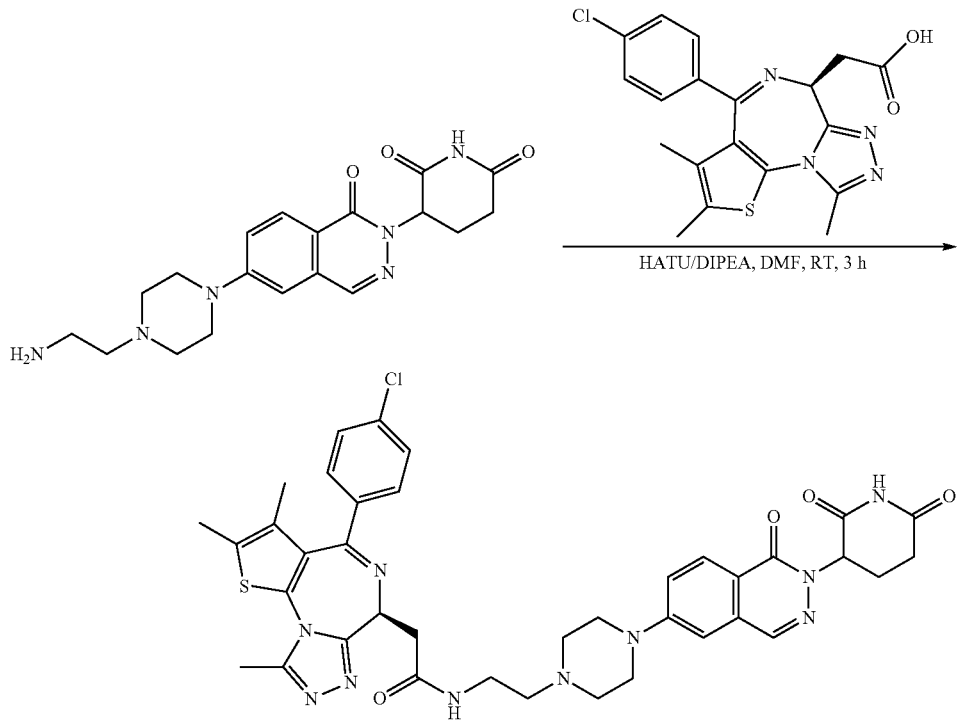

JQ-1 carboxylic acid (6.9 mg, 0.017 mmol), HATU (7.12 mg, 0.19 mmol) and DIPEA (113 μL, 0.63 mmol) were dissolved in DMF (1.5 ml) and the mixture was stirred for 1 hour at room temperature. 3-{6-[4-(2-aminoethyl)piperazin-1-yl]-1-oxo-1,2-dihydrophthalazin-2-yl}piperidine-2,6-dione (6 mg, 0.016 mmol) was added to reaction mixture. The mixture was stirred at room temperature for overnight. The reaction mixture was diluted with water and extracted with EA. The organic layer was washed with brine, dried over Na$_2$SO$_4$, and concentrated. Product was purified by MPLC (MC/Me 0→10%). Product was obtained as white solid (Yield: 7 mg, 59%).

MS (ESI, m/z): [M+$^1$]+=768.3

[NMR] $^1$H NMR (400 MHz, DMSO-d$_6$) δ ppm 11.01 (s, 1H) 8.18-8.28 (m, 3H) 8.04 (d, J=9.05 Hz, 1H) 7.39-7.53 (m, 5H) 7.25 (s, 1H) 5.75 (dd, J=12.10, 5.38 Hz, 1H) 4.51 (t, J=6.91 Hz, 1H) 3.19-3.28 (m, 8H) 2.85-2.98 (m, 1H) 2.54-2.66 (m, 9H) 2.40 (s, 3H) 2.08 (d, J=9.54 Hz, 1H) 1.62 (s, 3H)

Example 49: Synthesis of 2-((S)-4-(4-chlorophenyl)-2,3,9-trimethyl-6H-thieno[3,2-f][1,2,4]triazolo[4,3-a][1,4]diazepin-6-yl)-N-(2-(4-(3-(2,6-dioxopiperidin-3-yl)-4-oxo-3,4-dihydrophthalazin-6-yl)piperazin-1-yl)ethyl)acetamide

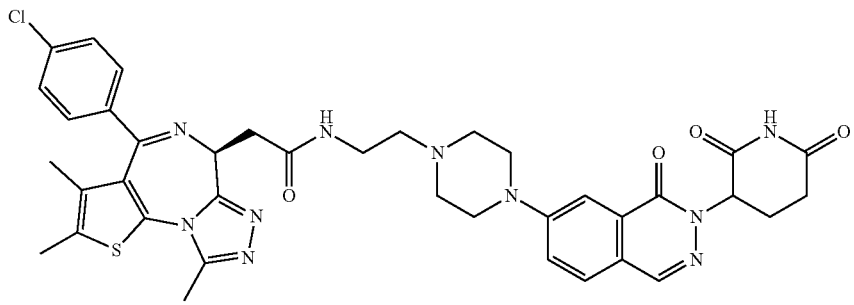 [SMILES: Cc1sc2c(c1C)C(c1ccc(Cl)cc1)=N[C@@H](CC(=O)NCCN1CCN(c3ccc4cnn(C5CCC(=O)NC5=O)c(=O)c4c3)CC1)c1nnc(C)n1-2]

The titled compound is synthesized through following procedure.

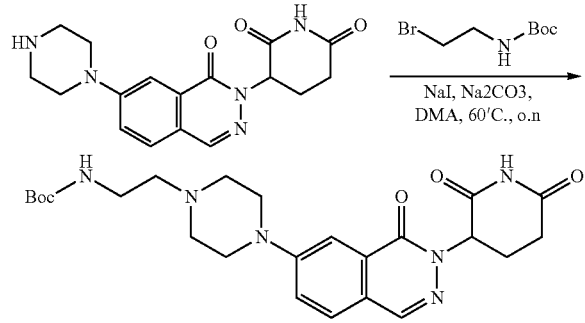

3-(1-oxo-7-(piperazin-1-yl)phthalazin-2(1H)-yl)piperidine-2,6-dione (41 mg, 0.12 mmol), tert-butyl N-(2-bromoethyl)carbamate (40.4 mg, 0.18 mmol), sodium iodide (36.0 mg, 0.24 mmol), Sodium Carbonate (38.5 mg, 0.36 mmol) were dissolved in DMAC (1 ml). The reaction mixture was stirred at 60° C. for 3 hours. After reaction was finished, the mixture was extracted with EtOAc and water. The organic layer was concentrated under vacuum. The reaction mixture was purified by MPLC. Product was obtained as yellow solid. (Yield: 10 mg, 18%). MS (ESI, m/z): [M+$^1$]+=[485.5].

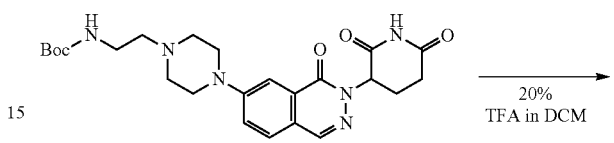

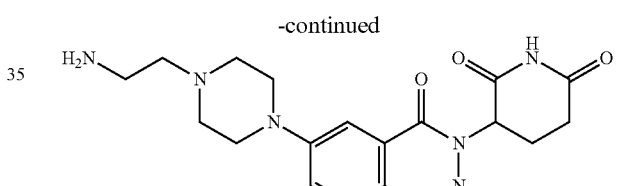

tert-butyl (2-(3-(2,6-dioxopiperidin-3-yl)-4-oxo-3,4-dihydrophthalazin-6-yl)piperazin-1-yl)ethyl)carbamate (10 mg, 0.021 mmol) was dissolved in 20% TFA in DCM (1 ml). The reaction mixture was stirred at room temperature for 1 hour. After reaction was finished, the resultant was concentrated by removing solvent under vacuum. The crude product is used in the next step without further purification. Product was obtained as oil (Yield: 8 mg, 100%). MS (ESI, m/z): [M+1]$^+$=[385.5].

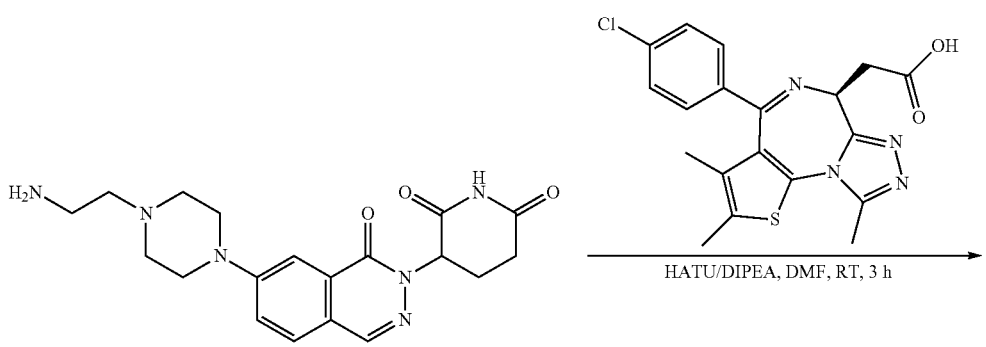

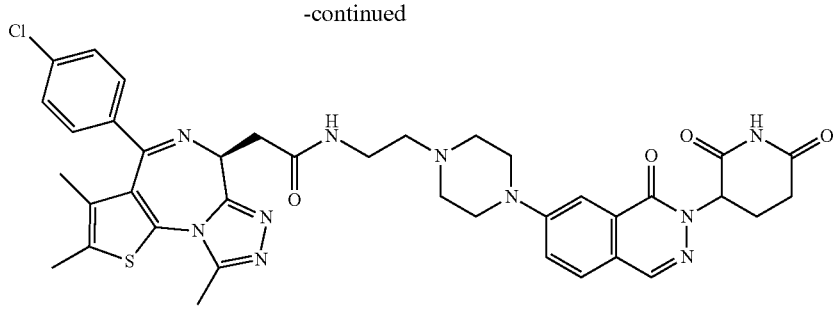

JQ-1 carboxylic acid (9.2 mg, 0.023 mmol), HATU (9.5 mg, 0.25 mmol) and DIPEA (0.015 mL, 0.083 mmol) were dissolved in DMF (1.5 ml) and the mixture was stirred for 1 hour at room temperature. 3-(7-(4-(2-aminoethyl)piperazin-1-yl)-1-oxophthalazin-2(1H)-yl)piperidine-2,6-dione (8 mg, 0.021 mmol) was added to reaction mixture. The mixture was stirred at room temperature for overnight. The reaction mixture was diluted with water and extracted with EA. The organic layer was washed with brine, dried over $Na_2SO_4$, and concentrated. Product was purified by MPLC. Product was obtained as white solid (Yield: 8 mg, 51%).

MS (ESI, m/z): [M+[1]]+=768.3

[NMR] $^1$H NMR (400 MHz, DMSO-$d_6$) δ ppm 11.02 (s, 1H) 8.18-8.30 (m, 2H) 7.79 (d, J=8.93 Hz, 1H) 7.61 (d, J=8.80 Hz, 1H) 7.38-7.53 (m, 6H) 5.77 (br. s., 1H) 4.51 (t, J=7.09 Hz, 1H) 3.19-3.28 (m, 8H) 2.86-3.00 (m, 1H) 2.54-2.65 (m, 9H) 2.40 (s, 3H) 2.10 (br. s., 1H) 1.62 (s, 3H)

Example 50: Synthesis of 2-((S)-4-(4-chlorophenyl)-2,3,9-trimethyl-6H-thieno[3,2-f][1,2,4]triazolo[4,3-a][1,4]diazepin-6-yl)-N-((1-(3-(2,6-dioxopiperidin-3-yl)-4-oxo-3,4-dihydrophthalazin-5-yl)pyrrolidin-3-yl)methyl)acetamide The titled compound is synthesized through following procedure:

50-1) Synthesis of tert-butyl 3-((2-(((S)-4-(4-chlorophenyl)-2,3,9-trimethyl-6H-thieno[3,2-f][1,2,4]triazolo[4,3-a][1,4]diazepin-6-yl)acetamido)methyl)pyrrolidin-1-carboxylate

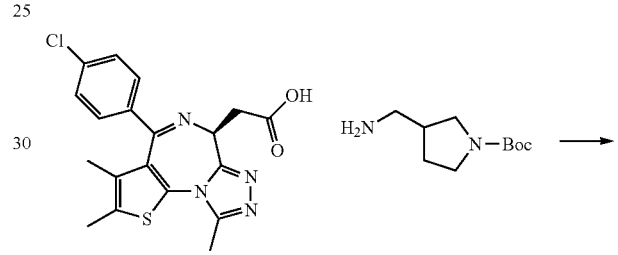

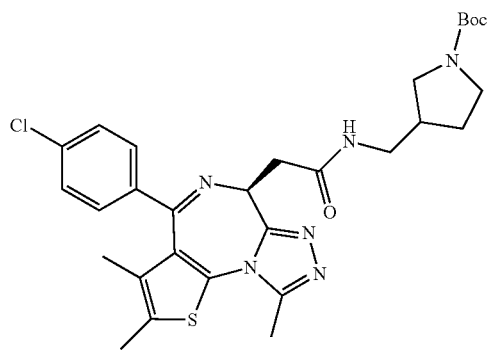

To a solution of JQ-1 carboxylic acid (98.9 mg, 0.247 mmol), tert-butyl 3-(aminomethyl)pyrrolidine-1-carboxylate (38 mg, 0.190 mmol) and DIPEA (0.132 ml, 0.759 mmol) in DMF (1 mL) was added HATU (86.6 mg, 0.228 mmol) at 0° C. and the mixture was stirred at room temperature for 1 hour. The reaction mixture was purified by reverse column chromatography to give the product. (Yield: 105 mg, 95%).

MS (ESI, m/z): [M+[1]]+=[583.2] and [585.2]

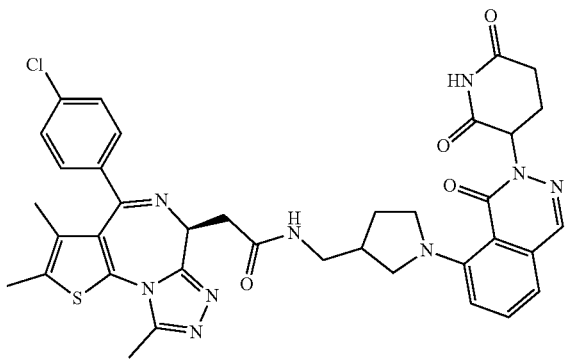 [SMILES: Cc1sc2c(c1C)C(c1ccc(Cl)cc1)=N[C@@H](CC(=O)NCC1CCN(c3cccc4cnn(C5CCC(=O)NC5=O)c(=O)c34)C1)c1nnc(C)n1-2]

50-2) Synthesis of 2-((S)-4-(4-chlorophenyl)-2,3,9-trimethyl-6H-thieno[3,2-f][1,2,4]triazolo[4,3-a][1,4]diazepin-6-yl)-N-(pyrrolidin-3-ylmethyl)acetamide

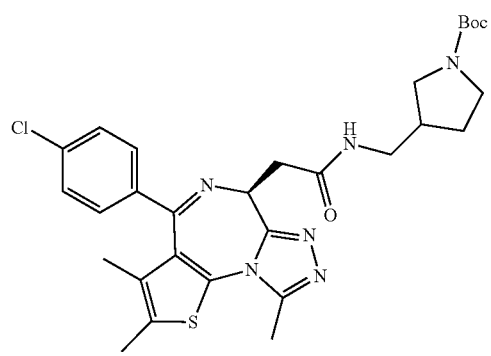

A solution of tert-butyl 3-((2-((S)-4-(4-chlorophenyl)-2,3,9-trimethyl-6H-thieno[3,2-f][1,2,4]triazolo[4,3-a][1,4]diazepin-6-yl)acetamido)methyl)pyrrolidine-1-carboxylate (30 mg, 0.050 mmol) in 20% TFA in DCM (0.6 mL) was stirred at room temperature. The reaction mixture was concentrated in vacuo and used for the next step without further purification. (Yield: 24.8 mg, quant.).

MS (ESI, m/z): [M+1]$^+$=[483.0] and [485.0]

50-3) Synthesis of 2-((S)-4-(4-chlorophenyl)-2,3,9-trimethyl-6H-thieno[3,2-f][1,2,4]triazolo[4,3-a][1,4]diazepin-6-yl)-N-((1-(3-(2,6-dioxopiperidin-3-yl)-4-oxo-3,4-dihydrophthalazin-5-yl)pyrrolidin-3-yl)methyl)acetamide

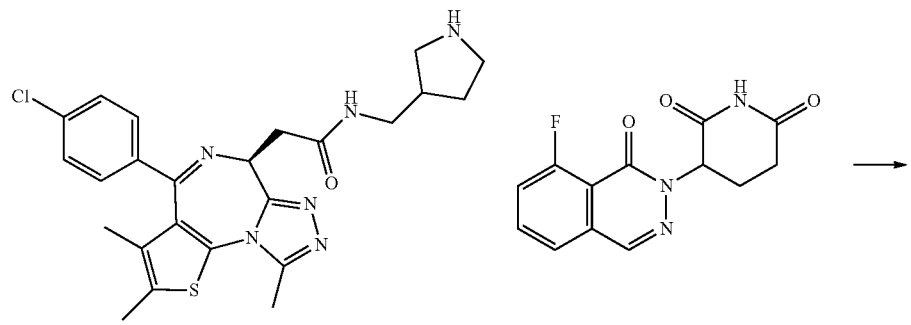

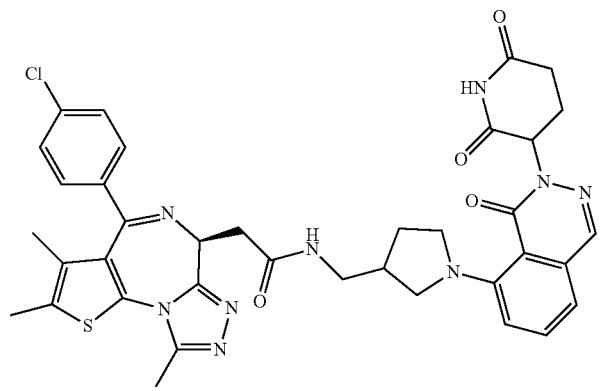

-continued

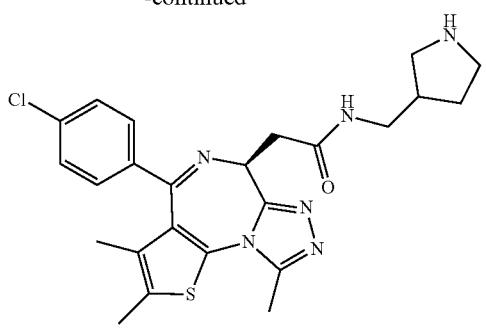

A solution of 2-((S)-4-(4-chlorophenyl)-2,3,9-trimethyl-6H-thieno[3,2-f][1,2,4]triazolo[4,3-a][1,4]diazepin-6-yl)-N-(pyrrolidin-3-ylmethyl)acetamide (24.8 mg, 0.051 mmol), 3-(8-fluoro-1-oxophthalazin-2(1H)-yl)piperidine-2,6-dione (14.1 mg, 0.051 mmol) and DIPEA (0.089 mL, 0.513 mmol) in NMP (1 mL) was stirred for 16 hours at 120° C. The reaction mixture was purified by reverse column chromatography to give the product.

(yield: 21 mg, 55.4%)

1H NMR (400 MHz, DMSO-d6) δ=10.98 (s, 1H), 8.39 (m, 1H), 8.19 (t. J=2.8 Hz, 1H), 7.65 (m, 1H), 7.45-7.35 (m, 4H), 7.17-8.05 (m, 2H), 5.61 (brs, 1H), 4.52 (m, 1H), 3.55-3.40 (m, 2H), 3.35-3.10 (m, 5H), 2.89 (m, 1H), 2.63-2.53 (m, 5H), 2.43 (m, 1H), 2.41 (s, 3H), 2.15-1.95 (m, 2H), 1.66 (m, 1H), 1.60 (s, 3H)

MS (ESI, m/z): [M+$^1$]+=738.2 and 740.2

Example 51: synthesis of 2-[(9S)-7-(4-chlorophenyl)-4,5,13-trimethyl-3-thia-1,8,11,12-tetraazatricyclo[8.3.0.0²,⁶]trideca-2(6),4,7,10,12-pentaen-9-yl]-N-(5-{[2-(2,6-dioxopiperidin-3-yl)-1-oxo-1,2-dihydrophthalazin-5-yl]amino}pentyl)acetamide

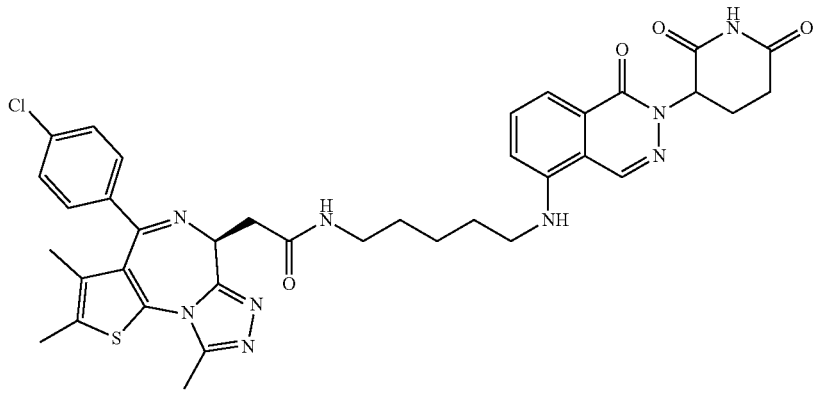 [SMILES: Cc1sc2c(c1C)C(c1ccc(Cl)cc1)=N[C@@H](CC(=O)NCCCCCNc1cccc3c(=O)n(C4CCC(=O)NC4=O)ncc13)c1nnc(C)n1-2]

The titled compound is synthesized through following procedure:

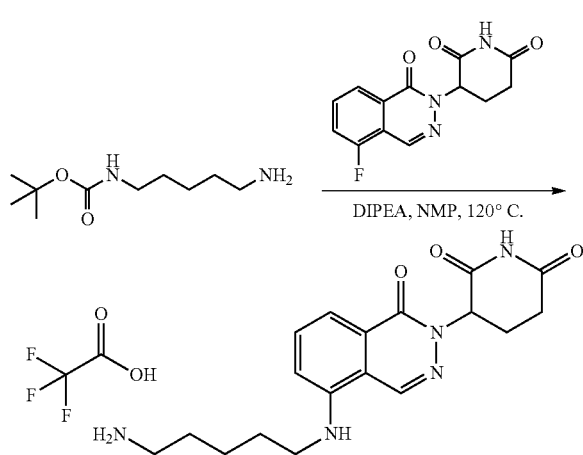

3-(5-fluoro-1-oxo-1,2-dihydrophthalazin-2-yl)piperidine-2,6-dione (100 mg, 0.363 mmol) and tert-butyl N-(5-aminopentyl)carbamate (110 mg, 0.545 mmol) were dissolved in NMP (2 mL), and DIPEA (517 μL, 2.91 mmol) was added in reaction mixture. The mixture was stirred 120° C. for overnight. The reaction was quenched by water, and the mixture was extracted with DCM, NH₄Cl and brine, and then dried over MgSO₄. TFA 20% solution (DCM:TFA=5:1) was add to the mixture and the mixture was stirred for 2 hours. The solvent was evaporated and dried in vacuo. (Yield: 60.4%, 100 mg)

MS (ESI, m/z): [M+¹]+=358.5

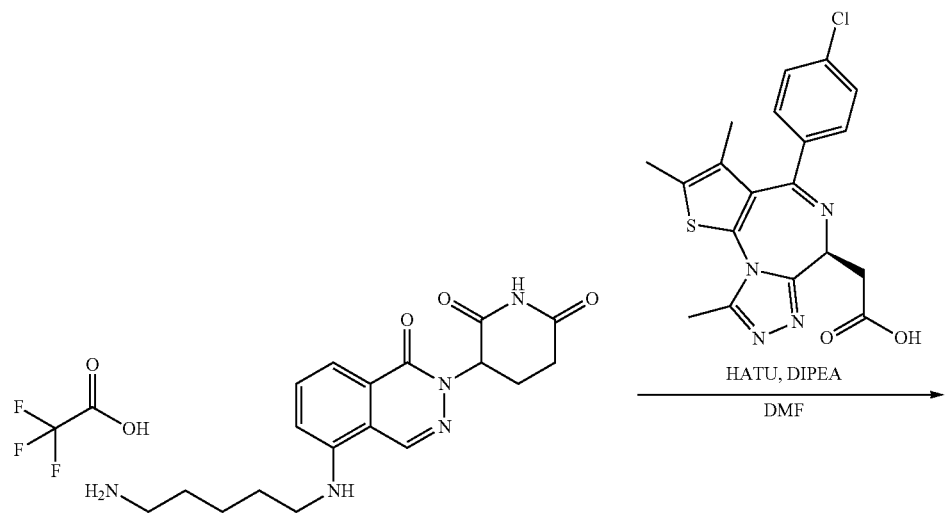

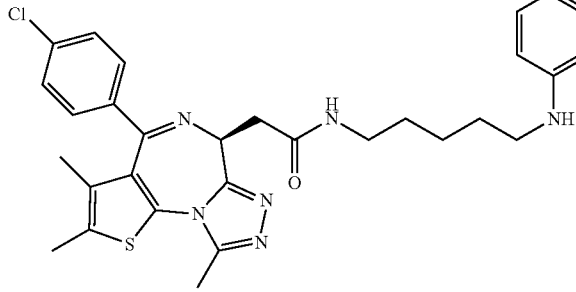

To a solution of 3-{5-[(5-aminopentyl)amino]-1-oxo-1,2-dihydrophthalazin-2-yl}piperidine-2,6-dione trifluoroacetic acid (100 mg, 0.212 mmol), 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetic acid (102 mg, 0.255 mmol), HATU (121 mg, 0.318 mmol) in DMF was added DIPEA (381 μL, 2.12 mmol). The mixture was stirred at room temperature for 3 hours. The reaction mixture was diluted with water and extracted with ethyl acetate. The organic layer was washed with brine, dried over Na$_2$SO$_4$, and concentrated. The desired product was separated by column chromatography. (Yield: 21.6%, 34 mg)

MS (ESI, m/z): [M+$^1$]+=740.2

[NMR] 1H NMR (400 MHz, DMSO-d6) δ ppm 11.02 (br. s., 1H), 8.63-8.74 (m, 1H), 8.46 (d, J=8.31 Hz, 1H), 8.20-8.30 (m, 1H), 7.57 (t, J=8.07 Hz, 1H), 7.34-7.52 (m, 4H), 6.93 (d, J=8.31 Hz, 1H), 6.73 (d, J=5.13 Hz, 1H), 4.44-4.56 (m, 1H), 3.22-3.30 (m, 1H), 3.09-3.22 (m, 3H), 2.84-2.98 (m, 1H), 2.55-2.67 (m, 5H), 2.32-2.44 (m, 3H), 2.01-2.13 (m, 1H), 1.60-1.74 (m, 3H), 1.48-1.60 (m, 5H), 1.44 (d, J=7.09 Hz, 2H), 1.19-1.35 (m, 3H)

Example 52: Synthesis of 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]-N-(5-{[3-(2,6-dioxopiperidin-3-yl)-4-oxo-3,4-dihydrophthalazin-5-yl]amino}pentyl)acetamide

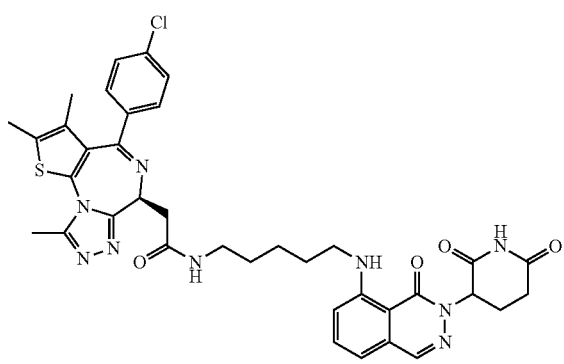 [SMILES: Cc1sc2c(c1C)C(c1ccc(Cl)cc1)=N[C@@H](CC(=O)NCCCCCNc1cccc3cnn(C4CCC(=O)NC4=O)c(=O)c13)c1nnc(C)n1-2]

The titled compound is synthesized through following procedure.

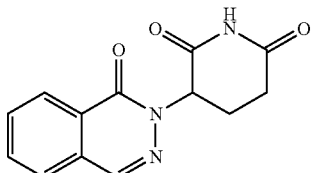

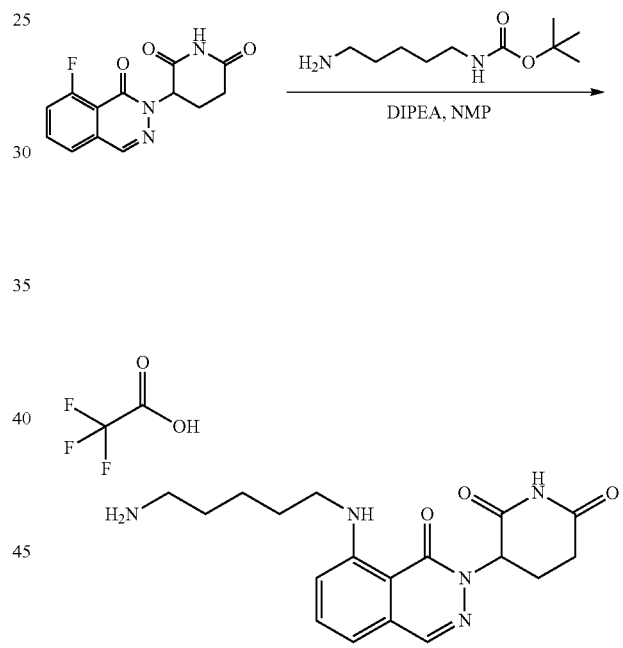

3-(8-fluoro-1-oxo-1,2-dihydrophthalazin-2-yl)piperidine-2,6-dione (100 mg, 0.363 mmol) and tert-butyl N-(5-aminopentyl)carbamate (110 mg, 0.545 mmol) were dissolved in NMP (2 mL), and DIPEA (517 μL, 2.91 mmol) was added in reaction mixture. The mixture was stirred 120° C. for overnight. The reaction was quenched by water and the mixture was extracted with DCM, NH$_4$Cl and brine, and then dried over MgSO$_4$. TFA 20% solution (DCM:TFA=5:1) was add to the mixture and stirred for 2 hours. The solvent was evaporated and dried in vacuo. (Yield: 58.4%, 100 mg)

MS (ESI, m/z): [M+$^1$]+=358.5

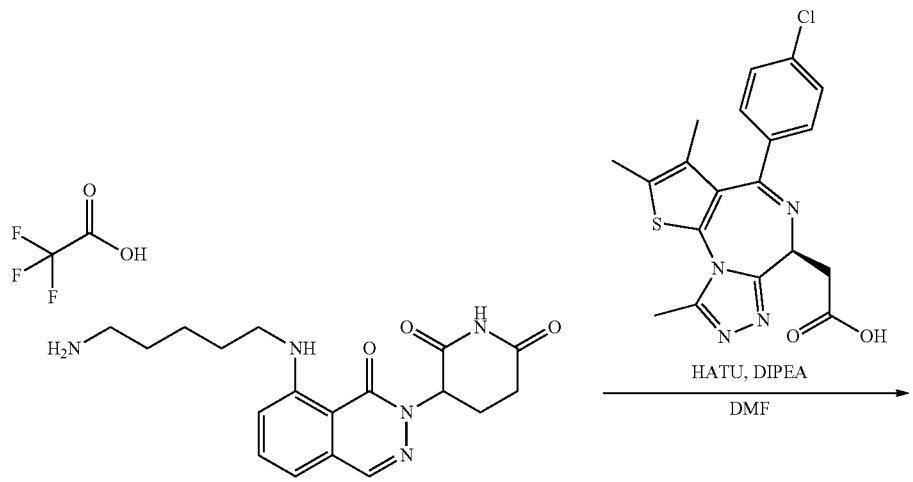

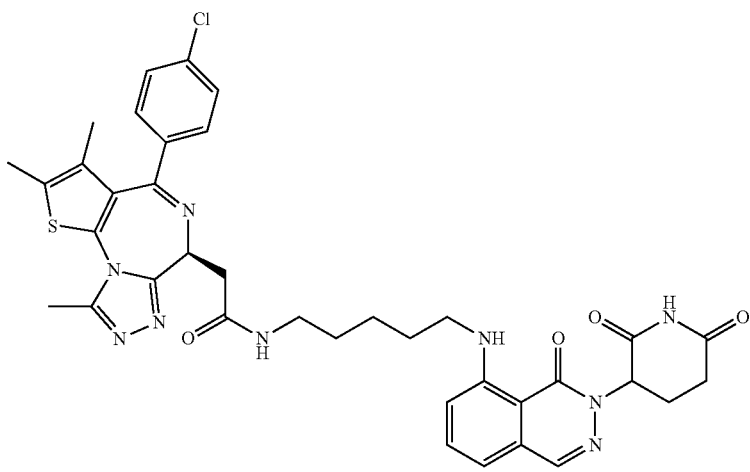

To a solution of 3-{8-[(5-aminopentyl)amino]-1-oxo-1,2-dihydrophthalazin-2-yl}piperidine-2,6-dione trifluoroacetic acid (100 mg, 0.212 mmol), 2-[(9S)-7-(4-chlorophenyl)-4,5,13-trimethyl-3-thia-1,8,11,12-tetraazatricyclo[8.3.0.0$^{2,6}$]trideca-2(6),4,7,10,12-pentaen-9-yl]acetic acid (102 mg, 0.255 mmol), HATU (121 mg, 0.318 mmol) in DMF was added DIPEA (378 μL, 2.12 mmol). The mixture was stirred at room temperature for 3 hours. The reaction mixture was diluted with water and extracted with ethyl acetate. The organic layer was washed with brine, dried over Na$_2$SO$_4$, and concentrated. The desired product was separated by column chromatography. (Yield: 68.8%, 108 mg).

MS (ESI, m/z): [M+$^1$]+=741.4

[NMR] 1H NMR (400 MHz, DMSO-d6) d ppm 11.03 (s, 1H), 8.71 (t, J=5.26 Hz, 1H), 8.17-8.26 (m, 2H), 7.63 (t, J=7.95 Hz, 1H), 7.38-7.50 (m, 4H), 6.79-6.94 (m, 2H), 5.71 (d, J=7.34 Hz, 1H), 4.51 (dd, J=8.07, 6.11 Hz, 1H), 3.07-3.29 (m, 3H), 2.81-2.94 (m, 1H), 2.53-2.65 (m, 5H), 2.40 (s, 3H), 2.03-2.15 (m, 1H), 1.59-1.73 (m, 5H), 1.37-1.59 (m, 4H), 1.20-1.31 (m, 4H)

Example 53: synthesis of 2-((S)-4-(4-chlorophenyl)-2,3,9-trimethyl-6H-thieno[3,2-f][1,2,4]triazolo[4,3-a][1,4]diazepin-6-yl)-N-((1-(3-(2,6-dioxopiperidin-3-yl)-4-oxo-3,4-dihydrophthalazin-5-yl)piperidine-4-yl)methyl)acetamide

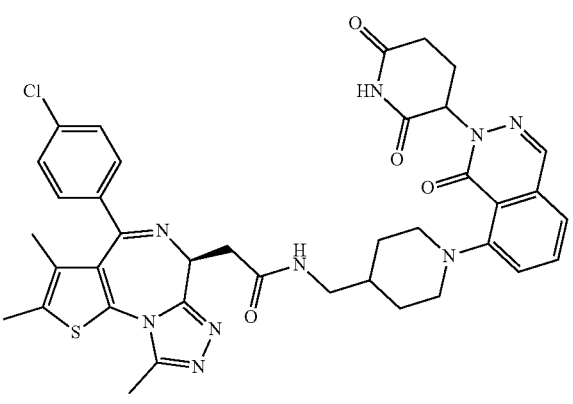 [SMILES: Cc1sc2c(c1C)C(c1ccc(Cl)cc1)=N[C@@H](CC(=O)NCC1CCN(c3cccc4cnn(C5CCC(=O)NC5=O)c(=O)c34)CC1)c1nnc(C)n1-2]

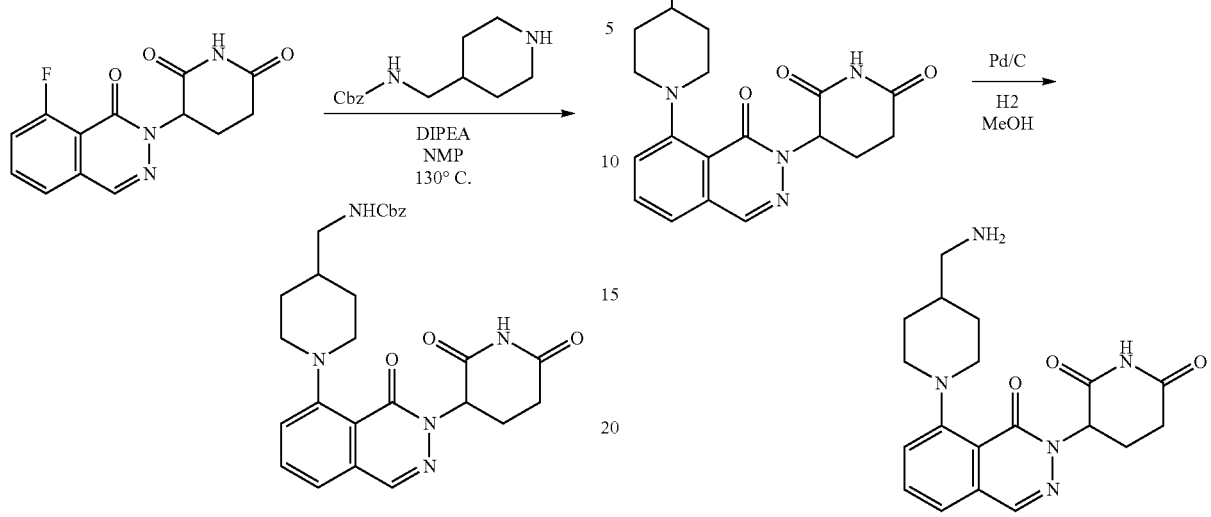

A solution of 3-(8-fluoro-1-oxophthalazin-2(1H)-yl)piperidine-2,6-dione (56.0 mg, 0.203 mmol), benzyl (piperidin-4-ylmethyl)carbamate (178 mg, 0.305 mmol) and DIPEA (0.134 mL, 0.814 mmol) in NMP (1 mL) was stirred for 17 hours at 130° C. The reaction mixture was purified by reverse column chromatography to give the product. (Yield: 73 mg, 71.3%).

MS (ESI, m/z): [M+1]$^+$=504.2

To a solution of benzyl ((1-(3-(2,6-dioxopiperidin-3-yl)-4-oxo-3,4-dihydrophthalazin-5-yl)piperidin-4-yl)methyl)carbamate (72 mg, 0.143 mmol) in 5 ml of MeOH was added Pd(OH)$_2$ (catalytic amounts) and the mixture was stirred under H$_2$ atmosphere for 16 hours at room temperature. The reaction mixture was filtered on celite and concentrated (Yield: 52 mg, 98.5%).

MS (ESI, m/z): [M+1]$^+$=370.2

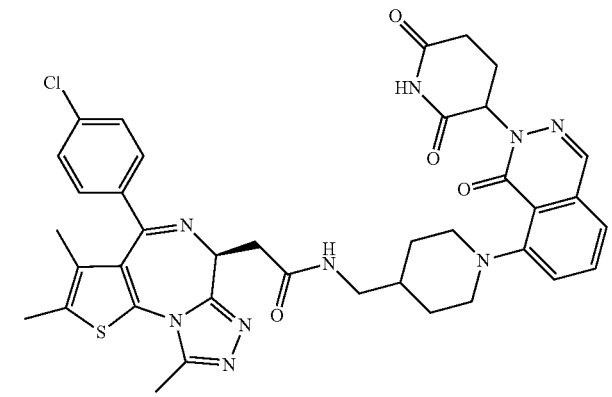

To a solution of 3-(8-(4-(aminomethyl)piperidin-1-yl)-1-oxophthalazin-2(1H)-yl)piperidine-2,6-dione (28 mg, 0.076 mmol), JQ-1 carboxylic acid (30.4 mg, 0.076 mmol), DIPEA (0.040 ml, 0.227 mmol) in DMF (0.5 mL) was added HATU (34.6 mg, 0.097 mmol) at 0° C. and the mixture was stirred at room temperature for 1 hour. The reaction mixture was purified by reverse column chromatography to give the product. (Yield: 24.7 mg, 43.4%).

1H NMR (400 MHz, DMSO-d6) δ=11.03 (s, 1H), 8.33 (m, 2H), 7.85 (brs, 1H), 7.55-7.30 (m, 6H), 5.80 (brs, 1H), 4.53 (m, 1H), 3.50 (m, 2H), 3.30-3.15 (m, 4H) 3.27 (m, 2H), 2.93-2.82 (m, 2H), 2.63-2.53 (m, 4H), 2.41 (s, 3H), 2.30 (m, 1H), 2.09 (m, 1H), 1.91 (m, 2H) 1.61 (s, 3H). 1.52 (m, 2H)

MS (ESI, m/z): [M+1]$^+$=752.2 and 754.2

Example 54: Synthesis of POI Ligand (Warhead)

Synthesis of SHP 099 Derivative

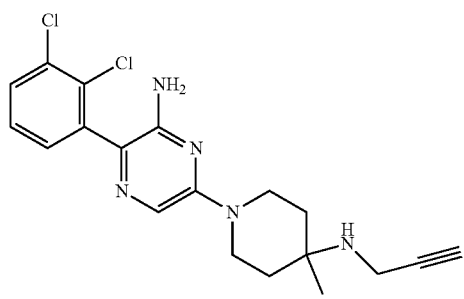 [SMILES: C#CCNC1(C)CCN(c2cnc(-c3cccc(Cl)c3Cl)c(N)n2)CC1]

54-1) Synthesis of 3-(2,3-dichlorophenyl)-6-(4-methyl-4-(prop-2-yn-1-ylamino)piperidine-1-yl)pyrazin-2-amine

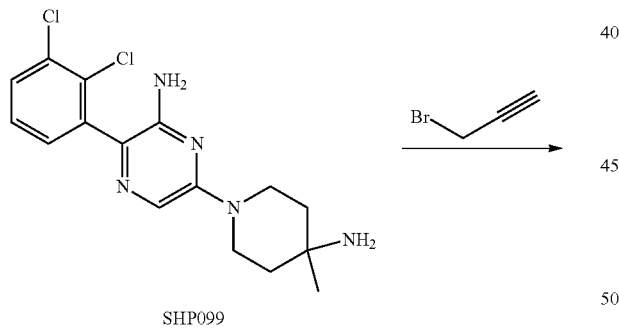

SHP099

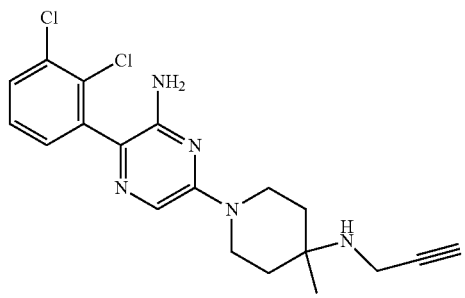

To a solution of 6-(4-amino-4-methylpiperidin-1-yl)-3-(2,3-dichlorophenyl)pyrazin-2-amine (802 mg, 2.28 mmol) and 3-bromoprop-1-yne (406 mg, 3.42 mmol) in 10 ml of 1,4-dioxane was added DIPEA (1.19 ml, 6.83 mmol) and the mixture was stirred for 4 hours at 90° C. The solvents were removed under reduced pressure. The residue was purified by silica gel chromatography (DCM/MeOH=99/1 to 95/5, gradient) to give product as yellow solid. (Yield: 314 mg, 35.3%).

MS (ESI, m/z): [M+1]$^+$=[390.0][392.0][394.0]

Example 55

Synthesis of 3-(4-((2-(2-(2-(2-(4-(((1-(6-amino-5-(2,3-dichlorophenyl)pyrazin-2-yl)-4-methylpiperidin-4-yl)amino)methyl)-1H-1,2,3-triazol-1-yl)ethoxy)ethoxy)ethoxy)ethyl)amino)-1,3-dioxo-2,3-dihydro-1H-inden-2-yl)piperidine-2,6-dione

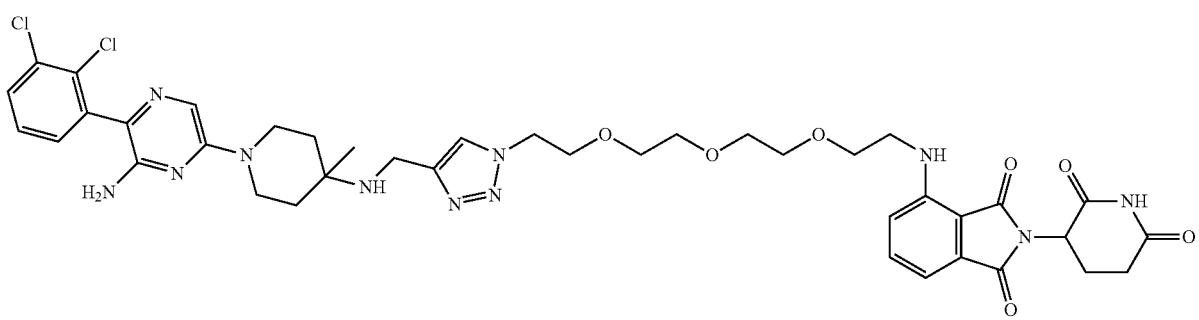 [SMILES: CC1(NCc2cn(CCOCCOCCOCCNc3cccc4c3C(=O)N(C3CCC(=O)NC3=O)C4=O)nn2)CCN(c2cnc(-c3cccc(Cl)c3Cl)c(N)n2)CC1]

Step 1) Synthesis of 4-((2-(2-(2-(2-azidoethoxy)ethoxy)ethoxy)ethyl)amino)-2-(2,6-dioxopiperidin-3-yl)isoindoline-1,3-dione

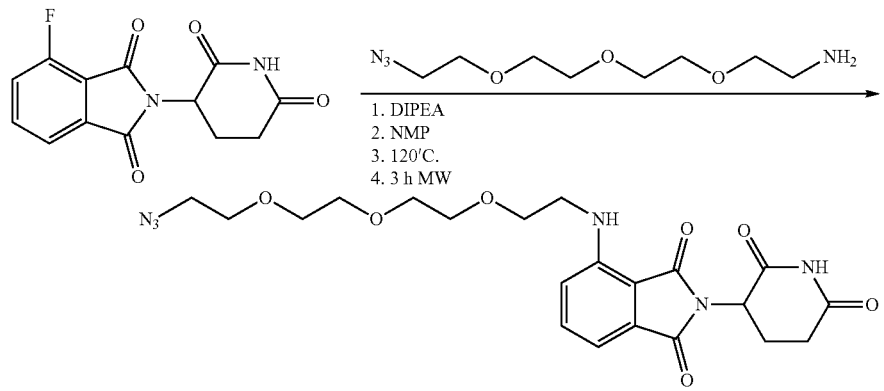

2-(2,6-dioxopiperidin-3-yl)-4-fluoro-2,3-dihydro-1H-isoindole-1,3-dione (100 mg, 0.363 mmol) and 1-[2-(2-aminoethoxy)ethoxy]-2-(2-azidoethoxy)ethane (87.2 mg, 0.4 mmol) and DIPEA (0.323 mL, 1.82 mmol) were dissolved in NMP (1 mL). The reaction mixture was stirred 120° C. for overnight. The reaction was quenched by water and extracted with DCM, NH₄Cl and brine, and then dried over MgSO₄. The reaction mixture was loaded on silica and separated by MPLC. The product was obtained as oil. (Yield: 60 mg, 35%).

Step 2) Synthesis of 3-(4-((2-(2-(2-(2-(4-(((1-(6-amino-5-(2,3-dichlorophenyl)pyrazin-2-yl)-4-methylpiperidin-4-yl)amino)methyl)-1H-1,2,3-triazol-1-yl)ethoxy)ethoxy)ethoxy)ethyl)amino)-1,3-dioxo-2,3-dihydro-1H-inden-2-yl)piperidine-2,6-dione

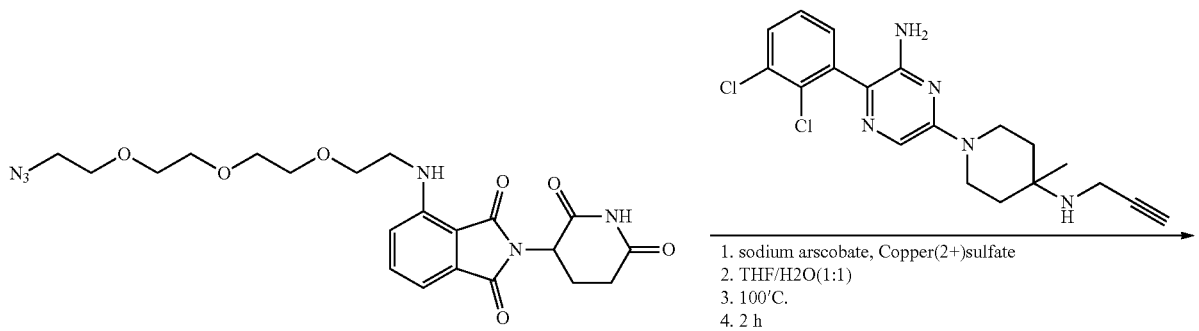

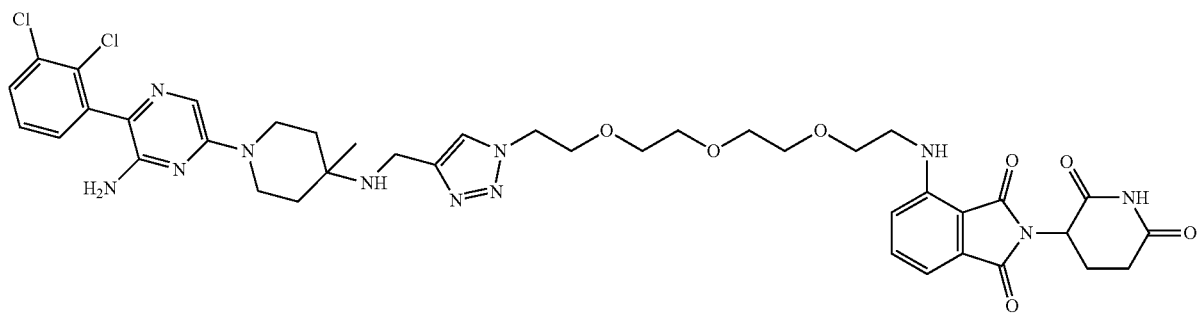

4-(12-azido-4,7,10-trioxa-1-azadodecan-1-yl)-2-(2,6-dioxopiperidin-3-yl)-2,3-dihydro-1H-isoindole-1,3-dione (50 mg, 0.105 mmol), and 3-(2,3-dichlorophenyl)-6-{4-methyl-4-[(prop-2-yn-1-yl)amino]piperidin-1-yl}pyrazin-2-amine (41.1 mg, 0.105 mmol) were dissolved in THF:H2O (1:1). The sodium ascorbate (4.17 mg, 0.021 mmol) and copper (2+) sulfate (3.36 mg, 0.021 mmol) were added in reaction mixture. The reaction mixture was reacted at 100° C. for 2 hours. After reaction was finished, the reaction mixture was cooled to room temperature and extracted with EA and water. The organic layer was dried over MgSO$_4$ and removed under vacuum. The product was purified by MPLC. The product was obtained as white solid.

(yield: 40 mg, 44%)

MS (ESI, m/z): [M+$^1$]+=864.8

[NMR] $^1$H NMR (400 MHz, DMSO-d$_6$) δ ppm 10.98 (s, 1H) 8.24 (t, J=5.56 Hz, 1H) 8.15 (d, J=1.22 Hz, 1H) 7.89 (d, J=8.80 Hz, 1H) 7.39-7.50 (m, 4H) 7.05 (dd, J=8.86, 2.26 Hz, 1H) 6.87 (t, J=5.14 Hz, 1H) 6.73 (d, J=2.08 Hz, 1H) 5.72 (dd, J=11.92, 5.07 Hz, 1H) 4.53 (dd, J=7.95, 6.24 Hz, 1H) 3.17-3.30 (m, 4H) 3.10 (d, J=6.11 Hz, 4H) 2.85-2.96 (m, 1H) 2.59 (s, 5H) 2.37 (s, 3H) 2.02-2.11 (m, 1H) 1.62 (d, J=7.34 Hz, 3H) 1.56 (d, J=1.71 Hz, 5H) 1.39-1.54 (m, 6H)

Example 56: Synthesis of 3-(8-((2-(2-(2-(4-(((1-(6-amino-5-(2,3-dichlorophenyl)pyrazin-2-yl)-4-methylpiperidin-4-yl)amino)methyl)-1H-1,2,3-triazol-1-yl)ethoxy)ethoxy)ethyl)amino)-1-oxophthalazin-2(1H)-yl)piperidine-2,6-dione 56-1) Synthesis of 3-(8-((2-(2-(2-azidoethoxy)ethoxy)ethyl)amino)-1-oxophthalazin-2(1H)-yl)piperidine-2,6-dione

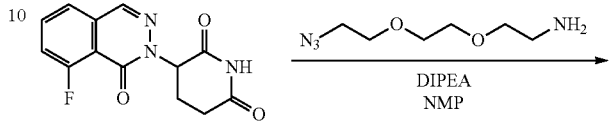

A solution of 3-(8-fluoro-1-oxophthalazin-2(1H)-yl)piperidine-2,6-dione (100 mg, 0.363 mmol), 2-(2-(2-azidoethoxy)ethoxy)ethan-1-amine (76 mg, 0.436 mmol) and DIPEA (0.19 mL, 1.09 mmol) in NMP (1 mL) was stirred for 16 hours at 110° C. The reaction mixture was purified by reverse column chromatography to give the product. (Yield: 89 mg, 57.4%).

MS (ESI, m/z): [M+$^1$]+=[430.0]

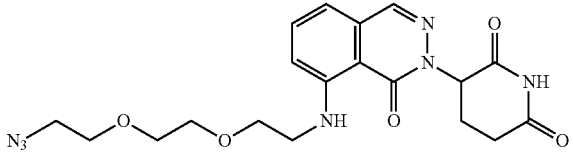

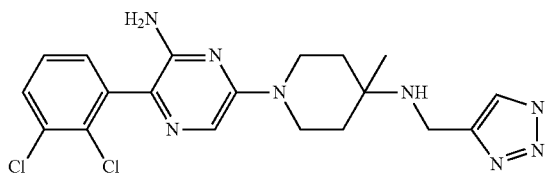

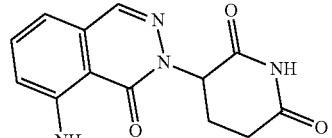

56-2) Synthesis of 3-(8-((2-(2-(2-(4-(((1-(6-amino-5-(2,3-dichlorophenyl)pyrazin-2-yl)-4-methylpiperidin-4-yl)amino)methyl)-1H-1,2,3-triazol-1-yl)ethoxy)ethoxy)ethyl)amino)-1-oxophthalazin-2(1H)-yl)piperidine-2,6-dione

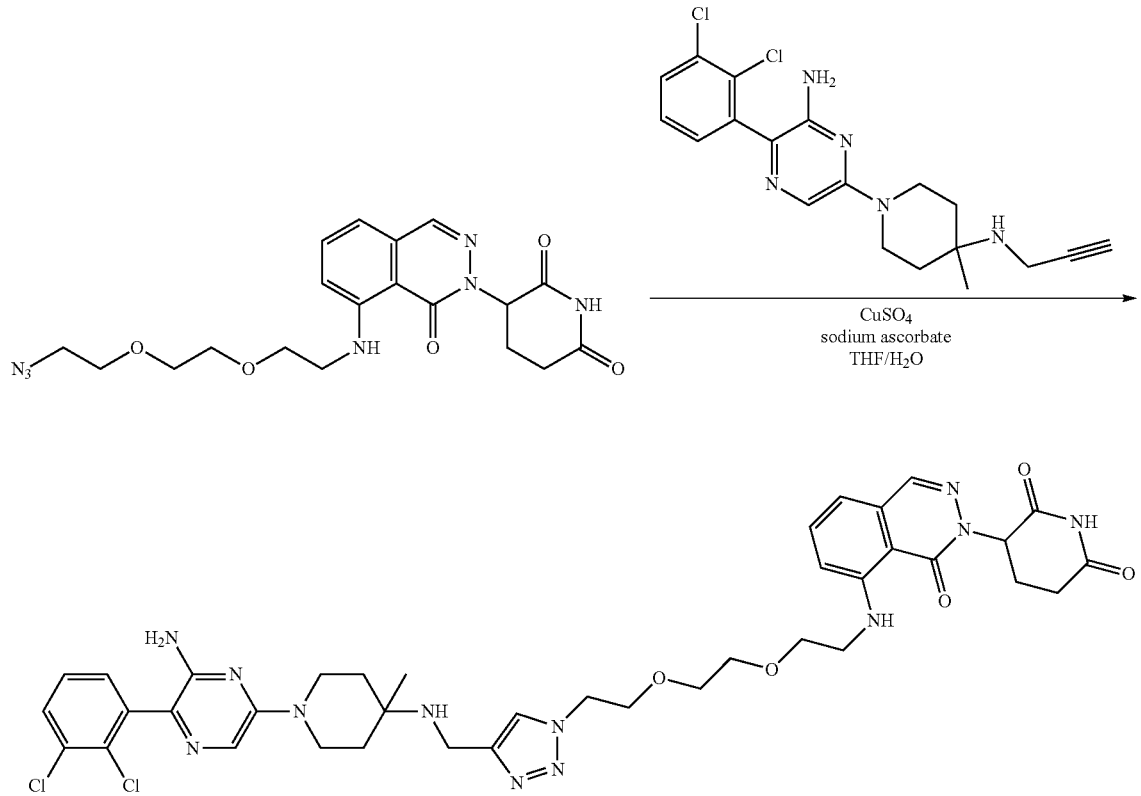 [SMILES: [N-]=[N+]=NCCOCCOCCNc1cccc2cnn(C3CCC(=O)NC3=O)c(=O)c12 ; C#CCNC1(C)CCN(c2cnc(-c3cccc(Cl)c3Cl)c(N)n2)CC1 ; "CuSO4sodium ascorbateTHF/H2O" ; CC1(NCc2cn(CCOCCOCCNc3cccc4cnn(C5CCC(=O)NC5=O)c(=O)c34)nn2)CCN(c2cnc(-c3cccc(Cl)c3Cl)c(N)n2)CC1]

To a suspension of 3-(8-((2-(2-(2-azidoethoxy)ethoxy)ethyl)amino)-1-oxophthalazin-2(1H)-yl)piperidine-2,6-dione (19.2 mg, 0.0446 mmol), 3-(2,3-dichlorophenyl)-6-(4-methyl-4-(prop-2-yn-1-ylamino)piperidin-1-yl)pyrazin-2-amine (17.4 mg, 0.0446 mmol) and sodium ascorbate (24 mg, 0.121 mmol) in 2 ml of TFA/H$_2$O (1/1, v/v) was added CuSO$_4$ (9 mg, 0.0564 mmol) at 0° C. and the mixture was stirred at room temperature for 1 hour. To a reaction mixture was added 30 ml of ethyl acetate and the resultant was extracted. The organic layer was dried over MgSO$_4$ and concentrated under reduced pressure. The residue was purified by silica column chromatography to give the product (yield: 19 mg, 51.9%).

1H NMR (400 MHz, DMSO-d6) δ=11.3 (s, 1H), 8.83 (t, J=4.7 Hz, 1H), 8.22 (s, 1H), 7.94 (brs, 1H), 7.64 (t, J=8.0 Hz, 1H), 7.62 (dd, J=8.0, 1.5 Hz, 1H), 7.47 (s, 1H), 7.39 (t, J=7.8 Hz, 1H), 7.30 (dd, J=7.6, 1.7 Hz, 1H), 6.92 (d, J=8.4 Hz, 1H), 6.90 (d, J=8.4 Hz, 1H), 5.70 (m, 1H), 5.62 (brs, 2H), 4.49 (t, J=4.9 Hz, 2H), 3.82 (t, J=5.1 Hz, 2H), 3.73 (brs, 2H), 3.63 (t, J=5.1 Hz, 2H), 3.56 (brs, 7H), 3.3 (brs, 4H), 2.89 (m, 1H), 2.63-2.47 (m, 2H), 2.07 (m, 1H), 1.60 (brs, 2H), 1.48 (brs, 2H), 1.14 (s, 3H).

MS (ESI, m/z): [M+1]$^+$=[819.4][821.4][823.4]

Example 57: Synthesis of 3-(6-((2-(2-(2-(4-(((1-(6-amino-5-(2,3-dichlorophenyl)pyrazin-2-yl)-4-methylpiperidin-4-yl)amino)methyl)-1H-1,2,3-triazol-1-yl)ethoxy)ethoxy)ethyl)amino)-1-oxophthalazin-2(1H)-yl)piperidine-2,6-dione

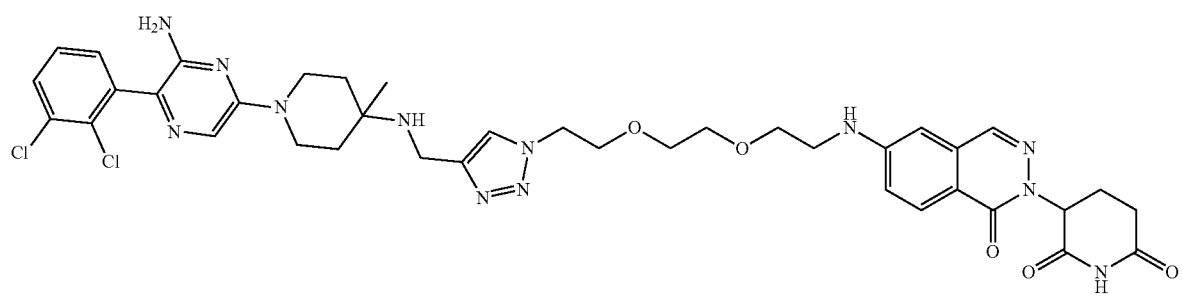 [SMILES: CC1(NCc2cn(CCOCCOCCNc3ccc4c(=O)n(C5CCC(=O)NC5=O)ncc4c3)nn2)CCN(c2cnc(-c3cccc(Cl)c3Cl)c(N)n2)CC1]

The titled compound is synthesized through following procedure.

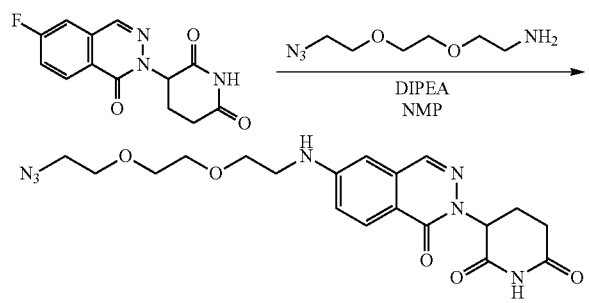

A solution of 3-(6-fluoro-1-oxophthalazin-2(1H)-yl)piperidine-2,6-dione (100 mg, 0.363 mmol), 2-(2-(2-azidoethoxy)ethoxy)ethan-1-amine (76 mg, 0.436 mmol) and DIPEA (0.19 mL, 1.09 mmol) in NMP (1 mL) was stirred for 16 hours at 110° C. The reaction mixture was purified by reverse column chromatography to give the product. (yield: 28 mg, 18%). MS (ESI, m/z): [M+1]$^+$=[430.0]

To a suspension of 3-(6-((2-(2-(2-azidoethoxy)ethoxy)ethyl)amino)-1-oxophthalazin-2(1H)-yl)piperidine-2,6-dione (19.2 mg, 0.0446 mmol), 3-(2,3-dichlorophenyl)-6-(4-methyl-4-(prop-2-yn-1-ylamino)piperidin-1-yl)pyrazin-2-amine (17.4 mg, 0.0446 mmol) and sodium ascorbate (24 mg, 0.121 mmol) in 2 ml of TFA/H$_2$O (1/1, v/v) was added CuSO$_4$ (9 mg, 0.0564 mmol) at 0° C. and the mixture was stirred at room temperature for 1 hour. To a reaction mixture was added 30 ml of ethyl acetate and the resultant was extracted. The organic layer was dried over MgSO$_4$ and concentrated under reduced pressure The residue was purified by silica column chromatography to give the product (yield: 8.2 mg, 22.4%)

1H NMR (400 MHz, DMSO-d6) δ=10.99 (s, 1H), 8.17 (s, 1H), 7.95 (s, 1H), 7.92 (d, J=9.0 Hz, 1H), 7.62 (d, J=7.80 Hz, 1H), 7.47 (s, 1H), 7.38 (t, J=7.8 Hz, 1H), 7.30 (d, J=7.6 Hz, 1H), 7.11 (d, J=9.0 Hz, 1H), 6.91 (m, 1H), 6.8 (s, 1H), 5.73 (m, 1H), 5.61 (brs, 2H), 4.48 (t, J=4.9 Hz, 2H), 3.81 (t, J=5.1 Hz, 2H), 3.75 (brs, 2H), 3.56 (brs, 9H), 3.3 (brs, 4H), 2.90 (m, 1H), 2.64-2.43 (m, 2H), 2.07 (m, 1H), 1.62 (brs, 2H), 1.48 (brs, 2H), 1.15 (s, 3H).

MS (ESI, m/z): [M+1]$^+$=[819.4][821.4][823.4]

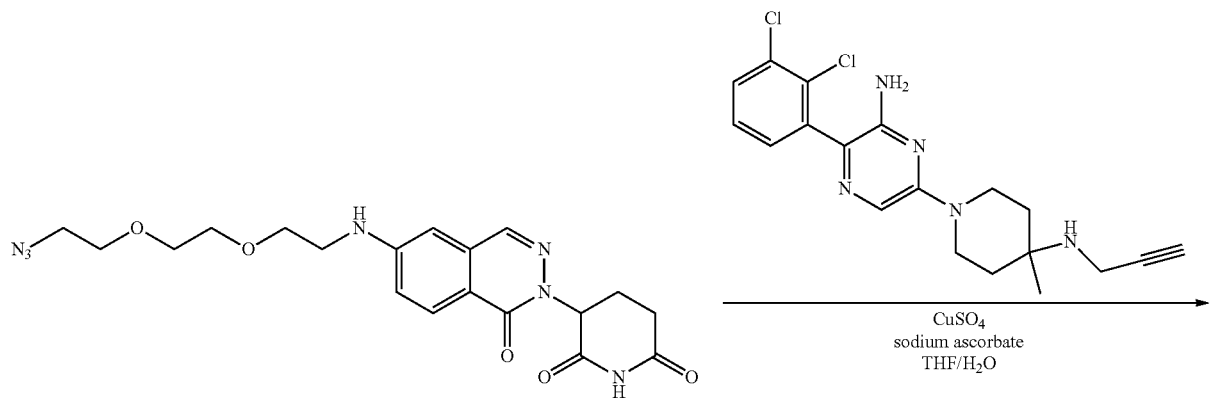

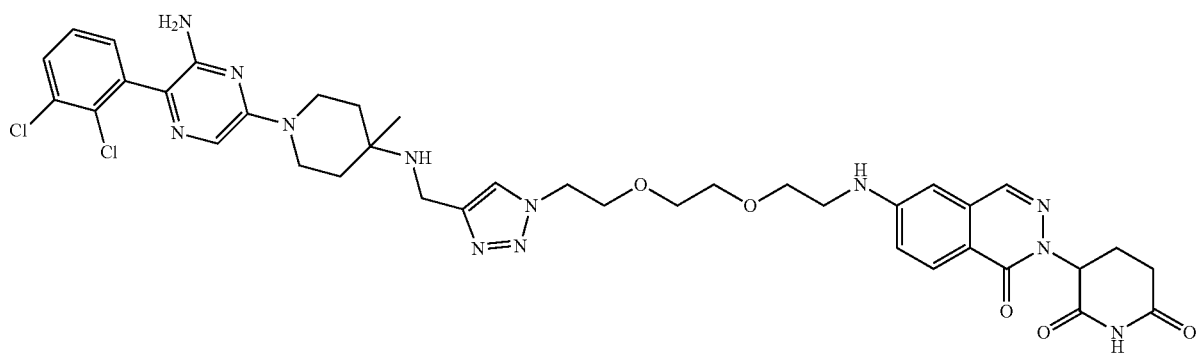

Example 58: Synthesis of 3-(6-((2-(2-(2-(2-(4-(((1-(6-amino-5-(2,3-dichlorophenyl)pyrazin-2-yl)-4-methylpiperidin-4-yl)amino)methyl)-1H-1,2,3-triazol-1-yl)ethoxy)ethoxy)ethoxy)ethyl)amino)-1-oxophthalazin-2(1H)-yl)piperidine-2,6-dione

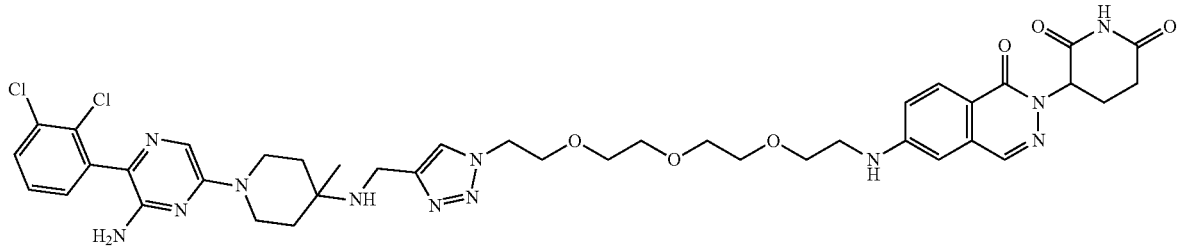 [SMILES: CC1(NCc2cn(CCOCCOCCOCCNc3ccc4c(=O)n(C5CCC(=O)NC5=O)ncc4c3)nn2)CCN(c2cnc(-c3cccc(Cl)c3Cl)c(N)n2)CC1]

The titled compound is synthesized through following procedure.

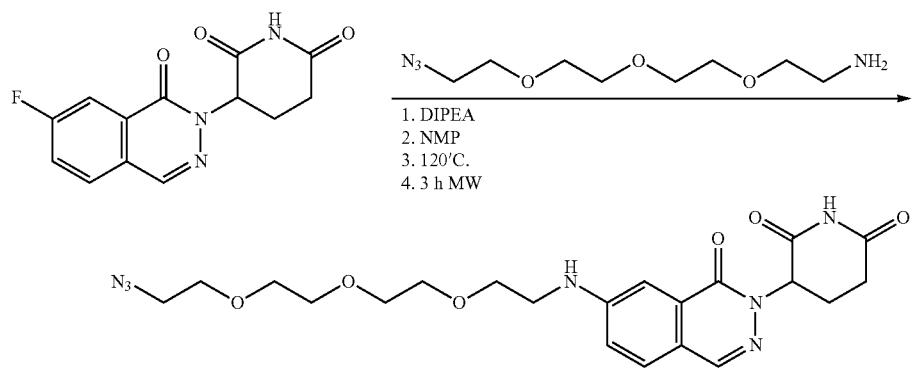

3-(6-fluoro-1-oxophthalazin-2(1H)-yl)piperidine-2,6-dione (100 mg, 0.363 mmol) and 1-[2-(2-aminoethoxy)ethoxy]-2-(2-azidoethoxy)ethane (87.2 mg, 0.4 mmol) and DIPEA (0.323 mL, 1.82 mmol) were dissolved in NMP (1 mL). The reaction mixture was stirred 120° C. for overnight.

The reaction was quenched by water and the resultant was extracted with DCM, NH₄Cl and brine, and then dried over MgSO₄. The reaction mixture was loaded on silica and separated by MPLC. The product was obtained as oil. (Yield: 65 mg, 37%).

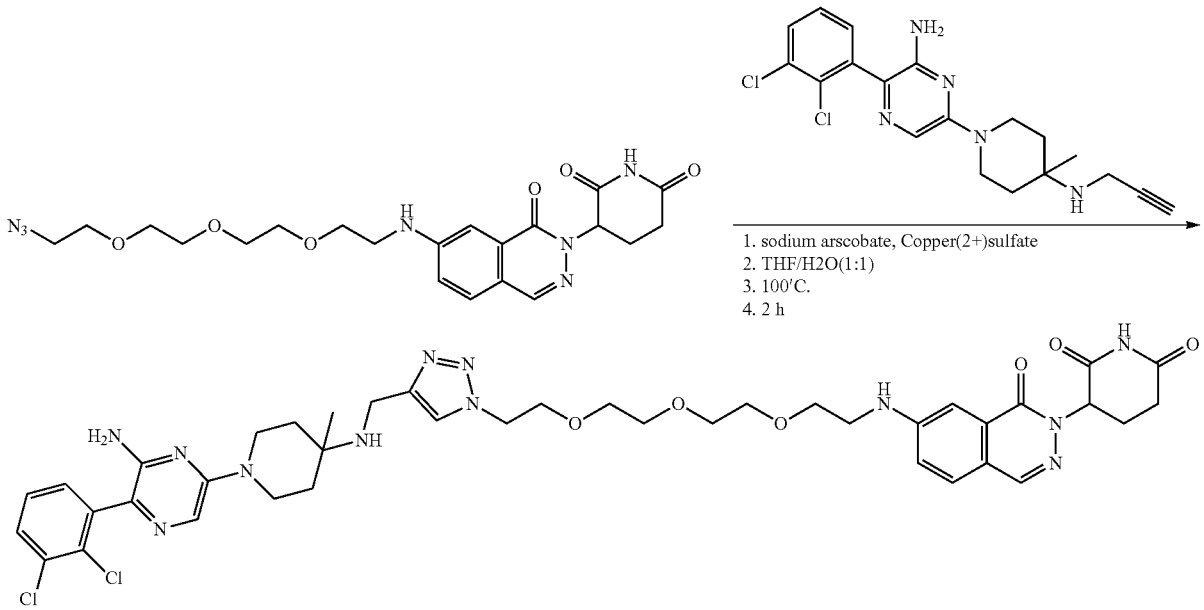

3-(6-((2-(2-(2-(2-azidoethoxy)ethoxy)ethoxy)ethyl)amino)-1-oxophthalazin-2(1H)-yl)piperidine-2,6-dione (54 mg, 0.114 mmol) and 3-(2,3-dichlorophenyl)-6-{4-methyl-4-[(prop-2-yn-h-yl)amino]piperidin-1-yl}pyrazin-2-amine (44.6 mg, 0.144 mmol) were dissolved in THF:H$_2$O (1:1). The sodium ascorbate (4.52 mg, 0.023 mmol) and copper (2+) sulfate (3.64 mg, 0.023 mmol) were added in reaction mixture. The reaction mixture was reacted at 100° C. for 2 hours. After reaction was finished, the reaction mixture was cooled to room temperature and extracted with EA and water. The organic layer was dried over MgSO$_4$ and removed under vacuum. The product was purified by MPLC. The product was obtained as white solid.
(yield: 15 mg, 15%),
MS (ESI, m/z): [M+$^1$]+=864.8

[NMR] $^1$H NMR (400 MHz, DMSO-d$_6$) δ ppm 10.99 (s, 1H) 8.17 (s, 1H) 7.91 (d, J=8.80 Hz, 1H) 7.62 (dd, J=8.01, 1.65 Hz, 1H) 7.50 (br. s., 1H) 7.39 (t, J=7.89 Hz, 1H) 7.29 (dd, J=7.70, 1.59 Hz, 1H) 7.11 (dd, J=8.93, 2.32 Hz, 1H) 6.89-7.05 (mi, 2H) 6.76-6.85 (m, 1H) 5.72 (dd, J=11.80, 5.56 Hz, 1H) 5.63 (br. s., 1H) 5.53 (s, 1H) 4.50 (br. s., 2H) 3.79 (t, J=5.01 Hz, 3H) 3.55-3.64 (m, 3H) 3.42-3.55 (m, 8H) 2.83-2.99 (m, 1H) 2.53-2.70 (m, 1H) 2.07 (dd, J=10.70, 5.07 Hz, 1H) 1.96 (d, J=12.72 Hz, 1H) 1.67 (br. s., 3H) 1.46 (br. s., 2H) 1.24 (s, 3H) 1.17 (br. s., 3H)

Example 59: Synthesis of 3-(7-((2-(2-(2-(2-(4-(((1-(6-amino-5-(2,3-dichlorophenyl)pyrazin-2-yl)-4-methylpiperidin-4-yl)amino)methyl)-1H-1,2,3-triazol-1-yl)ethoxy)ethoxy)ethoxy)ethyl)amino)-1-oxophthalazin-2(1H)-yl)piperidine-2,6-dione

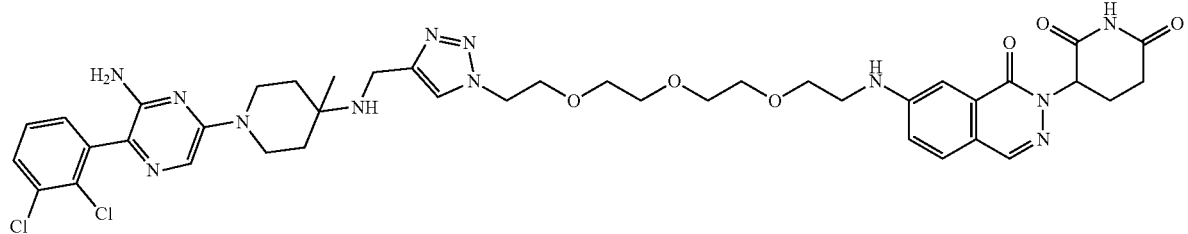 [SMILES: CC1(NCc2cn(CCOCCOCCOCCNc3ccc4cnn(C5CCC(=O)NC5=O)c(=O)c4c3)nn2)CCN(c2cnc(-c3cccc(Cl)c3Cl)c(N)n2)CC1]

The titled compound is synthesized through following procedure.

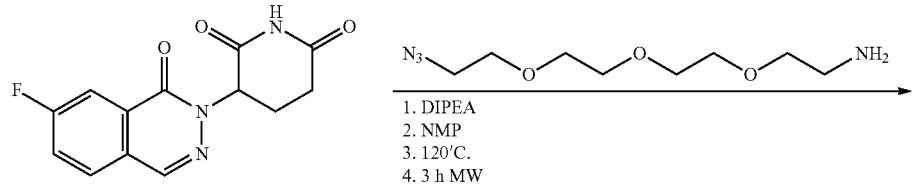

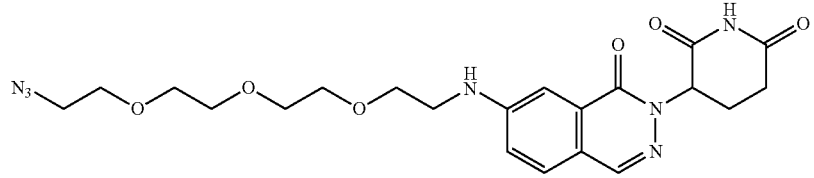

3-(7-fluoro-1-oxophthalazin-2(1H)-yl)piperidine-2,6-dione (100 mg, 0.363 mmol) and 1-[2-(2-aminoethoxy)ethoxy]-2-(2-azidoethoxy)ethane (87.2 mg, 0.4 mmol) and DIPEA (0.323 mL, 1.82 mmol) were dissolved in NMP (1 mL). The reaction mixture was stirred 120° C. for overnight. The reaction was quenched by water and the resultant was extracted with DCM, NH$_4$Cl and brine, and then dried over MgSO$_4$. The reaction mixture was loaded on silica and separated by MPLC. The product was obtained as oil. (Yield: 65 mg, 37%).

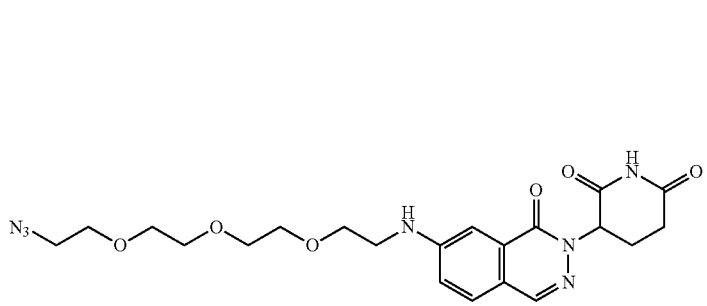
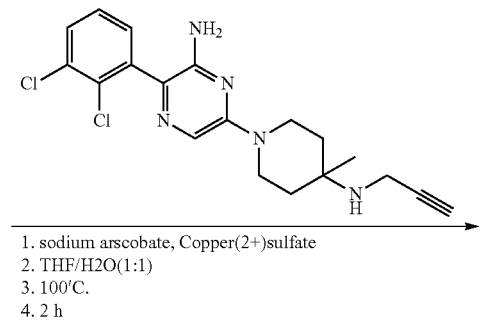

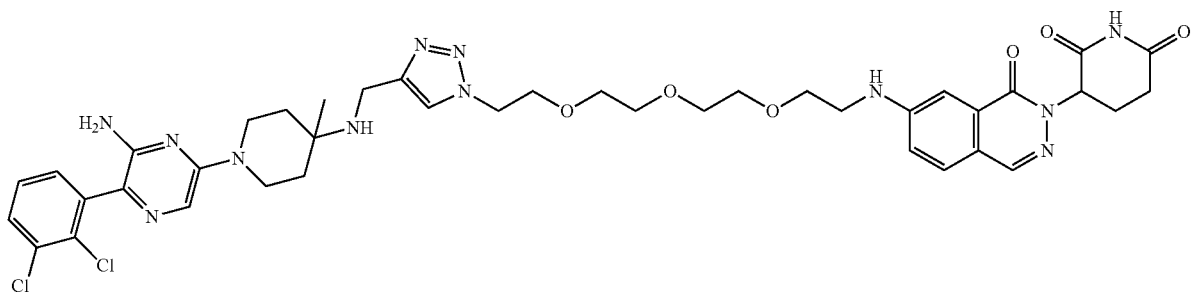

3-[7-(12-azido-4,7,10-trioxa-1-azadodecan-1-yl)-1-oxo-1,2-dihydrophthalazin-2-yl]piperidine-2,6-dione (42 mg, 0.088 mmol) and 3-(2,3-dichlorophenyl)-6-(4-methyl-4-[(prop-2-yn-1-yl)amino]piperidin-1-yl)pyrazin-2-amine (34.6 mg, 0.088 mmol) were dissolved in THF:H$_2$O (1:1). The sodium ascorbate (3.51 mg, 0.018 mmol) and copper (2+) sulfate (2.83 mg, 0.018 mmol) were added in reaction mixture. The reaction mixture was reacted at 100° C. for 2 hours. After reaction was finished, the reaction mixture was cooled to room temperature and extracted with EA and water. The organic layer was dried over MgSO$_4$ and removed under vacuum. The product was purified by MPLC. The product was obtained as white solid.

(yield: 16 mg, 21%)

MS (ESI, m/z): [M+1]$^+$=864.8

NMR] $^1$H NMR (400 MHz, DMSO-d$_6$) δ ppm 11.00 (s, 1H) 8.14 (s, 1H) 7.58-7.66 (m, 2H) 7.50 (br. s., 1H) 7.39 (t, J=7.83 Hz, 1H) 7.29 (dd, J=7.58, 1.59 Hz, 1H) 7.17-7.23 (m, 2H) 6.91 (t, J=5.62 Hz, 1H) 5.71-5.79 (m, 1H) 5.63 (br. s., 2H) 4.50 (br. s., 2H) 3.79 (t, J=5.14 Hz, 3H) 3.60 (t, J=5.56 Hz, 3H) 3.41-3.56 (m, 9H) 2.84-2.96 (m, 1H) 2.52-2.70 (m, 2H) 2.02-2.13 (m, 1H) 1.96 (d, J=13.69 Hz, 1H) 1.67 (br. s., 3H) 1.46 (br. s., 2H) 1.24 (s, 5H)

Example 60: 3-(8-((14-(4-(((1-(6-amino-5-(2,3-dichlorophenyl)pyrazin-2-yl)-4-methylpiperidin-4-yl)amino)methyl)-1H-1,2,3-triazol-1-yl)-3,6,9,12-tetraoxatetradecyl)amino)-1-oxophthalazin-2(1H)-yl)piperidine-2,6-dione

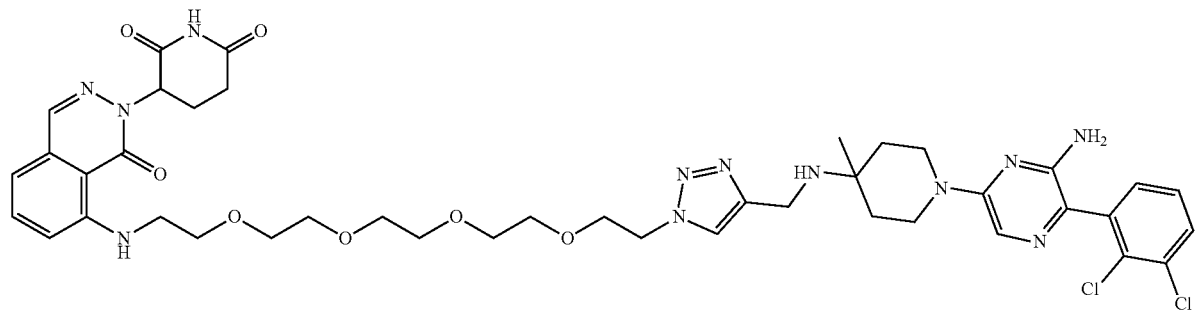 [SMILES: CC1(NCc2cn(CCOCCOCCOCCOCCNc3cccc4cnn(C5CCC(=O)NC5=O)c(=O)c34)nn2)CCN(c2cnc(-c3cccc(Cl)c3Cl)c(N)n2)CC1]

60-1) synthesis of 3-(2,3-dichlorophenyl)-6-(4-methyl-4-(prop-2-yn-1-ylamino)piperidine-1-yl)pyrazin-2-amine

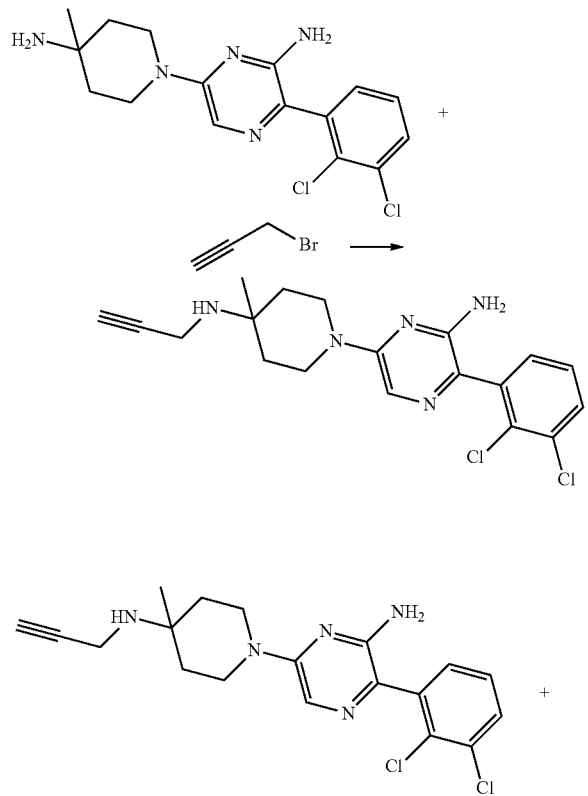

To a solution of 6-(4-amino-4-methylpiperidin-1-yl)-3-(2,3-dichlorophenyl)pyrazin-2-amine hydrochloride (2.5 g, 6.43 mmol) and 3-bromoprop-1-yne (918 mg, 7.72 mmol) in DMF (20 mL) were added $K_2CO_3$ (2.22 g, 16.1 mmol) followed by NaI (408 mg, 3.22 mmol). The mixture was heated at 80° C. for 5 hours. The reaction mixture was diluted with water (150 ml) and extracted with ethyl acetate (150 ml×2). The organic layer was washed with brine, dried over $Na_2SO_4$, and concentrated under reduced pressure. The residue was purified by MPLC with EA/Hex (20-80%) to afford the titled compound as an off-white solid (1.87 g, 4.79 mmol).

MS (ESI, m/z): [M+1]+=391.3

60-2) synthesis of 3-(8-((14-(4-(((1-(6-amino-5-(2,3-dichlorophenyl)pyrazin-2-yl)-4-methylpiperidin-4-yl)amino)methyl)-1H-1,2,3-triazol-1-yl)-3,6,9,12-tetraoxatetradecyl)amino)-1-oxophthalazin-2(1H)-yl)piperidine-2,6-dione

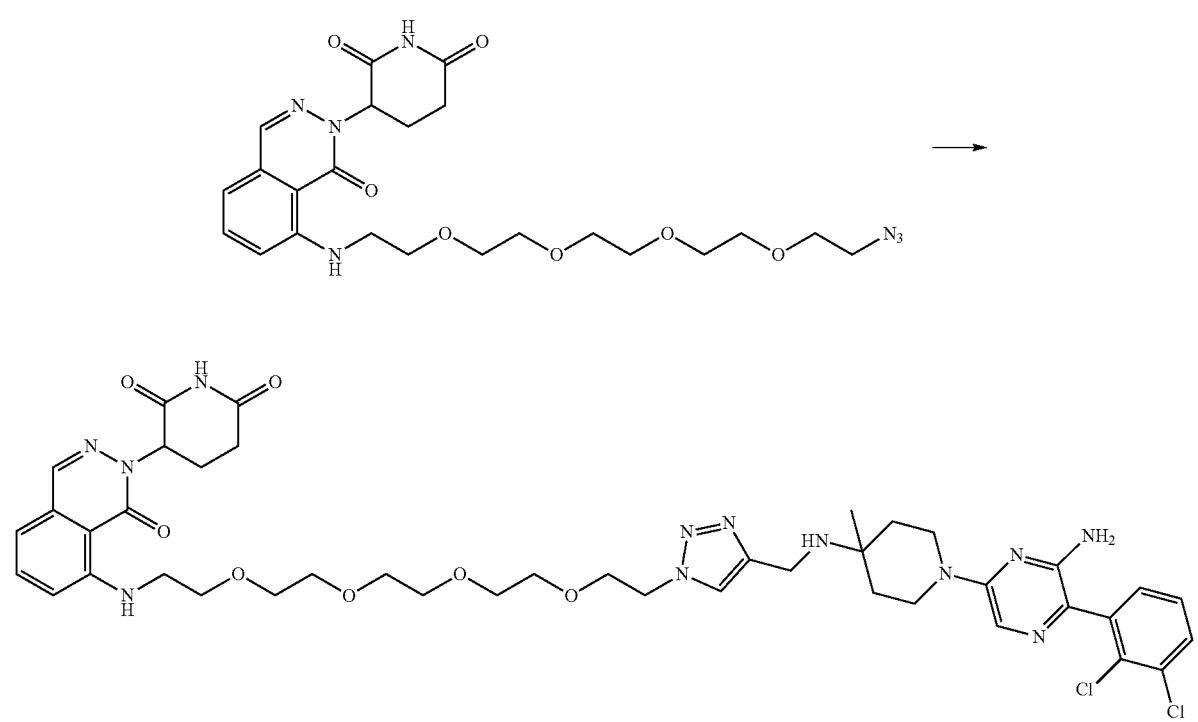

To a 3-(2,3-dichlorophenyl)-6-{4-methyl-4-[(prop-2-yn-1-yl)amino]piperidin-1-yl}pyrazin-2-amine (30 mg, 0.077 mmol) and 3-[8-(15-azido-4,7,10,13-tetraoxa-1-azapentadecan-1-yl)-1-oxo-1,2-dihydrophthalazin-2-yl]piperidine-2,6-dione (39.8 mg, 0.077 mmol) in THF/H$_2$O (5 mL/5 mL) were added Sodium ascorbate (3.04 mg, 0.0015 mmol) and copper sulfate (2.45 mg, 0.0015 mmol) at 25° C. The reaction was done in 2 hours. The reaction mixture was poured into 50 mL of water and extracted with EA (50 mL×2), and dried over MgSO$_4$. The reaction mixture was loaded on silica and separated by column chromatography. (DCM/MeOH 0%→10%) to afford the titled compound as a white crystal (Yield: 42 mg, 60.2%).

MS (ESI, m/z): [M+1]$^+$=908.8

$^1$H NMR (400 MHz, DMSO-d$_6$) δ 11.04 (s, 1H), 9.12 (br, 1H), 8.23 (s, 1H), 8.12 (s, 1H), 7.65 (m, 2H), 7.30-7.45 (m, 2H), 6.92 (m, 2H), 5.70 (br, 1H), 4.59 (m, 2H), 4.30 (m, 2H), 4.28 (s, 1H), 3.82 (m, 2H), 3.67 (m, 2H), 3.57-3.48 (m, 17H), 3.37 (m, 2H), 2.84-3.10 (m, 6H), 1.86-2.15 (m, 4H), 1.52 (s, 3H).

Example 61: synthesis of 3-(8-((17-(4-(((1-(6-amino-5-(2,3-dichlorophenyl)pyrazin-2-yl)-4-methylpiperidin-4-yl)amino)methyl)-1H-1,2,3-triazol-1-yl)-3,6,9,12,15-pentaoxaheptadecyl)amino)-1-oxophthalazin-2(1H)-yl)piperidine-2,6-dione

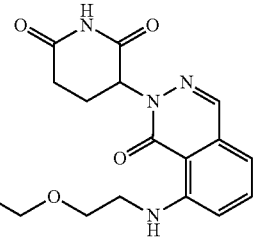

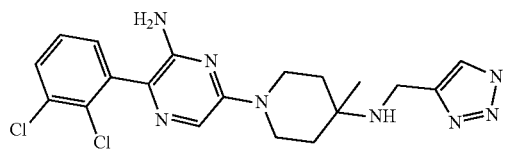

The titled compound is synthesized through following procedure.

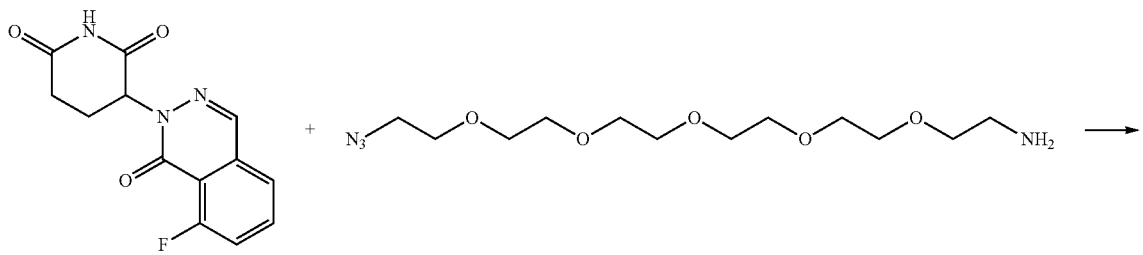

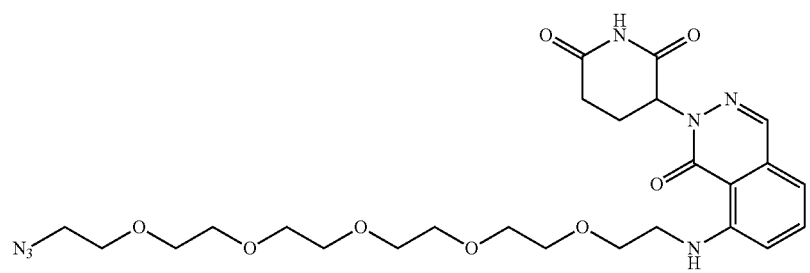

To a solution of 3-(8-fluoro-1-oxo-1,2-dihydrophthalazin-2-yl)piperidine-2,6-dione (100 mg; 0.36 mmol) and 17-azido-3,6,9,12,15-pentaoxaheptadecan-1-amine (96.3 mg, 0.44 mmol) in NMP (3 mL) was added ethylbis(propan-2-yl)amine (141 mg, 1.1 mmol) at room temperature. The reaction mixture was heated at 110° C. for 16 hours. After cooling, the reaction mixture was poured into water (10 mL) and extracted with ethyl acetate (20 mL×2). The resultant was extracted with combined ethyl acetate, dried over MgSO$_4$ and concentrated under reduced pressure. The resulting residue was purified by column chromatography with DCM/MeOH (0~10%) to afford the titled compound (103 mg, 55%). MS (ESI, m/z): [M+1]$^+$=[562.35].

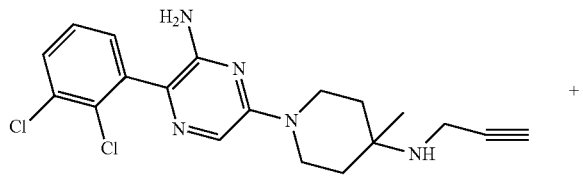

+

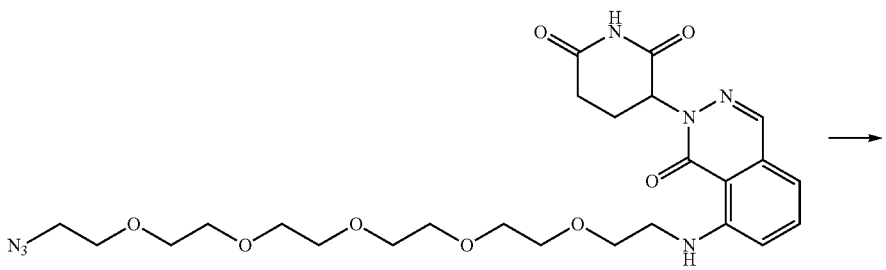

→

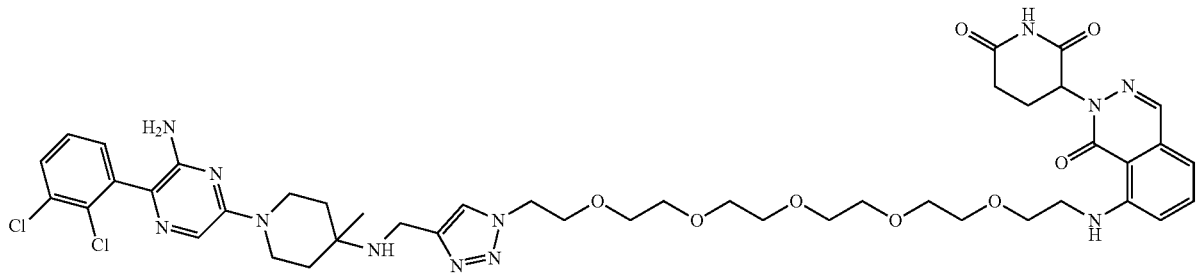

To a 3-(2,3-dichlorophenyl)-6-{4-methyl-4-[(prop-2-yn-1-yl)amino]piperidin-1-yl}pyrazin-2-amine (30 mg, 0.077 mmol) and 3-[8-(18-azido-4,7,10,13,16-pentaoxa-1-azaoctadecan-1-yl)-1-oxo-1,2-dihydrophthalazin-2-yl]piperidine-2,6-dione (43.2 mg, 0.077 mmol) in THF/H$_2$O (5 mL/5 mL) were added Sodium ascorbate (3.04 mg, 0.0015 mmol) and copper sulfate (2.45 mg, 0.0015 mmol) at 25° C. The reaction was done in 2 hours. The reaction mixture was poured into 50 mL of water and extracted with EA (50 mL×2), and dried over MgSO$_4$. The reaction mixture was loaded on silica and separated by column chromatography (DCM/MeOH 0%→10%) to afford the titled compound as a white crystal (56 mg, 76.9%).

MS (ESI, m/z): [M+$^1$]+=953.6

$^1$H NMR (400 MHz, DMSO-d$_6$) δ 11.04 (s, 1H), 9.10 (br, 1H), 8.23 (s, 1H), 8.12 (s, 1H), 7.63 (m, 2H), 7.29-7.42 (m, 2H), 6.93 (m, 2H), 5.57-5.64 (br, 1H), 4.38-4.42 (m, 2H), 4.32 (m, 2H), 4.28 (s, 1H), 3.82 (m, 2H), 3.67-3.74 (m, 4H), 3.57-3.48 (m, 19H), 3.37 (m, 2H), 2.84-3.10 (m, 6H), 1.86-2.15 (m, 4H), 1.52 (s, 3H).

Example 62: Synthesis of N1-(3-((3-amino-5-((3S,4S)-4-amino-3-methyl-2-oxa-8-azaspiro[4.5]decan-8-yl)pyrazin-2-yl)thio)-2-chlorophenyl)-N4-(3-(2-(2-(3-((3-(2,6-dioxopiperidin-3-yl)-4-oxo-3,4-dihydrophthalazin-5-yl)amino)propoxy)ethoxy)ethoxy)propyl)succinamide The titled compound is synthesized through following procedure:

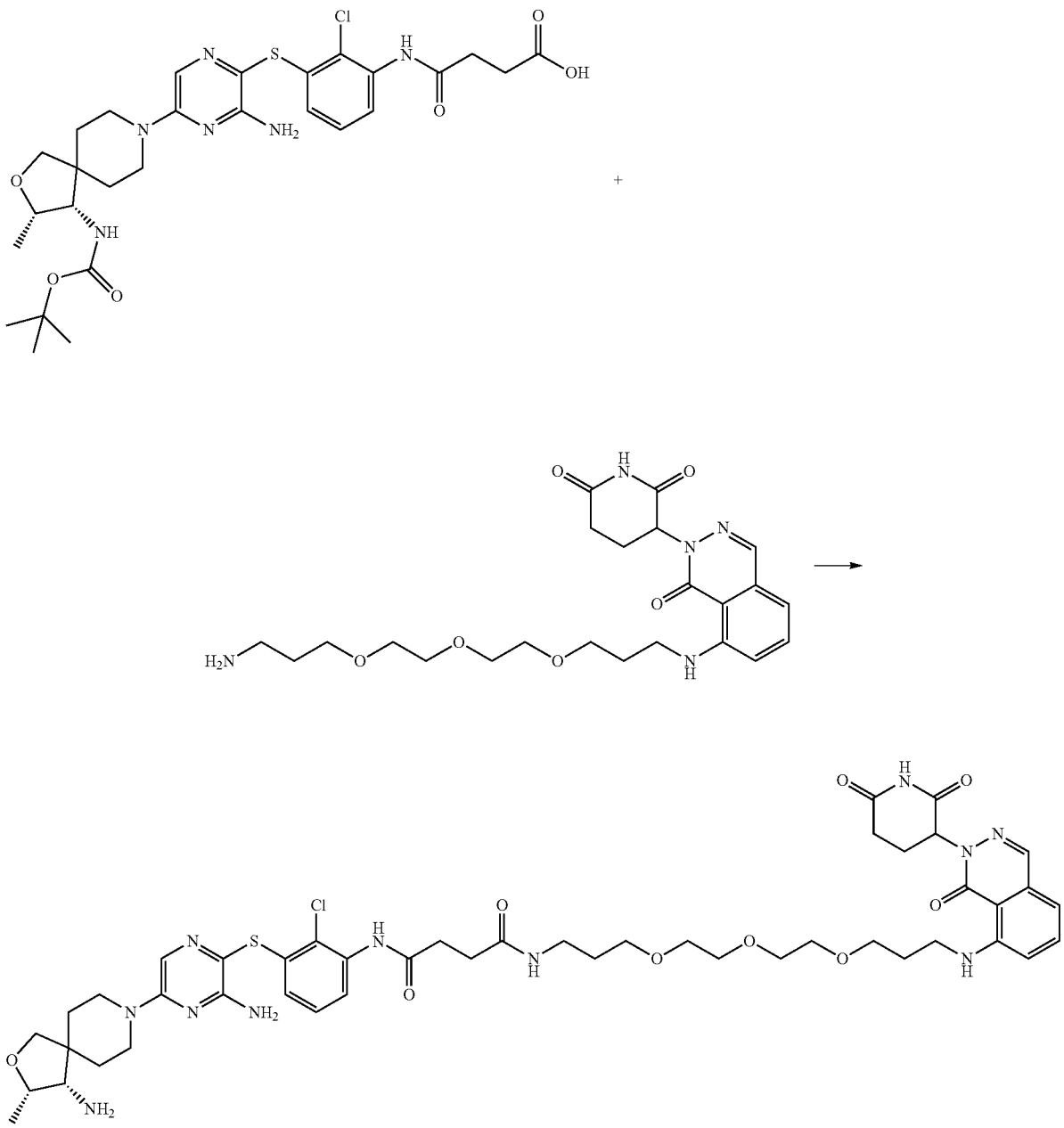 [SMILES: C[C@@H]1OCC2(CCN(c3cnc(Sc4cccc(NC(=O)CCC(=O)O)c4Cl)c(N)n3)CC2)[C@@H]1NC(=O)OC(C)(C)C ; NCCCOCCOCCOCCCNc1cccc2cnn(C3CCC(=O)NC3=O)c(=O)c12 ; C[C@@H]1OCC2(CCN(c3cnc(Sc4cccc(NC(=O)CCC(=O)NCCCOCCOCCOCCCNc5cccc6cnn(C7CCC(=O)NC7=O)c(=O)c56)c4Cl)c(N)n3)CC2)[C@@H]1N]

To a solution of 4-((3-((3-amino-5-((3S,4S)-4-((tert-butoxycarbonyl)amino)-3-methyl-2-oxa-8-azaspiro[4.5]decan-8-yl)pyrazin-2-yl)thio)-2-chlorophenyl)amino)-4-oxobutanoic acid (15 mg, 0.024 mmol) in DMF (1 mL) was added 3-[8-(14-amino-5,8,11-trioxa-1-azatetradecan-1-yl)-1-oxo-1,2-dihydrophthalazin-2-yl]piperidine-2,6-dione hydrochloride (14.9 mg, 0.029 mmol) and HATU (10 mg, 0.0266 mmol) followed by ethylbis(propan-2-yl)amine (9.38 mg, 0.073 mmol) at an ambient temperature. After the reaction was complete, the reaction mixture was poured into water and extracted with ethyl acetate (50 mL×2). The organic layer was separated, dried over MgSO₄, filtered, and concentrated to give a crude product. The crude product was purified by column chromatography to afford the boc-protected compound, which was treated with 4N—HCl in dioxane (3 mL). The reaction was monitored with LCMS.

The resultant was concentrated under reduced pressure to furnish the titled compound
(13.1 mg, 51.5%)
MS (ESI, m/z): [M+$^1$]+=979.6.
$^1$H NMR (400 MHz, DMSO-d$_6$) δ 11.05 (s, 1H), 9.61 (br, 1H), 8.21 (s, 1H), 8.19 (m, 1H), 7.75 (m, 3H), 6.95 (m, 3H), 3.40-3.65 (m, 22H), 3.21 (m, 2H), 2.90 (m, 2H), 2.72 (m, 6H), 2.43 (m, 4H), 1.75 (m, 4H), 1.52 (m, 2H), 1.23-1.35 (m, 8H).

Example 63: synthesis of N1-(3-((3-amino-5-(4-amino-4-methylpiperidin-1-yl)pyrazin-2-yl)thio)-2-chlorophenyl)-N4-(3-(2-(2-(3-((3-(2,6-dioxopiperidin-3-yl)-4-oxo-3,4-dihydrophthazin-5-yl)amino)propoxy)ethoxy)ethoxy)propyl)succinamide The titled compound is synthesized through following procedure.

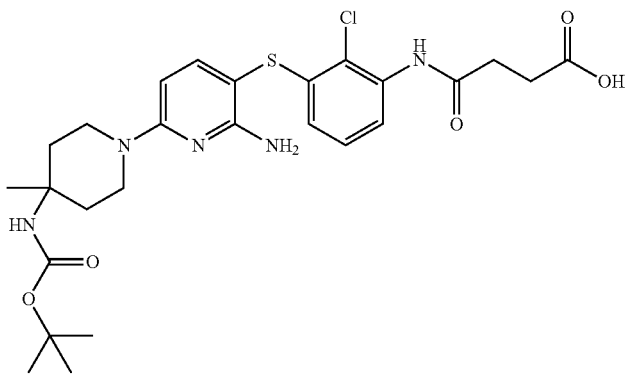

+

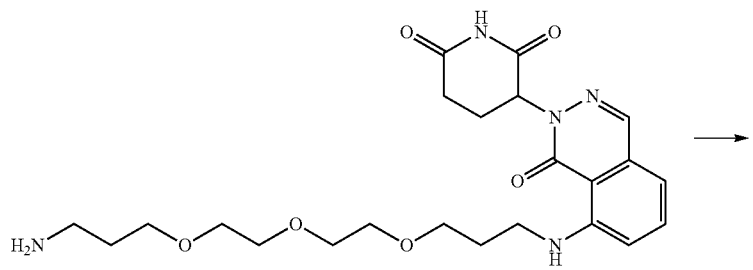

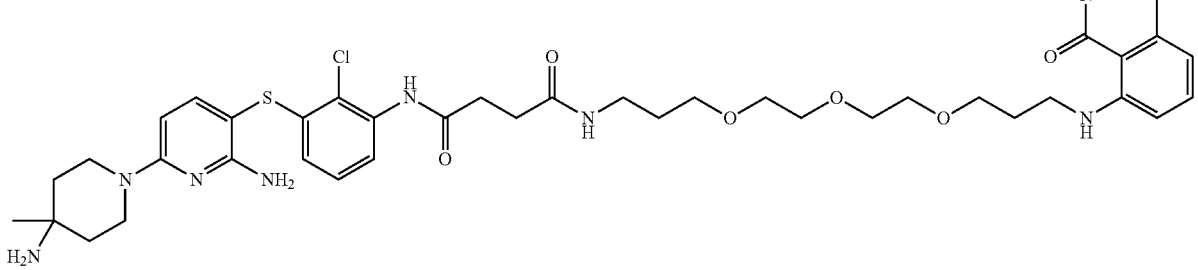

To a solution of 4-((3-((3-amino-5-(4-{[(tert-butoxycarbonyl)amino]-4-methylpiperidin-1-yl)pyrazin-2-yl]thio)-2-chlorophenyl)amino)-4-oxobutanoic acid (15 mg, 0.027 mmol) in DMF (5 mL) was added 3-[8-(14-amino-5,8,11-trioxa-1-azatetradecan-1-yl)-1-oxo-1,2-dihydrophthalazin-2-yl]piperidine-2,6-dione (12.6 mg, 0.026 mmol) and HATU (12.1 mg, 0.032 mmol) followed by ethylbis(propan-2-yl)amine (17.2 mg, 0.133 mmol) at an ambient temperature. After the reaction was complete, the reaction mixture was poured into water and extracted with ethyl acetate (50 mL×2). The organic layer was separated, dried over MgSO$_4$, filtered, and concentrated to give a crude product. The crude product was purified by MPLC to afford the boc-protected compound, which was treated with 4N—HCl in dioxane (3 mL). The reaction was monitored with LCMS. The resultant was concentrated under reduced pressure to furnish the titled compound.

(13.5 mg, 51.1%)

MS (ESI, m/z): [M+$^1$]+=922.6

Example 64: Synthesis of N1-(3-((3-amino-5-(4-amino-4-methylpiperidin-1-yl)pyrazin-2-yl)thio)-2-chlorophenyl)-N4-(14-((3-(2,6-dioxopiperidin-3-yl)-4-oxo-3,4-dihydrophthalazin-5-yl)amino)-3,6,9,12-tetraoxatetradecyl)succinamide The titled compound is synthesized through following procedure.

To a solution of 4-((3-((3-amino-5-(4-((tert-butoxycarbonyl)amino)-4-methylpiperidine-1-yl)pyrazin-2-yl]thio)-2-chlorophenyl)amino)-4-oxobutanoic acid (15 mg, 0.027 mmol) in DMF (5 mL) was added 3-[8-(15-amino-4,7,10,13-tetraoxa-1-azapentadecan-1-yl)-1-oxo-1,2-dihydrophthalazin-2-yl]piperidine-2,6-dione (15.7 mg, 0.032 mmol) and HATU (7.51 mg, 0.032 mmol) followed by ethylbis(propan-2-yl)amine (17.2 mg, 0.133 mmol) at an ambient temperature. After the reaction was complete, the reaction mixture was poured into water and extracted with ethyl acetate (50 mL×2). The organic layer was separated, dried over MgSO$_4$, filtered, and concentrated to give a crude product. The crude product was purified by MPLC to afford the boc-protected compound, which was treated with 4N—HCl in dioxane (3 mL). The reaction was monitored with LCMS. The resultant was concentrated under reduced pressure to furnish the titled compound (Yield: 16.2 mg, 60.3%).

MS (ESI, m/z): [M+$^1$]+=938.4.

δ ppm 11.12 (s, 1H) 9.52 (s, 1H) 8.25 (m, 2H) 7.73-7.78 (m, 2H) 7.30 (s, 1H) 7.12 (m, 1H) 6.87 (m, 2H) 6.42 (m, 1H) 6.09 (s, 2H) 5.74 (m, 1H) 3.75 (m, 2H) 3.50 (m, 12H) 3.39 (br., 3H) 3.20 (m, 3H) 3.10 (m, 2H) 2.90 (m, 4H) 2.54-2.65 (m, 4H) 2.39 (m, 2H) 2.07 (m, 1H) 1.82 (m, 2H) 1.60 (m, 3H) 1.50 (br, 5H) 1.13 (s, 3H).

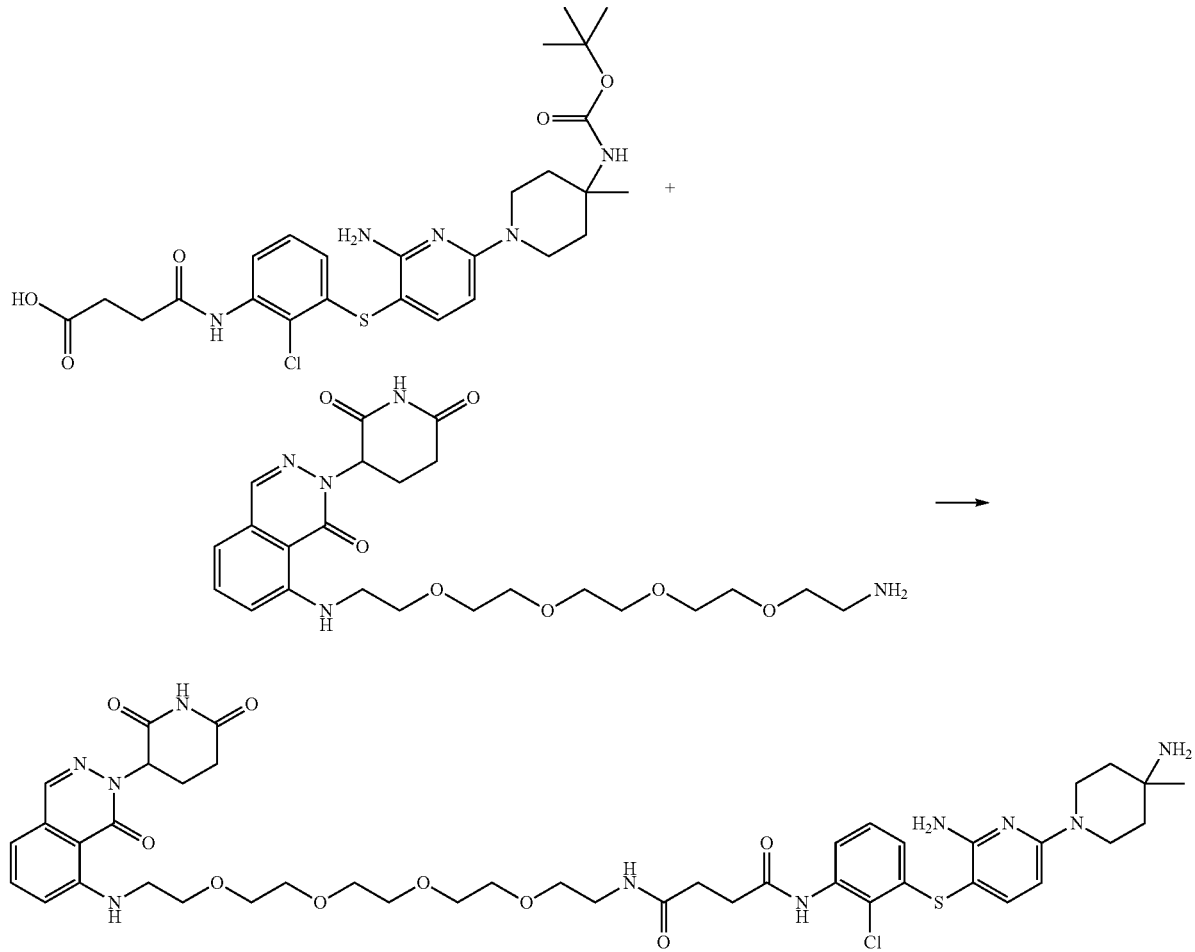

Example 65: N1-(3-((3-amino-5-(4-amino-4-methylpiperidin-1-yl)pyrazin-2-yl)thio)-2-chlorophenyl)-N4-(3-(2-(2-(3-((3-(2,6-dioxopiperidin-3-yl)-4-oxo-3,4-dihydrophthalazin-6-yl)amino)propoxy)ethoxy)ethoxy)propyl)succinamide

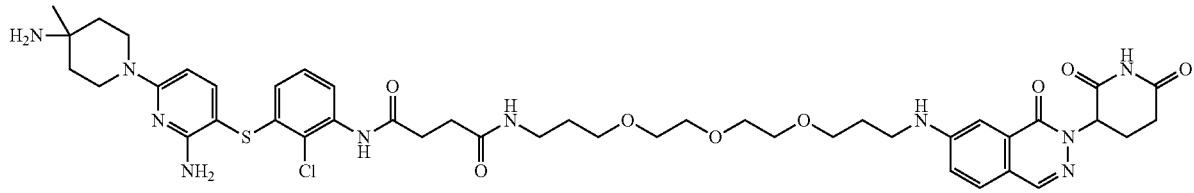 [SMILES: CC1(N)CCN(c2ccc(Sc3cccc(NC(=O)CCC(=O)NCCCOCCOCCOCCCNc4ccc5cnn(C6CCC(=O)NC6=O)c(=O)c5c4)c3Cl)c(N)n2)CC1]

The titled compound is synthesized through following procedure.

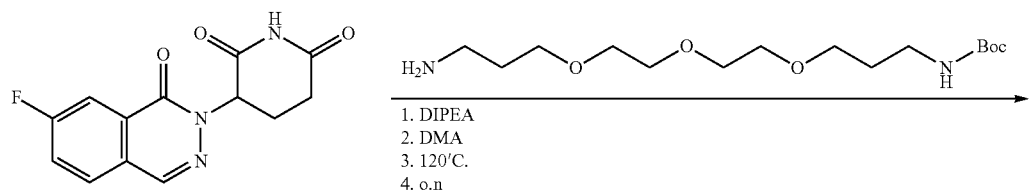

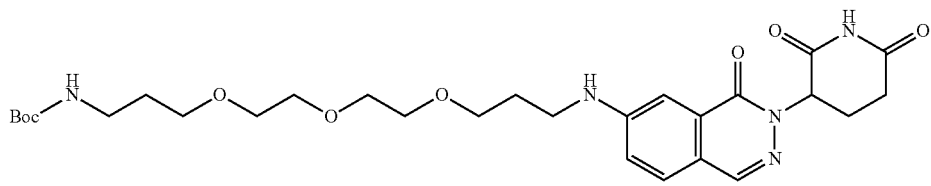

3-(7-fluoro-1-oxophthalazin-2(1H)-yl)piperidine-2,6-dione (200.0 mg, 0.727 mmol) and 1tert-butyl N-(3-{2-[2-(3-aminopropoxy)ethoxy]ethoxy}propyl)carbamate (233.0 mg, 0.727 mmol) and DIPEA (0.633 mL, 3.63 mmol) were dissolved in NMP (2 mL). The reaction mixture was stirred 120° C. for overnight. The reaction was quenched by water and the resultant was extracted with DCM, NH$_4$Cl and brine, and then dried over MgSO$_4$. The reaction mixture was loaded on silica and separated by MPLC. The product was obtained as oil. (Yield: 120 mg, 29%). MS (ESI, m/z): [M+1]$^+$=[576.5].

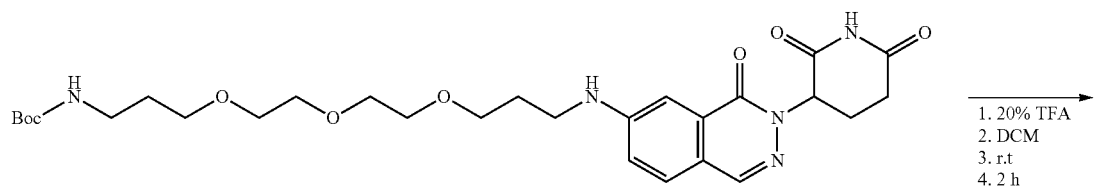

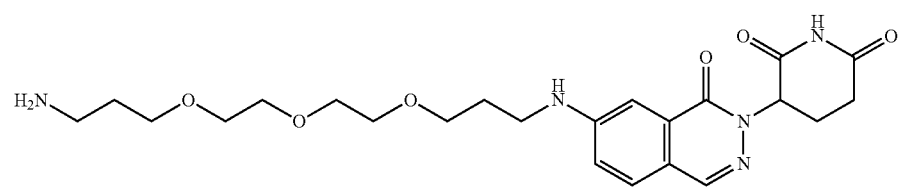

tert-butyl (3-(2-(2-(3-((3-(2,6-dioxopiperidin-3-yl)-4-oxo-3,4-dihydrophthalazin-6-yl)amino)propoxy)ethoxy)ethoxy)propyl)carbamate (50 mg, 0.087 mmol) was dissolved in 20% TFA in DCM. After reaction was finished, reaction mixture was concentrated under reduced pressure. The product was directly used in next step. (Yield: 40 mg, 97%). MS (ESI, m/z): [M+1]$^+$=[476.5].

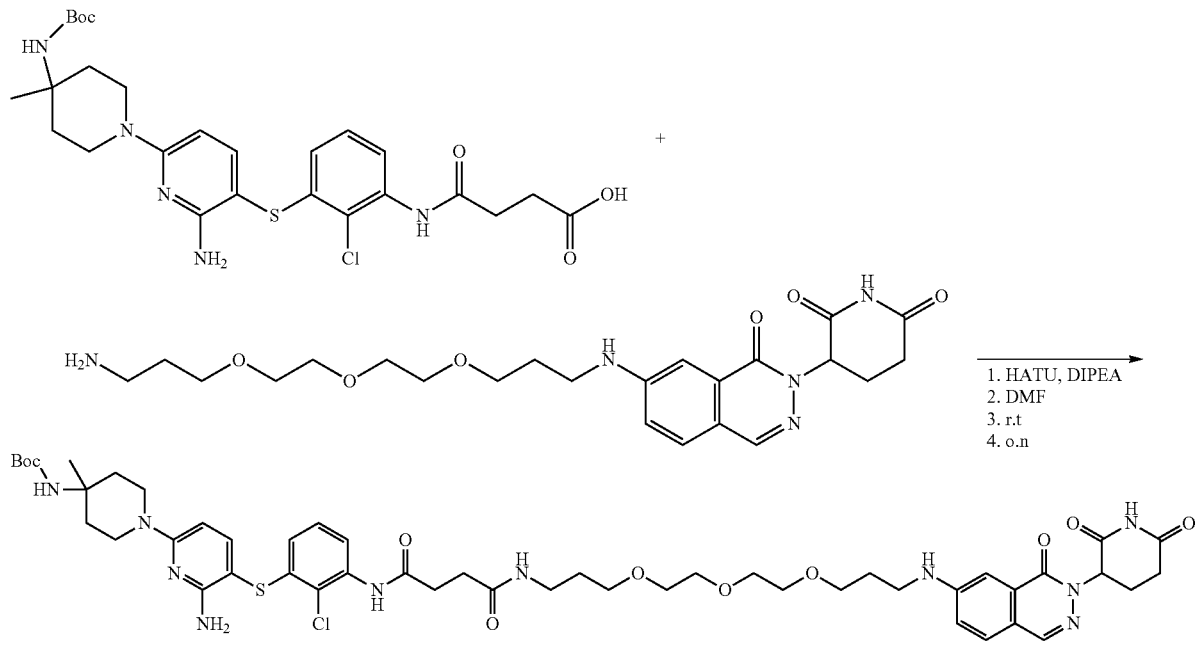

4-((3-((3-amino-5-(4-((tert-butoxycarbonyl)amino)-4-methylpiperidine-1I-yl)pyrazin-2-yl]thio)-2-chlorophenyl)amino)-4-oxobutanoic acid (26.1 mg, 0.046 mmol), HATU (26.4 mg, 0.069 mmol), DIPEA (0.04 mL, 0.231 mmol) and 3-[7-(14-amino-5,8,11-trioxa-1-azatetradecan-1-yl)-1-oxo-1,2-dihydrophthalazin-2-yl]piperidine-2,6-dione (22 mg, 0.046 mmol) were dissolved in DMF. The reaction mixture and stirred for 3 hours at room temperature. After reaction was finished, the reaction mixture was extracted with EA and water. The organic layer was dried over MgSO$_4$ and removed under vacuum. The product was purified by MPLC. The product was obtained as a white solid. (Yield: 30 mg, 64%). MS (ESI, m/z): [M+1]$^+$=[1023.5].

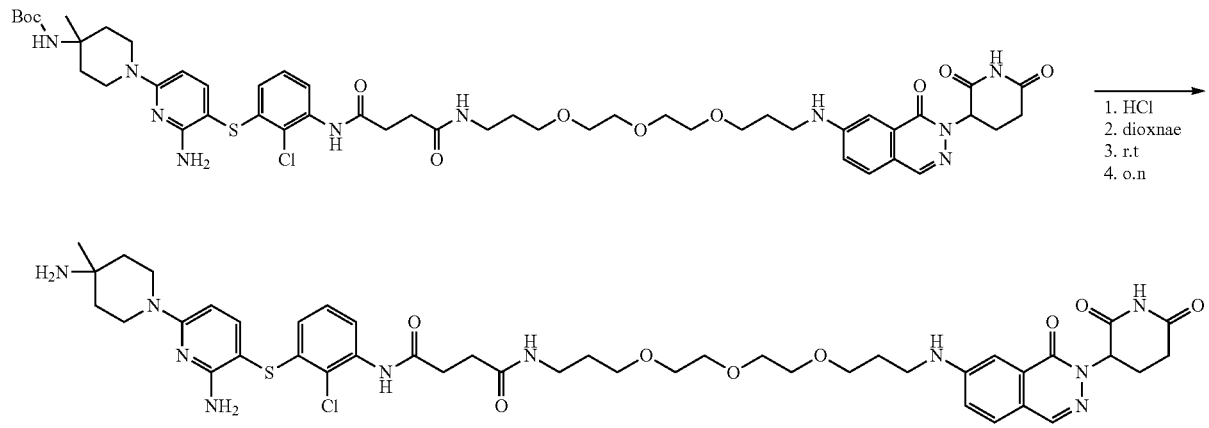

tert-butyl (1-(6-amino-5-((2-chloro-3-(1-((3-(2,6-dioxopiperidin-3-yl)-4-oxo-3,4-dihydrophthalazin-6-yl)amino-15-oxo-4,7,10-trioxa-14-azaoctadecan-18-amido)phenyl)thio)pyrazin-2-yl)-4-methylpiperidin-4-yl)carbamate (30 mg, 0.029 mmol) was dissolved in 1,4 dioxane. 4N—HCl in 1.4 dioxane was added and the mixture was stirred at room temperature for 3 hours. The reaction mixture was concentrated under reduced pressure. The product was purified by amino silica column MPLC. (Yield: 15 mg, 55%).

MS (ESI, m/z): [M+$^1$]+=923.5

[NMR] $^1$H NMR (400 MHz, DMSO-d$_6$) δ ppm 9.55 (s, 1H) 8.14 (s, 1H) 7.86 (t, J=5.26 Hz, 1H) 7.58-7.66 (m, 2H) 7.45 (d, J=7.95 Hz, 1H) 7.10-7.19 (m, 3H) 6.87 (t, J=5.14 Hz, 1H) 6.41 (d, J=8.07 Hz, 1H) 6.09 (s, 2H) 5.74 (d, J=6.85 Hz, 1H) 3.56-3.70 (m, 2H) 3.42-3.56 (m, 8H) 3.39 (br. s., 3H) 3.15-3.24 (m, 3H) 3.03-3.12 (m, 2H) 2.83-2.97 (m, 1H) 2.54-2.65 (m, 4H) 2.39 (t, J=7.03 Hz, 2H) 2.07 (d, J=10.64 Hz, 1H) 1.82 (t, J=6.54 Hz, 2H) 1.60 (quin, J=6.57 Hz, 3H) 1.47 (br. s., 5H) 1.14 (s, 3H)

Example 66: synthesis of N1-(3-((3-amino-5-((3S,4S)-4-amino-3-methyl-2-oxa-8-azaspiro[4.5]decan-8-yl)pyrazin-2-yl)thio)-2-chlorophenyl)-N4-(3-(2-(2-(3-((3-(2,6-dioxopiperidin-3-yl)-4-oxo-3,4-dihydrophthalazin-6-yl)amino)propoxy)ethoxy)ethoxy)propyl)succinamide

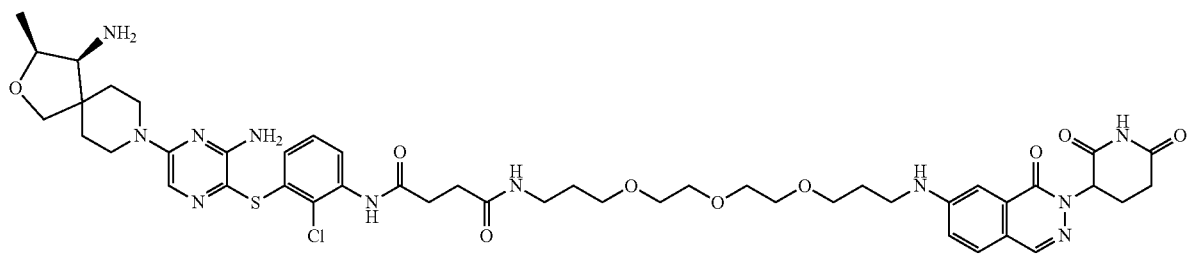 [SMILES: C[C@@H]1OCC2(CCN(c3cnc(Sc4cccc(NC(=O)CCC(=O)NCCCOCCOCCOCCCNc5ccc6cnn(C7CCC(=O)NC7=O)c(=O)c6c5)c4Cl)c(N)n3)CC2)[C@@H]1N]

The titled compound is synthesized through following procedure:

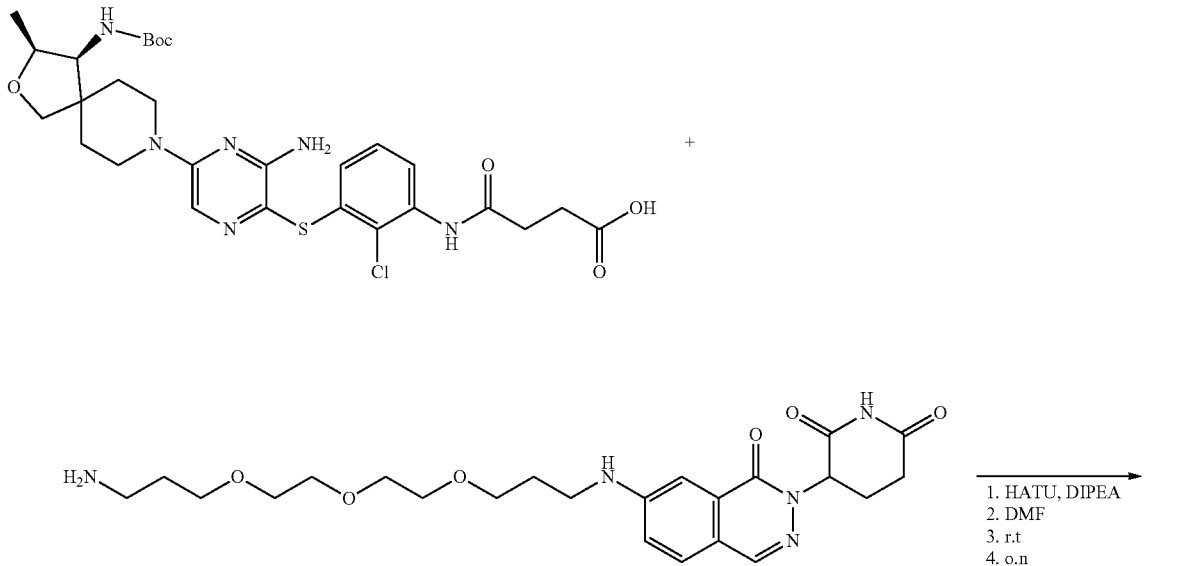

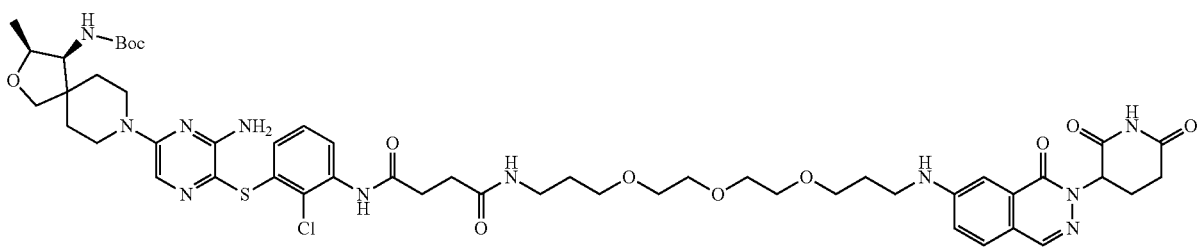

4-((3-((3-amino-5-((3S,4S)-4-((tert-butoxycarbonyl)amino)-3-methyl-2-oxa-8-azaspiro[4.5]decan-8-yl)pyrazin-2-yl)thio)-2-chlorophenyl)amino)-4-oxobutanoic acid (28.7 mg, 0.046 mmol), HATU (26.4 mg, 0.069 mmol), DIPEA (0.04 mL, 0.231 mmol) and 3-[7-(14-amino-5,8,11-trioxa-1-azatetradecan-1-yl)-1-oxo-1,2-dihydrophthalazin-2-yl]piperidine-2,6-dione (22 mg, 0.046 mmol) were dissolved in DMF. The reaction mixture was stirred for 3 hours at room temperature. After reaction was finished, the reaction mixture was extracted with EA and water. The organic layer was dried over MgSO$_4$ and removed under vacuum. The product was purified by MPLC. The product was obtained as white solid. (Yield: 30 mg, 60%). MS (ESI, m/z): [M+$^1$]+= [1080.5].

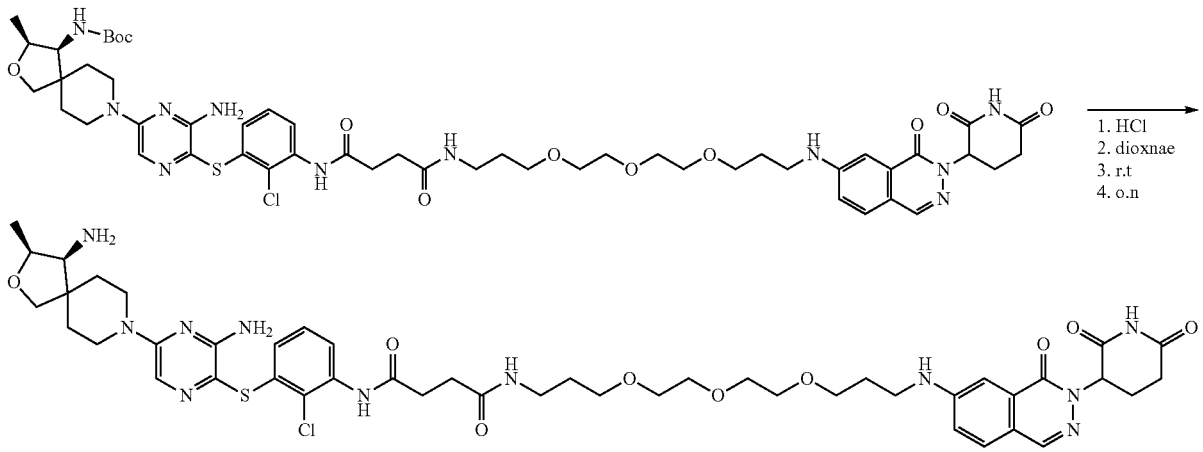

tert-butyl ((3S,4S)-8-(6-amino-5-((2-chloro-3-(1-((3-(2,6-dioxopiperidin-3-yl)-4-oxo-3,4-dihydrophthalazin-6-yl)amino)-15-oxo-4,7,10-trioxa-14-azaoctadecan-18-amido)phenyl)thio)pyrazin-2-yl)-3-methyl-2-oxa-8-azaspiro[4.5]decan-4-yl)carbamate (30 mg, 0.028 mmol) was dissolved in 1,4 dioxane. 4N—HCl in 1.4 dioxane was added and the mixture was stirred at room temperature for 3 hours. The reaction mixture was concentrated under reduced pressure. The product was purified by amino silica column MPLC. (Yield: 15 mg, 55%).

MS (ESI, m/z): [M+$^1$]+=980.5

[NMR] $^1$H NMR (400 MHz, DMSO-d$_6$) δ ppm 11.00 (s, 1H) 9.57 (s, 1H) 8.14 (s, 1H) 8.04 (br. s., 2H) 7.87 (t, J=5.20 Hz, 1H) 7.60-7.69 (m, 2H) 7.46 (d, J=8.19 Hz, 1H) 7.10-7.20 (m, 3H) 6.42 (d, J=6.72 Hz, 1H) 5.74 (d, J=6.60 Hz, 1H) 4.17-4.25 (m, 2H) 4.12 (d, J=12.84 Hz, 1H) 3.90 (d, J=9.05 Hz, 1H) 3.68 (d, J=9.29 Hz, 4H) 3.30-3.40 (m, 8H) 3.21 (t, J=6.72 Hz, 3H) 2.99-3.13 (m, 4H) 2.84-2.97 (m, 2H) 2.54-2.64 (m, 3H) 2.35-2.44 (m, 2H) 2.07 (d, J=9.78 Hz, 1H) 1.78-1.86 (m, 2H) 1.67-1.77 (m, 2H) 1.53-1.65 (m, 3H) 1.19-1.30 (m, 3H)

Example 67: N-[3-({3-amino-5-[(3S,4S)-4-amino-3-methyl-2-oxa-8-azaspiro[4.5]decan-8-yl]pyrazin-2-yl}sulfanyl)-2-chlorophenyl]-N'-(17-{[3-(2,6-dioxopiperidin-3-yl)-4-oxo-3,4-dihydrophthalazin-5-yl]amino}-3,6,9,12,15-pentaoxaheptadecan-1-yl)butanediamide Hydrochloride

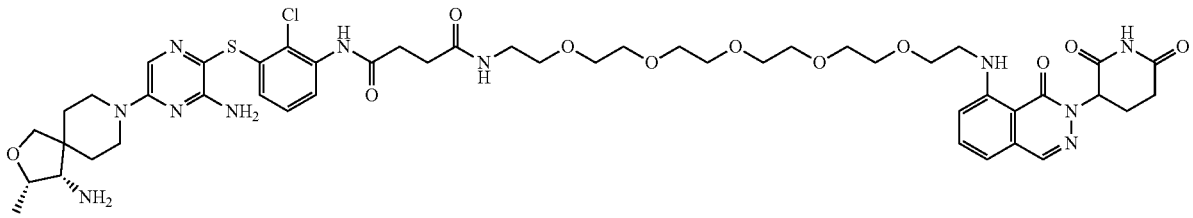 [SMILES: C[C@@H]1OCC2(CCN(c3cnc(Sc4cccc(NC(=O)CCC(=O)NCCOCCOCCOCCOCCOCCNc5cccc6cnn(C7CCC(=O)NC7=O)c(=O)c56)c4Cl)c(N)n3)CC2)[C@@H]1N]

The titled compound is synthesized through following procedure.

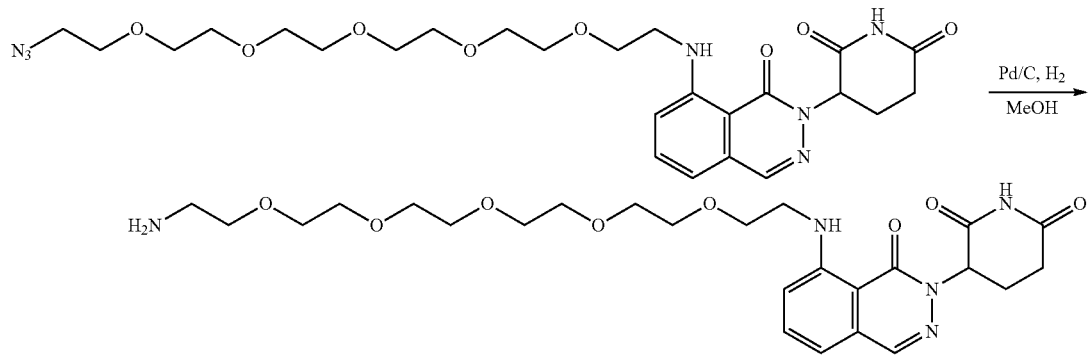

3-[8-(18-azido-4,7,10,13,16-pentaoxa-1-azaoctadecan-1-yl)-1-oxo-1,2-dihydrophthalazin-2-yl]piperidine-2,6-dione (240 mg, 0.427 mmol) was added to a solution of Pd/C (4.5 mg, 0.0427 mmol) in Methanol and the mixture was stirred at room temperature for 14 hours under hydrogen atmosphere. The mixture were filtered by Celite and volatile was removed under reduced pressure to afford a crude residue. (83.0%, 190 mg)

MS (ESI, m/z): [M+1]$^+$=536.3

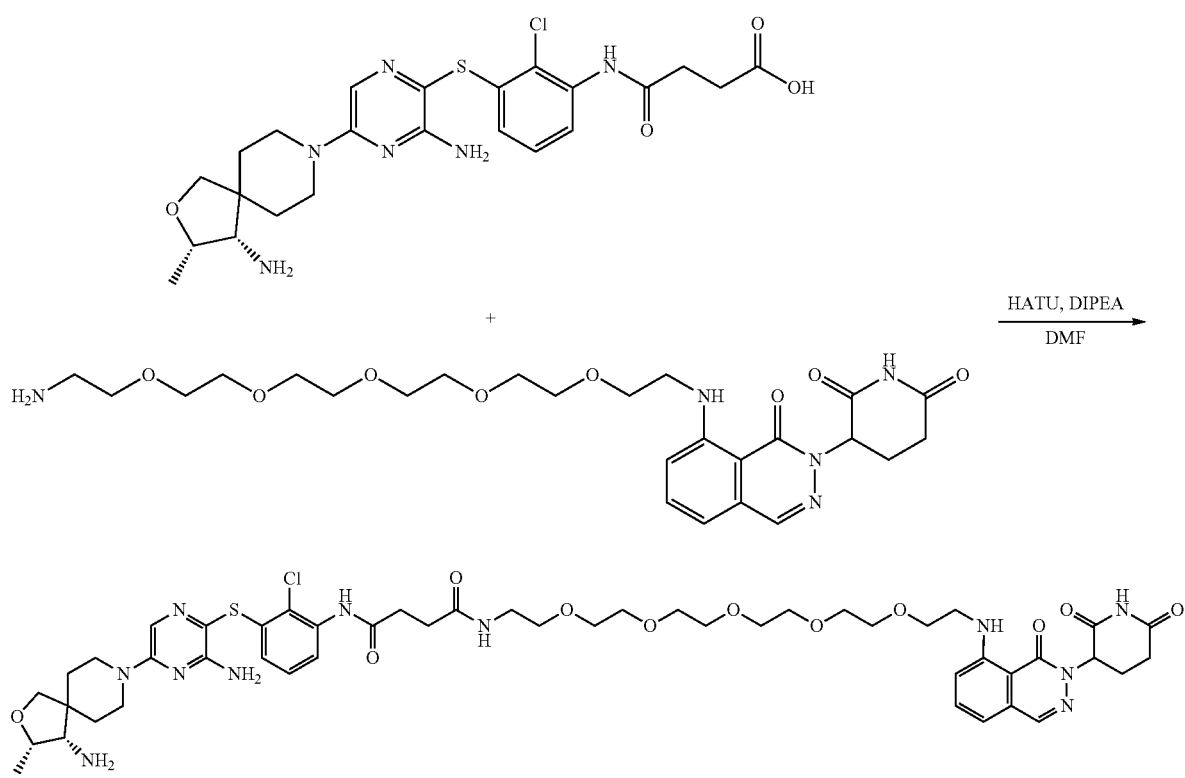

To a solution of 3-[8-(18-amino-4,7,10,13,16-pentaoxa-1-azaoctadecan-1-yl)-1-oxo-1,2-dihydrophthalazin-2-yl]piperidine-2,6-dione (8.64 mg, 0.016 mmol), 3-{[3-({3-amino-5-[(3S,4S)-4-{(tert-butoxy)carbonyl]amino}-3-methyl-2-oxa-8-azaspiro[4.5]decan-8-yl]pyrazin-2-yl}sulfanyl)-2-chlorophenyl]carbamoyl}propanoic acid (15 mg, 0.024 mmol), HATU (9.2 mg, 0.024 mmol) in DMF was added DIPEA (8.6 uL, 0.048 mmol). The mixture was stirred at room temperature overnight. The reaction mixture was diluted with water and extracted with ethyl acetate. The organic layer was washed with brine, dried over Na$_2$SO$_4$, and concentrated. The desired product was separated by column chromatography. MS (ESI, m/z): [M+]$^+$=[1040.6].

Example 68: synthesis of N-(3-{[3-amino-5-(4-amino-4-methylpiperidin-1-yl)pyrazin-2-yl]sulfanyl}-2-chlorophenyl)-N'-(17-{[3-(2,6-dioxopiperidin-3-yl)-4-oxo-3,4-dihydrophthalazin-5-yl]amino}-3,6,9,12,15-pentaoxaheptadecan-1-yl)butanediamide Hydrochloride

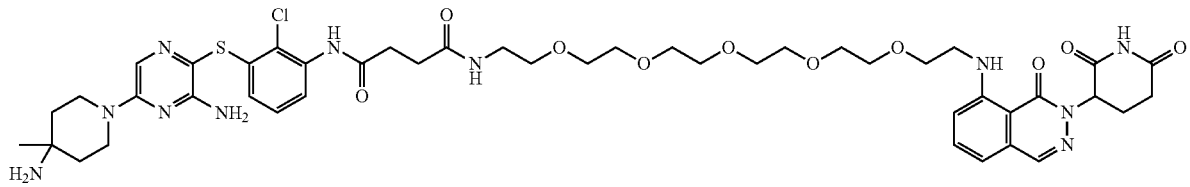 [SMILES: CC1(N)CCN(c2cnc(Sc3cccc(NC(=O)CCC(=O)NCCOCCOCCOCCOCCOCCNc4cccc5cnn(C6CCC(=O)NC6=O)c(=O)c45)c3Cl)c(N)n2)CC1]

The titled compound is synthesized through following procedure.

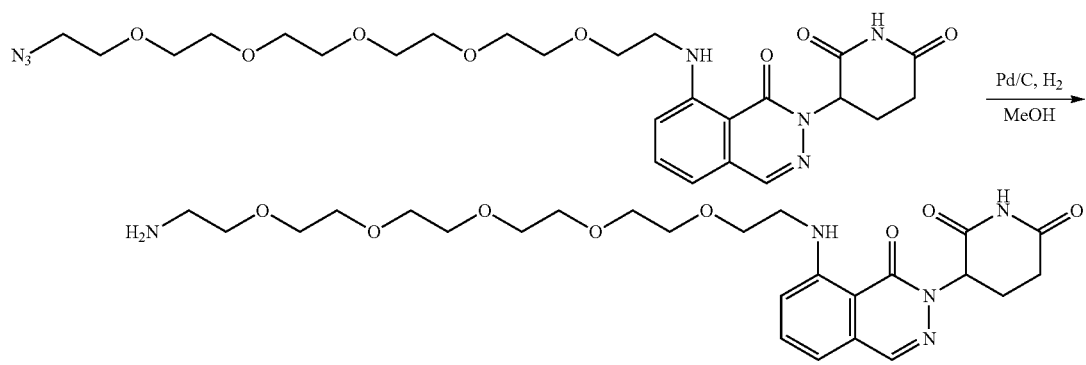

3-[8-(18-azido-4,7,10,13,16-pentaoxa-1-azaoctadecan-1-yl)-1-oxo-1,2-dihydrophthalazin-2-yl]piperidine-2,6-dione (240 mg, 0.427 mmol) was added to a solution of Pd/C (4.55 mg, 0.0427 mmol) in Methanol and the mixture was stirred at room temperature for 14 hours under hydrogen atmosphere. The mixture was filtered by Celite and volatile was removed under reduced pressure to afford a crude residue. (83.01%, 190 mg).

MS (ESI, m/z): [M+$^1$]+=536.7

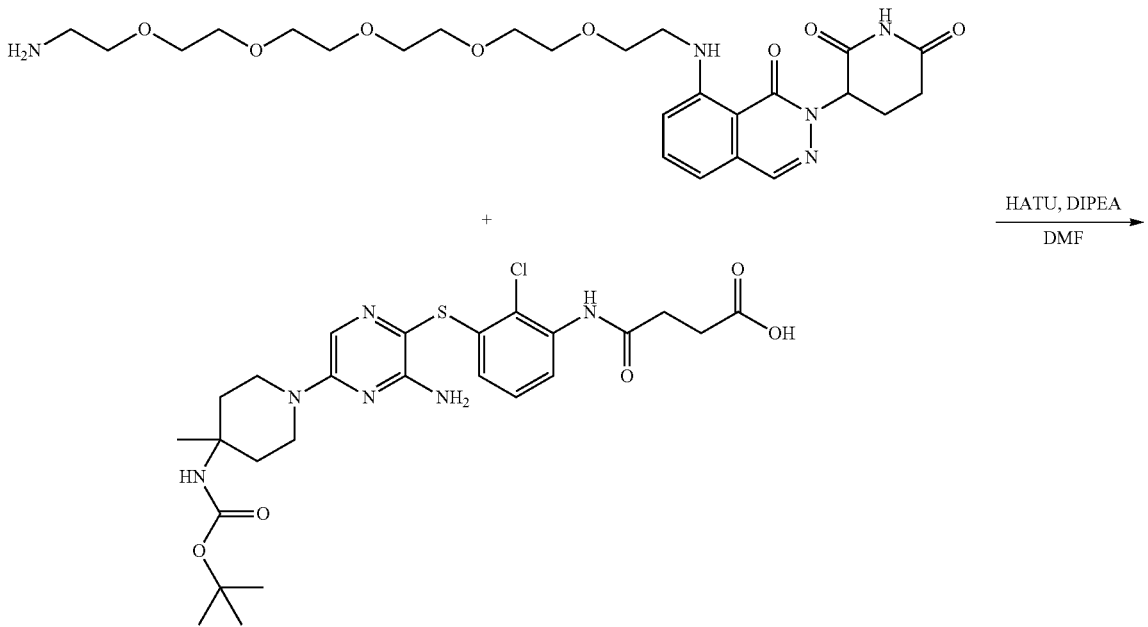

-continued

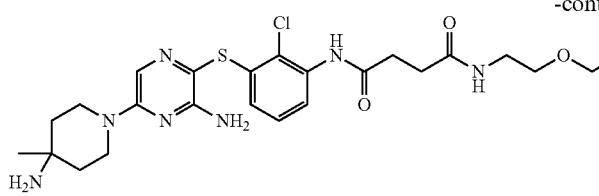 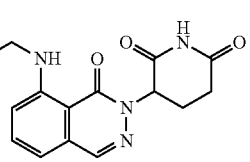

To a solution of 3-[(3-{[3-amino-5-(4-{[(tert-butoxy)carbonyl]amino}-4-methylpiperidin-1-yl)pyrazin-2-yl]sulfanyl}-2-chlorophenyl)carbamoyl]propanoic acid (15 mg, 0.0266 mmol), 3-[8-(18-amino-4,7,10,13,16-pentaoxa-1-azaoctadecan-1-yl)-1-oxo-1,2-dihydrophthaazin-2-yl]piperidine-2,6-dione (14.2 mg, 0.0266 mmol), HATU (9.38 mg, 0.0399 mmol) in DMF was added DIPEA (23.7 µL, 0.133 mmol). The mixture was stirred at room temperature overnight. The reaction mixture was diluted with water and extracted with ethyl acetate. The organic layer was washed with brine, dried over Na$_2$SO$_4$, and concentrated. The desired product was separated by column chromatography. (Yield: 56.4%, 15.3 mg).

MS (ESI, m/z): [M+1]$^+$=983.6

Example 69: N-[3-({3-amino-5-[(3S,4S)-4-amino-3-methyl-2-oxa-8-azaspiro[4.5]decan-8-yl]pyrazin-2-yl}sulfanyl)-2-chlorophenyl]-N'-(14-{[3-(2,6-dioxopiperidin-3-yl)-4-oxo-3,4-dihydrophthalazin-5-yl]amino}-3,6,9,12-tetraoxatetradecan-1-yl) butanediamide Hydrochloride

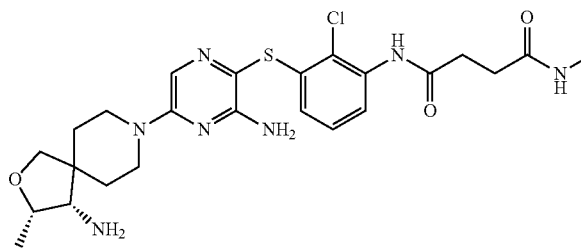 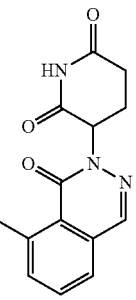

The titled compound is synthesized through following procedure:

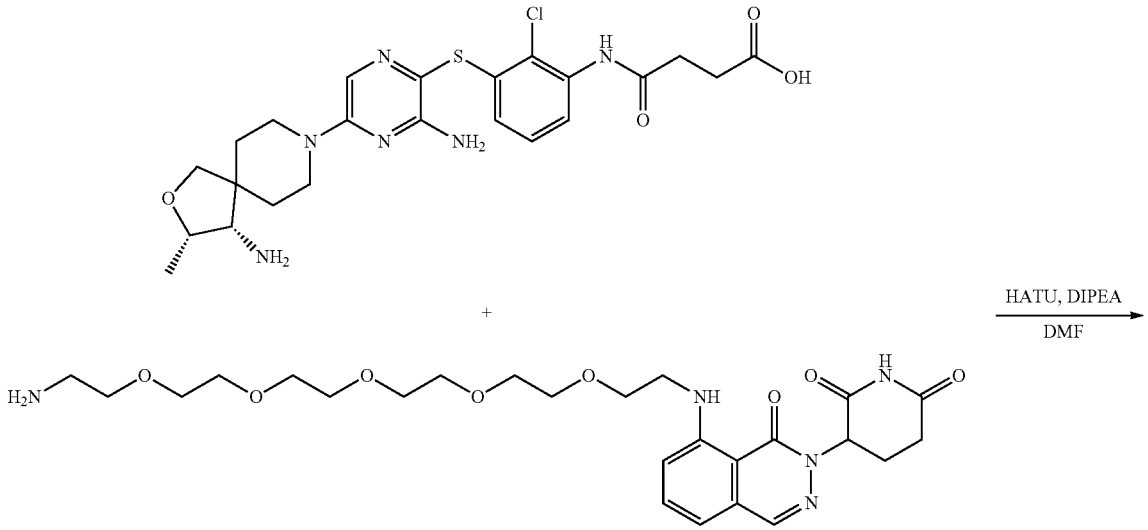

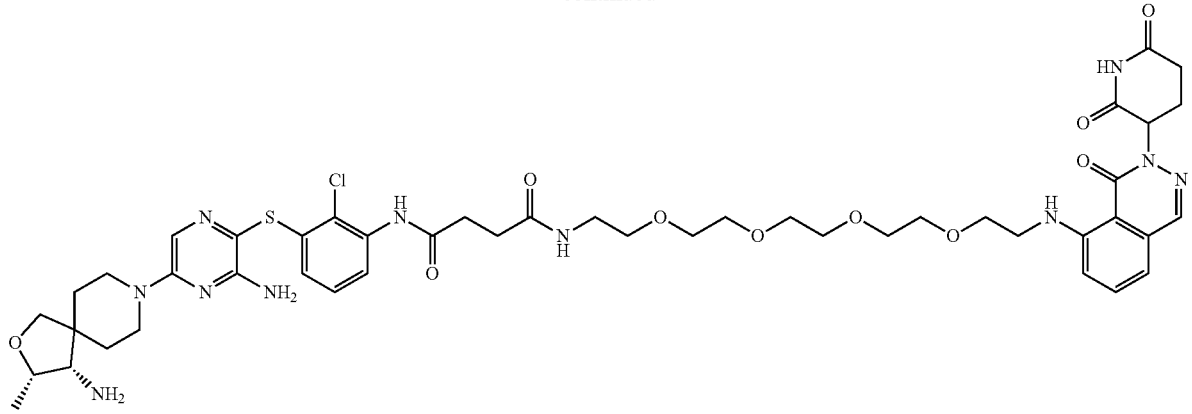 [SMILES: C[C@@H]1OCC2(CCN(c3cnc(Sc4cccc(NC(=O)CCC(=O)NCCOCCOCCOCCOCCCc5cccc6cnn(C7CCC(=O)NC7=O)c(=O)c56)c4Cl)c(N)n3)CC2)[C@@H]1N]

To a solution of 3-[8-(15-amino-4,7,10,13-tetraoxa-1-azapentadecan-1-yl)-1-oxo-1,2-dihydrophthalazin-2-yl]piperidine-2,6-dione (7.93 mg, 0.016 mmol), 3-{[3-({3-amino-5-[(3S,4S)-4-{[(tert-butoxy)carbonyl]amino}-3-methyl-2-oxa-8-azaspiro[4.5]decan-8-yl]pyrazin-2-yl}sulfanyl)-2-chlorophenyl]carbamoyl}propanoic acid (15 mg, 0.024 mmol), HATU (9.2 mg, 0.024 mmol) in DMF was added DIPEA (8.61 μL, 0.048 mmol). The mixture was stirred at room temperature overnight. The reaction mixture was diluted with water and extracted with ethyl acetate. The organic layer was washed with brine, dried over Na$_2$SO$_4$, and concentrated. The desired product was separated by column chromatography. (Yield: 53.4%, 8.89 mg).

MS (ESI, m/z): [M+1]$^+$=[996.5]

Example 70: Synthesis of N-[3-({3-amino-5-[(3S,4S)-4-amino-3-methyl-2-oxa-8-azaspiro[4.5]decan-8-yl]pyrazin-2-yl}sulfanyl)-2-chlorophenyl]-N'-{3-[4-(3-{[3-(2,6-dioxopiperidin-3-yl)-4-oxo-3,4-dihydrophthalazin-5-yl]amino}propyl)piperazin-1-yl]propyl}butanediamide Trihydrochloride

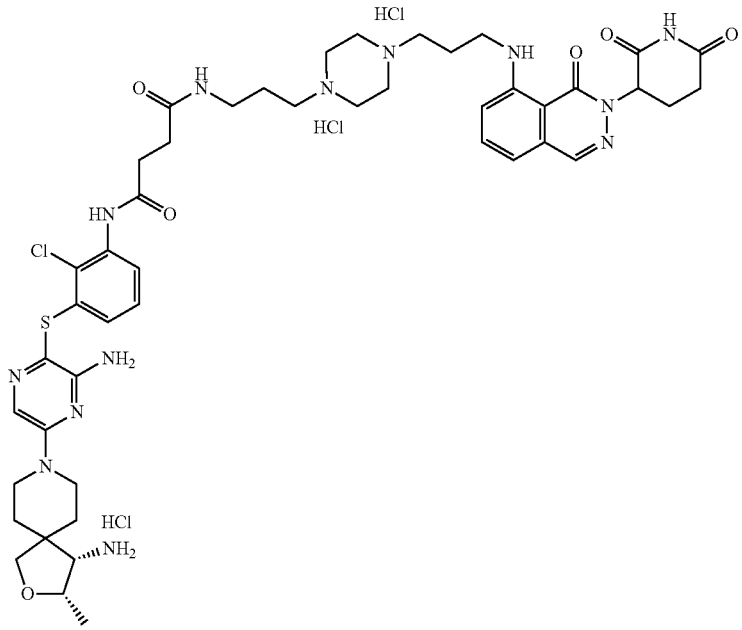 [SMILES: Cl ; C[C@@H]1OCC2(CCN(c3cnc(Sc4cccc(NC(=O)CCC(=O)NCCCN5CCN(CCCNc6cccc7cnn(C8CCC(=O)NC8=O)c(=O)c67)CC5)c4Cl)c(N)n3)CC2)[C@@H]1N ; Cl ; Cl]

The titled compound is synthesized through following procedure:

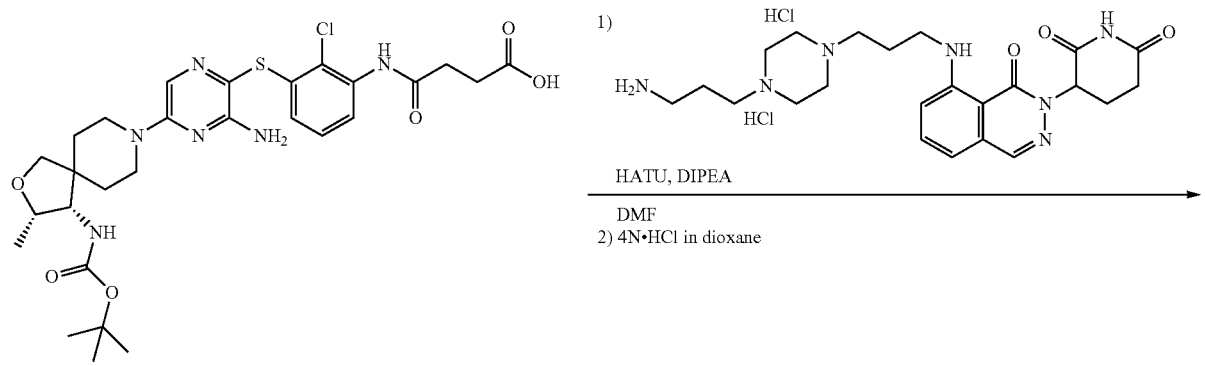

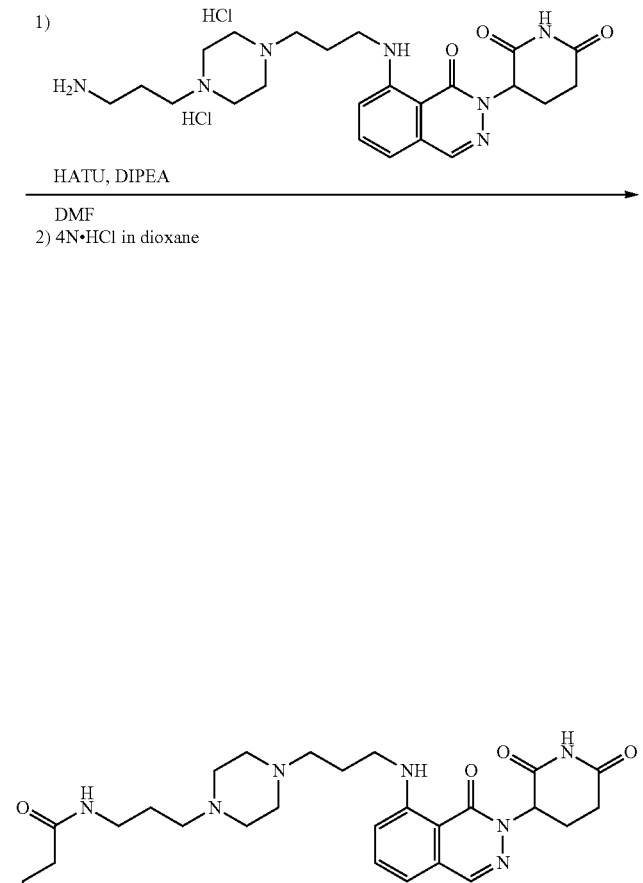

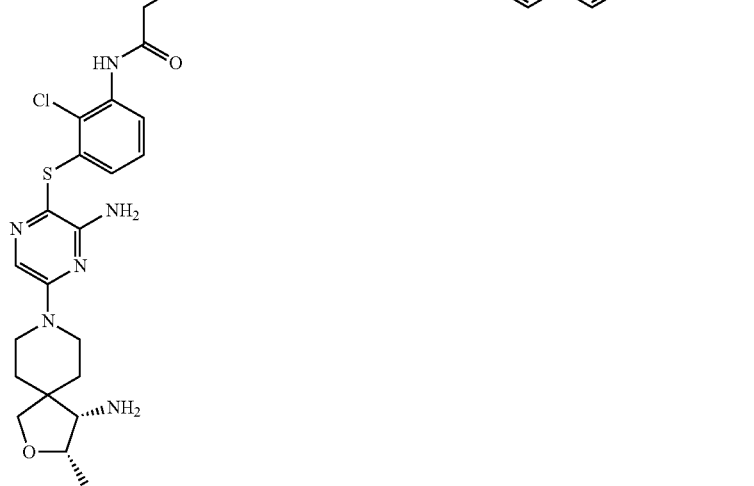

To a solution of 3-[8-({3-[4-(3-aminopropyl)piperazin-1-yl]propyl}amino)-1-oxo-1,2-dihydrophthalazin-2-yl]piperidine-2,6-dione dihydrochloride (8.52 mg, 0.0161 mmol), 3-{[3-({3-amino-5-[(3S,4S)-4-{[(tert-butoxy)carbonyl]amino}-3-methyl-2-oxa-8-azaspiro[4.5]decan-8-yl]pyrazin-2-yl}sulfanyl)-2-chlorophenyl]carbamoyl}propanoic acid (15 mg, 0.0241 mmol), HATU (9.2 mg, 0.0242 mmol) in DMF was added DIPEA (8.61 μL, 0.0484 mmol). The mixture was stirred at room temperature overnight. The reaction mixture was diluted with water and extracted with ethyl acetate. The organic layer was washed with brine, dried over $Na_2SO_4$, and concentrated.

The resulting compound was dissolved in DCM (2 ml), and 4N HCl in dioxane was added to the solution dropwise slowly, and sonicated for 10 minutes. The residue was evaporated and dissolved in MeOH. The solvent was evaporated and dried in vacuo. The desired product was separated by column chromatography. (Yield: 47.5%, 8.18 mg).

MS (ESI, m/z): [M+$^1$]+=960.0

Example 71: N1-(3-((3-amino-5-((3S,4S)-4-amino-3-methyl-2-oxa-8-azaspiro[4.5]decan-8-yl)pyrazin-2-yl)thio)-2-chlorophenyl)-N4-(3-(2-(2-(3-((3-(2,6-dioxopiperidin-3-yl)-1-methyl-4-oxo-3,4-dihydrophthalazin-5-yl)amino)propoxy)ethoxy)ethoxy)propyl)succinamide

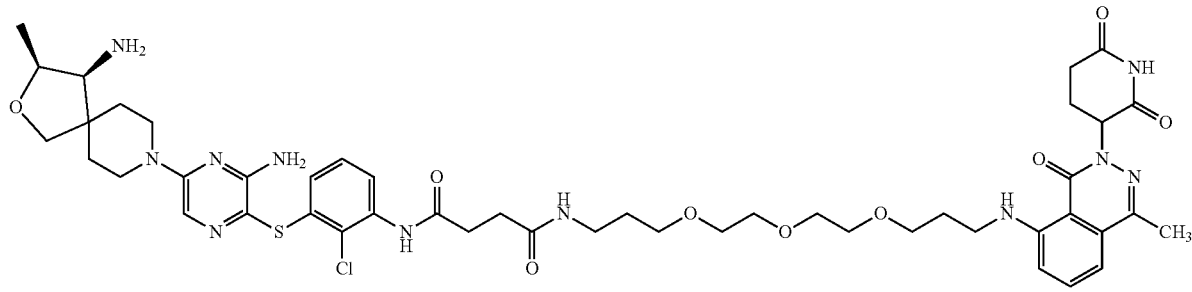 [SMILES: Cc1nn(C2CCC(=O)NC2=O)c(=O)c2c(NCCCOCCOCCOCCCNC(=O)CCC(=O)Nc3cccc(Sc4ncc(N5CCC6(CC5)CO[C@@H](C)[C@H]6N)nc4N)c3Cl)cccc12]

20

The titled compound is synthesized through following procedure:

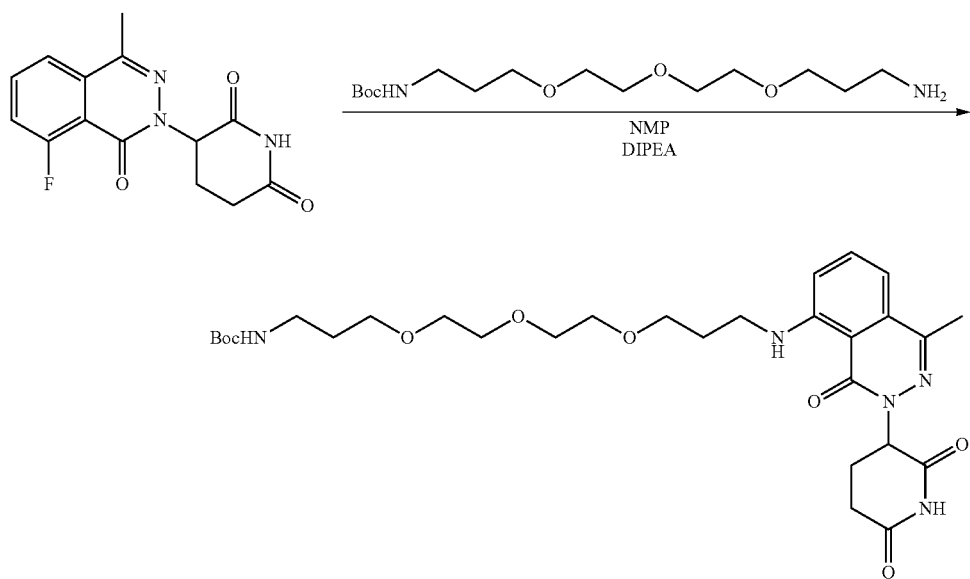

A solution of 3-(8-fluoro-4-methyl-1-oxophthalazin-2(1H)-yl)piperidine-2,6-dione (150 mg, 0.519 mmol), tert-butyl (3-(2-(2-(3-aminopropoxy)ethoxy)ethoxy)propyl)carbamate (199 mg, 0.622 mmol) and DIPEA (0.271 mL, 1.56 mmol) in NMP (1 mL) was stirred for 16 hours at 120° C. The reaction mixture was purified by reverse column chromatography to give the product. (Yield: 236 mg, 77.2%). MS (ESI, m/z): [M+$^1$]+=[590.2]

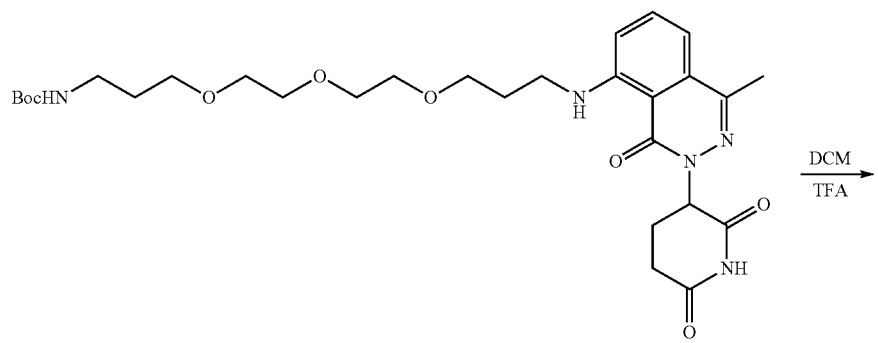

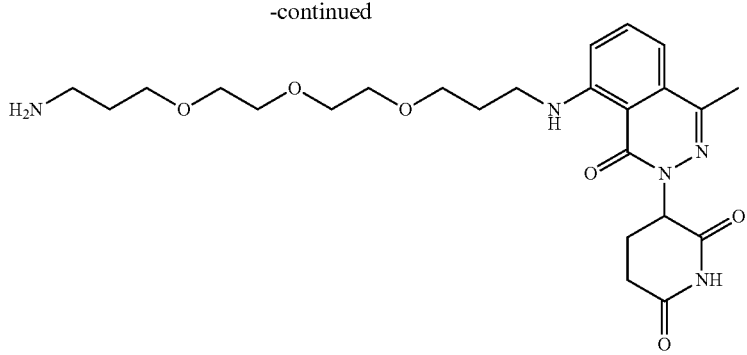
To a solution of tert-butyl (3-(2-(2-(3-((3-(2,6-dioxopiperidin-3-yl)-1-methyl-4-oxo-3,4-dihydrophthaazin-5-yl)amino)propoxy)ethoxy)ethoxy)propyl)carbamate (20 mg, 0.034 mmol) in 0.3 ml of DCM was added 0.1 ml of TFA and the mixture was stirred at room temperature for 1 hour. The reaction mixture was concentrated in vacuo and used for the next step without further purification. (Yield: 16.6 mg, quant.). MS (ESI, mu/z): [M+1]$^+$=[490.2]
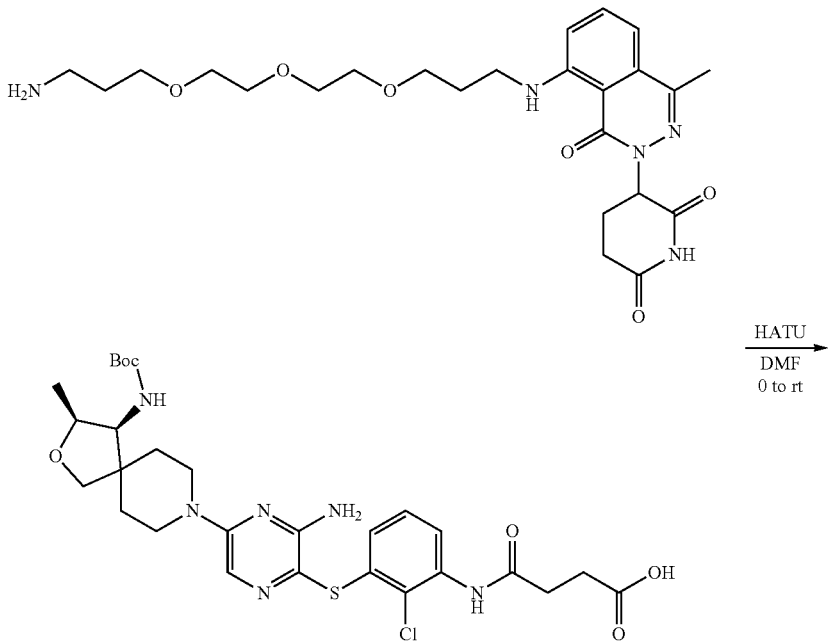
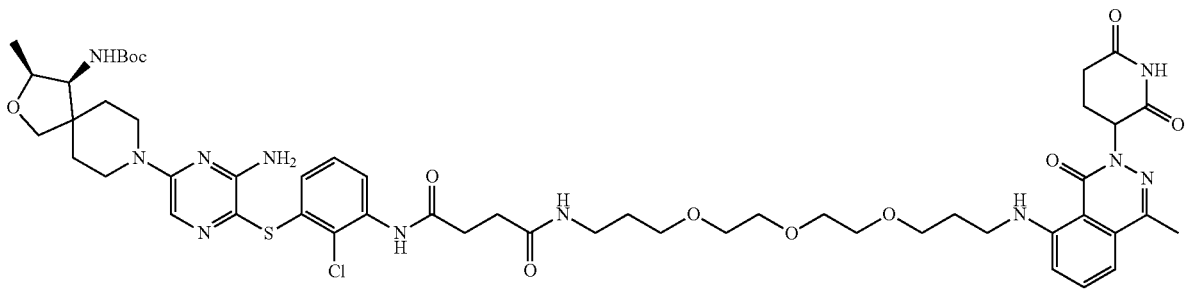

To a solution of 3-(8-((3-(2-(2-(3-aminopropoxy)ethoxy)ethoxy)propyl)amino)-4-methyl-1-oxophthalazin-2(1H)-yl)piperidine-2,6-dione (16.6 mg, 0.034 mmol), 4-((3-((3-amino-5-((3S,4S)-4-((tert-butoxycarbonyl)amino)-3-methyl-2-oxa-8-azaspiro[4.5]decan-8-yl)pyrazin-2-yl)thio)-2-chlorophenyl)amino)-4-oxobutanoic acid (20 mg, 0.032 mmol) and DIPEA (0.028 ml, 0.16 mmol) in DMF (1 mL) was added HATU (19.3 mg, 0.051 mmol) at 0° C. and the mixture was stirred at room temperature for 1 hour. The reaction mixture was purified by reverse column chromatography to give the product. (Yield: 31 mg, 83.7%). MS (ESI, m/z): [M+1]$^+$=[1092.6]

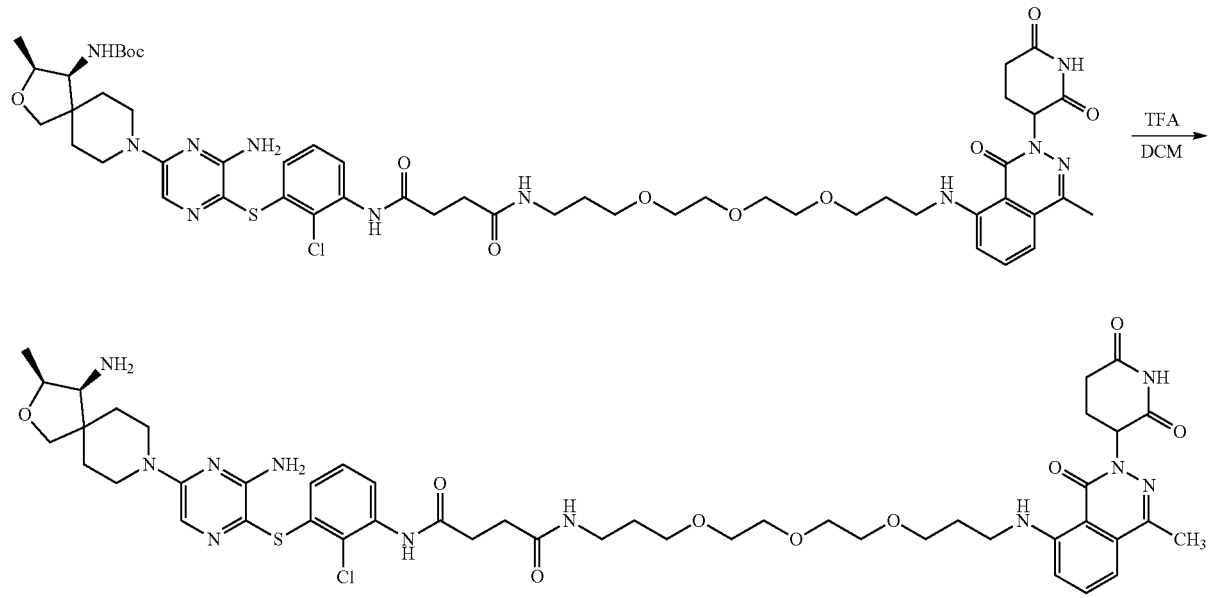

To a solution of tert-butyl ((3S,4S)-8-(6-amino-5-((2-chloro-3-(1-((3-(2,6-dioxopiperidin-3-yl)-1-methyl-4-oxo-3,4-dihydrophthalazin-5-yl)amino)-15-oxo-4,7,10-trioxa-14-azaoctadecan-18-amido)phenyl)thio)pyrazin-2-yl)-3-methyl-2-oxa-8-azaspiro[4.5]decan-4-yl)carbamate (31 mg, 0.028 mmol) in 0.3 ml of DCM was added 0.1 ml of TFA and the mixture was stirred at room temperature for 1 hour. The reaction mixture was concentrated in vacuo. The reaction mixture was purified by amino silica gel column chromatography to give the product. (Yield: 17.5 mg, 62.2%).

1H NMR (400 MHz, DMSO-d6) δ=10.99 (s, 1H), 9.55 (s, 1H), 8.96 (t, J=5.3 Hz, 1H), 7.86 (t, J=5.6 Hz, 1H), 7.66 (t, J=8.1 Hz, 1H), 7.63 (s, 1H), 7.45 (d, J=7.6 Hz, 1H), 7.14 (t, J=8.1 Hz, 1H), 6.91 (d, J=8.2 Hz, 1H), 6.91 (d, J=7.6 Hz, 1H), 6.11 (s, 2H), 5.63 (m, 1H), 4.08 (m, 1H), 3.86 (m, 2H), 3.68 (d, J=8.07 Hz, 1H), 3.57-3.47 (m, 10H), 3.47-3.42 (m, 2H), 3.37 (m, 4H), 3.27 (m, 4H), 3.08 (q, J=6.77 Hz, 2H), 2.95 (d, J=4.9 Hz, 1H), 2.91-2.83 (m, 1H), 2.66-2.53 (m, 4H), 2.41 (s, 3H), 2.39 (m, 2H), 2.07 (m, 1H), 1.85 (q, J=6.5 Hz, 2H), 1.72-1.40 (m, 6H), 1.35-1.15 (m, 2H), 1.09 (d, J=6.6 Hz, 3H)

MS (ESI, m/z): [M+1]$^+$=[992.6][994.6]

Example 72: synthesis of N1-(3-((3-amino-5-(4-amino-4-methylpiperidin-1-yl)pyrazin-2-yl)thio)-2-chlorophenyl)-N4-(3-(2-(2-(3-((2-(2,6-dioxopiperidin-3-yl)-1-oxo-1,2-dihydrophthalazin-6-yl)amino)propoxy)ethoxy)ethoxy)propyl)succinamide

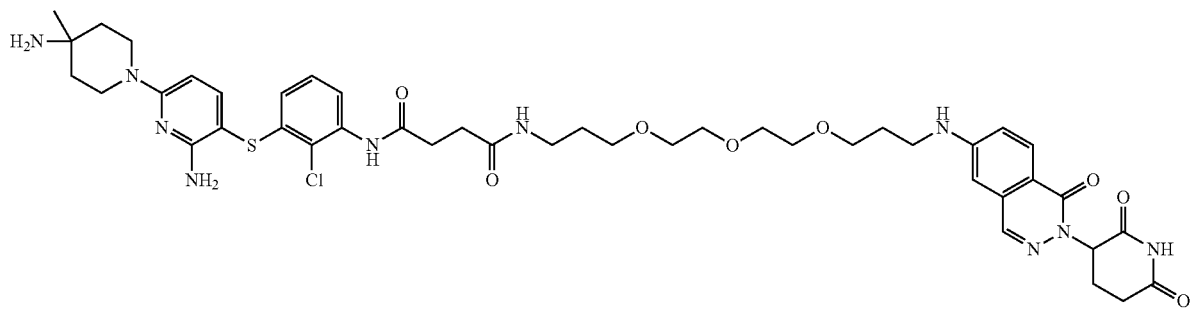 [SMILES: CC1(N)CCN(c2ccc(Sc3cccc(NC(=O)CCC(=O)NCCCOCCOCCOCCCNc4ccc5c(=O)n(C6CCC(=O)NC6=O)ncc5c4)c3Cl)c(N)n2)CC1]

The titled compound is synthesized through following procedure:

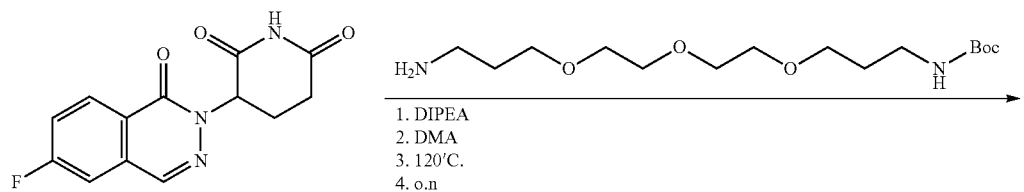

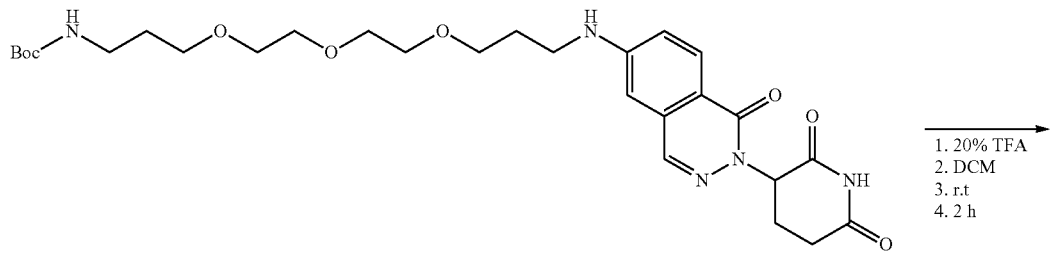

3-(6-fluoro-1-oxophthalazin-2(1H)-yl)piperidine-2,6-dione (200.0 mg, 0.727 mmol), tert-butyl N-(3-{2-[2-(3-aminopropoxy)ethoxy]ethoxy}propyl)carbamate (233.0 mg, 0.727 mmol) and DIPEA (0.633 mL, 3.63 mmol) were dissolved in NMP (2 mL). The reaction mixture was stirred 120° C. for overnight. The reaction was quenched by water and the resultant was extracted with DCM, NH$_4$Cl and brine, and then dried over MgSO$_4$. The reaction mixture was loaded on silica and separated by MPLC. The product was obtained as oil. (Yield: 150 mg, 38%). MS (ESI, m/z): [M+$^1$]+=[576.5].

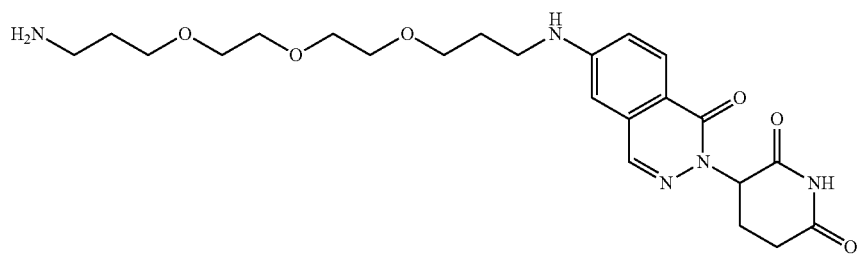

tert-butyl N-(3-{2-[2-(3-{[2-(2,6-dioxopiperidin-3-yl)-1-oxo-1,2-dihydrophthalazin-6-yl]amino}propoxy)ethoxy]ethoxy}propyl)carbamate (31 mg, 0.054 mmol) was dissolved in 20% TFA in DCM. After reaction was finished, reaction mixture was concentrated under reduced pressure. The product was directly used in next step. (Yield: 25 mg, 97%). MS (ESI, m/z): [M+$^1$]+=[476.5].

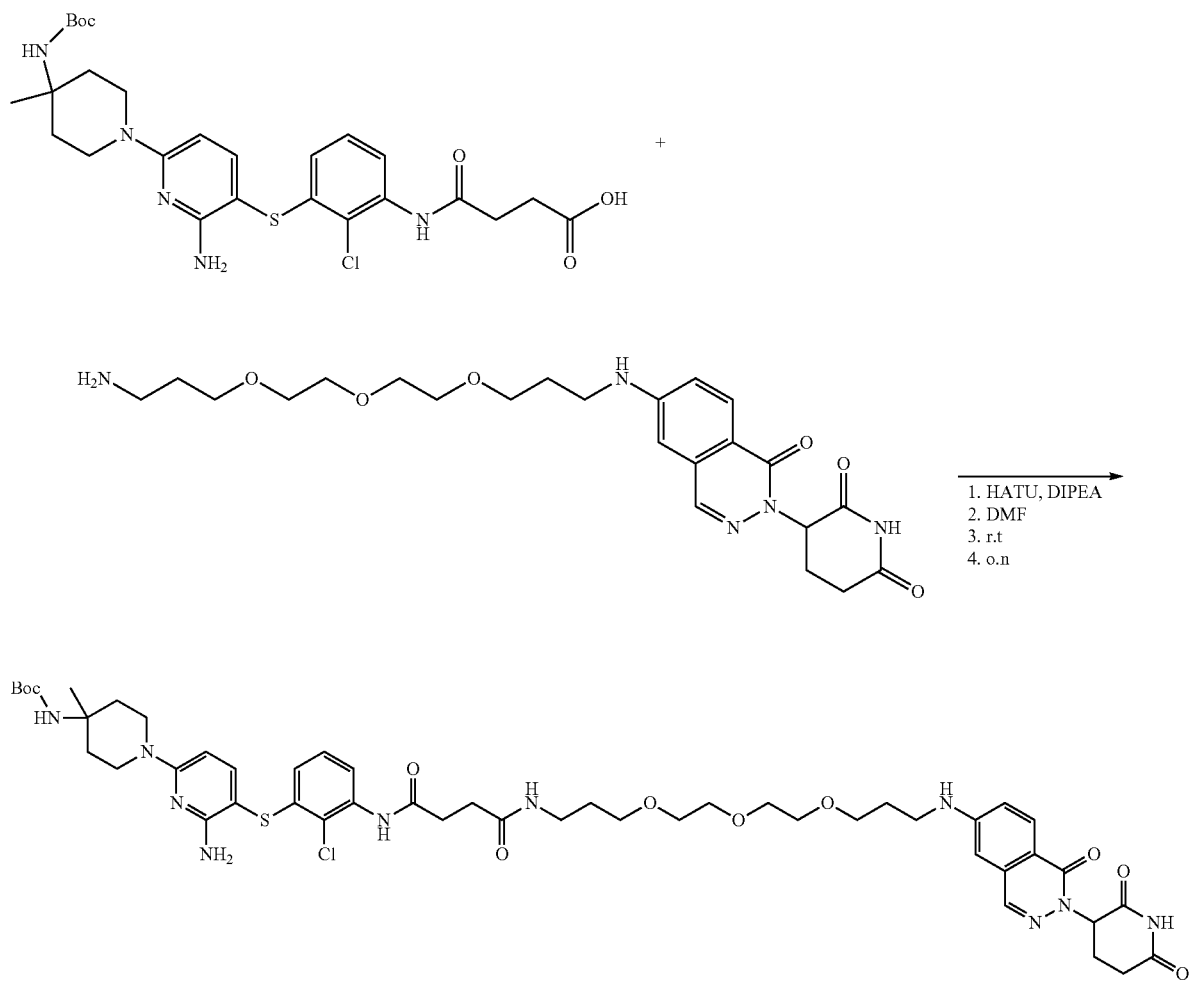

4-((3-((3-amino-5-(4-(((tert-butoxycarbonyl)amino}-4-methylpiperidin-1-yl)pyrazin-2-yl)thio)-2-chlorophenyl)amino-4-oxobutanoic acid (29.7 mg, 0.052 mmol), HATU (30.0 mg, 0.079 mmol), DIPEA (0.05 mL, 0.263 mmol) and 3-[6-(14-amino-5,8,11-trioxa-1-azatetradecan-1-yl)-1-oxo-1,2-dihydrophthalazin-2-yl]piperidine-2,6-dione (25 mg, 0.052 mmol) were dissolved in DMF. The reaction mixture and stirred for 3 hours at room temperature. After reaction was finished, the reaction mixture was extracted with EA and water. The organic layer was dried over MgSO$_4$ and removed under vacuum. The product was purified by MPLC. The product was obtained as white solid. (Yield: 30 mg, 56%). MS (ESI, m/z): [M+]$^+$=[1023.5]

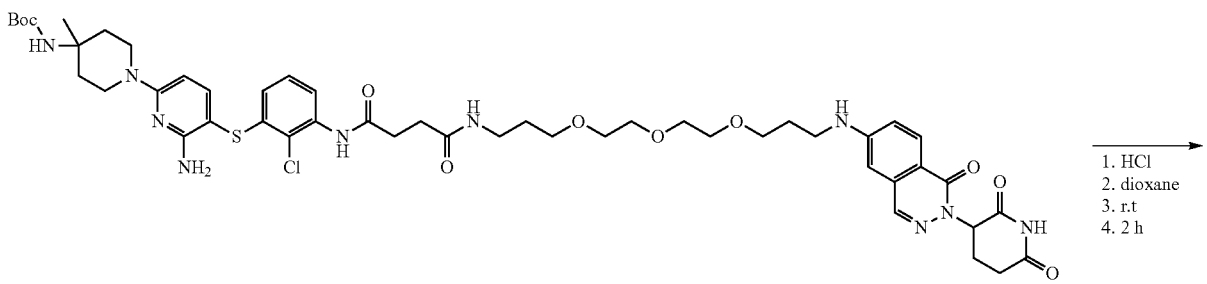

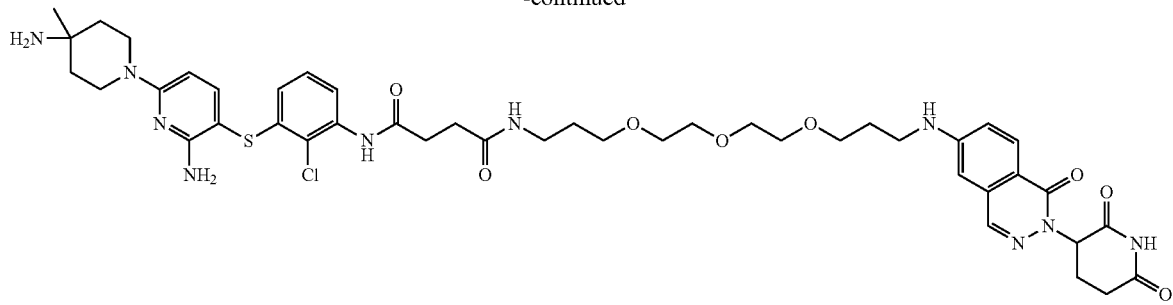

tert-butyl (1-(6-amino-5-((2-chloro-3-(1-((2-(2,6-di-oxopiperidin-3-yl)-1-oxo-1,2-dihydrophthalazine-6-yl)amino-15-우소-4,7,10-trioxa-azaoctadecan-19-amido)phenyl)thio)pyrazin-2-yl)-4-methylpiperidin-4-yl)carbamate (30 mg, 0.029 mmol) was dissolved in 1,4 dioxane. 4M HCl in 1.4 dioxane was added and the mixture was stirred at room temperature for 3 hours. The reaction mixture was concentrated under reduced pressure. The product was purified by amino silica column MPLC. (Yield: 17 mg, 35%).

MS (ESI, m/z): [M+1]+=923.5

[NMR] $^1$H NMR (400 MHz, DMSO-$d_6$) δ ppm 9.56 (s, 1H) 8.42 (s, 2H) 8.18 (s, 1H) 7.91 (d, J=8.68 Hz, 1H) 7.86 (s, 1H) 7.62 (s, 1H) 7.45 (d, J=8.07 Hz, 1H) 7.14 (t, J=8.07 Hz, 1H) 7.07 (d, J=8.68 Hz, 1H) 6.89 (s, 1H) 6.76 (s, 1H) 6.41 (d, J=7.95 Hz, 1H) 6.10 (s, 2H) 5.73 (s, 1H) 3.63 (br. s., 2H) 3.43-3.56 (m, 8H) 3.20 (d, J=5.38 Hz, 3H) 3.08 (d, J=5.26 Hz, 2H) 2.89 (br. s., 1H) 2.67 (s, 1H) 2.54-2.64 (m, 4H) 2.39 (t, J=6.85 Hz, 2H) 2.07 (br. s., 1H) 1.82 (t, J=6.24 Hz, 2H) 1.60 (t, J=7.03 Hz, 3H) 1.49 (br. s., 5H) 1.14 (s, 3H)

Example 73: N1-(3-((3-amino-5-((3S,4S)-4-amino-3-methyl-2-oxa-8-azaspiro[4.5]decan-8-yl)pyrazin-2-yl)thio)-2-chlorophenyl)-N4-(3-(2-(2-(3-((2-(2,6-dioxopiperidin-3-yl)-1-oxo-1,2-dihydrophthalazin-6-yl)amino)propoxy)ethoxy)ethoxy)propyl)succinamide

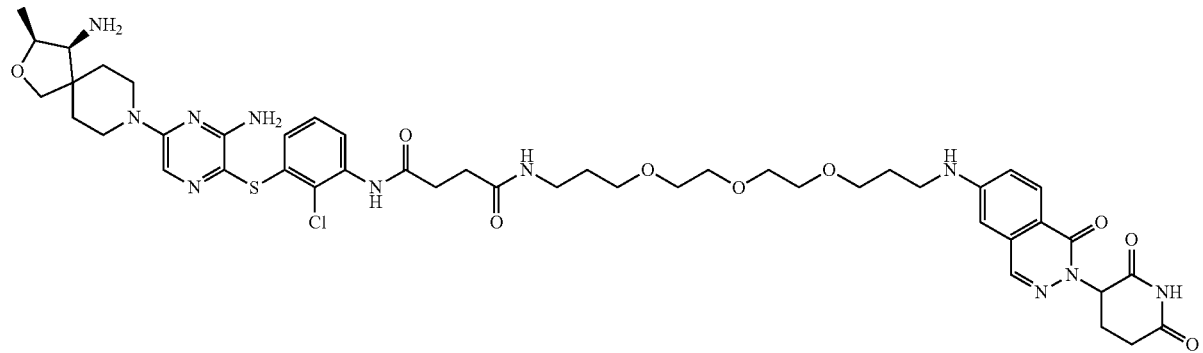 [SMILES: C[C@@H]1OCC2(CCN(c3cnc(Sc4cccc(NC(=O)CCC(=O)NCCCOCCOCCOCCCNc5ccc6c(=O)n(C7CCC(=O)NC7=O)ncc6c5)c4Cl)c(N)n3)CC2)[C@@H]1N]

The titled compound is synthesized through following procedure:

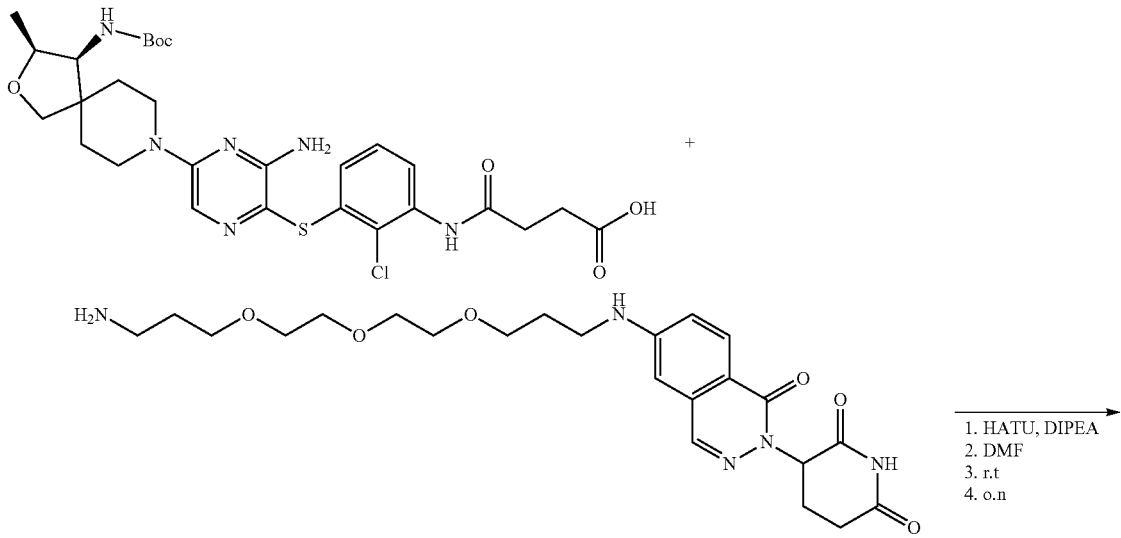

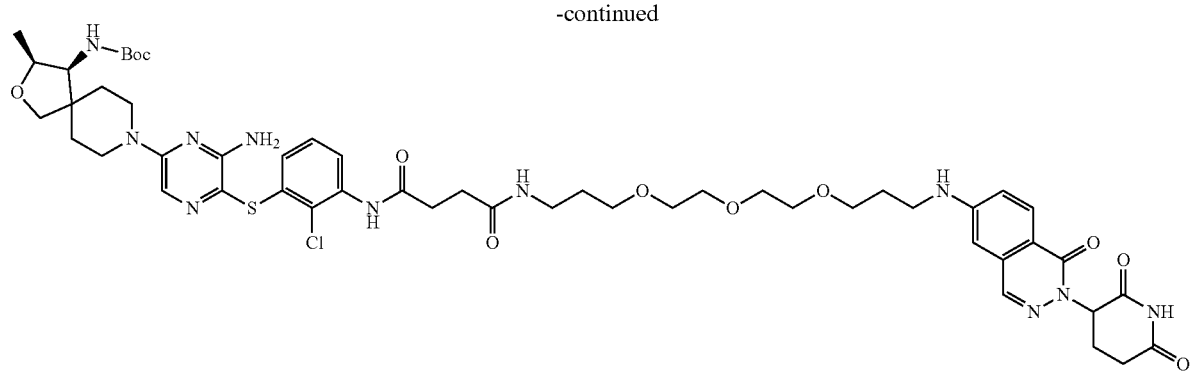

4-((3-((3-amino-5-((3S,4S)-4-((tert-butoxycarbonyl)amino)-3-methyl-2-oxa-8-azaspiro[4.5]decan-8-yl)pyrazin-2-yl)thio)-2-chlorophenyl)amino)-4-oxobutanoic acid (32.7 mg, 0.053 mmol), HATU (30.0 mg, 0.079 mmol), DIPEA (0.05 mL, 0.263 mmol) and 3-[6-(14-amino-5,8,11-trioxa-1-azatetradecan-1-yl)-1-oxo-1,2-dihydrophthalazin-2-yl]piperidine-2,6-dione (25 mg, 0.053 mmol) were dissolved in DMF. The reaction mixture and stirred for 3 hours at room temperature. After reaction was finished, the reaction mixture was extracted with EA and water. The organic layer was dried over MgSO$_4$ and removed under vacuum. The product was purified by MPLC. The product was obtained as white solid. (Yield: 40 mg, 71%). MS (ESI, m/z): [M+1]$^+$= [1080.5].

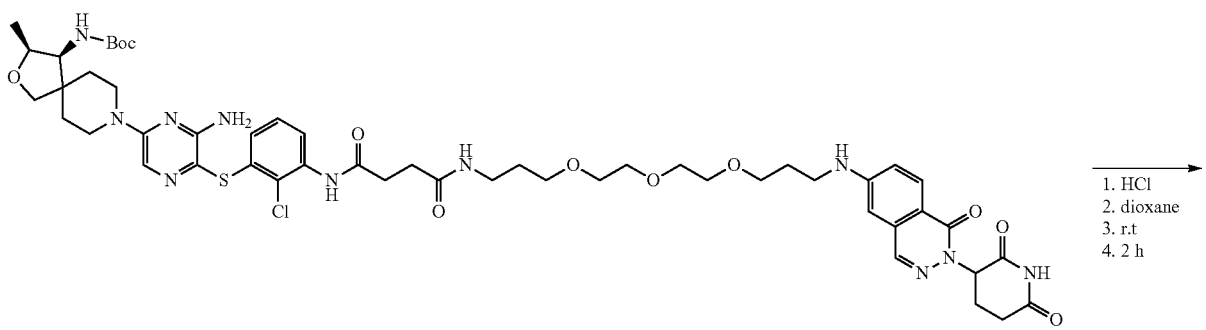

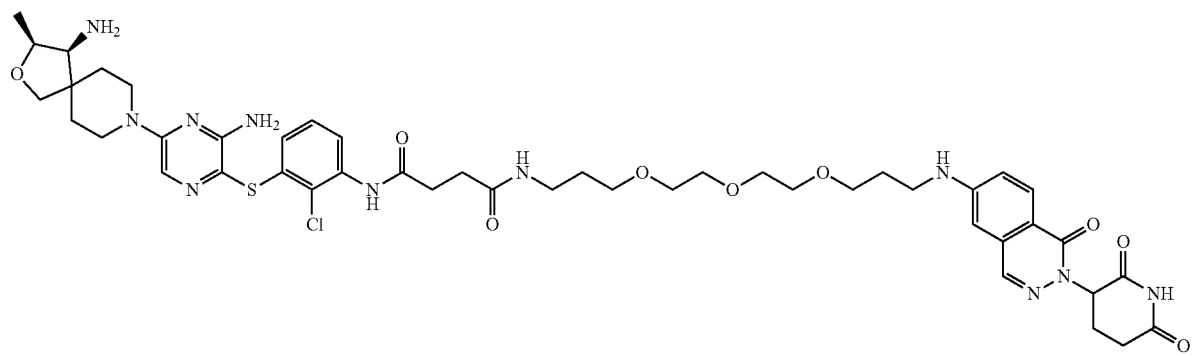

tert-butyl ((3S,4S)-8-(6-amino-5-((2-chloro-3-(1-((2-(2,6-dioxopiperidin-3-yl)-1-oxo-1,2-dihydrophthalazin-6-yl)amino)-15-oxo-4,7,10-trioxa-14-azaoctadecan-18-amido)phenyl)thio)pyrazin-2-yl)-3-methyl-2-oxa-8-azaspiro[4.5]decan-4-yl)carbamate (30 mg, 0.028 mmol) was dissolved in 1,4 dioxane. 4M-HCl in 1.4 dioxane was added and the mixture was stirred at room temperature for 3 hours. The reaction mixture was concentrated under reduced pressure. The product was purified by amino silicagel column MPLC. (Yield: 17 mg, 35%).

MS (ESI, m/z): [M+$^1$]+=980.5

[NMR] $^1$H NMR (400 MHz, DMSO-d$_6$) δ ppm 10.99 (br. s., 1H) 7.03-7.19 (m, 2H) 9.55 (s, 1H) 8.18 (s, 1H) 7.81-7.95 (m, 2H) 7.62 (s, 1H) 7.45 (d, J=7.95 Hz, 1H) 6.88 (t, J=5.26 Hz, 1H) 6.76 (d, J=2.08 Hz, 1H) 6.42 (d, J=7.95 Hz, 1H) 6.10 (s, 2H) 5.72 (dd, J=12.10, 5.14 Hz, 1H) 4.07 (quin, J=6.05 Hz, 1H) 3.86 (br. s., 2H) 3.68 (d, J=8.56 Hz, 1H) 3.44-3.58 (m, 10H) 3.15-3.24 (m, 4H) 3.08 (q, J=6.52 Hz, 3H) 2.84-2.96 (m, 2H) 2.53-2.66 (m, 4H) 2.35-2.43 (m, 2H) 2.02-2.11 (m, 1H) 1.77-1.87 (m, 2H) 1.72 (t, J=9.72 Hz, 1H) 1.60 (quin, J=6.57 Hz, 4H) 1.54 (br. s., 1H) 1.48 (br. s., 1H) 1.09 (d, J=6.48 Hz, 3H)

Example 74: N$^1$-(3-((3-amino-5-((3S,4S)-4-amino-3-methyl-2-oxa-8-azaspiro[4.5]decan-8-yl)pyrazin-2-yl)thio)-2-chlorophenyl)-N4-(12-((3-(2,6-dioxopiperidin-3-yl)-4-oxo-3,4-dihydrophthalazin-5-yl)amino)-12-oxododecyl)succinamide

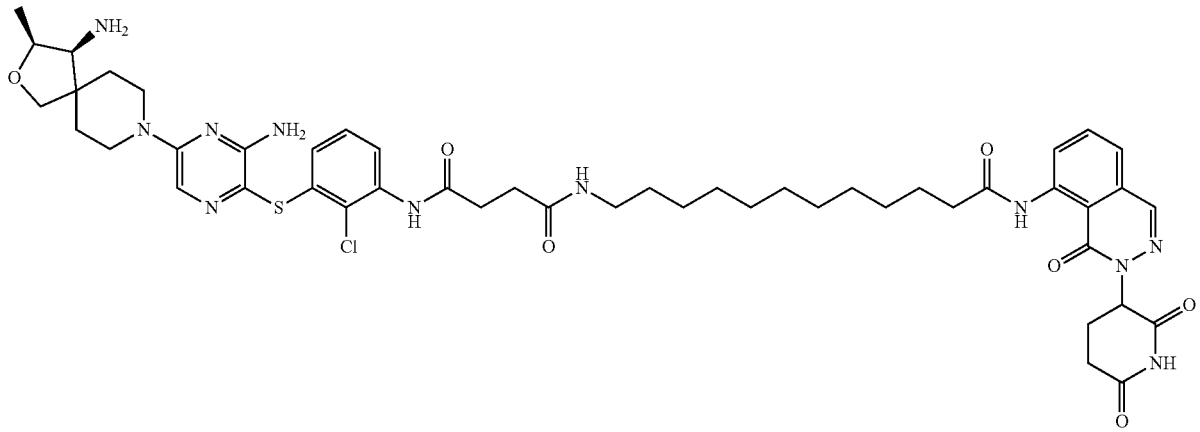 [SMILES: C[C@@H]1OCC2(CCN(c3cnc(Sc4cccc(NC(=O)CCC(=O)NCCCCCCCCCCCC(=O)Nc5cccc6cnn(C7CCC(=O)NC7=O)c(=O)c56)c4Cl)c(N)n3)CC2)[C@@H]1N]

The titled compound is synthesized through following procedure.

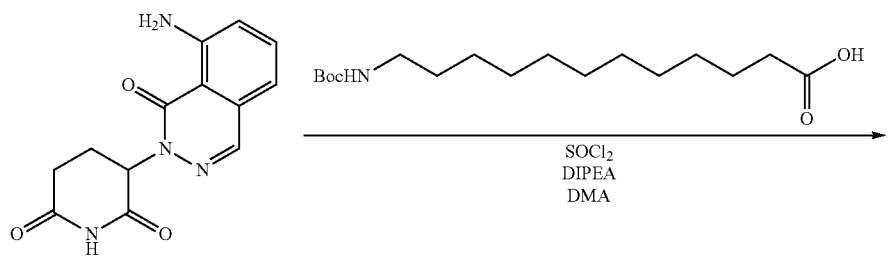

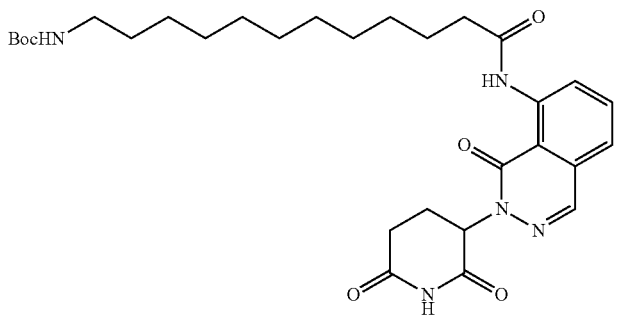

To a solution of 3-(8-amino-1-oxophthalazin-2(1H)-yl)piperidine-2,6-dione (14 mg, 0.051 mmol), 12-{[(tert-butoxy)carbonyl]amino}dodecanoic acid (40.6 mg, 0.129 mmol) and DIPEA (40 mg, 0.0309 mmol) in 0.3 ml of DMAC was added $SOCl_2$ (16.5 mg, 0.139 mmol) at 0° C. and the mixture was stirred for 16 hours at 50° C. The reaction mixture was purified by Reverse phase column chromatography (water (0.1% FA)/ACN (0.1% FA)=95/1 to 0/100 gradient) to give the product. (Yield: 9.1 mg, 31.6%). MS (ESI, m/z): [M+$^1$]+=[568.2]

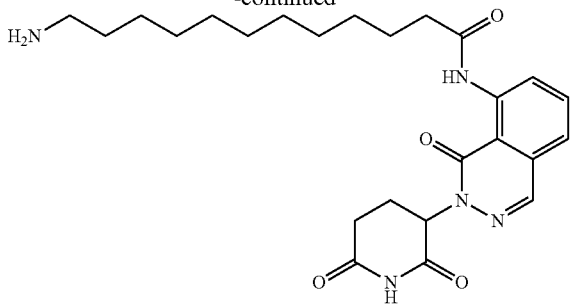

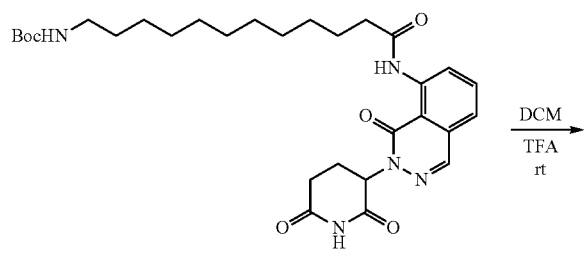

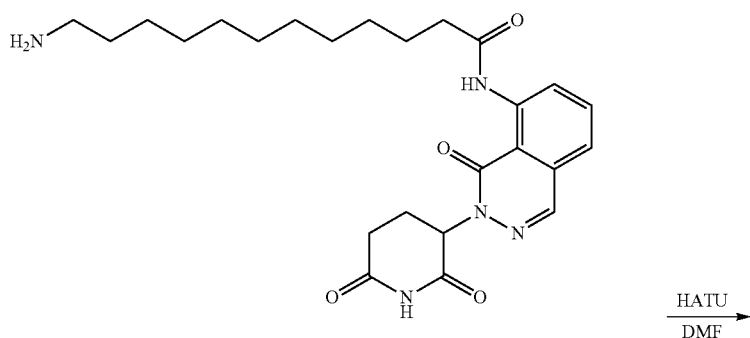

To a solution of tert-butyl (12-((3-(2,6-dioxopiperidin-3-yl)-4-oxo-3,4-dihydrophthalazin-5-yl)amino)-12-oxododecyl)carbamate (9.1 mg, 0.016 mmol) in 0.5 ml of DCM was added 0.1 ml of TFA and the mixture was stirred at room temperature for 1 hour. The reaction mixture was concentrated in vacuo and used for the next step without further purification. (Yield: 7.5 mg, quant.). MS (ESI, m/z): [M+$^1$]+=[470.2]

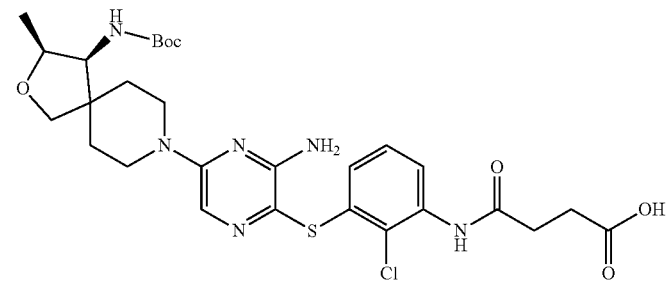

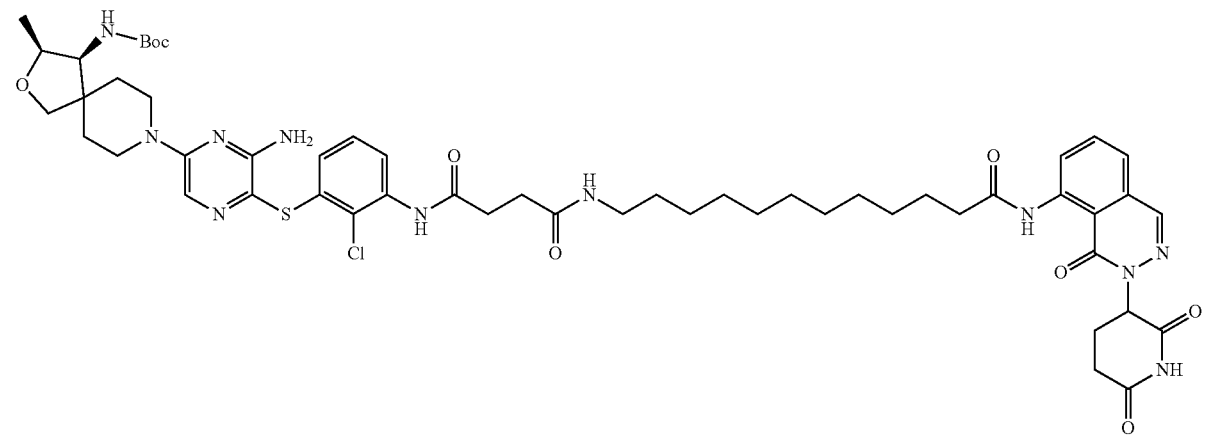

231

To a solution of 12-amino-N-(3-(2,6-dioxopiperidin-3-yl)-4-oxo-3,4-dihydrophthaazin-5-yl)dodecanamide (7.5 mg, 0.016 mmol), 4-((3-((3-amino-5-((3S,4S)-4-((tert-butoxycarbonyl)amino)-3-methyl-2-oxa-8-azaspiro[4.5]decan-8-yl)pyrazin-2-yl)thio)-2-chlorophenyl)amino)-4-oxobutanoic acid (9.92 mg, 0.016 mmol) and DIPEA (0.014 ml, 0.08 mmol) in DMF (0.4 mL) was added HATU (9.1 mg, 0.024 mmol) at 0 T and the mixture was stirred at room temperature for 1 hour. The reaction mixture was purified by reverse column chromatography to give the product (Yield: 10 mg, 58.4%). L MS (ESI, m/z): [M+1]*=[1072.2] and [1074.2].

232

To a solution of tert-butyl ((3S,4S)-8-(6-amino-5-((2-chloro-3-(4-((12-((3-(2,6-dioxopiperidin-3-yl)-4-oxo-3,4-dihydrophthalazin-5-yl)amino)-12-oxododecyl)amino)-4-oxobutanamido)phenyl)thio)pyrazin-2-yl)-3-methyl-2-oxa-8-azaspiro[4.5]decan-4-yl)carbamate (10 mg, 0.093 mmol) in 0.3 ml of DCM was added 0.1 ml of TFA and the mixture was stirred at room temperature for 1 hour. The reaction mixture was concentrated in vacuo. The reaction mixture was purified by amino silica gel column chromatography to give the product. (Yield: 5.4 mg, 34.8%).

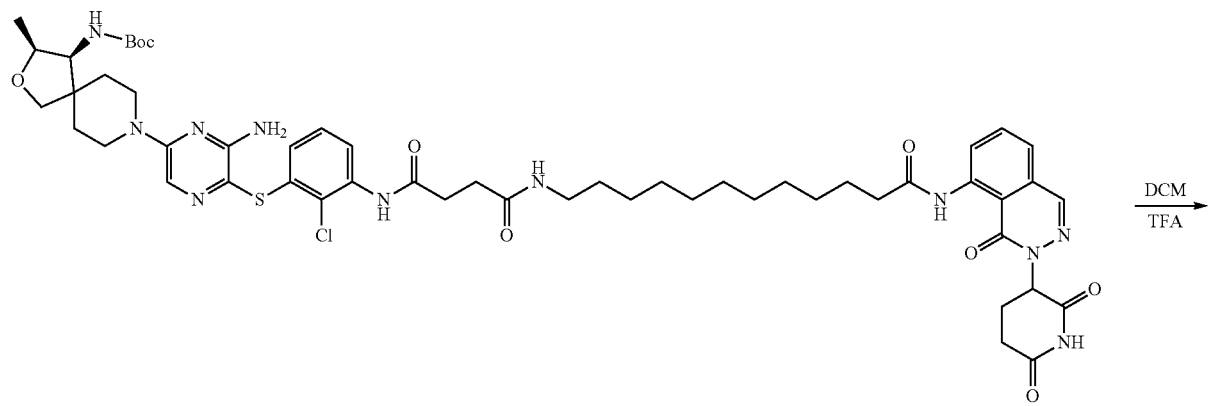

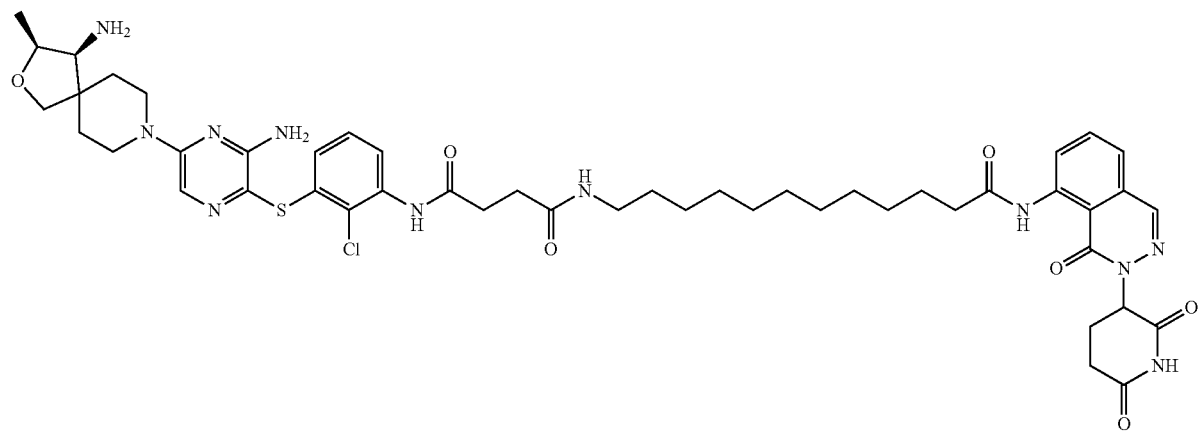

1H NMR (400 MHz, DMSO-d6) δ=12.25 (s, 1H), 9.55 (s, 1H), 8.92 (d, J=8.3 Hz, 1H), 8.51 (s, 1H), 7.94 (t, J=8.1 Hz, 1H), 7.84 (t, J=5.5 Hz, 1H), 7.62 (s, 1H), 7.61 (d, J=8.1 Hz, 1H), 7.45 (d, J=7.1 Hz, 1H), 7.14 (t, J=8.1 Hz, 1H), 6.42 (dd, J=7.9, 1.3 Hz, 1H), 6.10 (s, 2H), 5.85 (m, 1H), 4.05 (m, 1H), 3.82 (m, 2H), 3.57 (dd, J=74.09, 8.07 Hz, 2H), 3.26 (m, 2H), 3.07 (q, J=6.09 Hz, 2H), 2.93 (m, 1H), 2.90 (d, J=9.05 Hz, 1H), 2.69-2.55 (m, 4H), 2.43 (t, J=7.2 Hz, 2H), 2.39 (t, J=7.2 Hz, 2H), 2.15 (m, 1H), 1.72-1.56 (m, 4H), 1.55-1.40 (m, 2H), 1.4-1.15 (m, 19H), 1.08 (d, J=6.4 Hz, 3H).

MS (ESI, m/z): [M+1]$^+$=[972.6][974.6]

Example 75: N-(3-((3-amino-5-((3S,4S)-4-amino-3-methyl-2-oxa-8-azaspiro[4.5]decan-8-yl)pyrazin-2-yl)thio)-2-chlorophenyl)-4-(4-(3-(2-(2-((3-(2,6-dioxopiperidin-3-yl)-4-oxo-3,4-dihydrophthalazin-5-yl)amino)ethoxy)ethoxy)propanoyl)piperazin-1-yl)-4-oxobutanamide

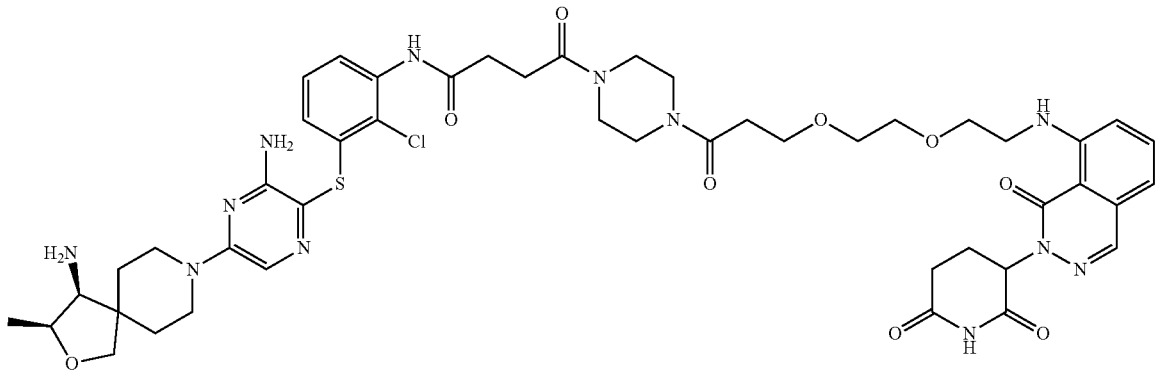 [SMILES: C[C@@H]1OCC2(CCN(c3cnc(Sc4cccc(NC(=O)CCC(=O)N5CCN(C(=O)CCOCCOCCNc6cccc7cnn(C8CCC(=O)NC8=O)c(=O)c67)CC5)c4Cl)c(N)n3)CC2)[C@@H]1N]

The titled compound is synthesized through following procedure.

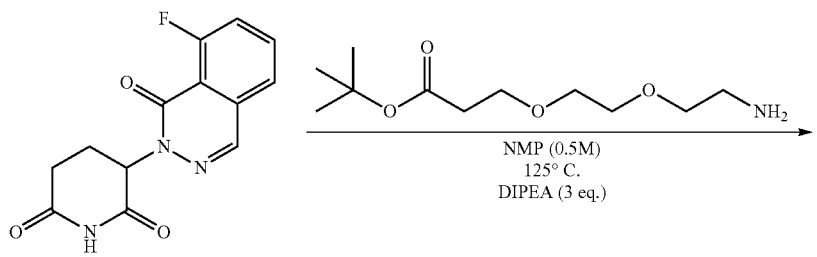

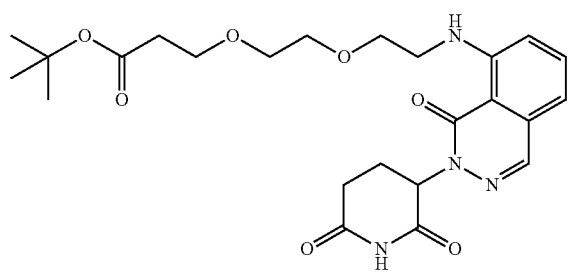

The solution of 3-(8-amino-1-oxophthalazin-2(1H)-yl)piperidine-2,6-dione (200 mg, 0.727 mmol), tert-butyl 3-(2-(2-aminoethoxy)ethoxy)propanoate (203 mg, 0.872 mmol) and DIPEA (0.38 ml, 2.18 mmol) in 1.5 ml of NMP was stirred for 20 hours at 125° C. The reaction mixture was purified by Reverse phase column chromatography (water (0.1% FA)/ACN (0.1% FA)=95/1 to 0/100 gradient) to give the product. (Yield: 320 mg, 90.14%). MS (ESI, m/z): [M+1]⁺=[489.0]

To a tert-butyl 3-(2-(2-((3-(2,6-dioxopiperidin-3-yl)-4-oxo-3,4-dihydrophthalazin-5-yl)amino)ethoxy)ethoxy)propanoate (320 mg, 0.655 mmol) in 5 ml of DCM was added 1 ml of TFA and the mixture was stirred at room temperature for 1 hour. The reaction mixture was concentrated in vacuo and used for the next step without further purification. (Yield: 325 mg, 0.43 TFA salts, quant.). MS (ESI, m/z): [M+¹]+=[433.0]

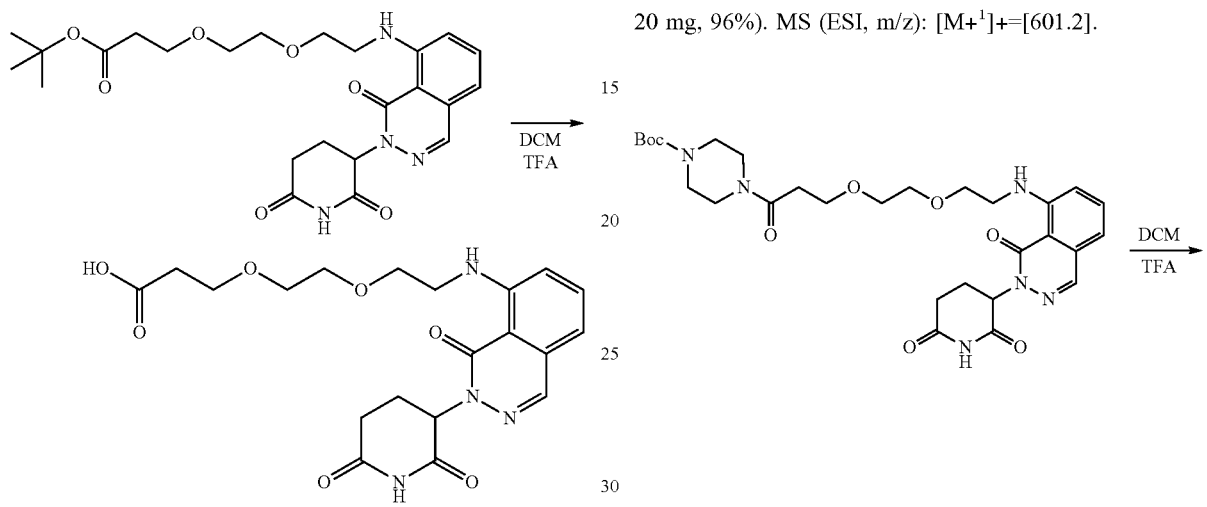

To a solution of 3-(2-(2-((3-(2,6-dioxopiperidin-3-yl)-4-oxo-3,4-dihydrophthalazin-5-yl)amino)ethoxy)ethoxy)propanoic acid (15 mg, 0.0347 mmol), tert-butyl piperazine-1-carboxylate (11.6 mg, 0.052 mmol) and DIPEA (0.018 ml, 0.104 mmol) in DMF (0.4 mL) was added HATU (19.8 mg, 0.052 mmol) at 0° C. and the mixture was stirred at room temperature for 1 hour. The reaction mixture was purified by reverse column chromatography to give the product (Yield: 20 mg, 96%). MS (ESI, m/z): [M+¹]+=[601.2].

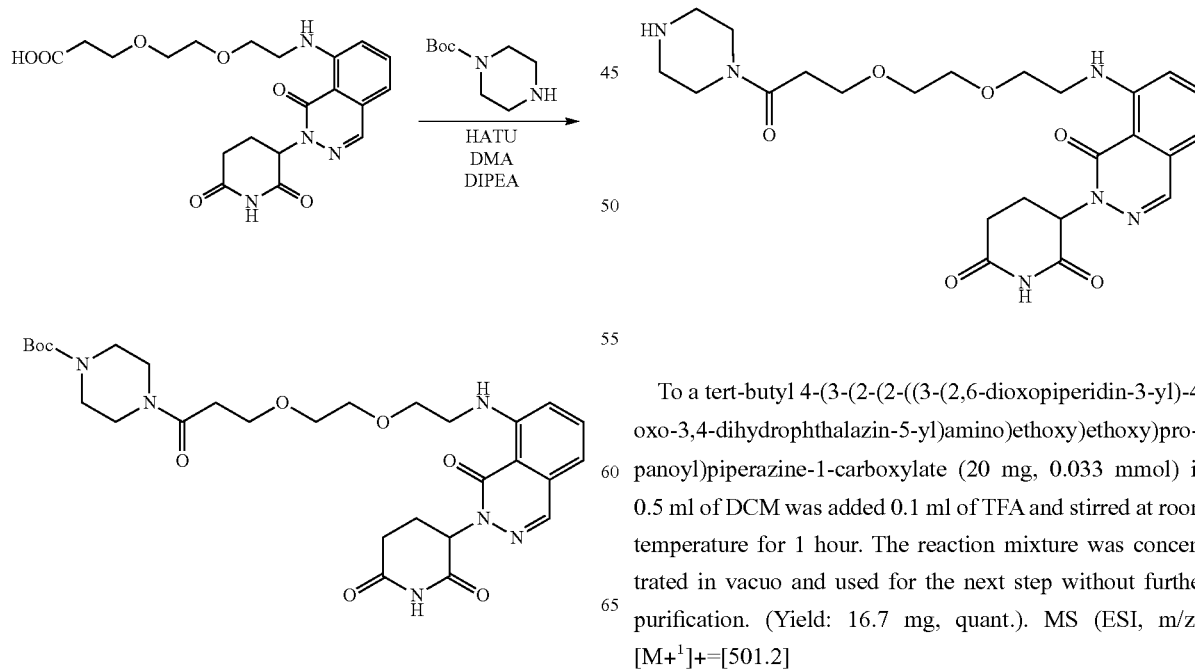

To a tert-butyl 4-(3-(2-(2-((3-(2,6-dioxopiperidin-3-yl)-4-oxo-3,4-dihydrophthalazin-5-yl)amino)ethoxy)ethoxy)propanoyl)piperazine-1-carboxylate (20 mg, 0.033 mmol) in 0.5 ml of DCM was added 0.1 ml of TFA and stirred at room temperature for 1 hour. The reaction mixture was concentrated in vacuo and used for the next step without further purification. (Yield: 16.7 mg, quant.). MS (ESI, m/z): [M+¹]+=[501.2]

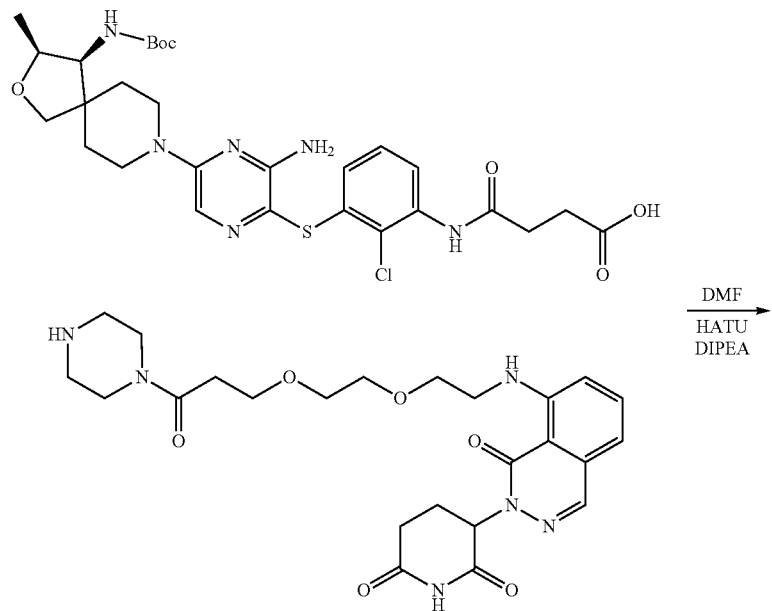

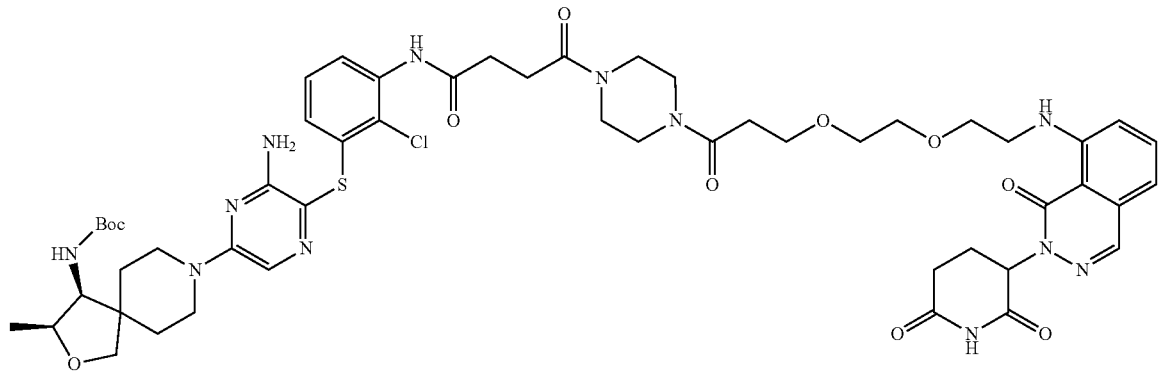

To a solution of 3-(1-oxo-8-((2-(2-(3-oxo-3-(piperazin-1-yl)propoxy)ethoxy)ethyl)amino)phthalazin-2(1H)-yl)piperidine-2,6-dione (16.7 mg, 0.033 mmol), 4(3-((3-amino-5-((3S,4S)-4-((tert-butoxycarbonyl)amino)-3-methyl-2-oxa-8-azaspiro[4.5]decan-8-yl)pyrazin-2-yl)thio)-2-chlorophenyl)amino)-4-oxobutanoic acid (18.6 mg, 0.030 mmol) and DIPEA (0.035 ml, 0.2 mmol) in DMF (0.4 mL) was added HATU (15.2 mg, 0.040 mmol) at 0° C. and the mixture was stirred at room temperature for 1 hour. The reaction mixture was purified by reverse column chromatography to give the product (Yield: 16.3 mg, 44.3%). MS (ESI, m/z): [M+1]$^+$= 1103.81 and [1105.6].

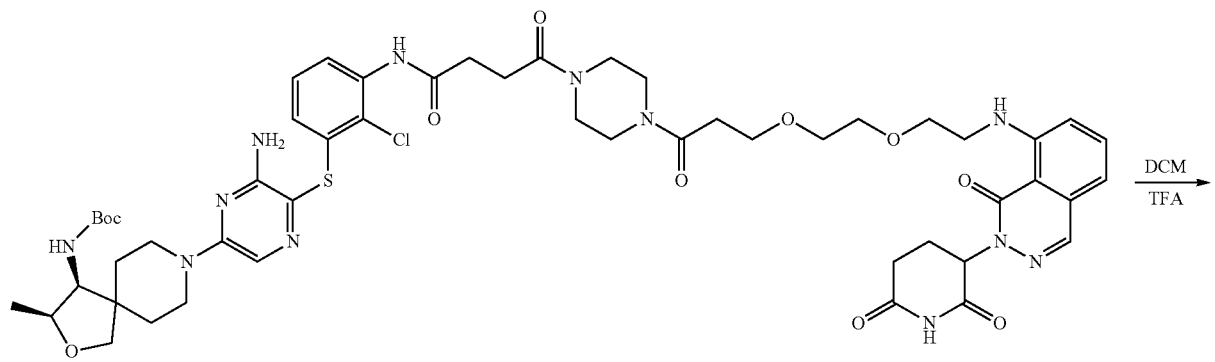

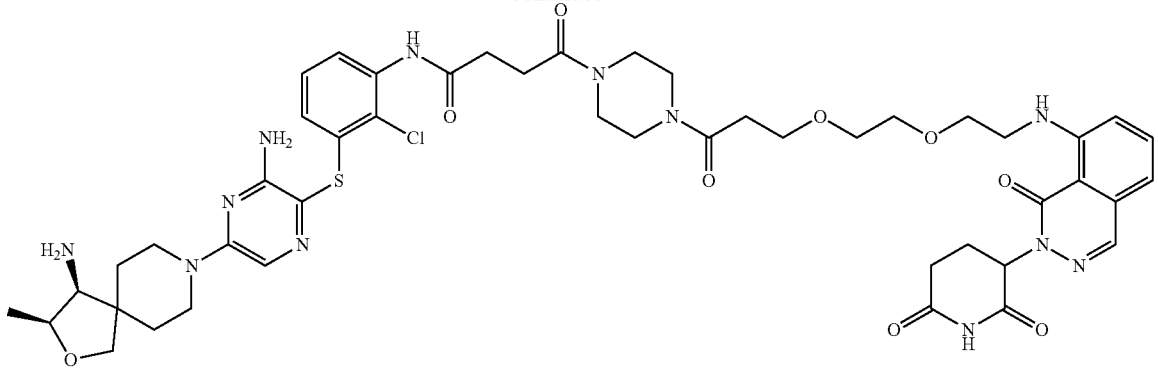

To a solution of ((3S,4S)-8-(6-amino-5-((2-chloro-3-(4-(4-(3-(2-(2-((3-(2,6-dioxopiperidin-3-yl)-4-oxo-3,4-dihydrophthalazin-5-yl)amino)ethoxy)ethoxy)propanoyl)piperazin-1-yl)-4-oxobutanamido)phenyl)thio)pyrazin-2-yl)-3-methyl-2-oxa-8-azaspiro[4.5]decan-4-yl)carbamate (16.3 mg, 0.0148 mmol) in 0.3 ml of DCM was added 0.1 ml of TFA and the mixture was stirred at room temperature for 1 hour. The reaction mixture was concentrated in vacuo. The reaction mixture was purified by amino silicagel column chromatography to give the product.

(yield: 12 mg, 81%).

1H NMR (400 MHz, DMSO-d6) δ=11.03 (s, 1H), 9.54 (s, 1H), 8.83 (s, 1H), 8.22 (s, 1H), 7.65 (t, J=7.8 Hz, 1H), 7.63 (s, 1H), 7.48 (d, J=7.3 Hz, 1H), 7.14 (t, J=8.1 Hz, 1H), 6.92 (d, J=8.1 Hz, 1H), 6.91 (d, J=8.1 Hz, 1H), 6.42 (dd, J=8.1, 1.5 Hz, 1H), 6.10 (s, 2H), 5.72 (m, 1H), 4.08 (m, 1H), 3.87 (m, 2H), 3.72-3.6 (m, 5H), 3.6-3.5 (m, 4H), 3.5-3.35 (m, 11H), 3.26 (m, 2H), 2.95 (d, J=5.1 Hz, 1H), 2.89 (m, 1H), 2.64 (s, 4H), 2.58-2.5 (m, 4H), 2.10 (m, 1H), 1.76-1.40 (m, 4H), 1.09 (d, J=6.6 Hz, 3H).

MS (ESI, m/z): [M+¹]+=[1003.6][1005.6]

Example 76: N-(3-((3-amino-5-((3S,4S)-4-amino-3-methyl-2-oxa-8-azaspiro[4.5]decan-8-yl)pyrazin-2-yl)thio)-2-chlorophenyl)-4-(4-(3-(2-(2-(2-((3-(2,6-dioxopiperidin-3-yl)-4-oxo-3,4-dihydrophthalazin-5-yl)amino)ethoxy)ethoxy)ethoxy)propanoyl)piperazin-1-yl)-4-oxobutanamide

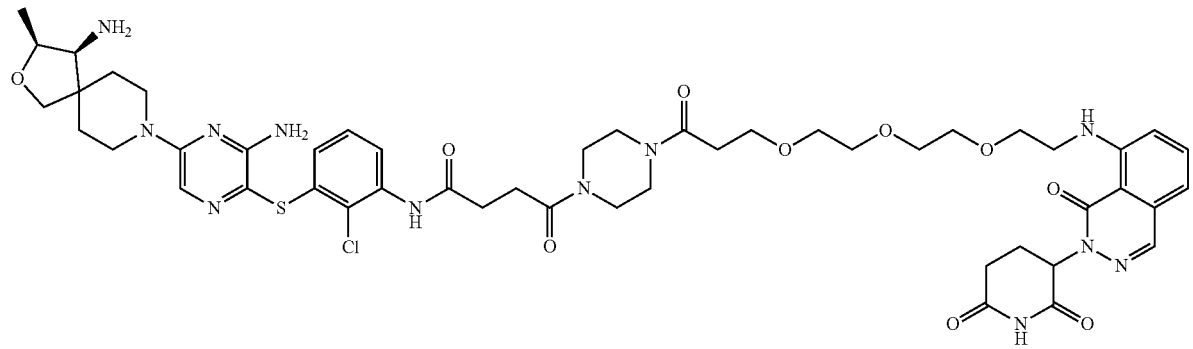 [SMILES: C[C@@H]1OCC2(CCN(c3cnc(Sc4cccc(NC(=O)CCC(=O)N5CCN(C(=O)CCOCCOCCOCCNc6cccc7cnn(C8CCC(=O)NC8=O)c(=O)c67)CC5)c4Cl)c(N)n3)CC2)[C@@H]1N]

The titled compound is synthesized through following procedure.

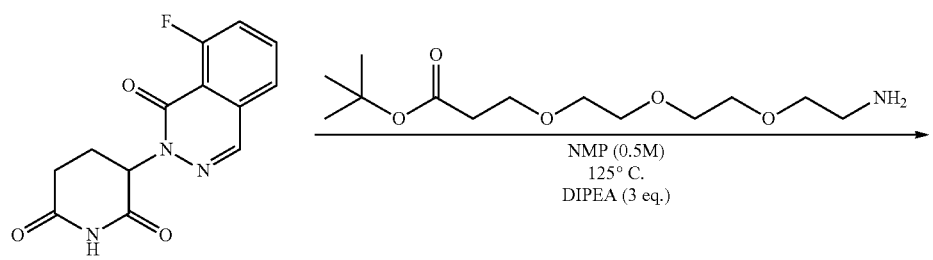

-continued

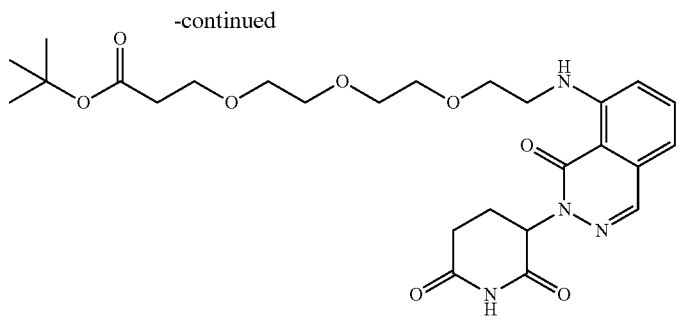

The solution of 3-(8-amino-1-oxophthalazin-2(1H)-yl)piperidine-2,6-dione (200 mg, 0.727 mmol), tert-butyl 3-(2-(2-(2-aminoethoxy)ethoxy)ethoxy)propanoate (242 mg, 0.872 mmol) and DIPEA (0.38 ml, 2.18 mmol) in 1.5 ml of NMP was stirred for 20 hours at 125° C. The reaction mixture was purified by Reverse phase column chromatography (water (0.1% FA)/ACN (0.1% FA)=95/1 to 0/100 gradient) to give the product (Yield: 360 mg, 93%). MS (ESI, m/z): [M+1]⁺=[533.2]

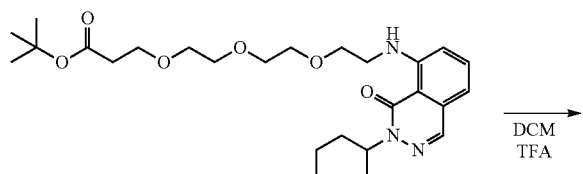 $\xrightarrow{\text{DCM} \atop \text{TFA}}$

-continued

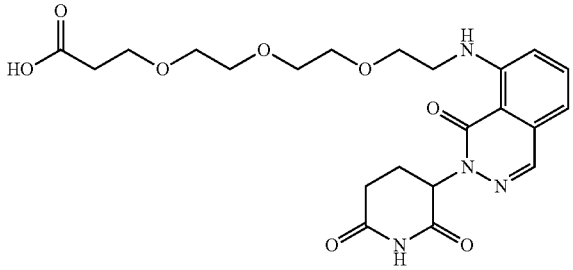

To a tert-butyl 3-(2-(2-(2-((3-(2,6-dioxopiperidin-3-yl)-4-oxo-3,4-dihydrophthalazin-5-yl)amino)ethoxy)ethoxy)ethoxy)propanoate (360 mg, 0.676 mmol) in 5 ml of DCM was added 1 ml of TFA and the mixture was stirred at room temperature for 1 hour. The reaction mixture was concentrated in vacuo and used for the next step without further purification. (Yield: 479 mg, 1.37 TFA salts, quant.). MS (ESI, nm/z): [M+1]⁺=[477.0]

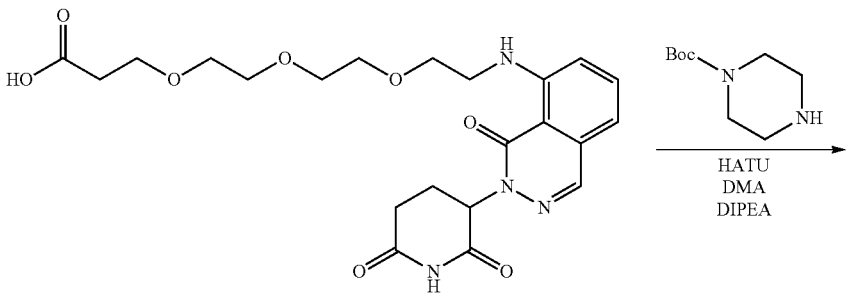 $\xrightarrow{\text{HATU} \atop \text{DMA} \atop \text{DIPEA}}$

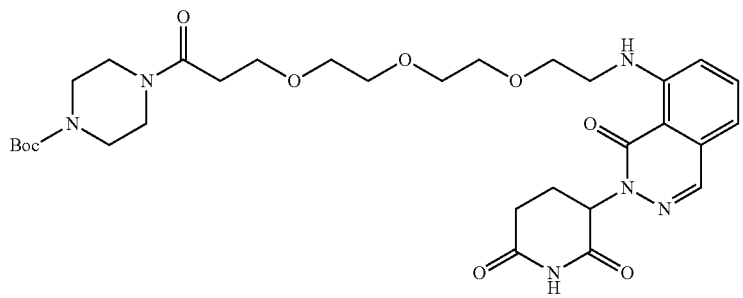

To a solution of 3-(2-(2-(2-((3-(2,6-dioxopiperidin-3-yl)-4-oxo-3,4-dihydrophthalazin-5-yl)amino)ethoxy)ethoxy)ethoxy)propanoic acid (17 mg, 0.0357 mmol), tert-butyl piperazine-1-carboxylate (11.9 mg, 0.0535 mmol) and DIPEA (0.0186 ml, 0.107 mmol) in DMF (0.4 mL) was added HATU (20.3 mg, 0.054 mmol) at 0° C. and the mixture was stirred at room temperature for 1 hour. The reaction mixture was purified by reverse column chromatography to give the product (Yield: 22 mg, 95.6%). MS (ESI, m/z): [M+1]$^+$=[645.2].

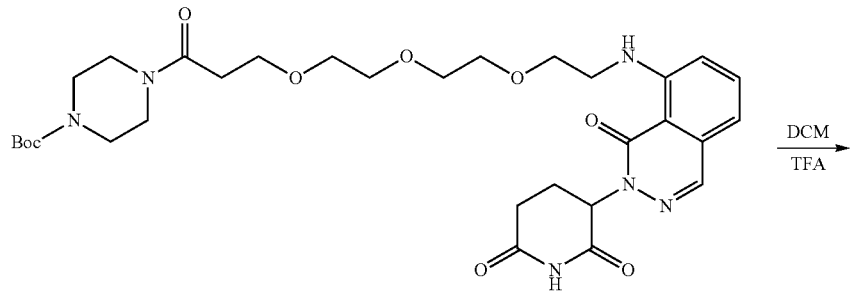

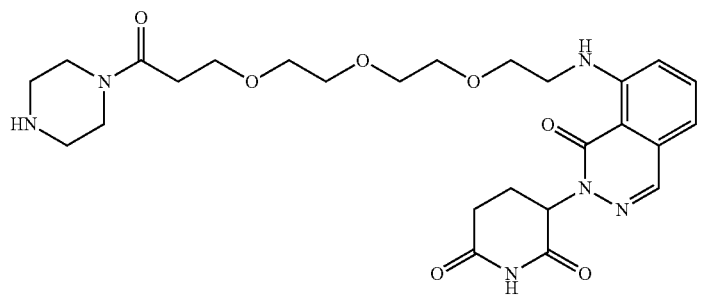

To a 4-(3-(2-(2-(2-((3-(2,6-dioxopiperidin-3-yl)-4-oxo-3,4-dihydrophthalazin-5-yl)amino)ethoxy)ethoxy)ethoxy)propanoyl)piperazine-1-carboxylate (22 mg, 0.034 mmol) in 0.5 ml of DCM was added 0.1 ml of TFA and the mixture was stirred at room temperature for 1 hour. The reaction mixture was concentrated in vacuo and used for the next step without further purification. (Yield: 19.4 mg, quant.). MS (ESI, m/z): [M+$^1$]+=[545.2]

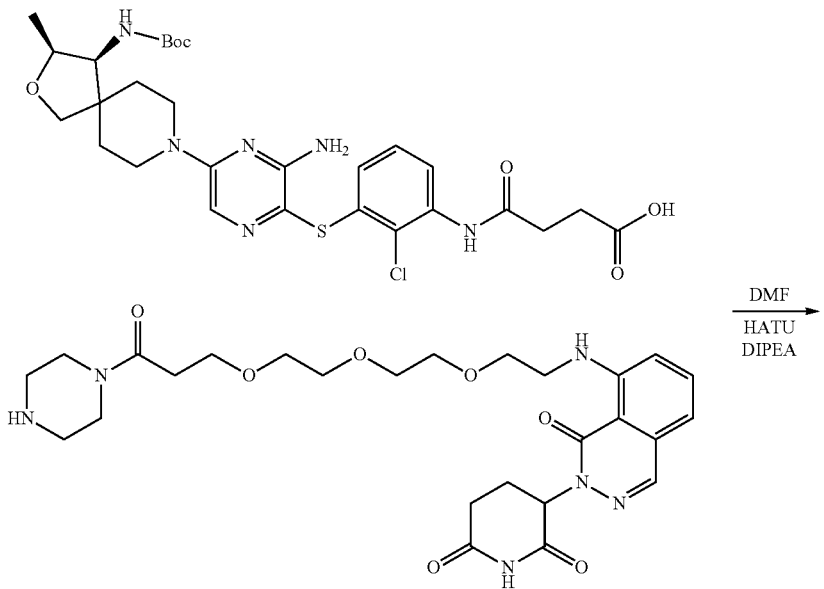

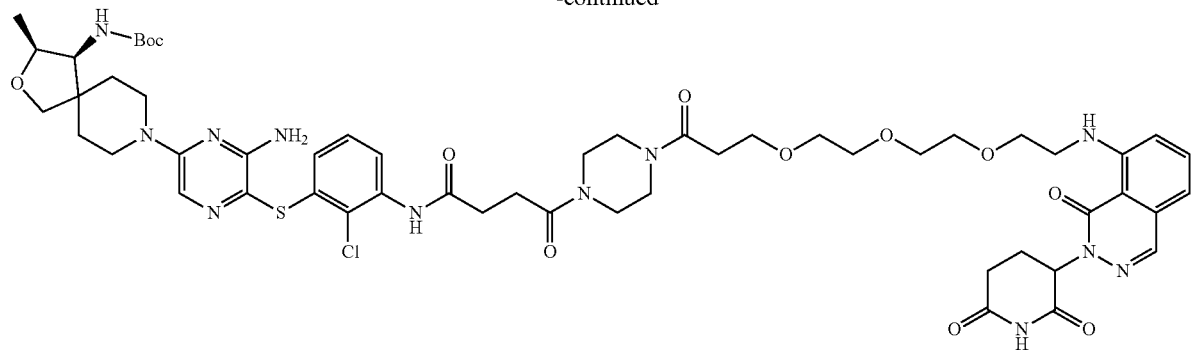

To a solution of 3-(1-oxo-8-((2-(2-(2-(3-oxo-3-(piperazin-1-yl)propoxy)ethoxy)ethoxy)ethyl)amino)phthalazin-2(1H)-yl)piperidine-2,6-dione (19.4 mg, 0.035 mmol), 4-((3-((3-amino-5-((3S,4S)-4-((tert-butoxycarbonyl)amino)-3-methyl-2-oxa-8-azaspiro[4.5]decan-8-yl)pyrazin-2-yl)thio)-2-chlorophenyl)amino)-4-oxobutanoic acid (17.7 mg, 0.028 mmol) and DIPEA (0.037 ml, 0.214 mmol) in DMF (0.4 mL) was added HATU (17.6 mg, 0.046 mmol) at 0° C. and the mixture was stirred at room temperature for 1 hour. The reaction mixture was purified by reverse column chromatography to give the product (Yield: 22 mg, 53.7%). MS (ESI, m/z): [M+$^1$]+=[1147.6] and [1149.6].

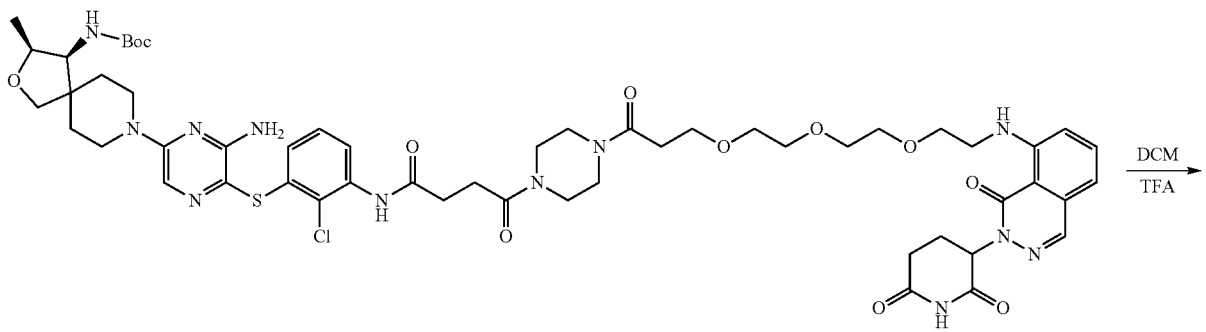

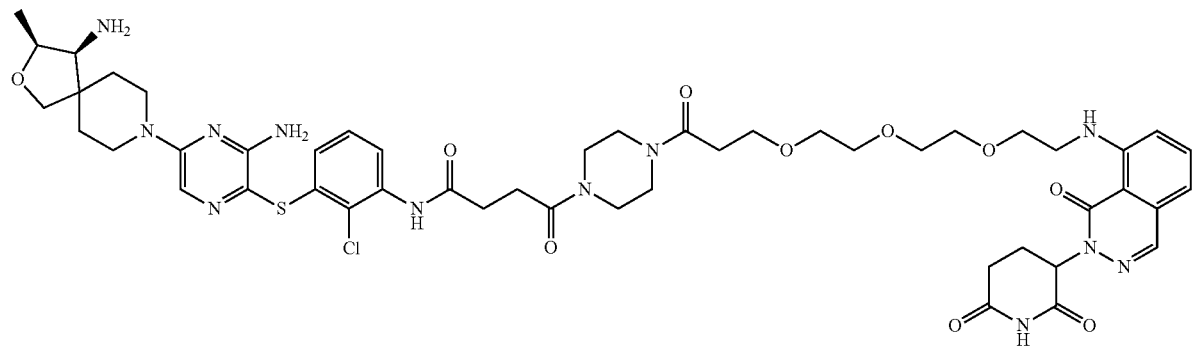

To a solution of tert-butyl ((3S,4S)-8-(6-amino-5-((2-chloro-3-(4-(4-(3-(2-(2-(2-((3-(2,6-dioxopiperidin-3-yl)-4-oxo-3,4-dihydrophthalazin-5-yl)amino)ethoxy)ethoxy)ethoxy)propanoyl)piperazin-1-yl)-4-oxobutanamido)phenyl)thio)pyrazin-2-yl)-3-methyl-2-oxa-8-azaspiro[4.5]decan-4-yl)carbamate (22 mg, 0.019 mmol) in 0.3 ml of DCM was added 0.1 ml of TFA and the mixture was stirred at room temperature for 1 hour. The reaction mixture was concentrated in vacuo. The reaction mixture was purified by amino silicagel column chromatography to give the product. (Yield: 15.5 mg, 77.2%).

1H NMR (400 MHz, DMSO-d6) δ=11.03 (s, 1H), 9.55 (s, 1H), 8.82 (s, 1H), 8.23 (s, 1H), 7.66 (s, 1H), 7.64 (t, J=7.8 Hz, 1H), 7.48 (d, J=7.3 Hz, 1H), 7.14 (t, J=8.1 Hz, 1H), 6.92 (d, J=8.1 Hz, 1H), 6.91 (d, J=8.1 Hz, 1H), 6.42 (dd, J=8.1, 1.5 Hz, 1H), 6.15 (s, 2H), 5.71 (m, 1H), 4.18 (m, 1H), 4.12 (m, 2H), 3.86 (m, 1H), 3.72-3.6 (m, 5H), 3.6-3.5 (m, 4H), 3.52-3.45 (m, 4H), 3.45-3.35 (m, 11H), 3.12 (m, 1H), 3.04 (m, 3H), 2.90 (m, 1H), 2.65 (s, 4H), 2.58-2.5 (m, 3H), 2.09 (m, 1H), 1.76-1.40 (m, 4H), 1.23-1.1 (m, 3H).

MS (ESI, m/z): [M+$^{1}$]+=[1047.6][1049.6]

Example 77: N-(3-((3-amino-5-((3S,4S)-4-amino-3-methyl-2-oxa-8-azaspiro[4.5]decan-8-yl)pyrazin-2-yl)thio)-2-chlorophenyl)-4-(4-(1-((3-(2,6-dioxopiperidin-3-yl)-4-oxo-3,4-dihydrophthalazin-5-yl)amino)-3,6,9,12-tetraoxapentadecan-15-oyl)piperazin-1-yl)-4-oxobutanamide

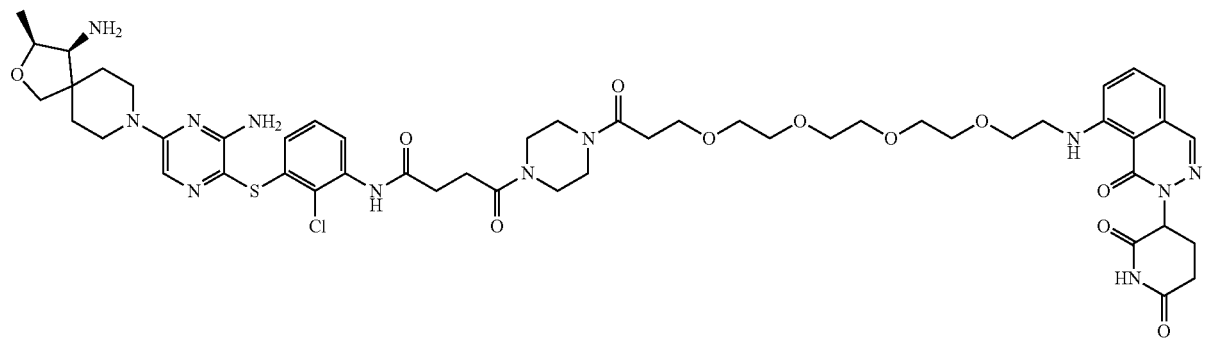 [SMILES: C[C@@H]1OCC2(CCN(c3cnc(Sc4cccc(NC(=O)CCC(=O)N5CCN(C(=O)CCOCCOCCOCCOCCNc6cccc7cnn(C8CCC(=O)NC8=O)c(=O)c67)CC5)c4Cl)c(N)n3)CC2)[C@@H]1N]

The titled compound is synthesized through following procedure.

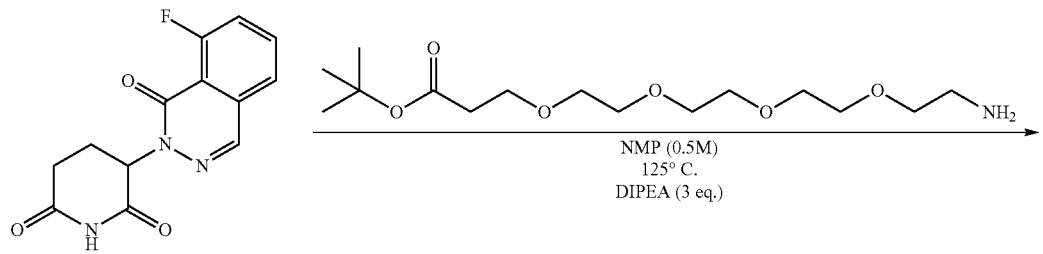

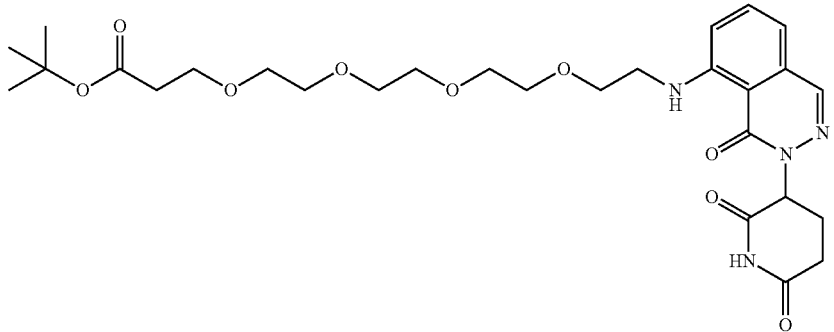

The solution of 3-(8-amino-1-oxophthalazin-2(1H)-yl)piperidine-2,6-dione (200 mg, 0.727 mmol), tert-butyl 1-amino-3,6,9,12-tetraoxapentadecan-15-oate (280 mg, 0.872 mmol) and DIPEA (0.38 ml, 2.18 mmol) in 1.5 ml of NMP was stirred for 20 hours at 125° C. The reaction mixture was purified by Reverse phase column chromatography (water (0.1% FA)/ACN (0.1% FA)=95/1 to 0/100 gradient) to give the product (Yield: 360 mg, 85.9%). MS (ESI, m/z): [M+$^1$]+=[577.2]

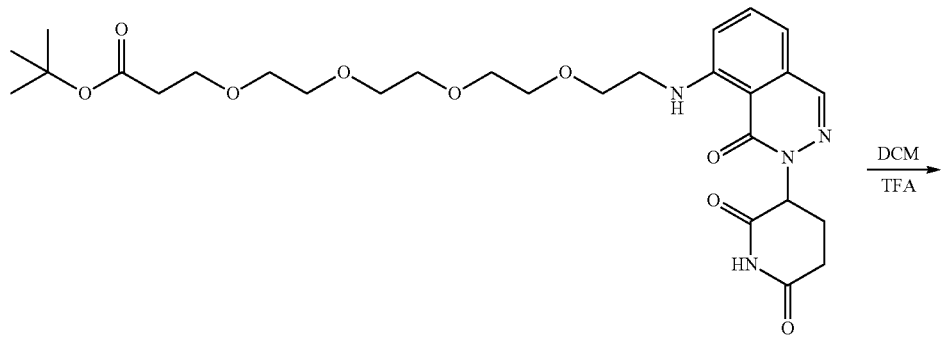

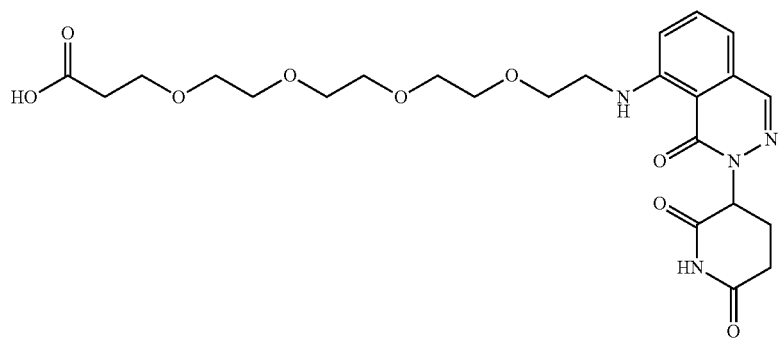

To a tert-butyl 1-((3-(2,6-dioxopiperidin-3-yl)-4-oxo-3,4-dihydrophthalazin-5-yl)amino)-3,6,9,12-tetraoxapentadecan-15-oate (360 mg, 0.624 mmol) in 5 ml of DCM was added 1 ml of TFA and the mixture was stirred at room temperature for 1 hour. The reaction mixture was concentrated in vacuo and used for the next step without further purification. (Yield: 564 mg, 1.92 TFA salts, quant.). MS (ESI, m/z): [M+$^1$]+=[521.0].

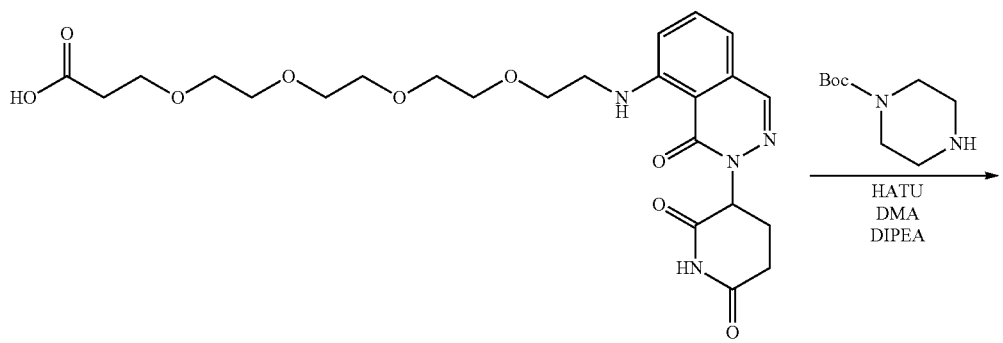

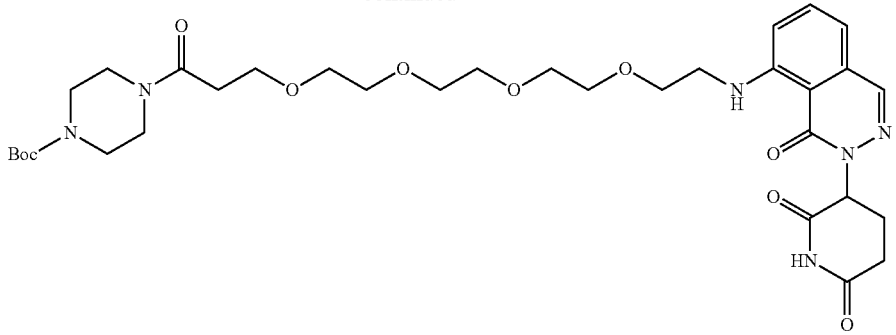

To a solution of 1-((3-(2,6-dioxopiperidin-3-yl)-4-oxo-3,4-dihydrophthalazin-5-yl)amino)-3,6,9,12-tetraoxapentadecan-15-oic acid (18.6 mg, 0.0357 mmol), tert-butyl piperazine-1-carboxylate (11.9 mg, 0.0535 mmol) and DIPEA (0.0186 ml, 0.107 mmol) in DMF (0.4 mL) was added HATU (20.3 mg, 0.054 mmol) at 0° C. and the mixture was stirred at room temperature for 1 hour. The reaction mixture was purified by reverse column chromatography to give the product. (Yield: 24 mg, 99%). MS (ESI, m/z): [M+$^1$]+= [689.4].

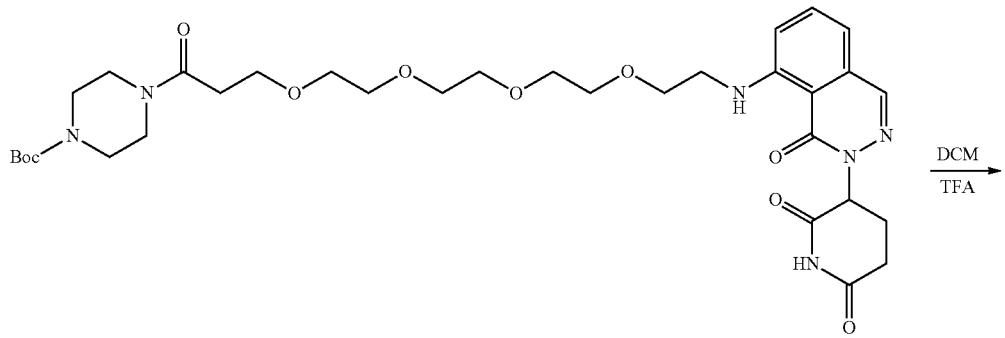

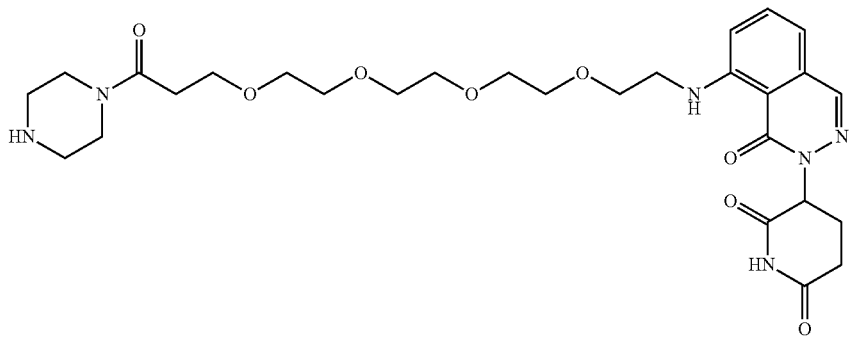

To a tert-butyl 4-(1-((3-(2,6-dioxopiperidin-3-yl)-4-oxo-3,4-dihydrophthalazin-5-yl)amino)-3,6,9,12-tetraoxapentadecan-15-oyl)piperazine-1-carboxylate (24 mg, 0.035 mmol) in 0.5 ml of DCM was added 0.1 ml of TFA and the mixture was stirred at room temperature for 1 hour. The reaction mixture was concentrated in vacuo and used for the next step without further purification. (Yield: 21 mg, quant.). MS (ESI, m/z): [M+1]$^+$=[589.2].

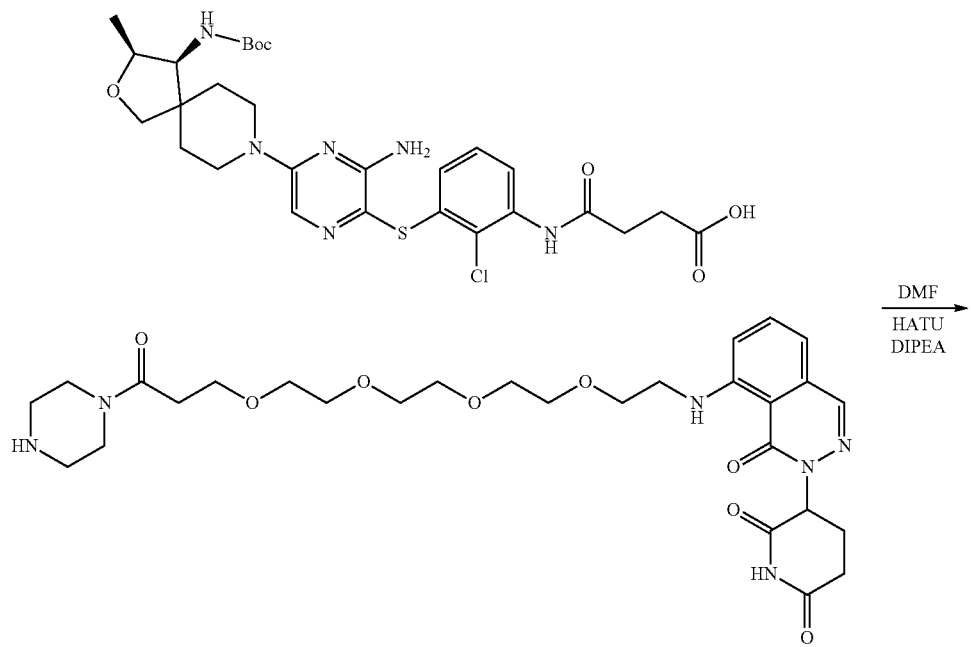

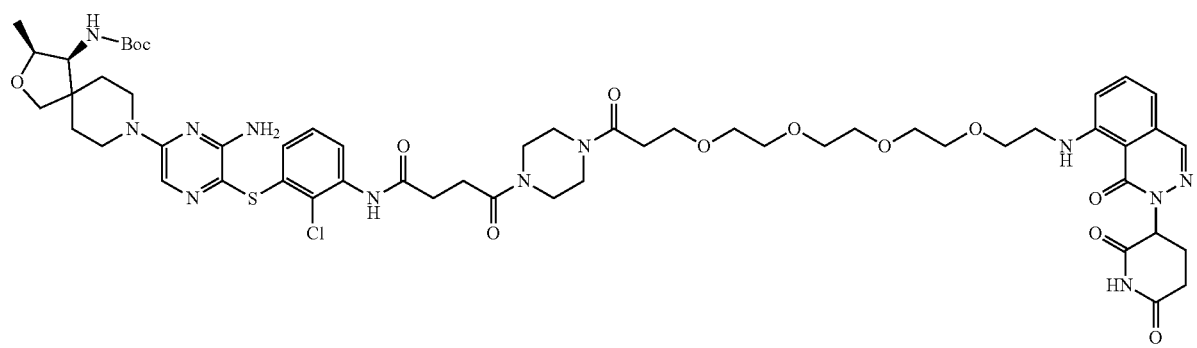

To a solution of 3-(1-oxo-8-((15-oxo-15-(piperazin-1-yl)-3,6,9,12-tetraoxapentadecyl)amino)phthalazin-2(1H)-yl)piperidine-2,6-dione (21 mg, 0.035 mmol), 4-((3-((3-amino-5-((3S,4S)-4-((tert-butoxycarbonyl)amino)-3-methyl-2-oxa-8-azaspiro[4.5]decan-8-yl)pyrazin-2-yl)thio)-2-chlorophenyl)amino)-4-oxobutanoic acid (17.7 mg, 0.028 mmol) and DIPEA (0.037 ml, 0.214 mmol) in DMF (0.4 mL) was added HATU (17.6 mg, 0.046 mmol) at 0° C. and the mixture was stirred at room temperature for 1 hour. The reaction mixture was purified by reverse column chromatography to give the product. (Yield: 19.2 mg, 45%). MS (ESI, m/z): [M+1]$^+$=[1191.8] and [1193.6].

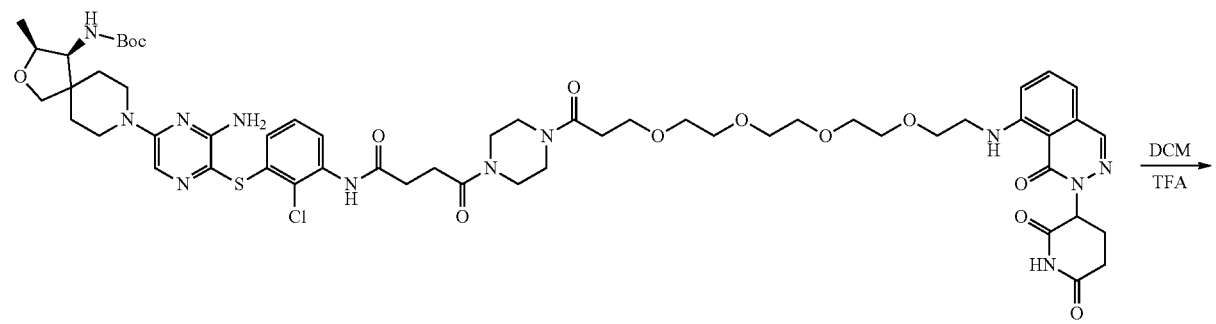

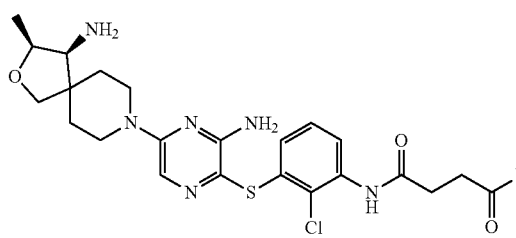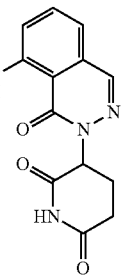

To a solution of tert-butyl ((3S,4S)-8-(6-amino-5-((2-chloro-3-(4-(4-(1-((3-(2,6-dioxopiperidin-3-yl)-4-oxo-3,4-dihydrophthalazin-5-yl)amino)-3,6,9,12-tetraoxapentadecan-15-oyl)piperazin-1-yl)-4-oxobutanamido)phenyl)thio)pyrazin-2-yl)-3-methyl-2-oxa-8-azaspiro[4.5]decan-4-yl)carbamate (19.2 mg, 0.016 mmol) in 0.3 ml of DCM was added 0.1 ml of TFA and the mixture was stirred at room temperature for 1 hour. The reaction mixture was concentrated in vacuo. The reaction mixture was purified by amino silica gel column chromatography to give the product. (Yield: 17.2 mg, 97%).

1H NMR (400 MHz, DMSO-d6) δ=11.03 (s, 1H), 9.55 (s, 1H), 8.84 (s, 1H), 8.23 (s, 1H), 7.67 (s, 1H), 7.65 (t, J=7.8 Hz, 1H), 7.49 (d, J=7.3 Hz, 1H), 7.14 (t, J=8.1 Hz, 1H), 6.92 (d, J=8.2 Hz, 1H), 6.91 (d, J=8.1 Hz, 1H), 6.42 (dd, J=8.1, 1.5 Hz, 1H), 6.16 (s, 2H), 5.71 (m, 1H), 4.20 (m, 2H), 4.15 (m, 1H), 3.89 (m, 1H), 3.72-3.6 (m, 5H), 3.6-3.5 (m, 5H), 3.52-3.45 (m, 4H), 3.45-3.35 (m, 13H), 3.1 (m, 3H), 3.04 (m, 1H), 2.90 (m, 1H), 2.65 (s, 4H), 2.58-2.5 (m, 3H), 2.09 (m, 1H), 1.76-1.40 (m, 4H), 1.23-1.1 (m, 3H).

MS (ESI, m/z): [M+¹]+=[1091.6][1093.6]

Example 78: N-(3-((3-amino-5-((3S,4S)-4-amino-3-methyl-2-oxa-8-azaspiro[4.5]decan-8-yl)pyrazin-2-yl)thio)-2-chlorophenyl)-4-(4-(1-((3-(2,6-dioxopiperidin-3-yl)-4-oxo-3,4-dihydrophthalazin-5-yl)amino)-3,6,9,12,15-pentaoxaoctadecan-18-oyl)piperazin-1-yl)-4-oxobutanamide

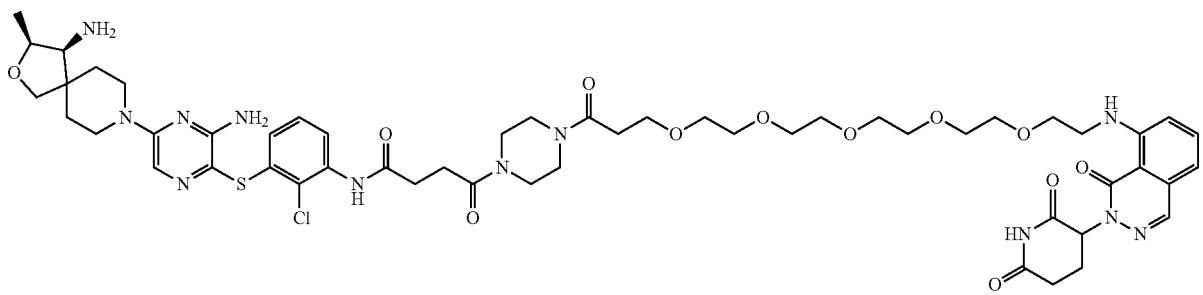 [SMILES: C[C@@H]1OCC2(CCN(c3cnc(Sc4cccc(NC(=O)CCC(=O)N5CCN(C(=O)CCOCCOCCOCCOCCOCCNc6cccc7cnn(C8CCC(=O)NC8=O)c(=O)c67)CC5)c4Cl)c(N)n3)CC2)[C@@H]1N]

The titled compound is synthesized through following procedure.

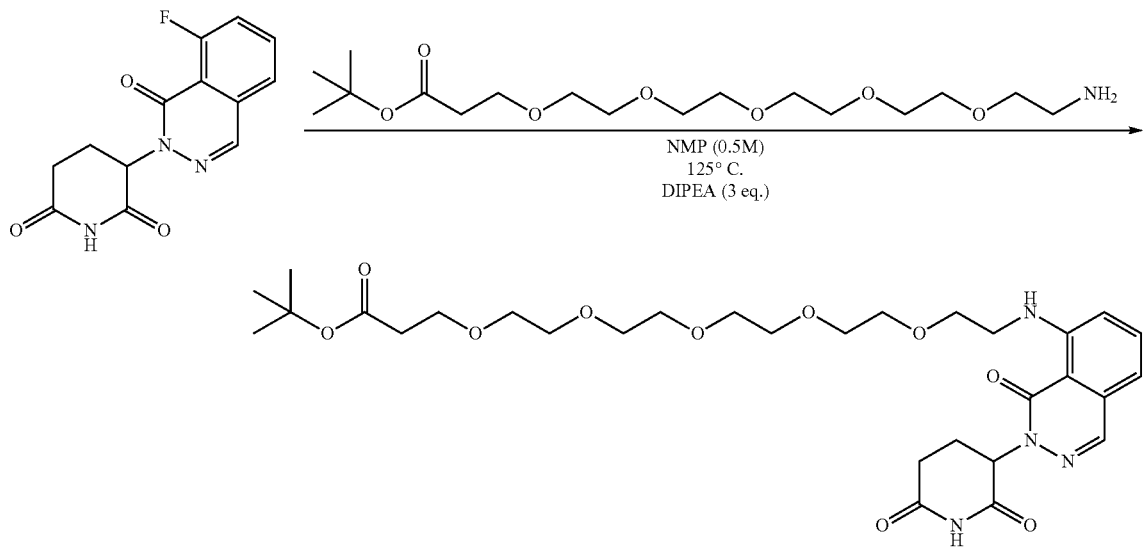

The solution of 3-(8-amino-1-oxophthalazin-2(1H)-yl)piperidine-2,6-dione (200 mg, 0.727 mmol), tert-butyl 1-amino-3,6,9,12,15-pentaoxaoctadecan-18-oate (319 mg, 0.872 mmol) and DIPEA (0.38 ml, 2.18 mmol) in 1.5 ml of NMP was stirred for 20 hours at 125° C. The reaction mixture was purified by Reverse phase column chromatography (water (0.1% FA)/ACN (0.1% FA)=95/1 to 0/100 gradient) to give the product. (Yield: 416 mg, 92.3%). MS (ESI, m/z): [M+$^1$]+=[621.2].

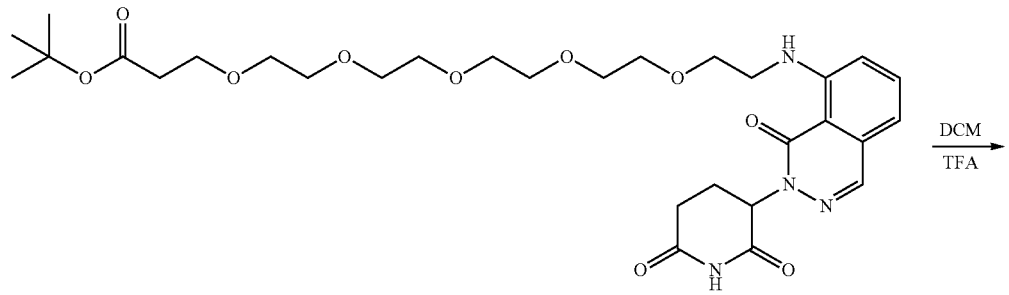

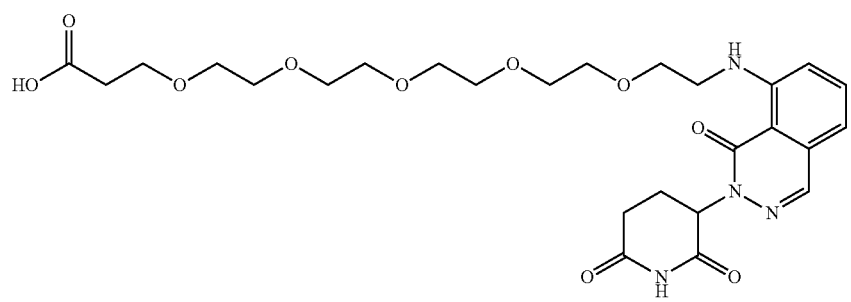

To a tert-butyl 1-((3-(2,6-dioxopiperidin-3-yl)-4-oxo-3,4-dihydrophthalazin-5-yl)amino)-3,6,9,12,15-pentaoxaoctadecan-18-oate (416 mg, 0.670 mmol) in 5 ml of DCM was added 1 ml of TFA and the mixture was stirred at room temperature for 1 hour. The reaction mixture was concentrated in vacuo and used for the next step without further purification. (Yield: 652 mg, 2.8 TFA salts, quant.). MS (ESI, m/z): [M+$^1$]+=[565.2].

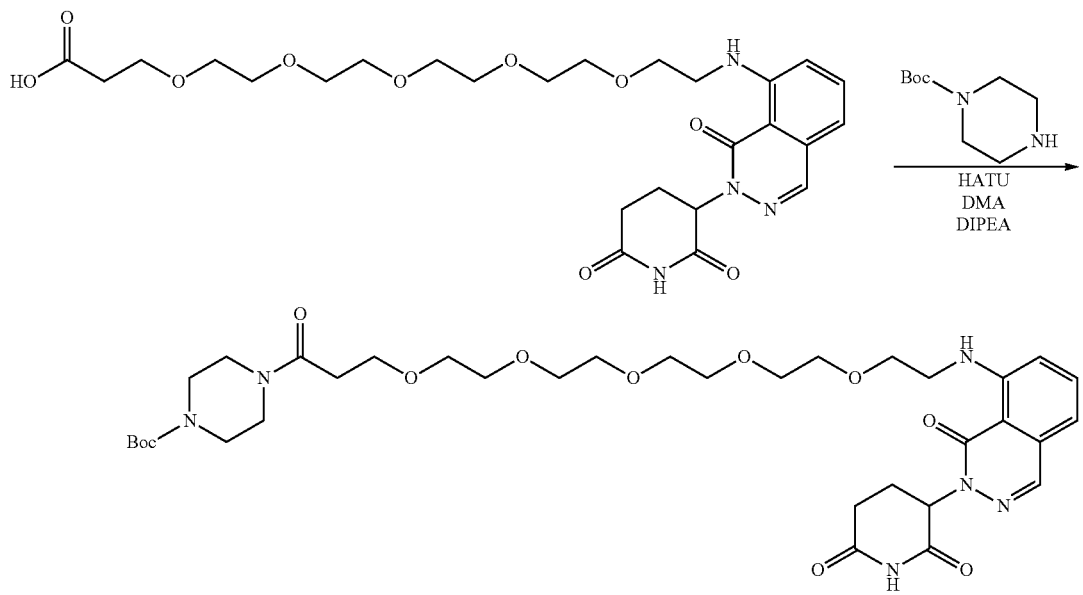

To a solution of 1-((3-(2,6-dioxopiperidin-3-yl)-4-oxo-3,4-dihydrophthalazin-5-yl)amino)-3,6,9,12,15-pentaoxaoctadecan-18-oic acid (20.1 mg, 0.0357 mmol), tert-butyl piperazine-1-carboxylate (11.9 mg, 0.0535 mmol) and DIPEA (0.0186 ml, 0.107 mmol) in DMF (0.4 mL) was added HATU (20.3 mg, 0.054 mmol) at 0° C. and the mixture was stirred at room temperature for 1 hour. The reaction mixture was purified by reverse column chromatography to give the product. (Yield: 26 mg, 99%). MS (ESI, m/z): [M+$^1$]+= [733.4].

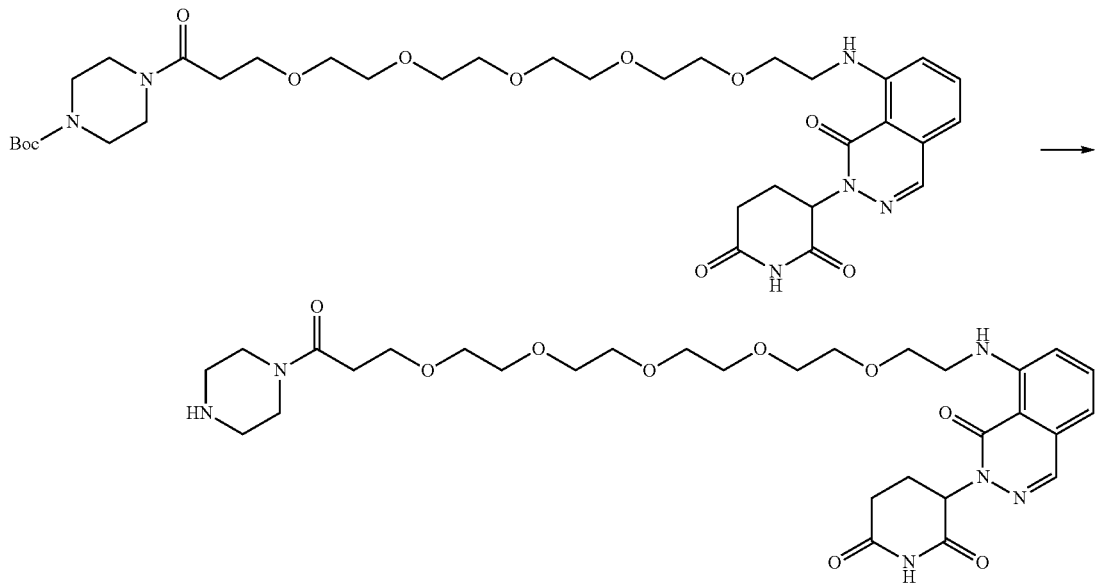

To a tert-butyl 4-(1-((3-(2,6-dioxopiperidin-3-yl)-4-oxo-3,4-dihydrophthalazin-5-yl)amino)-3,6,9,12,15-pentaoxaoctadecan-18-oyl)piperazine-1-carboxylate (26 mg, 0.035 mmol) in 0.5 ml of DCM was added 0.1 ml of TFA and the mixture was stirred at room temperature for 1 hour. The reaction mixture was concentrated in vacuo and used for the next step without further purification. (Yield: 22.6 mg, quant.). MS (ESI, m/z): [M+$^1$]+=[633.2]

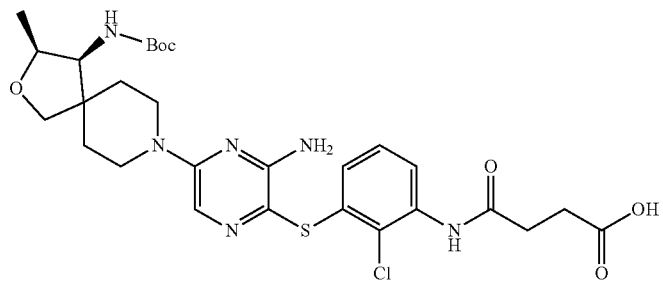

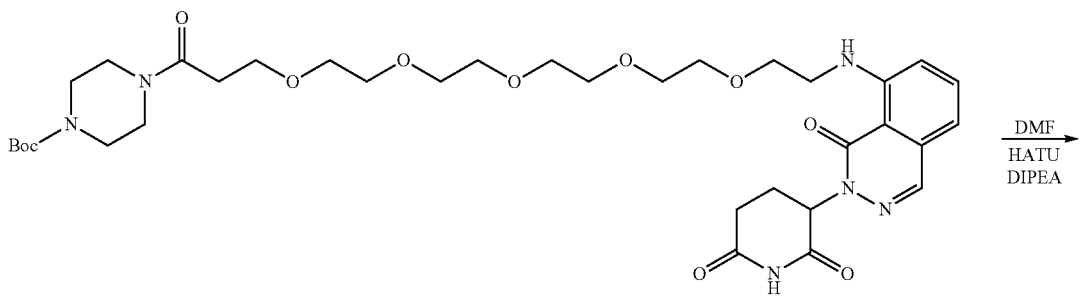

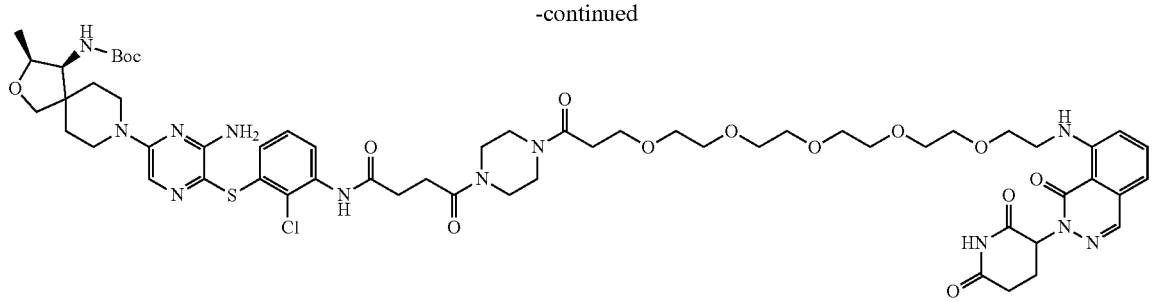

To a solution of 3-(1-oxo-8-((18-oxo-18-(piperazin-1-yl)-3,6,9,12,15-pentaoxaoctadecyl)amino)phthalazin-2(1H)-yl)piperidine-2,6-dione (26 mg, 0.035 mmol), 4-((3-((3-amino-5-((3S,4S)-4-((tert-butoxycarbonyl)amino)-3-methyl-2-oxa-8-azaspiro[4.5]decan-8-yl)pyrazin-2-yl)thio)-2-chlorophenyl)amino)-4-oxobutanoic acid (17.7 mg, 0.028 mmol) and DIPEA (0.037 ml, 0.214 mmol) in DMF (0.4 mL) was added HATU (17.6 mg, 0.046 mmol) at 0° C. and the mixture was stirred at room temperature for 1 hour. The reaction mixture was purified by reverse column chromatography to give the product. (Yield: 22 mg, 48%). MS (ESI, m/z): [M+$^1$]+=[1235.8] and [1237.8].

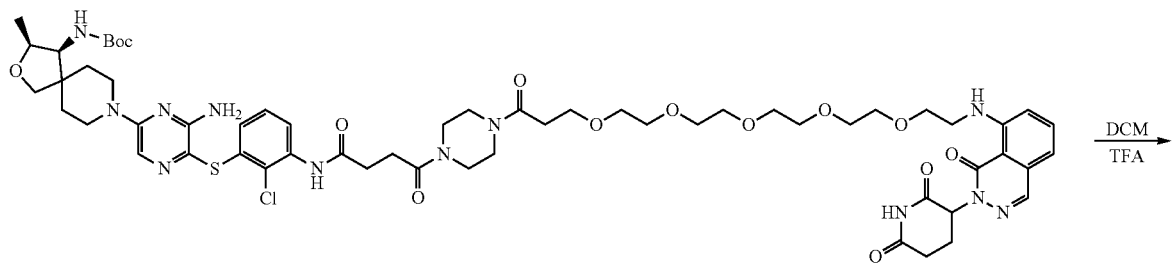

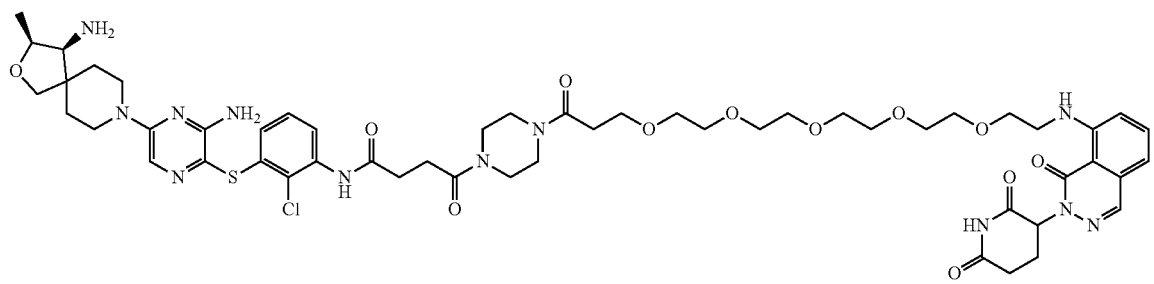

To a solution of tert-butyl ((3S,4S)-8-(6-amino-5-((2-chloro-3-(4-(4-(1-((3-(2,6-dioxopiperidin-3-yl)-4-oxo-3,4-dihydrophthalazin-5-yl)amino)-3,6,9,12,15-pentaoxaoctadecan-18-oyl)piperazin-1-yl)-4-oxobutanamido)phenyl)thio)pyrazin-2-yl)-3-methyl-2-oxa-8-azaspiro[4.5]decan-4-yl)carbamate (22 mg, 0.018 mmol) in 0.3 ml of DCM was added 0.1 ml of TFA and stirred at room temperature for 1 hour. The reaction mixture was concentrated in vacuo. The reaction mixture was purified by amino silica gel column chromatography to give the product. (Yield: 16 mg, 79%).

1H NMR (400 MHz, DMSO-d6) δ=11.05 (s, 1H), 9.54 (s, 1H), 8.83 (t, J=5.3 Hz, 1H), 8.22 (s, 1H), 7.64 (t, J=7.8 Hz, 1H), 7.62 (s, 1H), 7.48 (d, J=7.3 Hz, 1H), 7.14 (t, J=8.1 Hz, 1H), 6.92 (d, J=8.2 Hz, 1H), 6.91 (d, J=8.1 Hz, 1H), 6.42 (dd, J=8.1, 1.5 Hz, 1H), 6.10 (s, 2H), 5.71 (m, 1H), 4.06 (m, 2H), 3.84 (m, 2H), 3.72-3.6 (m, 5H), 3.6-3.5 (m, 5H), 3.52-3.45 (m, 4H), 3.45-3.35 (m, 15H), 3.3-3.1 (m, 5H), 3.04 (m, 1H), 2.90 (m, 1H), 2.65 (s, 4H), 2.58-2.5 (m, 3H), 2.09 (m, 1H), 1.76-1.40 (m, 4H), 1.08 (d, J=6.4 Hz, 3H).

MS (ESI, m/z): [M+$^1$]+=[1135.8][1137.8]

Example 79: N-(3-((3-amino-5-((3S,4S)-4-amino-3-methyl-2-oxa-8-azaspiro[4.5]decan-8-yl)pyrazin-2-yl)thio)-2-chlorophenyl)-4-(4-(1-((3-(2,6-dioxopiperidin-3-yl)-4-oxo-3,4-dihydrophthalazin-5-yl)amino)-3,6,9,12,15,18-hexaoxahenicosane-21-oyl)piperazin-1-yl)-4-oxobutanamide

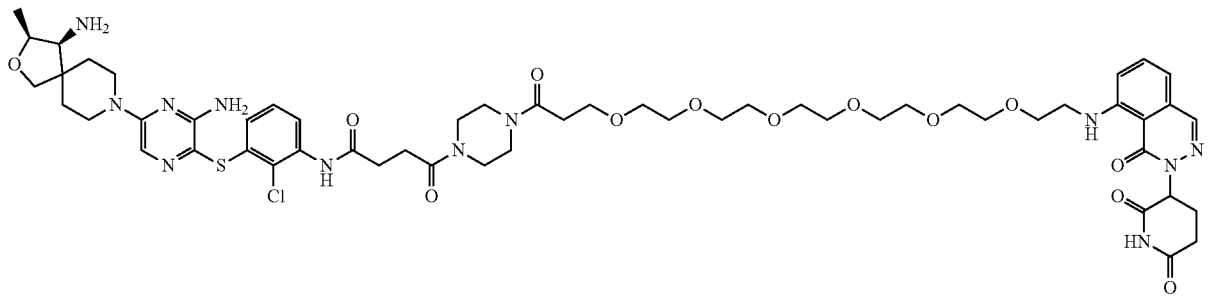 [SMILES: C[C@@H]1OCC2(CCN(c3cnc4c(n3)Nc3ccc(NC(=O)CCC(=O)N5CCN(C(=O)CCOCCOCCOCCOCCOCCOCCNc6cccc7cnn(C8CCC(=O)NC8=O)c(=O)c67)CC5)c(Cl)c3S4)CC2)[C@@H]1N]

The titled compound is synthesized through following procedure:

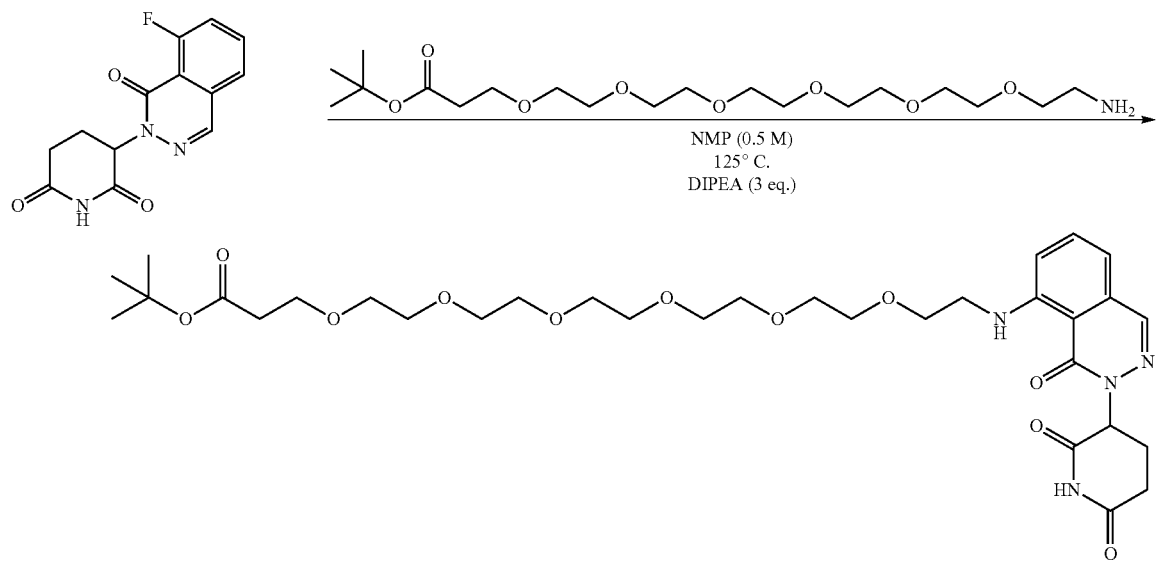

The solution of 3-(8-amino-1-oxophthalazin-2(1H)-yl)piperidine-2,6-dione (200 mg, 0.727 mmol), tert-butyl 1-amino-3,6,9,12,15,18-hexaoxahenicosan-21-oate (357 mg, 0.872 mmol) and DIPEA (0.38 ml, 2.18 mmol) in 1.5 ml of NMP was stirred for 20 hours at 125° C. The reaction mixture was purified by Reverse phase column chromatography (water (0.1% FA)/ACN (0.1% FA)=95/1 to 0/100 gradient) to give the product. (Yield: 439 mg, 90.9%). MS (ESI, m/z): [M+$^1$]+=[665.4].

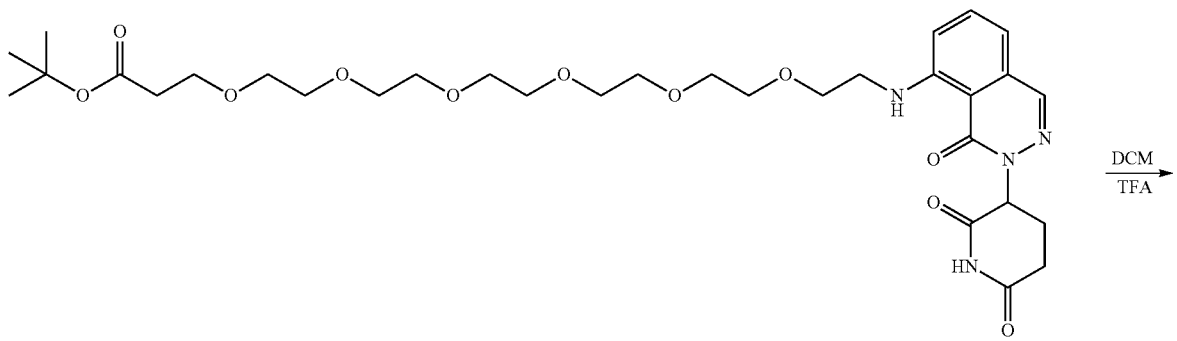

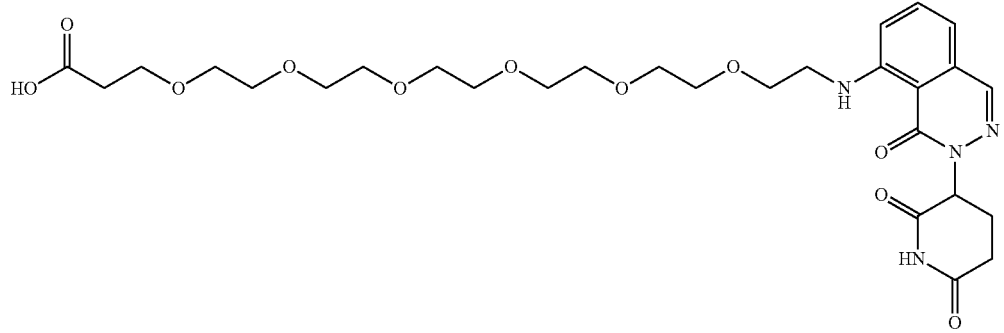

To a tert-butyl 1-((3-(2,6-dioxopiperidin-3-yl)-4-oxo-3,4-dihydrophthalazin-5-yl)amino)-3,6,9,12,15,18-hexaoxahenicosan-21-oate (439 mg, 0.660 mmol) in 5 ml of DCM was added 1 ml of TFA and the mixture was stirred at room temperature for 1 hour. The reaction mixture was concentrated in vacuo and used for the next step without further purification. (Yield: 659 mg, 2.2 TFA salts, quant.). MS (ESI, m/z): [M+1]$^+$=[609.2].

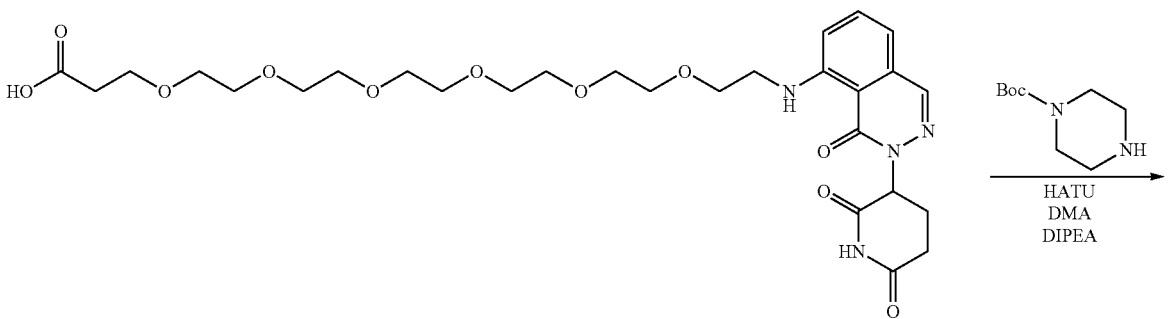

To a solution of 1-((3-(2,6-dioxopiperidin-3-yl)-4-oxo-3,4-dihydrophthalazin-5-yl)amino)-3,6,9,12,15,18-hexaoxahenicosan-21-oic acid (21.7 mg, 0.0357 mmol), tert-butyl piperazine-1-carboxylate (11.9 mg, 0.0535 mmol) and DIPEA (0.0186 ml, 0.107 mmol) in DMF (0.4 mL) was added HATU (20.3 mg, 0.054 mmol) at 0° C. and the mixture was stirred at room temperature for 1 hour. The reaction mixture was purified by reverse column chromatography to give the product. (Yield: 28 mg, quant.). MS (ESI, m/z): [M+$^1$]+=[777.4].

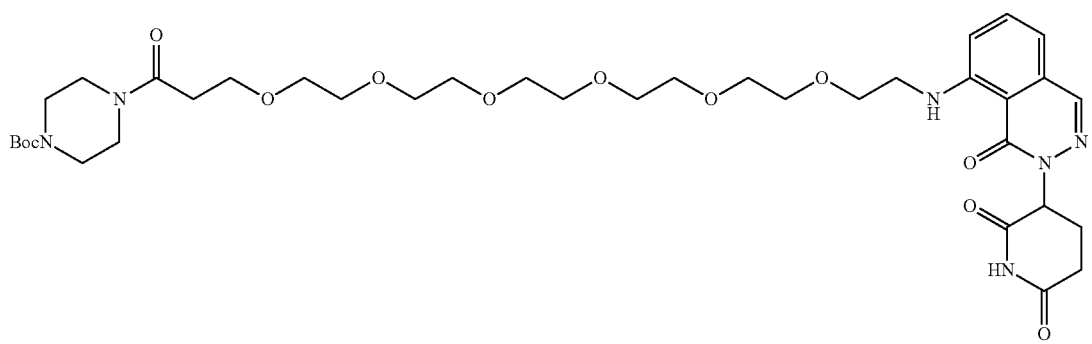

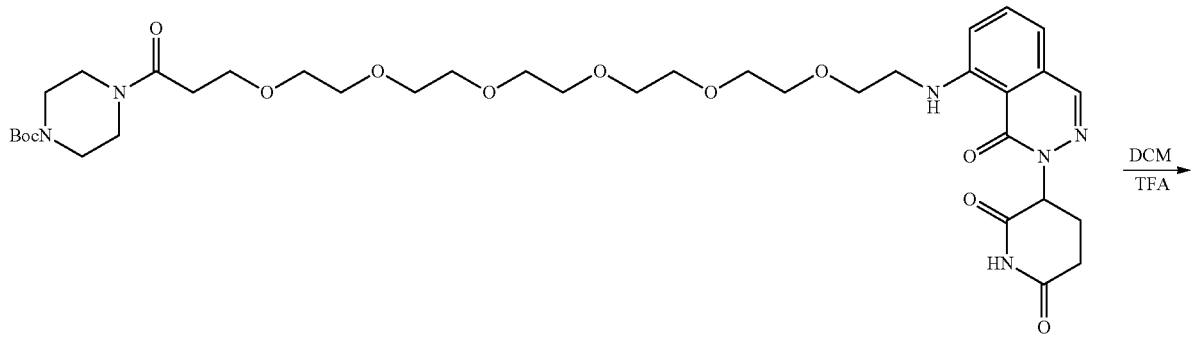
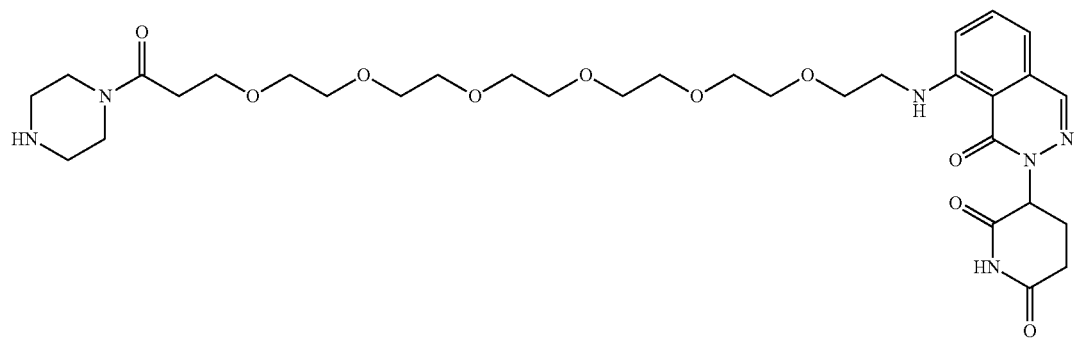
To a tert-butyl 4-(1-((3-(2,6-dioxopiperidin-3-yl)-4-oxo-3,4-dihydrophthalazin-5-yl)amino)-3,6,9,12,15,18-hexaoxahenicosan-21-oyl)piperazine-1-carboxylate (28 mg, 0.035 mmol) in 0.5 ml of DCM was added 0.1 ml of TFA and the mixture was stirred at room temperature for 1 hour. The reaction mixture was concentrated in vacuo and used for the next step without further purification. (Yield: 24 mg, quant.) MS (ESI, mu/z): [M+1]$^+$=[677.4].
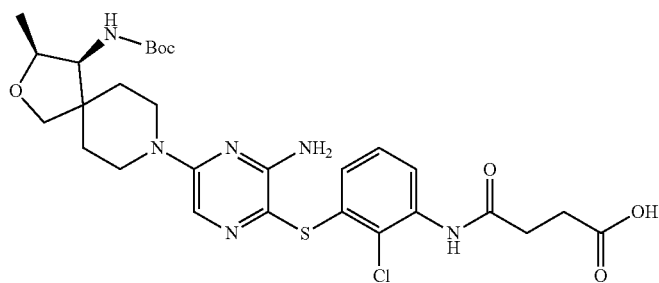
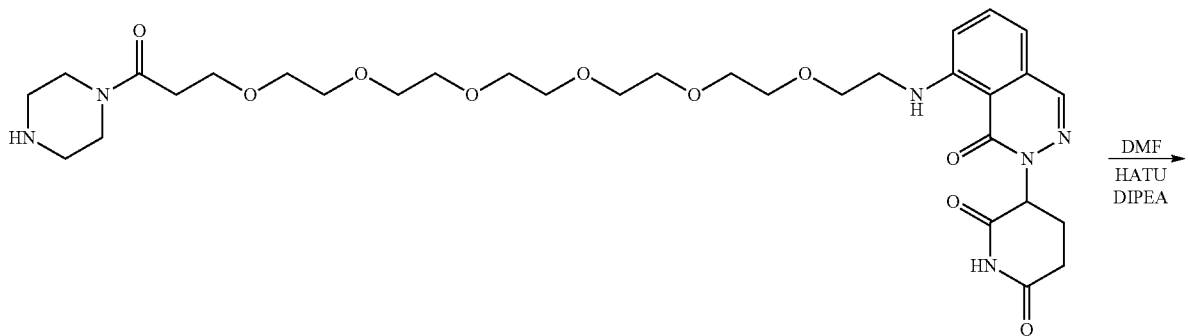

-continued

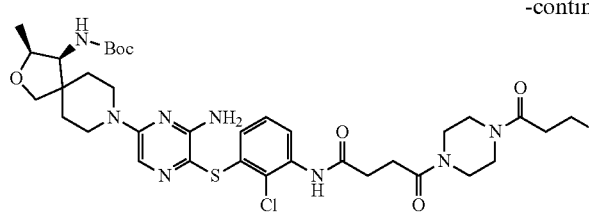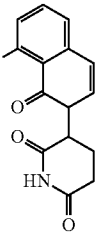

To a solution of 3-(1-oxo-8-((21-oxo-21-(piperazin-1-yl)-3,6,9,12,15,18-hexaoxahenicosyl)amino)phthalazin-2(1H)-yl)piperidine-2,6-dione (24 mg, 0.035 mmol), 4-((3-((3-amino-5-((3S,4S)-4-((tert-butoxycarbonyl)amino)-3-methyl-2-oxa-8-azaspiro[4.5]decan-8-yl)pyrazin-2-yl)thio)-2-chlorophenyl)amino-4-oxobutanoic acid (17.5 mg, 0.028 mmol) and DIPEA (0.037 ml, 0.214 mmol) in DMF (0.4 mL) was added HATU (17.6 mg, 0.046 mmol) at 0° C. and the mixture was stirred at room temperature for 1 hour. The reaction mixture was purified by reverse column chromatography to give the product.

(yield: 23 mg, 50.6%)

MS (ESI, m/z): [M+$^1$]+=[1279.6][1281.6]

3.04 (m, 2H), 2.90 (m, 2H), 2.65 (s, 4H), 2.58-2.5 (m, 3H), 2.09 (m, 1H), 1.76-1.40 (m, 4H), 1.08 (d, J=6.5 Hz, 3H).

MS (ESI, m/z): [M+$^1$]+=[1179.4][1181.4]

Example C

CRBN Binding Affinity Evaluation.

1. CRBN Binding Affinity Measurement [NanoBRET Assay]

[1] Evaluation Method

The binding affinity of the synthesized compounds to CRBN E3 ligase was measured using PROMEGA NANO-

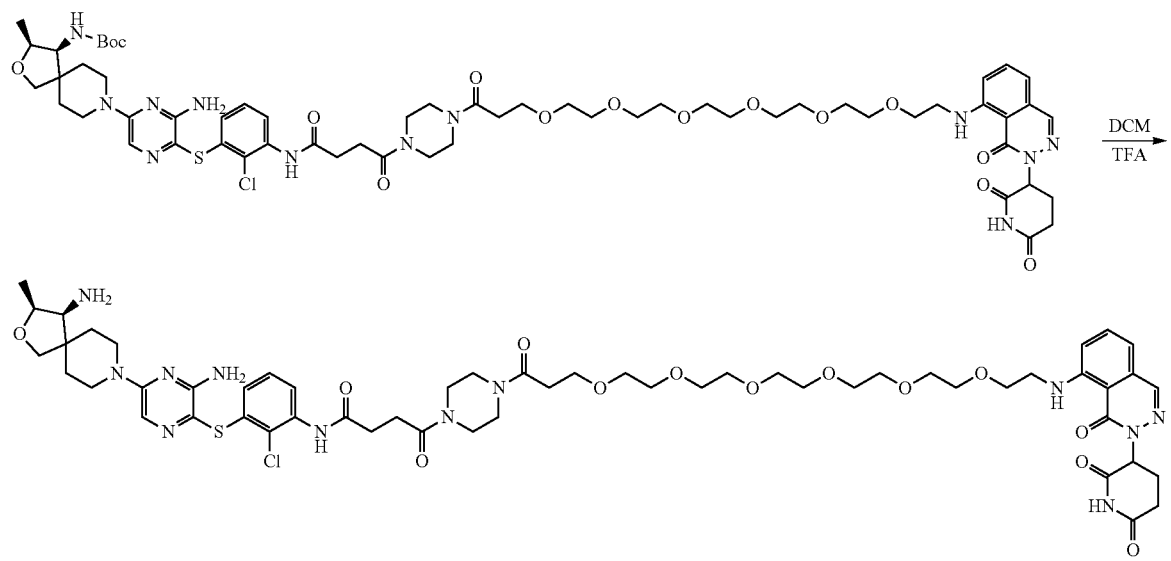

To a solution of tert-butyl ((3S,4S)-8-(6-amino-5-((2-chloro-3-(4-(4-(1-((3-(2,6-dioxopiperidin-3-yl)-4-oxo-3,4-dihydrophthalazin-5-yl)amino)-3,6,9,12,15,18-hexaoxahenicosan-21-oyl)piperazin-1-yl)-4-oxobutanamido)phenyl)thio)pyrazin-2-yl)-3-methyl-2-oxa-8-azaspiro[4.5]decan-4-yl)carbamate (23 mg, 0.018 mmol) in 0.3 ml of DCM was added 0.1 ml of TFA and the mixture was stirred at room temperature for 1 hour. The reaction mixture was concentrated in vacuo. The reaction mixture was purified by amino silicagel column chromatography to give the product (Yield: 11.4 mg, 53.77%).

1H NMR (400 MHz, DMSO-d6) δ=11.01 (s, 1H), 9.54 (s, 1H), 8.83 (t, J=5.3 Hz, 1H), 8.22 (s, 1H), 7.64 (t, J=7.8 Hz, 1H), 7.62 (s, 1H), 7.48 (d, J=7.3 Hz, 1H), 7.14 (t, J=8.1 Hz, 1H), 6.92 (d, J=8.2 Hz, 1H), 6.92 (d, J=8.1 Hz, 1H), 6.42 (dd, J=8.1, 1.5 Hz, 1H), 6.10 (s, 2H), 5.71 (m, 1H), 4.06 (m, 1H), 3.82 (m, 2H), 3.72-3.6 (m, 5H), 3.6-3.5 (m, 5H), 3.52-3.45 (m, 4H), 3.45-3.35 (m, 17H), 3.3-3.1 (m, 5H),

BRET™ Intracellular E3 ligase Assay, CRBN [cat #N2910]. Bioluminescence resonance energy transfer (BRET) assay is a method that the transfer of luminescence energy of POI into a bound fluorescent tracer is measured. When a synthesized compound is bound to the POI, the binding of fluorescent tracer to the POI is decreased, and accordingly decreased transfer of the luminescence energy is measured. Thus, the affinity of a compound to the POI can be measure.

[2] Culture of Cell Lines and Expression of NanoLuc-CRBN Fusion Vector

HEK 293T cells purchased from the Korean Cell Line Bank were cultured in a DMEM (Welgene) medium with 10% fetal bovine serum, penicillin [100 U/ml] and streptomycin [100 mg/ml]. The cultured cell lines were detached from the culture dish using Trypsin-EDTA (Gibco), and attached to a culture dish at a concentration of $2 \times 10^5$ cells/ml. 9.0 mg/ml of DDB1 expression vector and 1.0 mg/ml of NanoLuc-CRBN fusion vector were transfected using LIPOFECTAMINE™ 3000.

[3] Treatment with Compound and Measurement of CRBN Binding Affinity

At 24 hours after transfection, the cell lines were detached from the culture dish using Trypsin-EDTA (Gibco), aliquoted into a 384-white well plate at a concentration of $2 \times 10^5$ cells/ml, treated with nanoBRET tracer, and mixed for 15 seconds. Then, the cell lines were treated with a compound prepared at various concentrations, and then mixed for 15 seconds. Then, cell walls were broken by using digitonin, and the mixture was reacted for 25 minutes. Then, the mixture was treated with luciferase substrate. The luminescence intensity and the fluorescence intensity were measure at donor emission wavelength (450 nm) and at acceptor emission wavelength (610 nm), and then BRET ratio was calculated and normalized. BRET ratio was calculated by the following formula:

BRET ratio: Acceptor/Donor×1000

[4] CRBN Binding Affinity of the Compound

Figure 2:
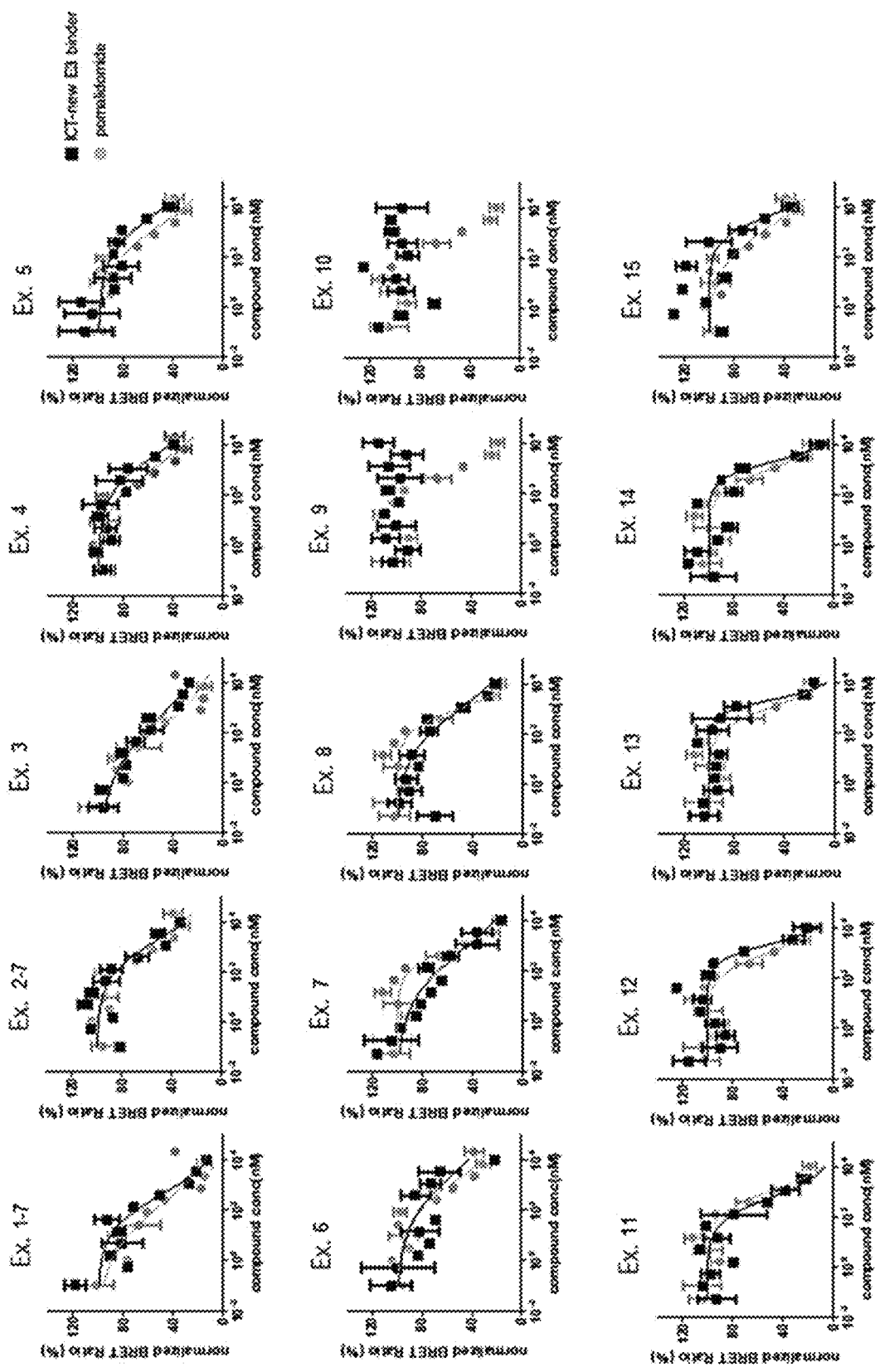
FIG. 2 illustrates CRBN ligand affinity.

The binding affinity of the synthesized compound to CRBN was measured using BRET assay. As shown in the results of Table 2 and FIG. 2, most of the compounds exhibit a binding affinity equivalent to that of pomalidomide, and in particular, the compounds of Examples 7, 8 and 11 exhibit excellent CRBN binding affinity.

TABLE 1

| BRET ratio $IC_{50}$ | | |
|---|---|---|
| PROTAC compound | $IC_{50}$ (μM) | $IC_{50}$ (μM) Pomalidomide |
| Ex. 1-7 | 0.38 | 0.15 |
| Ex. 2-7 | 2.0 | 1.80 |
| Ex. 3 | 0.42 | 0.15 |
| Ex. 4 | 5.2 | 1.80 |
| Ex. 5 | 7.5 | 1.80 |
| Ex. 6 | 4.6 | 1.80 |
| Ex. 7 | 0.54 | 1.02 |
| Ex. 8 | 0.98 | 1.02 |
| Ex. 9 | Na | 1.02 |
| Ex. 10 | Na | 1.02 |
| Ex. 11 | 0.56 | 1.02 |
| Ex. 12 | 2.20 | 1.02 |
| Ex. 13 | 2.00 | 1.02 |
| Ex. 14 | 1.90 | 1.02 |
| Ex. 15 | 4.50 | 1.02 |

Pomalidomide: comparator drug for assay comparison

Example D

Evaluation of BRD4 Targeted PROTAC

[1] Culture of Cell Lines and Treatment with Compound

Human breast cancer cell line [MDA-MB-231] was cultured in RPMI medium with 10% petal bovine serum, penicillin [100 U/ml] and streptomycin [100 mg/ml]. The synthesized compound was prepared as a stock solution of 10 mM or 50 mM dissolved in DMSO [dimethyl sulfoxide], and it was sequentially diluted to treat the cell line.

[2] Evaluation of BRD4 Targeted PROTAC's Ability for BRD4 Protein Degradation

Figure 3:
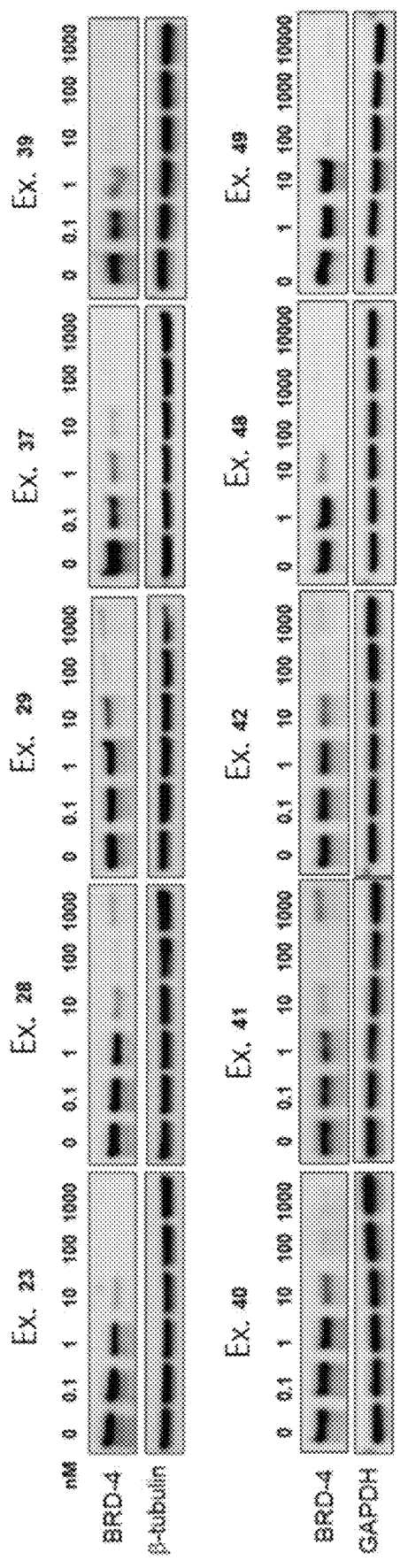
FIG. 3 shows the proteolytic efficacy of the BRD4-targeted PROTAC to which the E3 ligase binder is applied.

To evaluate the PROTAC's degradation ability to BRD4 expressed in cells, the cells were aliquoted into a 6 well plate at a concentration of $5 \times 10^5$ cells/ml, and then the sample was treated for 24 hours. In order to conduct western blotting assay to confirm protein expression, the cell treated with the compound was treated for 30 minutes with 70 μL of RIPA buffer wherein protease inhibitor is added. Then, cell lysate was collected on ice using a scraper and centrifuged at 4° C. 15,000 rpm for 30 minutes to obtain a supernatant containing protein. Then, SDS-PAGE is conducted for 10 μg of protein per each sample, and the protein is transferred to a membrane. The protein is reacted with antibodies of anti-BRD4, anti-tubulin and anti-GAPDH at 4° C. for 16 hours, and then, reacted with secondary antibodies at room temperature for 1 hour. The protein expression is confirmed using SUPERSIGNAL™ WEST PICO PLUS chemiluminescence substrate and image analyzer. The protein expression was normalized based on the expression value of β-tublin or GAPDH. The amount of protein expression in each sample was measured in % based on the sample treated with 0.1% DMSO vehicle which was set to 100%. The amount of protein expression was quantified using the IMAGE J PROGRAM. The change in the amount of protein expression due to the treatment of compound ($DC_{50}$: the concentration of compounds where the 50% inhibition of protein expression is achieved) was calculated using GRAPHICPAD PRISM 8.0 software. As shown in the results of Table 3 and FIG. 3, the compounds of Example 23, Example 28, Example 29, Example 37, Example 39, Example 40, Example 41, Example 42, Example 48 and Example 49 effectively degraded BRD4.

Figure 4:
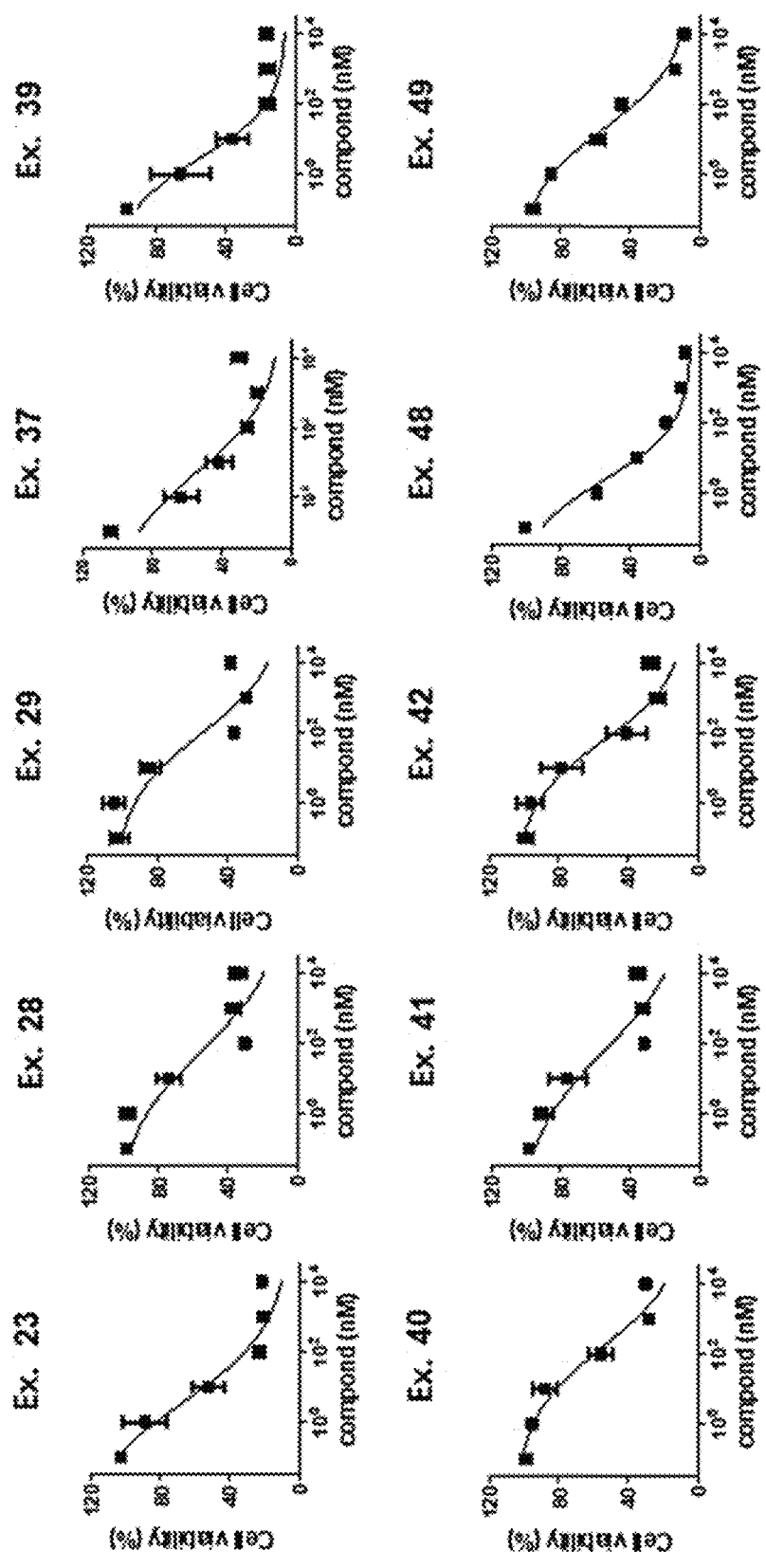
FIG. 4 shows the effect of inhibiting cancer cell proliferation of BRD4-targeted PROTAC to which E3 ligase binder is applied.

[3] Evaluation of Anti-Proliferative Activity Against Cancer Cell by BRD4 Targeted PROTAC In order to observe inhibition of cell growth, cells were aliquoted into concentrations of 5,000 cells/well at 96 well plates, and then were treated with samples prepared at various concentrations for 72 hours. The cell survival was calculated by steps of adding in each well 10 ml of water soluble tetrazolium salt (WST-8) which produces formazon in response to dehydrogenase present in the electron transport chain in mitochondria, incubating for 2 hours, measuring the absorbance at 450 nm, and calculating by GraphicPad Prism 8.0 software. The $IC_{50}$ value (the concentration of compounds where 50% inhibition of cell proliferation is achieved) is the average of three independent measurement results. The results are shown in the table below. As shown in the results of Table 3 and FIG. 4, the compounds of Example 23, Example 28, Example 29, Example 37, Example 39, Example 40, Example 41, Example 42, Example 48 and Example 49 which effectively degraded BRD4 inhibited effectively cancer cell proliferation at the below of concentration 250 nM.

TABLE 2

| $DC_{50}$ and $IC_{50}$ of BRD4-targeted PROTAC with novel E3 ligase binder | | |
|---|---|---|
| PROTAC compound | $DC_{50}$ (nM) | $IC_{50}$ (nM) |
| Ex. 23 | 2.6 | 32.2 |
| Ex. 25 | — | 232 |
| Ex. 26 | — | 126 |
| Ex. 27 | — | 640 |
| Ex. 28 | 3.3 | 33.1 |
| Ex. 29 | 3.7 | 98.6 |
| Ex. 30 | — | >1000 |
| Ex. 31 | — | >1000 |
| Ex. 32 | — | >1000 |
| Ex. 33 | 171 | >1000 |
| Ex. 34 | 38.6 | >1000 |

TABLE 2-continued

DC$_{50}$ and IC$_{50}$ of BRD4-targeted PROTAC with novel E3 ligase binder

| PROTAC compound | DC$_{50}$ (nM) | IC$_{50}$ (nM) |
|---|---|---|
| Ex. 35 | 274.6 | >1000 |
| Ex. 36 | 663 | >1000 |
| Ex. 37 | 0.173 | <1.0 |
| Ex. 38 | 66.5 | 568 |
| Ex. 39 | 0.575 | <1.0 |
| Ex. 40 | 10.9 | 227 |
| Ex. 41 | 4.4 | 137 |
| Ex. 42 | 10.7 | 20.3 |
| Ex. 43 | 184.9 | >1000 |
| Ex. 44 | 930.1 | >1000 |
| Ex. 45 | 108.3 | >1000 |
| Ex. 46 | na | >1000 |
| Ex. 47 | 52.26 | 754 |
| Ex. 48 | 5.9 | 2.15 |
| Ex. 49 | 40.7 | 30.6 |
| Ex. 50 | na | 622 |
| Ex. 51 | na | 101 |
| Ex. 52 | na | 127 |
| Ex. 53 | na | >1000 |

Example E

Evaluation for SHP2 Targeted PROTAC

[1] Culture of Cell Line and Treatment with Compound

Human hematologic cancer cell line [MV-4-11] was cultured in IMDM medium with 10% fetal bovine serum, penicillin [100 U/ml] and streptomycin [100 mg/ml]. The synthesized compound was prepared with a stock solution of 10 mM or 50 mM dissolved in DMSO [dimethyl sulfoxide], and it was sequentially diluted to treat the cell line.

[2] Evaluation of SHP2 Targeted PROTAC's Ability for SHP2 Protein Degradation

Figure 5:
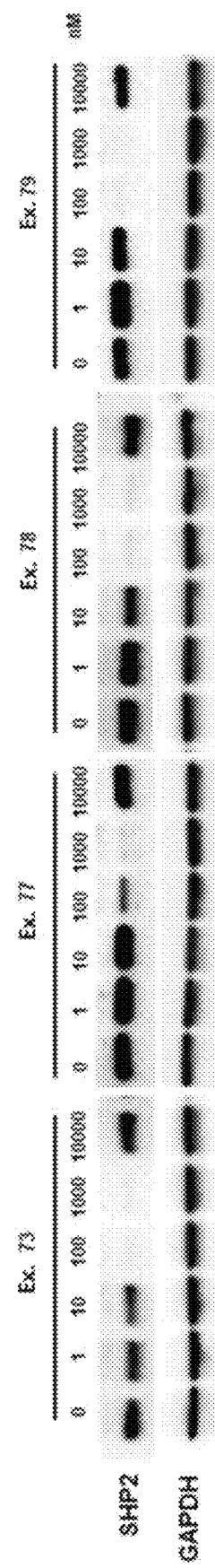
FIG. 5 shows the proteolytic efficacy of SHP2-targeted PROTAC to which the E3 ligase binder is applied.
Figure 6:
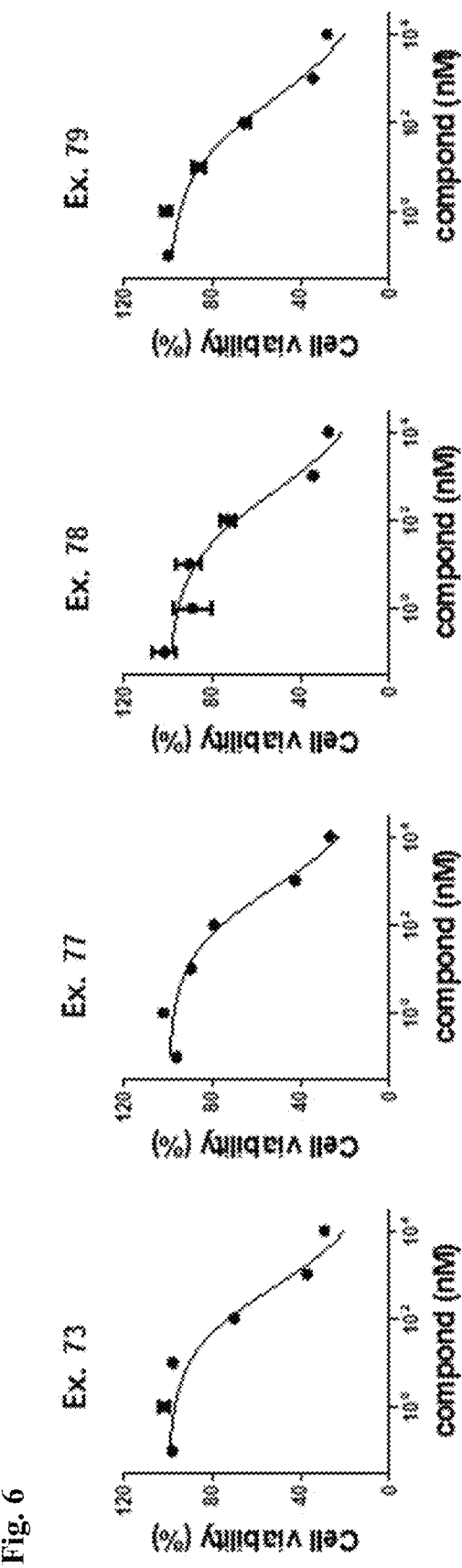
FIG. 6 shows the effect of inhibiting cancer cell proliferation of SHP2-targeted PROTAC to which E3 ligase binder is applied.

To observe the PROTAC's degradation ability to SHP2 expressed in cells, the cells were aliquoted into a 12 well plate at a concentrations of 3×10$^5$ cells/well, and then the sample was treated for 24 hours. In order to conduct western blotting assay to confirm protein expression, the cell treated with the compound was treated for 30 minutes with 70 μL of RIPA buffer with wherein protease inhibitor is added. Then, cell lysate was collected on ice using a scraper and centrifuged at 4° C. 15,000 rpm for 30 minutes to obtain a supernatant containing protein. Then, SDS-PAGE is conducted for 10 μg of protein per sample, and the protein is transferred to a membrane. The protein is reacted with antibodies of anti-SHP2 and anti-GAPDH at 4° C. for 16 hours, and then, reacted with the secondary antibodies at room temperature for 1 hour. The protein expression is confirmed using SuperSignal™ West Pico PLUS chemiluminescence substrate and image analyzer. The protein expression inhibition was normalized based on the expression value of GAPDH. The amount of protein expression in each sample was measured based on the sample treated with 0.1% DMSO vehicle which was set to 100%. The amount of protein expression was quantified using the Image J program. The change in the amount of protein expression due to the treatment of compound (DC$_{50}$: the concentration of compounds where the 50% inhibition of protein expression is achieved) was calculated using GraphicPad Prism 8.0 software. As shown in the results of Table 4 and FIG. 5, the compounds of Example 73, Example 77, Example 78 and Example 79 effectively degraded SHP2.

[3] Evaluation of Anti-Proliferative Activity Against Cancer Cell by SHP2 Targeted PROTAC In order to observe inhibition of cell growth, cells were aliquoted into concentrations of 7,000 cells/well at 96 well plates, and then were treated with samples prepared at various concentrations for 72 hours. The cell survival was calculated by steps of adding in each well 10 ml of water soluble tetrazolium salt (WST-8) which produces formazon in response to dehydrogenase present in the electron transport chain in mitochondria, incubating for 3 hours, measuring the absorbance at 450 nm, and calculating GRAPHICPAD PRISM 8.0 software. The results are shown in the table below. As shown in the results of Table 3 and FIG. 5, the compounds of Example 73, Example 77, Example 78 and Example 79 effectively which effectively degrade SHP2 inhibited effectively cancer cell proliferation.

TABLE 3

DC$_{50}$ and IC$_{50}$ of SHP2-targeted PROTAC with novel E3 ligase binder

| PROTAC compound | DC$_{50}$ (nM) | IC$_{50}$ (nM) |
|---|---|---|
| Ex. 73 | 29.9 | 507 |
| Ex. 77 | 70.19 | 685 |
| Ex. 78 | 24.1 | 422 |
| Ex. 79 | 23.6 | 337 |

Example F

Experimental Material and Methods

1. Cultivation of A549 Cell Lines

The human lung cancer cell line A549 was purchased from the Korean Cell Line Bank.

RPMI (Gibco), FBS (Gibco), penicillin/streptomycin (PS) (Gibco), 100 mm$^2$ cell culture dish (SPL), 6-well culture plate (NEST), PBS pH 7.4 (Gibco), Trypsin-EDTA (Gibco), counting chamber (Hematocytometer) (INCYTO) and 0.4% trypan blue solution (SIGMA) were used for cell culture.

2. Treatment with PROTAC Compound of the Present Invention

5×10$^5$ cells were seeded for each well of the 6 well plate (SPL company), and the cells were cultured with a total of 1.5 mL of the culture medium volume. The cultured cells were treated with various concentrations (0 nM, 0.1 nM, 0.3 nM, 1 nM, 3 nM, 10 nM, 30 nM, 100 nM, 300 nM, 1000 nM, 3000 nM, 10000 nM) of PROTAC compound according to the present invention and cultured for 24 hours.

3. Western Blotting

For SDS-PAGE and Western blotting, 1×RIPA lysis buffer (Rockland), 100× protease inhibitor cocktail (CST), BCA protein assay kit (ThermoScientific), bovine serum albumin (GenDEPOT), 4-15% Mini-PROTEAN TGX stain-free gel (Bio-rad), 10× tris/glycine/SDS buffer (Bio-rad), Trans-blot turbo 5× transfer buffer (Bio-rad), 10×TBS (Bio-rad), 10% Tween 20 (Bio-rad), Color protein standard broad range (Bio-rad), Non-Reducing Lane Marker Sample buffer (ThermoScientific), Blotting-Grade Blocker (Bio-rad), BRD4 (E2A7X) Rabbit mAb (CST), beta-Tubulin Rabbit Ab (CST), Goat pAb to Rb IgG (HRP)(abcam), SUPERSIGNAL™ WEST PICO PLUS chemiluminescence substrate (ThermoScientific) were used. For cell lysis, a lysis buffer was added and cell lysate was obtained using a cell scraper.

Specifically, cells were treated with 70 μl of 1×RIPA buffer containing protease inhibitors. Cell lysate was collected on ice using a scraper and incubated for 30 minutes. Then, cells were centrifuged at 4° C. 15,000 rpm for 30 minutes to obtain a cell lysate.

The standard curve was obtained using BCA assay, and the protein mass in the lysate was quantified by substituting the standard curve. The mixture was incubated at 37° C. for 30 minutes using a sample solution of 1 µl and a BCA solution of 200 µl. The absorbance was measured at 562 nm. Samples were prepared by adding a sample buffer to reach 10 µg per well.

SDS-PAGE was conducted by setting a running time of 70 minutes at 110 V in a 4-15% Mini-PROTEAN TGX stain-free gel (15 wells). A transfer was conducted using a trans-blot turbo transfer system (Bio-rad). Blocking was conducted using a blocking-grade blocker (Bio-rad) for 1 hour. Then, it was washed with 1×TBS containing 0.1% tween 20, and reacted with anti-BRD4 antibody (1:3000) or anti-beta-tubulin antibody (1:3000) in bovine serum albumin as a primary antibody at 4° C. for 16 hours. After washing three times for 10 minutes with 1×TBS containing 0.1% tween 20, it was reacted with anti-rabbit antibody (1:10000) in the blotting-grade blocker as a secondary antibody at room temperature for 1 hour. Then, after washing three times for 10 minutes with 1×TBS containing 0.1% tween 20, detection was conducted with SUPERSIGNAL™ WEST PICO PLUS chemiluminescence substrate.

For result analysis, final blot data were obtained using an image analyzer (GE).

Table 4 shows each $DC_{50}$ (50% degradation concentration) for BRR4 of the PROTAC compound according to the present invention:

TABLE 4

| PROTAC compound | $DC_{50}$ [1] | $DC_{50}$ [2] |
|---|---|---|
| Ex. 21 | 1600 nM | 242 nM |
| Ex. 23 | 11.3 nM | 10.9 nM |
| Ex. 25 | 56.86 nM | 49.63 nM |
| Ex. 26 | 22.02 nM | 567.9 nM |
| Ex. 27 | 9.21 nM | 11.87 nM |
| Ex. 28 | 25.26 nM | 298.8 nM |

$DC_{50}$ [1]: $DC_{50}$ value is calculated by comparing band intensity with that of a sample which is not treated with a PROTAC compound as a controlled group.

$DC_{50}$ [2]: $DC_{50}$ value is calculated by comparing the band intensity relative to that of beta-tubulin with that of the controlled group.

As a result of the experiment, it can be seen that the PROTAC compound containing a piperidinedione derivative according to the present invention has a very excellent effect of degradation on BRD4, which is known as POI for treatment of cancer.

INDUSTRIAL APPLICABILITY

The piperidinedione derivatives according to the present invention and the PROTAC compounds containing the same can be usefully used as an anticancer agent.

The invention claimed is:

1. A compound of Formula 1 or a pharmaceutical acceptable salt thereof:

[Formula 1]

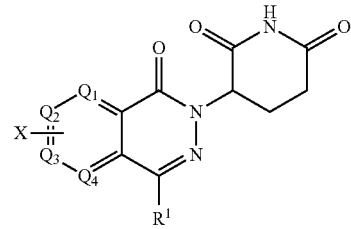

wherein

X is hydrogen, halogen, amino, nitro, hydroxy, $C_1$ to $C_6$ straight or branched alkyloxy, or 4 to 8 membered heterocyclic group including oxygen or nitrogen, $Q_1$ to $Q_4$ are each independently C—F, C—Cl, C—H, C—X or N, provided that at least one of $Q_1$ to $Q_4$ is C—X, $R^1$ is hydrogen, nitro, amino, carbonyl, $C_1$ to $C_6$ straight, branched or cyclic alkyl, or $C_1$ to $C_6$ straight, branched or cyclic alkyl substituted with halogen.

2. The compound of Formula 1 or a pharmaceutical acceptable salt thereof according to claim 1, wherein X is hydrogen, fluoro, chloro, bromo, amino, nitro, hydroxy, piperazinyl group, methoxy or ethoxy, $Q_1$ to $Q_4$ are each independently C—H or C—X, and $R^1$ is hydrogen, amino, methyl, ethyl, cyclopropyl or $CF_3$.

3. The compound of Formula 1 or a pharmaceutical acceptable salt thereof according to claim 1, wherein the compound of Formula 1 is selected from the group consisting of following compounds:

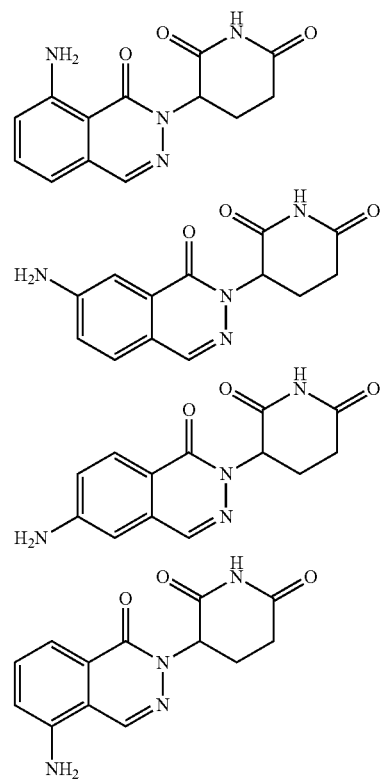

277
-continued
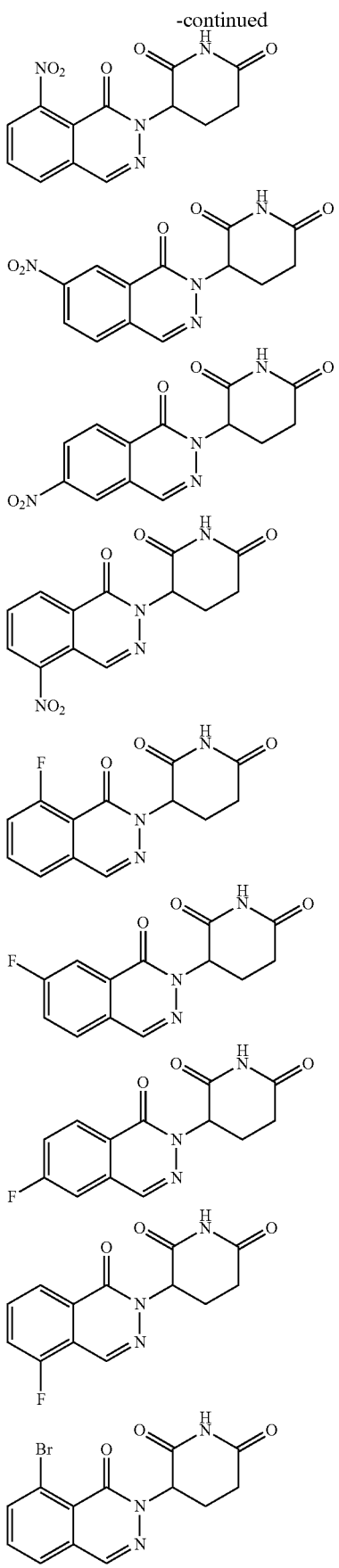
278
-continued
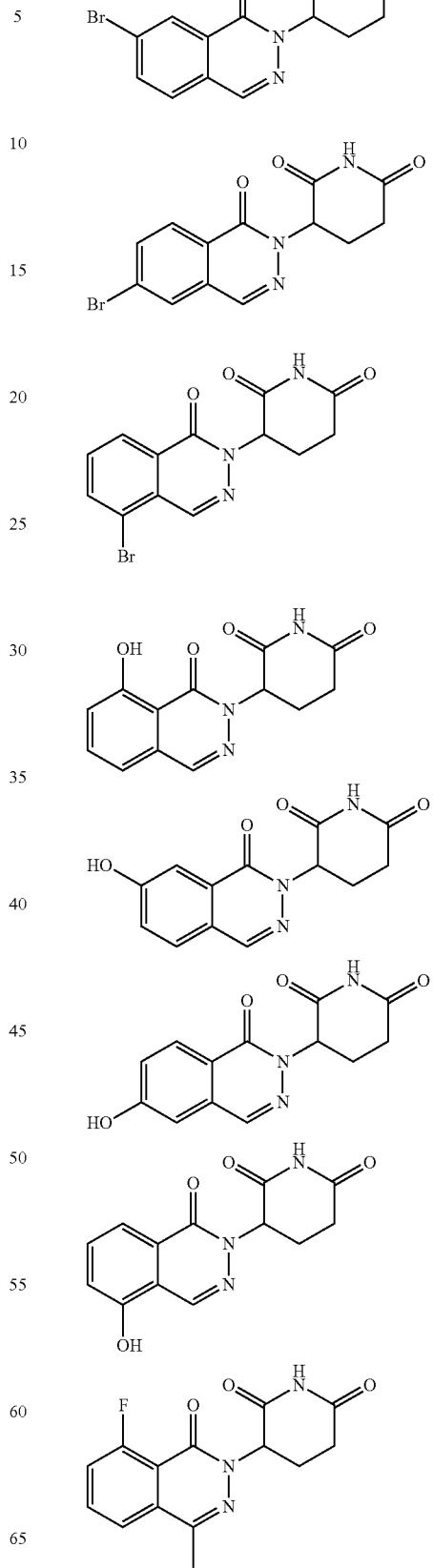

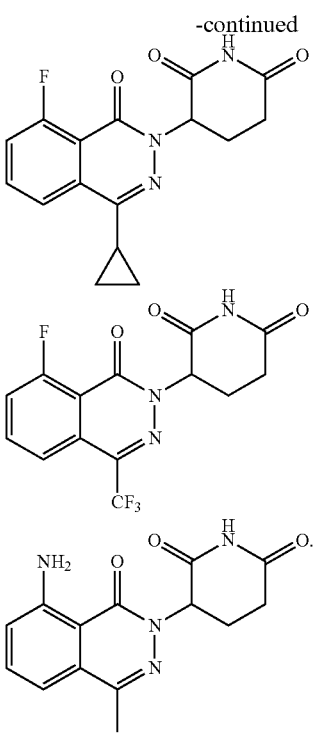

4. A compound or a pharmaceutically acceptable salt thereof, wherein the compound is selected from the group consisting of following compounds:

3-(8-nitro-1-oxophthalazin-2 (1H)-yl) piperidine-2,6-dione;
3-(8-nitro-1-oxophthalazin-2 (1H)-yl) piperidine-2,6-dione;
3-(5-nitro-1-oxophthalazin-2 (1H)-yl) piperidine-2,6-dione;
3-(5-amino-1-oxophthalazin-2 (1H)-yl) piperidine-2,6-dione;
3-(8-fluoro-1-oxophthalazin-2 (1H)-yl) piperidine-2,6-dione;
3-(5-fluoro-1-oxo-1,2-dihydrophthalazin-2-yl) piperidine-2,6-dione;
3-(6-fluoro-1-oxophthalazin-2 (1H)-yl) piperidine-2,6-dione;
3-(7-fluoro-1-oxophthalazin-2 (1H)-yl) piperidine-2,6-dione;
3-(8-fluoro-4-methyl-1-oxophthalazin-2 (1H)-yl) piperidine-2,6-dione;
3-(8-amino-4-methyl-1-oxophthalazin-2 (1H)-yl) piperidine-2,6-dione;
3-(1-oxo-6-(piperazin-1-yl) phthalazin-2 (1H)-yl) piperidine-2,6-dione;
3-(1-oxo-7-(piperazin-1-yl) phthalazin-2 (1H)-yl) piperidine-2,6-dione;
3-(8-methoxy-1-oxophthalazin-2 (1H)-yl) piperidine-2,6-dione;
3-(7-methoxy-1-oxophthalazin-2 (1H)-yl) piperidine-2,6-dione;
3-(6-methoxy-1-oxophthalazin-2 (1H)-yl) piperidine-2,6-dione;
3-(5-methoxy-1-oxophthalazin-2 (1H)-yl) piperidine-2,6-dione;
3-(6-bromo-1-oxophthalazin-2 (1H)-yl) piperidine-2,6-dione; and
3-(1-oxo-8-(piperazin-1-yl) phthalazin-2 (1H)-yl) piperidine-2,6-dione 2HCl.

* * * * *